US011060071B2

(12) United States Patent
Hansen et al.

(10) Patent No.: US 11,060,071 B2
(45) Date of Patent: Jul. 13, 2021

(54) INCREASED BIOSYNTHESIS OF BENZYLISOQUINOLINE ALKALOIDS AND BENZYLISOQUINOLINE ALKALOID PRECURSORS IN A RECOMBINANT HOST CELL

(71) Applicant: River Stone Biotech LLC, Cambridge, MA (US)

(72) Inventors: Esben Halkjaer Hansen, Frederiksberg (DK); Markus Schwab, Lorrach (DK); Philipp Berninger, Basel (CH); Fanny Delgrange, Hagenthal-le-Haut (FR); Franziska Grassinger, Basel (CH)

(73) Assignee: RIVER STONE BIOTECH, LLC, Cambridge, MA (US)

( * ) Notice: Subject to any disclaimer, the term of this patent is extended or adjusted under 35 U.S.C. 154(b) by 0 days.

(21) Appl. No.: 16/324,284

(22) PCT Filed: Aug. 9, 2017

(86) PCT No.: PCT/EP2017/070253
§ 371 (c)(1),
(2) Date: Feb. 8, 2019

(87) PCT Pub. No.: WO2018/029282
PCT Pub. Date: Feb. 15, 2018

(65) Prior Publication Data

US 2019/0338255 A1 Nov. 7, 2019

Related U.S. Application Data

(60) Provisional application No. 62/524,120, filed on Jun. 23, 2017, provisional application No. 62/372,356, filed on Aug. 9, 2016.

(51) Int. Cl.
*C12N 9/04* (2006.01)
*C12N 9/02* (2006.01)
*C12P 17/12* (2006.01)

(52) U.S. Cl.
CPC ......... *C12N 9/0006* (2013.01); *C12N 9/0008* (2013.01); *C12P 17/12* (2013.01); *C12Y 101/01001* (2013.01); *C12Y 101/01006* (2013.01); *C12Y 101/0109* (2013.01); *C12Y 101/01021* (2013.01); *C12Y 101/01026* (2013.01); *C12Y 101/01034* (2013.01); *C12Y 101/01035* (2013.01); *C12Y 101/01041* (2013.01); *C12Y 101/01046* (2013.01); *C12Y 101/01049* (2013.01); *C12Y 101/01076* (2013.01); *C12Y 101/05003* (2013.01)

(58) Field of Classification Search
None
See application file for complete search history.

(56) References Cited

FOREIGN PATENT DOCUMENTS

| | | | |
|---|---|---|---|
| WO | WO2011058446 | A2 | 5/2011 |
| WO | WO2015066642 | * | 5/2015 |
| WO | WO2015066642 | A1 | 7/2015 |
| WO | WO2016179296 | A1 | 11/2016 |
| WO | WO2016183023 | A1 | 11/2016 |

OTHER PUBLICATIONS

Chica et al. CurrOpin Biotechnol. Aug. 16, 2005(4):378-84. (Year: 2005).*
Singh et al. Curr Protein PeptSci. 2017, 18, 1-11 (Year: 2017).*
Kizeretal. Appl Environ Microbiol. May 2008 74(10):3229-41. (Year: 2008).*
Pratheretal. CurrOpin Biotechnol. Oct. 19, 2008(5):468-74. (Year: 2008).*
Accession P53111.01—Oct. 1996 (Year: 1996).*
Accession Q12068. Oct. 25, 2004 (Year: 2004).*
Hawkins. Metabolic Engineering of *Saccharomyces cerevisiae* for the Production of Benzylisoquinoline Alkaloids (2009) PHD Thesis. (Year: 2009).*
Thodey et al. Nat Chem Biol. Oct. 10, 2014(10):837-44 (Year: 2014).*
Chenna R., et al. Multiple sequence alignment with the Clustal series of programs. Nucl. Acids Res. vol. 31, No. 13, pp. 3497-3500 (2003).
Fossati E., et al. Synthesis of Morphinan Alkaloids in *Saccharomyces cerevisiae*. PLoS ONE 10(4): e0124459 (2015).
Hagel JM & P. Facchini. Benzylisoquinoline Alkaloid Metabolism: A Century of Discovery and a Brave New World. Plant Cell Physiol. 54(5): 647-672 (2013).
Hawkins K.M. & C.D. Smolke. Production of benzylisoquinoline alkaloids in *Saccharomyces cerevisiae*. Nat Chem. Biol., 4:564-573 (2008).
Hawkins K., Metabolic Engineering of *Saccharomyces cerevisiae* for the Production of Benzylisoquinoline Alkaloids. PHD Thesis, CaltechTHESIS, XP055361294, p. 1-154 (Jan. 1, 2009).
Ilari A., et al. Structural Basis of Enzymatic (S)-Norcoclaurine Biosynthesis_ J Biol. Chem. vol. 284, No. 2, pp. 897-904 (2009).
Mnaimneh S., et al. Exploration of Essential Gene Functions via Titratable Promoter Alleles. Cell., vol. 118, 31-44 (2004).
Nakagawa A., et al. (R, S)-Tetrahydropapaveroline production by stepwise fermentation using engineered *Escherichia coli*. Sci. Rep., 4:6695 (2014).
Nakagawa A., et al. A bacterial platform for fermentative production of plant alkaloids. Nature Communications. 2:326 (2011).
Thodey K. et al., A microbial biomanufacturing platform for natural and semisynthetic opioids. Nat Chem. Biol., 10 (10):837-844 (2014).

* cited by examiner

*Primary Examiner* — Christian L Fronda
(74) *Attorney, Agent, or Firm* — McDonnell Boehnen Hulbert & Berghoff LLP

(57) ABSTRACT

Recombinant microorganisms, plants, and plant cells are disclosed that have been engineered to have reduced levels or activity of one or more alcohol dehydrogenases or aldehyde reductases thereby increasing the production of benzylisoquinoline alkaloids and/or benzylisoquinoline alkaloid precursors.

14 Claims, 4 Drawing Sheets

Specification includes a Sequence Listing.

FIG. 1

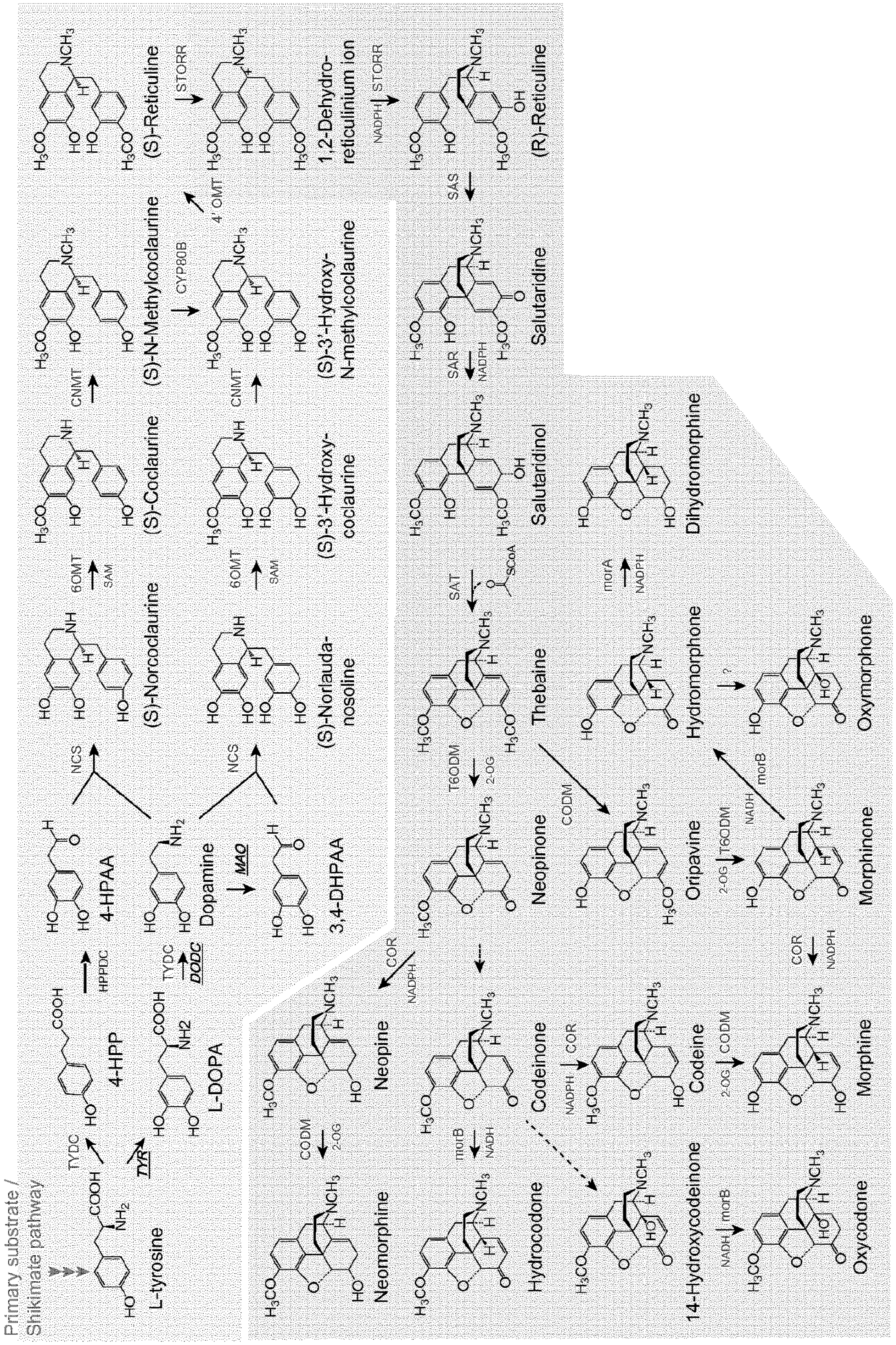

L-tyrosine
4-HPP
L-DOPA
4-HPAA
Dopamine
3,4-DHPAA
(S)-Norcoclaurine
(S)-Norlaudanosoline
(S)-Coclaurine
(S)-3'-Hydroxycoclaurine
(S)-N-Methylcoclaurine
(S)-3'-Hydroxy-N-methylcoclaurine
(S)-Reticuline
1,2-Dehydroreticulinium ion
(R)-Reticuline
Salutaridine
Salutaridinol
Thebaine
Neopinone
Neopine
Neomorphine
Codeinone
Hydrocodone
14-Hydroxycodeinone
Oxycodone
Codeine
Morphine
Oripavine
Morphinone
Hydromorphone
Oxymorphone
Dihydromorphine

SEQUENCE LISTING

<160> NUMBER OF SEQ ID NOS: 64

<210> SEQ ID NO 1
<211> LENGTH: 351
<212> TYPE: PRT
<213> ORGANISM: Saccharomyces cerevisiae

<400> SEQUENCE: 1

Met Pro Ser Gln Val Ile Pro Glu Lys Gln Lys Ala Ile Val Phe Tyr
1 5 10 15

Glu Thr Asp Gly Lys Leu Glu Tyr Lys Asp Val Thr Val Pro Glu Pro
20 25 30

Lys Pro Asn Glu Ile Leu Val His Val Lys Tyr Ser Gly Val Cys His
35 40 45

Ser Asp Leu His Ala Trp His Gly Asp Trp Pro Phe Gln Leu Lys Phe
50 55 60

Pro Leu Ile Gly Gly His Glu Gly Ala Gly Val Val Val Lys Leu Gly
65 70 75 80

-continued

Ser Asn Val Lys Gly Trp Lys Val Gly Asp Phe Ala Gly Ile Lys Trp
                85                  90                  95

Leu Asn Gly Thr Cys Met Ser Cys Glu Tyr Cys Glu Val Gly Asn Glu
            100                 105                 110

Ser Gln Cys Pro Tyr Leu Asp Gly Thr Gly Phe Thr His Asp Gly Thr
        115                 120                 125

Phe Gln Glu Tyr Ala Thr Ala Asp Ala Val Gln Ala Ala His Ile Pro
    130                 135                 140

Pro Asn Val Asn Leu Ala Glu Val Ala Pro Ile Leu Cys Ala Gly Ile
145                 150                 155                 160

Thr Val Tyr Lys Ala Leu Lys Arg Ala Asn Val Ile Pro Gly Gln Trp
                165                 170                 175

Val Thr Ile Ser Gly Ala Cys Gly Gly Leu Gly Ser Leu Ala Ile Gln
            180                 185                 190

Tyr Ala Leu Ala Met Gly Tyr Arg Val Ile Gly Ile Asp Gly Gly Asn
        195                 200                 205

Ala Lys Arg Lys Leu Phe Glu Gln Leu Gly Gly Glu Ile Phe Ile Asp
    210                 215                 220

Phe Thr Glu Glu Lys Asp Ile Val Gly Ala Ile Ile Lys Ala Thr Asn
225                 230                 235                 240

Gly Gly Ser His Gly Val Ile Asn Val Ser Val Ser Glu Ala Ala Ile
                245                 250                 255

Glu Ala Ser Thr Arg Tyr Cys Arg Pro Asn Gly Thr Val Val Leu Val
            260                 265                 270

Gly Met Pro Ala His Ala Tyr Cys Asn Ser Asp Val Phe Asn Gln Val
        275                 280                 285

Val Lys Ser Ile Ser Ile Val Gly Ser Cys Val Gly Asn Arg Ala Asp
    290                 295                 300

Thr Arg Glu Ala Leu Asp Phe Phe Ala Arg Gly Leu Ile Lys Ser Pro
305                 310                 315                 320

Ile His Leu Ala Gly Leu Ser Asp Val Pro Glu Ile Phe Ala Lys Met
                325                 330                 335

Glu Lys Gly Glu Ile Val Gly Arg Tyr Val Val Glu Thr Ser Lys
            340                 345                 350

<210> SEQ ID NO 2
<211> LENGTH: 1056
<212> TYPE: DNA
<213> ORGANISM: Saccharomyces cerevisiae

<400> SEQUENCE: 2
atgccttcgc aagtcattcc tgaaaaacaa aaggctattg tcttttatga gacagatgga 60
aaattggaat ataaagacgt cacagttccg gaacctaagc ctaacgaaat tttagtccac 120
gttaaatatt ctggtgtttg tcatagtgac ttgcacgcgt ggcacggtga ttggccattt 180
caattgaaat ttccattaat cggtggtcac gaaggtgctg gtgttgttgt taagttggga 240
tctaacgtta agggctggaa agtcggtgat tttgcaggta taaaatggtt gaatgggact 300
tgcatgtcct gtgaatattg tgaagtaggt aatgaatctc aatgtcctta tttggatggt 360
actggcttca cacatgatgg tacttttcaa gaatacgcaa ctgccgatgc cgttcaagct 420
gcccatattc caccaaacgt caatcttgct gaagttgccc caatcttgtg tgcaggtatc 480
actgtttata aggcgttgaa aagagccaat gtgataccag gccaatgggt cactatatcc 540
ggtgcatgcg gtggcttggg ttctctggca atccaatacg cccttgctat gggttacagg 600

```
gtcattggta tcgatggtgg taatgccaag cgaaagttat ttgaacaatt aggcggagaa    660

atattcatcg atttcacgga agaaaaagac attgttggtg ctataataaa ggccactaat    720

ggcggttctc atggagttat taatgtgtct gtttctgaag cagctatcga ggcttctacg    780

aggtattgta ggcccaatgg tactgtcgtc ctggttggta tgccagctca tgcttactgc    840

aattccgatg ttttcaatca agttgtaaaa tcaatctcca tcgttggatc ttgtgttgga    900

aatagagctg atacaaggga ggctttagat ttcttcgcca gaggtttgat caaatctccg    960

atccacttag ctggcctatc ggatgttcct gaaatttttg caaagatgga gaagggtgaa   1020

attgttggta gatatgttgt tgagacttct aaatga                             1056


<210> SEQ ID NO 3
<211> LENGTH: 360
<212> TYPE: PRT
<213> ORGANISM: Saccharomyces cerevisiae

<400> SEQUENCE: 3

Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
        275                 280                 285
```

```
Tyr Gly Leu Lys Ala Val Ser Ile Ser Tyr Ser Ala Leu Gly Ser Ile
    290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
            340                 345                 350

Gly Tyr Asp Lys Glu Phe Ser Asp
        355                 360
```

<210> SEQ ID NO 4
<211> LENGTH: 1083
<212> TYPE: DNA
<213> ORGANISM: Saccharomyces cerevisiae

<400> SEQUENCE: 4

```
atgtcttatc ctgagaaatt tgaaggtatc gctattcaat cacacgaaga ttggaaaaac      60

ccaaagaaga caaagtatga cccaaaacca ttttacgatc atgacattga cattaagatc     120

gaagcatgtg gtgtctgcgg tagtgatatt cattgtgcag ctggtcattg gggcaatatg     180

aagatgccgc tagtcgttgg tcatgaaatc gttggtaaag ttgtcaagct agggcccaag     240

tcaaacagtg ggttgaaagt cggtcaacgt gttggtgtag gtgctcaagt cttttcatgc     300

ttggaatgtg accgttgtaa gaatgataat gaaccatact gcaccaagtt tgttaccaca     360

tacagtcagc cttatgaaga cggctatgtg tcgcagggtg gctatgcaaa ctacgtcaga     420

gttcatgaac attttgtggt gcctatccca gagaatattc catcacattt ggctgctcca     480

ctattatgtg gtggtttgac tgtgtactct ccattggttc gtaacggttg cggtccaggt     540

aaaaaagttg gtatagttgg tcttggtggt atcggcagta tgggtacatt gatttccaaa     600

gccatggggg cagagacgta tgttatttct cgttcttcga gaaaaagaga agatgcaatg     660

aagatgggcg ccgatcacta cattgctaca ttagaagaag gtgattgggg tgaaaagtac     720

tttgacacct tcgacctgat tgtagtctgt gcttcctccc ttaccgacat tgacttcaac     780

attatgccaa aggctatgaa ggttggtggt agaattgtct caatctctat accagaacaa     840

cacgaaatgt tatcgctaaa gccatatggc ttaaaggctg tctccatttc ttacagtgct     900

ttaggttcca tcaaagaatt gaaccaactc ttgaaattag tctctgaaaa agatatcaaa     960

atttgggtgg aaacattacc tgttggtgaa gccggcgtcc atgaagcctt cgaaaggatg    1020

gaaaagggtg acgttagata tagatttacc ttagtcggct acgacaaaga attttcagac    1080

tag                                                                  1083
```

<210> SEQ ID NO 5
<211> LENGTH: 361
<212> TYPE: PRT
<213> ORGANISM: Saccharomyces cerevisiae

<400> SEQUENCE: 5

```
Met Leu Tyr Pro Glu Lys Phe Gln Gly Ile Gly Ile Ser Asn Ala Lys
1               5                   10                  15

Asp Trp Lys His Pro Lys Leu Val Ser Phe Asp Pro Lys Pro Phe Gly
            20                  25                  30

Asp His Asp Val Asp Val Glu Ile Glu Ala Cys Gly Ile Cys Gly Ser
        35                  40                  45

Asp Phe His Ile Ala Val Gly Asn Trp Gly Pro Val Pro Glu Asn Gln
```

-continued

```
    50                  55                  60

Ile Leu Gly His Glu Ile Ile Gly Arg Val Val Lys Val Gly Ser Lys
65                  70                  75                  80

Cys His Thr Gly Val Lys Ile Gly Asp Arg Val Gly Val Gly Ala Gln
                85                  90                  95

Ala Leu Ala Cys Phe Glu Cys Glu Arg Cys Lys Ser Asp Asn Glu Gln
            100                 105                 110

Tyr Cys Thr Asn Asp His Val Leu Thr Met Trp Thr Pro Tyr Lys Asp
        115                 120                 125

Gly Tyr Ile Ser Gln Gly Gly Phe Ala Ser His Val Arg Leu His Glu
    130                 135                 140

His Phe Ala Ile Gln Ile Pro Glu Asn Ile Pro Ser Pro Leu Ala Ala
145                 150                 155                 160

Pro Leu Leu Cys Gly Gly Ile Thr Val Phe Ser Pro Leu Leu Arg Asn
                165                 170                 175

Gly Cys Gly Pro Gly Lys Arg Val Gly Ile Val Gly Ile Gly Gly Ile
            180                 185                 190

Gly His Met Gly Ile Leu Leu Ala Lys Ala Met Gly Ala Glu Val Tyr
        195                 200                 205

Ala Phe Ser Arg Gly His Ser Lys Arg Glu Asp Ser Met Lys Leu Gly
    210                 215                 220

Ala Asp His Tyr Ile Ala Met Leu Glu Asp Lys Gly Trp Thr Glu Gln
225                 230                 235                 240

Tyr Ser Asn Ala Leu Asp Leu Leu Val Val Cys Ser Ser Ser Leu Ser
                245                 250                 255

Lys Val Asn Phe Asp Ser Ile Val Lys Ile Met Lys Ile Gly Gly Ser
            260                 265                 270

Ile Val Ser Ile Ala Ala Pro Glu Val Asn Glu Lys Leu Val Leu Lys
        275                 280                 285

Pro Leu Gly Leu Met Gly Val Ser Ile Ser Ser Ser Ala Ile Gly Ser
    290                 295                 300

Arg Lys Glu Ile Glu Gln Leu Leu Lys Leu Val Ser Glu Lys Asn Val
305                 310                 315                 320

Lys Ile Trp Val Glu Lys Leu Pro Ile Ser Glu Glu Gly Val Ser His
                325                 330                 335

Ala Phe Thr Arg Met Glu Ser Gly Asp Val Lys Tyr Arg Phe Thr Leu
            340                 345                 350

Val Asp Tyr Asp Lys Lys Phe His Lys
        355                 360
```

<210> SEQ ID NO 6
<211> LENGTH: 1086
<212> TYPE: DNA
<213> ORGANISM: Saccharomyces cerevisiae

<400> SEQUENCE: 6

```
atgctttacc cagaaaaatt tcagggcatc ggtatttcca acgcaaagga ttggaagcat      60

cctaaattag tgagttttga cccaaaaccc tttggcgatc atgacgttga tgttgaaatt     120

gaagcctgtg gtatctgcgg atctgatttt catatagccg ttggtaattg gggtccagtc     180

ccagaaaatc aaatccttgg acatgaaata attggccgcg tggtgaaggt tggatccaag     240

tgccacactg ggtaaaaat cggtgaccgt gttggtgttg gtgcccaagc cttggcgtgt      300

tttgagtgtg aacgttgcaa aagtgacaac gagcaatact gtaccaatga ccacgttttg     360
```

-continued

```
actatgtgga ctccttacaa ggacggctac atttcacaag gaggctttgc ctcccacgtg    420

aggcttcatg aacactttgc tattcaaata ccagaaaata ttccaagtcc gctagccgct    480

ccattattgt gtggtggtat tacagttttc tctccactac taagaaatgg ctgtggtcca    540

ggtaagaggg taggtattgt tggcatcggt ggtattgggc atatggggat tctgttggct    600

aaagctatgg gagccgaggt ttatgcgttt tcgcgaggcc actccaagcg ggaggattct    660

atgaaactcg gtgctgatca ctatattgct atgttggagg ataaaggctg gacagaacaa    720

tactctaacg ctttggacct tcttgtcgtt tgctcatcat ctttgtcgaa agttaatttt    780

gacagtatcg ttaagattat gaagattgga ggctccatcg tttcaattgc tgctcctgaa    840

gttaatgaaa agcttgtttt aaaaccgttg ggcctaatgg gagtatcaat ctcaagcagt    900

gctatcggat ctaggaagga aatcgaacaa ctattgaaat tagtttccga aaagaatgtc    960

aaaatatggg tggaaaaact tccgatcagc gaagaaggcg tcagccatgc ctttacaagg   1020

atggaaagcg gagacgtcaa atacagattt actttggtcg attatgataa gaaattccat   1080

aaatag                                                              1086
```

```
<210> SEQ ID NO 7
<211> LENGTH: 342
<212> TYPE: PRT
<213> ORGANISM: Saccharomyces cerevisiae

<400> SEQUENCE: 7

Met Ser Val Phe Val Ser Gly Ala Asn Gly Phe Ile Ala Gln His Ile
1               5                   10                  15

Val Asp Leu Leu Leu Lys Glu Asp Tyr Lys Val Ile Gly Ser Ala Arg
            20                  25                  30

Ser Gln Glu Lys Ala Glu Asn Leu Thr Glu Ala Phe Gly Asn Asn Pro
        35                  40                  45

Lys Phe Ser Met Glu Val Val Pro Asp Ile Ser Lys Leu Asp Ala Phe
    50                  55                  60

Asp His Val Phe Gln Lys His Gly Lys Asp Ile Lys Ile Val Leu His
65                  70                  75                  80

Thr Ala Ser Pro Phe Cys Phe Asp Ile Thr Asp Ser Glu Arg Asp Leu
                85                  90                  95

Leu Ile Pro Ala Val Asn Gly Val Lys Gly Ile Leu His Ser Ile Lys
            100                 105                 110

Lys Tyr Ala Ala Asp Ser Val Glu Arg Val Val Leu Thr Ser Ser Tyr
        115                 120                 125

Ala Ala Val Phe Asp Met Ala Lys Glu Asn Asp Lys Ser Leu Thr Phe
    130                 135                 140

Asn Glu Glu Ser Trp Asn Pro Ala Thr Trp Glu Ser Cys Gln Ser Asp
145                 150                 155                 160

Pro Val Asn Ala Tyr Cys Gly Ser Lys Lys Phe Ala Glu Lys Ala Ala
                165                 170                 175

Trp Glu Phe Leu Glu Glu Asn Arg Asp Ser Val Lys Phe Glu Leu Thr
            180                 185                 190

Ala Val Asn Pro Val Tyr Val Phe Gly Pro Gln Met Phe Asp Lys Asp
        195                 200                 205

Val Lys Lys His Leu Asn Thr Ser Cys Glu Leu Val Asn Ser Leu Met
    210                 215                 220

His Leu Ser Pro Glu Asp Lys Ile Pro Glu Leu Phe Gly Gly Tyr Ile
225                 230                 235                 240
```

```
Asp Val Arg Asp Val Ala Lys Ala His Leu Val Ala Phe Gln Lys Arg
                245                 250                 255

Glu Thr Ile Gly Gln Arg Leu Ile Val Ser Glu Ala Arg Phe Thr Met
            260                 265                 270

Gln Asp Val Leu Asp Ile Leu Asn Glu Asp Phe Pro Val Leu Lys Gly
        275                 280                 285

Asn Ile Pro Val Gly Lys Pro Gly Ser Gly Ala Thr His Asn Thr Leu
    290                 295                 300

Gly Ala Thr Leu Asp Asn Lys Lys Ser Lys Lys Leu Leu Gly Phe Lys
305                 310                 315                 320

Phe Arg Asn Leu Lys Glu Thr Ile Asp Asp Thr Ala Ser Gln Ile Leu
                325                 330                 335

Lys Phe Glu Gly Arg Ile
            340
```

```
<210> SEQ ID NO 8
<211> LENGTH: 1029
<212> TYPE: DNA
<213> ORGANISM: Saccharomyces cerevisiae

<400> SEQUENCE: 8

atgtcagttt tcgtttcagg tgctaacggg ttcattgccc aacacattgt cgatctcctg      60

ttgaaggaag actataaggt catcggttct gccagaagtc aagaaaaggc cgagaattta     120

acggaggcct ttggtaacaa cccaaaattc tccatggaag ttgtcccaga catatctaag     180

ctggacgcat ttgaccatgt tttccaaaag cacggcaagg atatcaagat agttctacat     240

acggcctctc cattctgctt tgatatcact gacagtgaac gcgatttatt aattcctgct     300

gtgaacggtg ttaagggaat tctccactca attaaaaaat acgccgctga ttctgtagaa     360

cgtgtagttc tcacctcttc ttatgcagct gtgttcgata tggcaaaaga aaacgataag     420

tctttaacat ttaacgaaga atcctggaac ccagctacct gggagagttg ccaaagtgac     480

ccagttaacg cctactgtgg ttctaagaag tttgctgaaa aagcagcttg ggaatttcta     540

gaggagaata gagactctgt aaaattcgaa ttaactgccg ttaacccagt ttacgttttt     600

ggtccgcaaa tgtttgacaa agatgtgaaa aaacacttga acacatcttg cgaactcgtc     660

aacagcttga tgcatttatc accagaggac aagataccgg aactatttgg tggatacatt     720

gatgttcgtg atgttgcaaa ggctcattta gttgccttcc aaaagaggga aacaattggt     780

caaagactaa tcgtatcgga ggccagattt actatgcagg atgttctcga tatccttaac     840

gaagacttcc ctgttctaaa aggcaatatt ccagtgggga aaccaggttc tggtgctacc     900

cataacaccc ttggtgctac tcttgataat aaaaagagta agaaattgtt aggtttcaag     960

ttcaggaact tgaaagagac cattgacgac actgcctccc aaattttaaa atttgagggc    1020

agaatataa                                                            1029
```

```
<210> SEQ ID NO 9
<211> LENGTH: 327
<212> TYPE: PRT
<213> ORGANISM: Saccharomyces cerevisiae

<400> SEQUENCE: 9

Met Ser Ser Leu Val Thr Leu Asn Asn Gly Leu Lys Met Pro Leu Val
1               5                   10                  15

Gly Leu Gly Cys Trp Lys Ile Asp Lys Lys Val Cys Ala Asn Gln Ile
            20                  25                  30
```

-continued

```
Tyr Glu Ala Ile Lys Leu Gly Tyr Arg Leu Phe Asp Gly Ala Cys Asp
        35                  40                  45

Tyr Gly Asn Glu Lys Glu Val Gly Glu Gly Ile Arg Lys Ala Ile Ser
    50                  55                  60

Glu Gly Leu Val Ser Arg Lys Asp Ile Phe Val Val Ser Lys Leu Trp
65                  70                  75                  80

Asn Asn Phe His His Pro Asp His Val Lys Leu Ala Leu Lys Lys Thr
                85                  90                  95

Leu Ser Asp Met Gly Leu Asp Tyr Leu Asp Leu Tyr Tyr Ile His Phe
            100                 105                 110

Pro Ile Ala Phe Lys Tyr Val Pro Phe Glu Glu Lys Tyr Pro Pro Gly
        115                 120                 125

Phe Tyr Thr Gly Ala Asp Asp Glu Lys Lys Gly His Ile Thr Glu Ala
    130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
            180                 185                 190

Ile Glu His His Pro Tyr Leu Thr Gln Glu His Leu Val Glu Phe Cys
        195                 200                 205

Lys Leu His Asp Ile Gln Val Val Ala Tyr Ser Ser Phe Gly Pro Gln
    210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255

Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
        275                 280                 285

Ile Glu Lys Lys Phe Thr Leu Thr Glu Gln Glu Leu Lys Asp Ile Ser
    290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325
```

<210> SEQ ID NO 10
<211> LENGTH: 984
<212> TYPE: DNA
<213> ORGANISM: Saccharomyces cerevisiae

<400> SEQUENCE: 10

```
atgtcttcac tggttactct taataacggt ctgaaaatgc ccctagtcgg cttagggtgc      60

tggaaaattg acaaaaaagt ctgtgcgaat caaatttatg aagctatcaa attaggctac     120

cgtttattcg atggtgcttg cgactacggc aacgaaaagg aagttggtga aggtatcagg     180

aaagccatct ccgaaggtct tgtttctaga aaggatatat ttgttgtttc aaagttatgg     240

aacaattttc accatcctga tcatgtaaaa ttagctttaa agaagacctt aagcgatatg     300

ggacttgatt atttagacct gtattatatt cacttcccaa tcgccttcaa atatgttcca     360

tttgaagaga aataccctcc aggattctat acgggcgcag atgacgagaa gaaaggtcac     420
```

```
atcaccgaag cacatgtacc aatcatagat acgtaccggg ctctggaaga atgtgttgat    480

gaaggcttga ttaagtctat tggtgtttcc aactttcagg gaagcttgat tcaagattta    540

ttacgtggtt gtagaatcaa gcccgtggct ttgcaaattg aacaccatcc ttatttgact    600

caagaacacc tagttgagtt ttgtaaatta cacgatatcc aagtagttgc ttactcctcc    660

ttcggtcctc aatcattcat tgagatggac ttacagttgg caaaaaccac gccaactctg    720

ttcgagaatg atgtaatcaa gaaggtctca caaaaccatc caggcagtac cacttcccaa    780

gtattgctta gatgggcaac tcagagaggc attgccgtca ttccaaaatc ttccaagaag    840

gaaaggttac ttggcaacct agaaatcgaa aaaaagttca ctttaacgga gcaagaattg    900

aaggatattt ctgcactaaa tgccaacatc agatttaatg atccatggac ctggttggat    960

ggtaaattcc ccacttttgc ctga                                            984
```

<210> SEQ ID NO 11
<211> LENGTH: 344
<212> TYPE: PRT
<213> ORGANISM: Saccharomyces cerevisiae

<400> SEQUENCE: 11

```
Met Ser Asn Thr Val Leu Val Ser Gly Ala Ser Gly Phe Ile Ala Leu
1               5                   10                  15

His Ile Leu Ser Gln Leu Leu Lys Gln Asp Tyr Lys Val Ile Gly Thr
            20                  25                  30

Val Arg Ser His Glu Lys Glu Ala Lys Leu Leu Arg Gln Phe Gln His
        35                  40                  45

Asn Pro Asn Leu Thr Leu Glu Ile Val Pro Asp Ile Ser His Pro Asn
    50                  55                  60

Ala Phe Asp Lys Val Leu Gln Lys Arg Gly Arg Glu Ile Arg Tyr Val
65                  70                  75                  80

Leu His Thr Ala Ser Pro Phe His Tyr Asp Thr Thr Glu Tyr Glu Lys
                85                  90                  95

Asp Leu Leu Ile Pro Ala Leu Glu Gly Thr Lys Asn Ile Leu Asn Ser
            100                 105                 110

Ile Lys Lys Tyr Ala Ala Asp Thr Val Glu Arg Val Val Val Thr Ser
        115                 120                 125

Ser Cys Thr Ala Ile Ile Thr Leu Ala Lys Met Asp Asp Pro Ser Val
    130                 135                 140

Val Phe Thr Glu Glu Ser Trp Asn Glu Ala Thr Trp Glu Ser Cys Gln
145                 150                 155                 160

Ile Asp Gly Ile Asn Ala Tyr Phe Ala Ser Lys Lys Phe Ala Glu Lys
                165                 170                 175

Ala Ala Trp Glu Phe Thr Lys Glu Asn Glu Asp His Ile Lys Phe Lys
            180                 185                 190

Leu Thr Thr Val Asn Pro Ser Leu Leu Phe Gly Pro Gln Leu Phe Asp
        195                 200                 205

Glu Asp Val His Gly His Leu Asn Thr Ser Cys Glu Met Ile Asn Gly
    210                 215                 220

Leu Ile His Thr Pro Val Asn Ala Ser Val Pro Asp Phe His Ser Ile
225                 230                 235                 240

Phe Ile Asp Val Arg Asp Val Ala Leu Ala His Leu Tyr Ala Phe Gln
                245                 250                 255

Lys Glu Asn Thr Ala Gly Lys Arg Leu Val Val Thr Asn Gly Lys Phe
            260                 265                 270
```

-continued

Gly Asn Gln Asp Ile Leu Asp Ile Leu Asn Glu Asp Phe Pro Gln Leu
275 280 285

Arg Gly Leu Ile Pro Leu Gly Lys Pro Gly Thr Gly Asp Gln Val Ile
290 295 300

Asp Arg Gly Ser Thr Thr Asp Asn Ser Ala Thr Arg Lys Ile Leu Gly
305 310 315 320

Phe Glu Phe Arg Ser Leu His Glu Ser Val His Asp Thr Ala Ala Gln
325 330 335

Ile Leu Lys Lys Gln Asn Arg Leu
340

<210> SEQ ID NO 12
<211> LENGTH: 1035
<212> TYPE: DNA
<213> ORGANISM: Saccharomyces cerevisiae

<400> SEQUENCE: 12
atgtctaata cagttctagt ttctggcgct tcaggtttta ttgccttgca tatcctgtca 60
caattgttaa aacaagatta taaggttatt ggaactgtga gatcccatga aaaagaagca 120
aaattgctaa gacaatttca acataaccct aatttaactt tagaaattgt tccggacatt 180
tctcatccaa atgctttcga taaggttctg cagaaacgtg gacgtgagat taggtatgtt 240
ctacacacgg cctctccttt tcattatgat actaccgaat atgaaaaaga cttattgatt 300
cccgcgttag aaggtacaaa aaacatccta aattctatca agaaatatgc agcagacact 360
gtagagcgtg ttgttgtgac ttcttcttgt actgctatta taacccttgc aaagatggac 420
gatcccagtg tggtttttac agaagagagt tggaacgaag caacctggga aagctgtcaa 480
attgatggga taaatgctta ctttgcatcc aagaagtttg ctgaaaaggc tgcctgggag 540
ttcacaaaag agaatgaaga tcacatcaaa ttcaaactaa caacagtcaa cccttctctt 600
ctttttggtc ctcaactttt cgatgaagat gtgcatggcc atttgaatac ttcttgcgaa 660
atgatcaatg gcctaattca taccccagta aatgccagtg ttcctgattt tcattccatt 720
tttattgatg taagggatgt ggccctagct catctgtatg ctttccagaa ggaaaatacc 780
gcgggtaaaa gattagtggt aactaacggt aaatttggaa accaagatat cctggatatt 840
ttgaacgaag attttccaca attaagaggt ctcattcctt tgggtaagcc tggcacaggt 900
gatcaagtca ttgaccgcgg ttcaactaca gataatagtg caacgaggaa aatacttggc 960
tttgagttca gaagtttaca cgaaagtgtc catgatactg ctgcccaaat tttgaagaag 1020
cagaacagat tatga 1035

<210> SEQ ID NO 13
<211> LENGTH: 376
<212> TYPE: PRT
<213> ORGANISM: Saccharomyces cerevisiae

<400> SEQUENCE: 13

Met Gln Val Ala Ile Pro Glu Thr Met Lys Ala Val Val Ile Glu Asp
1 5 10 15

Gly Lys Ala Val Val Lys Glu Gly Ile Pro Ile Pro Glu Leu Glu Glu
20 25 30

Gly Phe Val Leu Ile Lys Thr Leu Ala Val Ala Gly Asn Pro Thr Asp
35 40 45

Trp Ala His Ile Asp Tyr Lys Ile Gly Pro Gln Gly Ser Ile Leu Gly
50 55 60

-continued

```
Cys Asp Ala Ala Gly Gln Ile Val Lys Leu Gly Pro Ala Val Asn Pro
65                  70                  75                  80

Lys Asp Phe Ser Ile Gly Asp Tyr Ile Tyr Gly Phe Ile His Gly Ser
                85                  90                  95

Ser Val Arg Phe Pro Ser Asn Gly Ala Phe Ala Glu Tyr Ser Ala Ile
            100                 105                 110

Ser Thr Val Val Ala Tyr Lys Ser Pro Asn Glu Leu Lys Phe Leu Gly
        115                 120                 125

Glu Asp Val Leu Pro Ala Gly Pro Val Arg Ser Leu Glu Gly Val Ala
    130                 135                 140

Thr Ile Pro Val Ser Leu Thr Thr Ala Gly Leu Val Leu Thr Tyr Asn
145                 150                 155                 160

Leu Gly Leu Asp Leu Lys Trp Glu Pro Ser Thr Pro Gln Arg Lys Gly
                165                 170                 175

Pro Ile Leu Leu Trp Gly Gly Ala Thr Ala Val Gly Gln Ser Leu Ile
            180                 185                 190

Gln Leu Ala Asn Lys Leu Asn Gly Phe Thr Lys Ile Ile Val Val Ala
        195                 200                 205

Ser Arg Lys His Glu Lys Leu Leu Lys Glu Tyr Gly Ala Asp Glu Leu
    210                 215                 220

Phe Asp Tyr His Asp Ile Asp Val Val Glu Gln Ile Lys His Lys Tyr
225                 230                 235                 240

Asn Asn Ile Ser Tyr Leu Val Asp Cys Val Ala Asn Gln Asp Thr Leu
                245                 250                 255

Gln Gln Val Tyr Lys Cys Ala Ala Asp Lys Gln Asp Ala Thr Ile Val
            260                 265                 270

Glu Leu Lys Asn Leu Thr Glu Glu Asn Val Lys Lys Glu Asn Arg Arg
        275                 280                 285

Gln Asn Val Thr Ile Asp Ile Ile Arg Leu Tyr Ser Ile Gly Gly His
    290                 295                 300

Glu Val Pro Phe Gly Asn Ile Thr Leu Pro Ala Asp Ser Glu Ala Arg
305                 310                 315                 320

Lys Ala Ala Ile Lys Phe Ile Lys Phe Ile Asn Pro Lys Ile Asn Asp
                325                 330                 335

Gly Gln Ile Arg His Ile Pro Val Arg Val Tyr Lys Asn Gly Leu Cys
            340                 345                 350

Asp Val Pro His Ile Leu Lys Asp Ile Lys Tyr Gly Lys Asn Ser Gly
        355                 360                 365

Glu Lys Leu Val Ala Val Leu Asn
    370                 375


<210> SEQ ID NO 14
<211> LENGTH: 1131
<212> TYPE: DNA
<213> ORGANISM: Saccharomyces cerevisiae

<400> SEQUENCE: 14

atgcaagttg caattccaga aaccatgaag gctgtcgtca ttgaagacgg taaagcggtt      60

gttaaagagg gcattcccat tcctgaattg gaagaaggat tcgtattgat taagacactc     120

gctgttgctg gtaaccccac tgattgggca cacattgact acaagatcgg gcctcaagga     180

tctattctgg gatgtgatgc tgctggccaa attgtcaaat tgggcccagc tgtcaatcct     240

aaagactttt ctatcggtga ttatatttat gggttcattc acggatcttc cgtaaggttt     300

ccttccaatg gtgcttttgc tgaatattct gctatttcaa ctgtggttgc ctacaaatca     360
```

```
cccaatgaac tcaaattttt gggtgaggat gttctacctg ccggccctgt caggtctttg    420

gaaggtgtag ccactatccc agtgtcactg accacagccg gcttggtgtt gacctataac    480

ttgggcttgg acctgaagtg ggagccatca accccacaaa gaaaaggccc catcttatta    540

tggggcggtg caactgcagt aggtcagtcg ctcatccaat tagccaataa attgaatggc    600

ttcaccaaga tcattgttgt ggcttctcgg aagcacgaaa aacttttgaa agaatatggt    660

gctgatgaat tatttgatta tcatgatatt gacgtggtag aacaaattaa acacaagtac    720

aacaatatct cgtatttagt cgactgtgtc gcgaatcaag atacgcttca acaagtgtac    780

aaatgtgcgg ccgataaaca ggatgctaca attgttgaat taaaaaattt gacagaagaa    840

aacgtcaaaa aagagaacag gagacaaaac gttactattg acataataag gctatattca    900

ataggtggcc atgaagtacc atttggaaac attactttac cagccgactc agaagctagg    960

aaagctgcaa taaaatttat caaattcatc aatccaaaga ttaatgatgg acaaattcgc   1020

catattccag taagggtcta taagaacggg ctttgtgatg ttcctcatat cctaaaagac   1080

atcaaatatg gtaagaactc tggtgaaaaa ctcgttgccg tattaaacta g            1131
```

<210> SEQ ID NO 15
<211> LENGTH: 347
<212> TYPE: PRT
<213> ORGANISM: Saccharomyces cerevisiae

<400> SEQUENCE: 15

```
Met Thr Thr Asp Thr Thr Val Phe Val Ser Gly Ala Thr Gly Phe Ile
1               5                   10                  15

Ala Leu His Ile Met Asn Asp Leu Leu Lys Ala Gly Tyr Thr Val Ile
            20                  25                  30

Gly Ser Gly Arg Ser Gln Glu Lys Asn Asp Gly Leu Leu Lys Lys Phe
        35                  40                  45

Asn Asn Asn Pro Lys Leu Ser Met Glu Ile Val Glu Asp Ile Ala Ala
    50                  55                  60

Pro Asn Ala Phe Asp Glu Val Phe Lys Lys His Gly Lys Glu Ile Lys
65                  70                  75                  80

Ile Val Leu His Thr Ala Ser Pro Phe His Phe Glu Thr Thr Asn Phe
                85                  90                  95

Glu Lys Asp Leu Leu Thr Pro Ala Val Asn Gly Thr Lys Ser Ile Leu
            100                 105                 110

Glu Ala Ile Lys Lys Tyr Ala Ala Asp Thr Val Glu Lys Val Ile Val
        115                 120                 125

Thr Ser Ser Thr Ala Ala Leu Val Thr Pro Thr Asp Met Asn Lys Gly
    130                 135                 140

Asp Leu Val Ile Thr Glu Glu Ser Trp Asn Lys Asp Thr Trp Asp Ser
145                 150                 155                 160

Cys Gln Ala Asn Ala Val Ala Ala Tyr Cys Gly Ser Lys Lys Phe Ala
                165                 170                 175

Glu Lys Thr Ala Trp Glu Phe Leu Lys Glu Asn Lys Ser Ser Val Lys
            180                 185                 190

Phe Thr Leu Ser Thr Ile Asn Pro Gly Phe Val Phe Gly Pro Gln Met
        195                 200                 205

Phe Ala Asp Ser Leu Lys His Gly Ile Asn Thr Ser Ser Gly Ile Val
    210                 215                 220

Ser Glu Leu Ile His Ser Lys Val Gly Gly Glu Phe Tyr Asn Tyr Cys
225                 230                 235                 240
```

```
Gly Pro Phe Ile Asp Val Arg Asp Val Ser Lys Ala His Leu Val Ala
                245                 250                 255

Ile Glu Lys Pro Glu Cys Thr Gly Gln Arg Leu Val Leu Ser Glu Gly
            260                 265                 270

Leu Phe Cys Cys Gln Glu Ile Val Asp Ile Leu Asn Glu Glu Phe Pro
        275                 280                 285

Gln Leu Lys Gly Lys Ile Ala Thr Gly Glu Pro Ala Thr Gly Pro Ser
    290                 295                 300

Phe Leu Glu Lys Asn Ser Cys Lys Phe Asp Asn Ser Lys Thr Lys Lys
305                 310                 315                 320

Leu Leu Gly Phe Gln Phe Tyr Asn Leu Lys Asp Cys Ile Val Asp Thr
                325                 330                 335

Ala Ala Gln Met Leu Glu Val Gln Asn Glu Ala
            340                 345


<210> SEQ ID NO 16
<211> LENGTH: 1044
<212> TYPE: DNA
<213> ORGANISM: Saccharomyces cerevisiae

<400> SEQUENCE: 16

atgactactg ataccactgt tttcgtttct ggcgcaaccg gtttcattgc tctacacatt     60

atgaacgatc tgttgaaagc tggctataca gtcatcggct caggtagatc tcaagaaaaa    120

aatgatggct tgctcaaaaa atttaataac aatcccaaac tatcgatgga aattgtggaa    180

gatattgctg ctccaaacgc ctttgatgaa gttttcaaaa aacatggtaa ggaaattaag    240

attgtgctac acactgcctc cccattccat tttgaaacta ccaattttga aaaggattta    300

ctaacccctg cagtgaacgg tacaaaatct atcttggaag cgattaaaaa atatgctgca    360

gacactgttg aaaaagttat tgttacttcg tctactgctg ctctggtgac acctacagac    420

atgaacaaag gagatttggt gatcacggag gagagttgga ataaggatac atgggacagt    480

tgtcaagcca acgccgttgc cgcatattgt ggctcgaaaa agtttgctga aaaaactgct    540

tgggaatttc ttaaagaaaa caagtctagt gtcaaattca cactatccac tatcaatccg    600

ggattcgttt ttggtcctca aatgtttgca gattcgctaa aacatggcat aaatacctcc    660

tcagggatcg tatctgagtt aattcattcc aaggtaggtg gagaatttta taattactgt    720

ggcccattta ttgacgtgcg tgacgtttct aaagcccacc tagttgcaat tgaaaaacca    780

gaatgtaccg gccaaagatt agtattgagt gaaggtttat tctgctgtca agaaatcgtt    840

gacatcttga acgaggaatt ccctcaatta aagggcaaga tagctacagg tgaacctgcg    900

accggtccaa gctttttaga aaaaaactct tgcaagtttg acaattctaa gacaaaaaaa    960

ctactgggat tccagtttta caatttaaag gattgcatag ttgacaccgc ggcgcaaatg   1020

ttagaagttc aaaatgaagc ctaa                                          1044


<210> SEQ ID NO 17
<211> LENGTH: 348
<212> TYPE: PRT
<213> ORGANISM: Saccharomyces cerevisiae

<400> SEQUENCE: 17

Met Thr Thr Glu Lys Thr Val Val Phe Val Ser Gly Ala Thr Gly Phe
1               5                   10                  15

Ile Ala Leu His Val Val Asp Asp Leu Leu Lys Thr Gly Tyr Lys Val
            20                  25                  30
```

```
Ile Gly Ser Gly Arg Ser Gln Glu Lys Asn Asp Gly Leu Leu Lys Lys
        35                  40                  45

Phe Lys Ser Asn Pro Asn Leu Ser Met Glu Ile Val Glu Asp Ile Ala
    50                  55                  60

Ala Pro Asn Ala Phe Asp Lys Val Phe Gln Lys His Gly Lys Glu Ile
65                  70                  75                  80

Lys Val Val Leu His Ile Ala Ser Pro Val His Phe Asn Thr Thr Asp
                85                  90                  95

Phe Glu Lys Asp Leu Leu Ile Pro Ala Val Asn Gly Thr Lys Ser Ile
            100                 105                 110

Leu Glu Ala Ile Lys Asn Tyr Ala Ala Asp Thr Val Glu Lys Val Val
        115                 120                 125

Ile Thr Ser Ser Val Ala Ala Leu Ala Ser Pro Gly Asp Met Lys Asp
    130                 135                 140

Thr Ser Phe Val Val Asn Glu Glu Ser Trp Asn Lys Asp Thr Trp Glu
145                 150                 155                 160

Ser Cys Gln Ala Asn Ala Val Ser Ala Tyr Cys Gly Ser Lys Lys Phe
                165                 170                 175

Ala Glu Lys Thr Ala Trp Asp Phe Leu Glu Glu Asn Gln Ser Ser Ile
            180                 185                 190

Lys Phe Thr Leu Ser Thr Ile Asn Pro Gly Phe Val Phe Gly Pro Gln
        195                 200                 205

Leu Phe Ala Asp Ser Leu Arg Asn Gly Ile Asn Ser Ser Ser Ala Ile
    210                 215                 220

Ile Ala Asn Leu Val Ser Tyr Lys Leu Gly Asp Asn Phe Tyr Asn Tyr
225                 230                 235                 240

Ser Gly Pro Phe Ile Asp Val Arg Asp Val Ser Lys Ala His Leu Leu
                245                 250                 255

Ala Phe Glu Lys Pro Glu Cys Ala Gly Gln Arg Leu Phe Leu Cys Glu
            260                 265                 270

Asp Met Phe Cys Ser Gln Glu Ala Leu Asp Ile Leu Asn Glu Glu Phe
        275                 280                 285

Pro Gln Leu Lys Gly Lys Ile Ala Thr Gly Glu Pro Gly Ser Gly Ser
    290                 295                 300

Thr Phe Leu Thr Lys Asn Cys Cys Lys Cys Asp Asn Arg Lys Thr Lys
305                 310                 315                 320

Asn Leu Leu Gly Phe Gln Phe Asn Lys Phe Arg Asp Cys Ile Val Asp
                325                 330                 335

Thr Ala Ser Gln Leu Leu Glu Val Gln Ser Lys Ser
            340                 345


<210> SEQ ID NO 18
<211> LENGTH: 1047
<212> TYPE: DNA
<213> ORGANISM: Saccharomyces cerevisiae

<400> SEQUENCE: 18

atgactactg aaaaaaccgt tgtttttgtt tctggtgcta ctggtttcat tgctctacac      60

gtagtggacg atttattaaa aactggttac aaggtcatcg gttcgggtag gtcccaagaa     120

aagaatgatg gattgctgaa aaaatttaag agcaatccca acctttcaat ggagattgtc     180

gaagacattg ctgctccaaa cgcttttgac aaagtttttc aaaagcacgg caaagagatc     240

aaggttgtct tgcacatagc ttctccggtt cacttcaaca ccactgattt cgaaaaggat     300
```

-continued

```
ctgctaattc ctgctgtgaa tggtaccaag tccattctag aagcaatcaa aaattatgcc    360

gcagacacag tcgaaaaagt cgttattact tcttctgttg ctgcccttgc atctcccgga    420

gatatgaagg acactagttt cgttgtcaat gaggaaagtt ggaacaaaga tacttgggaa    480

agttgtcaag ctaacgcggt ttccgcatac tgtggttcca agaaatttgc tgaaaaaact    540

gcttgggatt ttctcgagga aaaccaatca agcatcaaat ttacgctatc aaccatcaac    600

ccaggatttg tttttggccc tcagctattt gccgactctc ttagaaatgg aataaatagc    660

tcttcagcca ttattgccaa tttggttagt tataaattag gcgacaattt ttataattac    720

agtggtcctt ttattgacgt tcgcgatgtt tcaaaagctc atttacttgc atttgagaaa    780

cccgaatgcg ctggccaaag actattctta tgtgaagata tgttttgctc tcaagaagcg    840

ctggatatct tgaatgagga atttccacag ttaaaaggca agatagcaac tggcgaacct    900

ggtagcggct caaccttttt gacaaaaaac tgctgcaagt gcgacaaccg caaaaccaaa    960

aatttattag gattccaatt taataagttc agagattgca ttgtcgatac tgcctcgcaa   1020

ttactagaag ttcaaagtaa aagctaa                                       1047
```

<210> SEQ ID NO 19
<211> LENGTH: 368
<212> TYPE: PRT
<213> ORGANISM: Saccharomyces cerevisiae

<400> SEQUENCE: 19

```
Met Lys Ala Val Val Ile Glu Asp Gly Lys Ala Val Val Lys Glu Gly
1               5                   10                  15

Val Pro Ile Pro Glu Leu Glu Glu Gly Phe Val Leu Ile Lys Thr Leu
            20                  25                  30

Ala Val Ala Gly Asn Pro Thr Asp Trp Ala His Ile Asp Tyr Lys Val
        35                  40                  45

Gly Pro Gln Gly Ser Ile Leu Gly Cys Asp Ala Ala Gly Gln Ile Val
    50                  55                  60

Lys Leu Gly Pro Ala Val Asp Pro Lys Asp Phe Ser Ile Gly Asp Tyr
65                  70                  75                  80

Ile Tyr Gly Phe Ile His Gly Ser Ser Val Arg Phe Pro Ser Asn Gly
                85                  90                  95

Ala Phe Ala Glu Tyr Ser Ala Ile Ser Thr Val Val Ala Tyr Lys Ser
            100                 105                 110

Pro Asn Glu Leu Lys Phe Leu Gly Glu Asp Val Leu Pro Ala Gly Pro
        115                 120                 125

Val Arg Ser Leu Glu Gly Ala Ala Thr Ile Pro Val Ser Leu Thr Thr
    130                 135                 140

Ala Gly Leu Val Leu Thr Tyr Asn Leu Gly Leu Asn Leu Lys Trp Glu
145                 150                 155                 160

Pro Ser Thr Pro Gln Arg Asn Gly Pro Ile Leu Leu Trp Gly Gly Ala
                165                 170                 175

Thr Ala Val Gly Gln Ser Leu Ile Gln Leu Ala Asn Lys Leu Asn Gly
            180                 185                 190

Phe Thr Lys Ile Ile Val Val Ala Ser Arg Lys His Glu Lys Leu Leu
        195                 200                 205

Lys Glu Tyr Gly Ala Asp Gln Leu Phe Asp Tyr His Asp Ile Asp Val
    210                 215                 220

Val Glu Gln Ile Lys His Lys Tyr Asn Asn Ile Ser Tyr Leu Val Asp
225                 230                 235                 240
```

-continued

```
Cys Val Ala Asn Gln Asn Thr Leu Gln Gln Val Tyr Lys Cys Ala Ala
                245                 250                 255

Asp Lys Gln Asp Ala Thr Val Val Glu Leu Thr Asn Leu Thr Glu Glu
            260                 265                 270

Asn Val Lys Lys Glu Asn Arg Arg Gln Asn Val Thr Ile Asp Arg Thr
        275                 280                 285

Arg Leu Tyr Ser Ile Gly Gly His Glu Val Pro Phe Gly Gly Ile Thr
    290                 295                 300

Phe Pro Ala Asp Pro Glu Ala Arg Arg Ala Ala Thr Glu Phe Val Lys
305                 310                 315                 320

Phe Ile Asn Pro Lys Ile Ser Asp Gly Gln Ile His His Ile Pro Ala
                325                 330                 335

Arg Val Tyr Lys Asn Gly Leu Tyr Asp Val Pro Arg Ile Leu Glu Asp
            340                 345                 350

Ile Lys Ile Gly Lys Asn Ser Gly Glu Lys Leu Val Ala Val Leu Asn
        355                 360                 365
```

<210> SEQ ID NO 20
<211> LENGTH: 1107
<212> TYPE: DNA
<213> ORGANISM: Saccharomyces cerevisiae

<400> SEQUENCE: 20

```
atgaaggctg tcgtcattga agacggtaaa gcggttgtca aagagggcgt tcccattcct      60

gaattggaag aaggattcgt attgattaag acactcgctg ttgctggtaa cccgactgat     120

tgggcacaca ttgactacaa ggtcgggcct caaggatcta ttctgggatg tgacgctgcc     180

ggccaaattg tcaaattggg cccagccgtc gatcctaaag acttttctat tggtgattat     240

atttatgggt tcattcacgg atcttccgta aggtttcctt ccaatggtgc ttttgctgaa     300

tattctgcta tttcaactgt ggttgcctac aaatcaccca atgaactcaa atttttgggt     360

gaagatgttc tacctgccgg ccctgtcagg tctttggaag gggcagccac tatcccagtg     420

tcactgacca cagctggctt ggtgttgacc tataacttgg gcttgaacct gaagtgggag     480

ccatcaaccc cacaaagaaa cggccccatc ttattatggg gcggtgcaac tgcagtaggt     540

cagtcgctca tccaattagc caataaattg aatggcttca ccaagatcat tgttgtggct     600

tctcggaaac acgaaaaact gttgaaagaa tatggtgctg atcaactatt tgattaccat     660

gatattgacg tggtagaaca aattaaacac aagtacaaca atatctcgta tttagtcgac     720

tgtgtcgcga atcaaaatac gcttcaacaa gtgtacaaat gtgcggccga taaacaggat     780

gctaccgttg tcgaattaac taatttgaca gaagaaaacg tcaaaaagga gaataggagg     840

caaaatgtca ctattgacag aacaagactg tattcaatag gcggccatga agtaccattt     900

ggtggcatta ctttccctgc tgacccagaa gccaggagag ctgccaccga attcgtcaag     960

ttcatcaatc caaagattag tgatgggcaa attcaccata ttccagcaag ggtctataag    1020

aacgggcttt acgatgttcc tcgtatcctg gaagacatta aaatcggtaa gaactctggt    1080

gaaaaactag ttgccgtatt aaactag                                        1107
```

<210> SEQ ID NO 21
<211> LENGTH: 345
<212> TYPE: PRT
<213> ORGANISM: Saccharomyces cerevisiae

<400> SEQUENCE: 21

```
Met Ser Val Ala Asp Leu Lys Asn Asn Ile His Lys Leu Asp Thr Gly
```

-continued 1               5                   10                  15

Tyr Gly Leu Met Ser Leu Thr Trp Arg Ala Glu Pro Ile Pro Gln Ser
            20                  25                  30

Gln Ala Phe Glu Ala Met His Arg Val Val Glu Leu Ser Arg Glu Arg
        35                  40                  45

Gly His Lys Ala Phe Phe Asn Val Gly Glu Phe Tyr Gly Pro Asp Phe
    50                  55                  60

Ile Asn Leu Ser Tyr Val His Asp Phe Phe Ala Lys Tyr Pro Asp Leu
65                  70                  75                  80

Arg Lys Asp Val Val Ile Ser Cys Lys Gly Gly Ala Asp Asn Ala Thr
                85                  90                  95

Leu Thr Pro Arg Gly Ser His Asp Asp Val Val Gln Ser Val Lys Asn
            100                 105                 110

Ser Val Ser Ala Ile Gly Gly Tyr Ile Asp Ile Phe Glu Val Ala Arg
        115                 120                 125

Ile Asp Thr Ser Leu Cys Thr Lys Gly Glu Val Tyr Pro Tyr Glu Ser
    130                 135                 140

Phe Glu Ala Leu Ala Glu Met Ile Ser Glu Gly Val Ile Gly Gly Ile
145                 150                 155                 160

Ser Leu Ser Glu Val Asn Glu Glu Gln Ile Arg Ala Ile His Lys Asp
                165                 170                 175

Trp Gly Lys Phe Leu Thr Cys Val Glu Val Glu Leu Ser Leu Phe Ser
            180                 185                 190

Asn Asp Ile Leu His Asn Gly Ile Ala Lys Thr Cys Ala Glu Leu Gly
        195                 200                 205

Leu Ser Ile Ile Cys Tyr Ser Pro Leu Gly Arg Gly Leu Leu Thr Gly
    210                 215                 220

Gln Leu Lys Ser Asn Ala Asp Ile Pro Glu Gly Asp Phe Arg Lys Ser
225                 230                 235                 240

Leu Lys Arg Phe Ser Asp Glu Ser Leu Lys Lys Asn Leu Thr Leu Val
                245                 250                 255

Arg Phe Leu Gln Glu Glu Ile Val Asp Lys Arg Pro Gln Asn Asn Ser
            260                 265                 270

Ile Thr Leu Ala Gln Leu Ala Leu Gly Trp Val Lys His Trp Asn Lys
        275                 280                 285

Val Pro Glu Tyr Ser Gly Ala Lys Phe Ile Pro Ile Pro Ser Gly Ser
    290                 295                 300

Ser Ile Ser Lys Val Asn Glu Asn Phe Asp Glu Gln Lys Thr Lys Leu
305                 310                 315                 320

Thr Asp Gln Glu Phe Asn Ala Ile Asn Lys Tyr Leu Thr Thr Phe His
                325                 330                 335

Thr Val Gly Asp Arg Tyr Glu Met Ala
            340                 345

<210> SEQ ID NO 22
<211> LENGTH: 1038
<212> TYPE: DNA
<213> ORGANISM: Saccharomyces cerevisiae

<400> SEQUENCE: 22
atgtctgtcg ccgatttgaa aaacaacatc cacaagttag atactggcta tggtttaatg 60
agtttgactt ggagagccga gcctatccct cagtcgcagg ctttcgaggc catgcacaga 120
gtggttgagt tatccagaga acgtgggcac aaggcctttt tcaacgttgg tgaattctat 180

-continued

```
ggtcccgatt ttattaattt gtcgtatgtt cacgacttct ttgcgaaata cccagatttg    240

agaaaggatg tggttatcag ttgtaaaggt ggtgcagaca atgctacctt aacccccaga    300

ggcagtcacg atgatgttgt acaaagcgta aagaattcag ttagtgctat tggtggctac    360

atcgacatct tcgaagtcgc aagaatcgac acttccctat gcacgaaagg agaggtctac    420

ccctacgaat cgttcgaagc gcttgctgag atgatctccg aaggcgttat tggcggtatt    480

tcattaagtg aagttaatga agagcaaatt agagctattc acaaggattg ggaaagttt    540

ttgacctgcg ttgaagtgga actttctttg ttcagtaatg acattttaca caacggaatt    600

gctaaaacat gtgctgaatt ggggttgtcc atcatctgct actccccact gggcagagga    660

ttgttgacag gtcaattgaa gtcaaacgct gatatccctg agggtgactt tagaaagtcg    720

ttaaagagat ttagcgacga gtctttgaaa aaaaacctga ccttggtcag gtttctacag    780

gaagaaatag tcgacaagcg cccacaaaac aactccatta ctcttgcaca actggctttg    840

ggatgggtta agcactggaa caaagttccg gaatacagtg gcgccaaatt tatcccaatt    900

ccaagtggct cttctatttc caaggttaat gaaaactttg atgaacagaa aaccaaactt    960

accgatcaag agttcaatgc cattaacaaa tatttgacta ctttccatac tgttggtgac   1020

agatacgaaa tggcgtaa                                                  1038
```

```
<210> SEQ ID NO 23
<211> LENGTH: 612
<212> TYPE: DNA
<213> ORGANISM: Coptis japonica

<400> SEQUENCE: 23

aagcttaaaa tgagaatgga agtcgtcttg gtcgttttct tgatgttcat tggtactatc     60

aactgcgaaa gattgatctt caatggtaga cctttgttgc acagagttac caaagaagaa    120

accgttatgt tgtaccacga attggaagtt gctgcttctg ctgatgaagt ttggtctgtt    180

gaaggttctc cagaattggg tttacatttg ccagatttgt tgccagctgg tatttttgcc    240

aagttcgaaa ttactggtga tggtggtgaa ggttccattt tggatatgac ttttccacca    300

ggtcaattcc cacatcatta cagagaaaag ttcgtctttt tcgaccacaa gaacagatac    360

aagttggtcg aacaaatcga tggtgatttc ttcgatttgg gtgttactta ctacatggac    420

accattagag ttgttgctac tggtccagat tcttgcgtta ttaagtctac tactgaatac    480

cacgtcaagc cagaatttgc taaaatcgtt aagccattga tcgataccgt tccattggct    540

attatgtctg aagctattgc caaggttgtc ttggaaaaca aacacaagtc atctgaatga    600

aagactccgc gg                                                        612
```

```
<210> SEQ ID NO 24
<211> LENGTH: 196
<212> TYPE: PRT
<213> ORGANISM: Coptis japonica

<400> SEQUENCE: 24

Met Arg Met Glu Val Val Leu Val Val Phe Leu Met Phe Ile Gly Thr
1               5                   10                  15

Ile Asn Cys Glu Arg Leu Ile Phe Asn Gly Arg Pro Leu Leu His Arg
            20                  25                  30

Val Thr Lys Glu Glu Thr Val Met Leu Tyr His Glu Leu Glu Val Ala
        35                  40                  45

Ala Ser Ala Asp Glu Val Trp Ser Val Glu Gly Ser Pro Glu Leu Gly
    50                  55                  60
```

Leu His Leu Pro Asp Leu Leu Pro Ala Gly Ile Phe Ala Lys Phe Glu
65 70 75 80

Ile Thr Gly Asp Gly Gly Glu Gly Ser Ile Leu Asp Met Thr Phe Pro
85 90 95

Pro Gly Gln Phe Pro His His Tyr Arg Glu Lys Phe Val Phe Phe Asp
100 105 110

His Lys Asn Arg Tyr Lys Leu Val Glu Gln Ile Asp Gly Asp Phe Phe
115 120 125

Asp Leu Gly Val Thr Tyr Tyr Met Asp Thr Ile Arg Val Val Ala Thr
130 135 140

Gly Pro Asp Ser Cys Val Ile Lys Ser Thr Thr Glu Tyr His Val Lys
145 150 155 160

Pro Glu Phe Ala Lys Ile Val Lys Pro Leu Ile Asp Thr Val Pro Leu
165 170 175

Ala Ile Met Ser Glu Ala Ile Ala Lys Val Val Leu Glu Asn Lys His
180 185 190

Lys Ser Ser Glu
195

<210> SEQ ID NO 25
<211> LENGTH: 363
<212> TYPE: PRT
<213> ORGANISM: Saccharomyces cerevisiae

<400> SEQUENCE: 25

Met Ile Gly Ser Ala Ser Asp Ser Ser Ser Lys Leu Gly Arg Leu Arg
1 5 10 15

Phe Leu Ser Glu Thr Ala Ala Ile Lys Val Ser Pro Leu Ile Leu Gly
20 25 30

Glu Val Ser Tyr Asp Gly Ala Arg Ser Asp Phe Leu Lys Ser Met Asn
35 40 45

Lys Asn Arg Ala Phe Glu Leu Leu Asp Thr Phe Tyr Glu Ala Gly Gly
50 55 60

Asn Phe Ile Asp Ala Ala Asn Asn Cys Gln Asn Glu Gln Ser Glu Glu
65 70 75 80

Trp Ile Gly Glu Trp Ile Gln Ser Arg Arg Leu Arg Asp Gln Ile Val
85 90 95

Ile Ala Thr Lys Phe Ile Lys Ser Asp Lys Lys Tyr Lys Ala Gly Glu
100 105 110

Ser Asn Thr Ala Asn Tyr Cys Gly Asn His Lys Arg Ser Leu His Val
115 120 125

Ser Val Arg Asp Ser Leu Arg Lys Leu Gln Thr Asp Trp Ile Asp Ile
130 135 140

Leu Tyr Val His Trp Trp Asp Tyr Met Ser Ser Ile Glu Glu Phe Met
145 150 155 160

Asp Ser Leu His Ile Leu Val Gln Gln Gly Lys Val Leu Tyr Leu Gly
165 170 175

Val Ser Asp Thr Pro Ala Trp Val Val Ser Ala Ala Asn Tyr Tyr Ala
180 185 190

Thr Ser Tyr Gly Lys Thr Pro Phe Ser Ile Tyr Gln Gly Lys Trp Asn
195 200 205

Val Leu Asn Arg Asp Phe Glu Arg Asp Ile Ile Pro Met Ala Arg His
210 215 220

Phe Gly Met Ala Leu Ala Pro Trp Asp Val Met Gly Gly Gly Arg Phe

-continued

```
225                 230                 235                 240

Gln Ser Lys Lys Ala Met Glu Glu Arg Arg Lys Asn Gly Glu Gly Ile
                245                 250                 255

Arg Ser Phe Val Gly Ala Ser Glu Gln Thr Asp Ala Glu Ile Lys Ile
            260                 265                 270

Ser Glu Ala Leu Ala Lys Ile Ala Glu Glu His Gly Thr Glu Ser Val
        275                 280                 285

Thr Ala Ile Ala Ile Ala Tyr Val Arg Ser Lys Ala Lys Asn Phe Phe
    290                 295                 300

Pro Ser Val Glu Gly Gly Lys Ile Glu Asp Leu Lys Glu Asn Ile Lys
305                 310                 315                 320

Ala Leu Ser Ile Asp Leu Thr Pro Asp Asn Ile Lys Tyr Leu Glu Ser
                325                 330                 335

Ile Val Pro Phe Asp Ile Gly Phe Pro Asn Asn Phe Ile Val Leu Asn
            340                 345                 350

Ser Leu Thr Gln Lys Tyr Gly Thr Asn Asn Val
        355                 360
```

<210> SEQ ID NO 26
<211> LENGTH: 1092
<212> TYPE: DNA
<213> ORGANISM: Saccharomyces cerevisiae

<400> SEQUENCE: 26

```
atgattgggt ccgcgtccga ctcatctagc aagttaggac gcctccgatt tctttctgaa      60

actgccgcta ttaaagtatc cccgttaatc ctaggagaag tctcatacga tggagcacgt     120

tcggattttc tcaaatcaat gaacaagaat cgagcttttg aattgcttga tactttttac     180

gaggcaggtg gaaatttcat tgatgccgca aacaactgcc aaaacgagca atcagaagaa     240

tggattggtg aatggataca gtccagaagg ttacgtgatc aaattgtcat tgcaaccaag     300

tttataaaaa gcgataaaaa gtataaagca ggtgaaagta acactgccaa ctactgtggt     360

aatcacaagc gtagtttaca tgtgagtgtg agggattctc tccgcaaatt gcaaactgat     420

tggattgata tactttacgt tcactggtgg gattatatga gttcaatcga agaatttatg     480

gatagtttgc atattctggt ccagcagggc aaggtcctct atttgggtgt atctgataca     540

cctgcttggg ttgtttctgc ggcaaactac tacgctacat cttatggtaa aactcccttt     600

agtatctacc aaggtaaatg gaacgtgttg aacagagatt ttgagcgtga tattattcca     660

atggctaggc atttcggtat ggccctcgcc ccatgggatg tcatgggagg tggaagattt     720

cagagtaaaa aagcaatgga ggaacggagg aagaatggag agggtattcg ttctttcgtt     780

ggcgcctccg aacaaacaga tgcagaaatc aagattagtg aagcattggc caagattgct     840

gaggaacatg gcactgagtc tgttactgct attgctattg cctatgttcg ctctaaggcg     900

aaaaattttt ttccgtcggt tgaaggagga aaaattgagg atctcaaaga gaacattaag     960

gctctcagta tcgatctaac gccagacaat ataaaatact tagaaagtat agttcctttt    1020

gacatcggat ttcctaataa ttttatcgtg ttaaattcct tgactcaaaa atatggtacg    1080

aataatgttt ag                                                        1092
```

<210> SEQ ID NO 27
<211> LENGTH: 329
<212> TYPE: PRT
<213> ORGANISM: Saccharomyces cerevisiae

<400> SEQUENCE: 27

```
Met Gly Ser Met Asn Lys Glu Gln Ala Phe Glu Leu Leu Asp Ala Phe
1               5                   10                  15

Tyr Glu Ala Gly Gly Asn Cys Ile Asp Thr Ala Asn Ser Tyr Gln Asn
            20                  25                  30

Glu Glu Ser Glu Ile Trp Ile Gly Glu Trp Met Lys Ser Arg Lys Leu
        35                  40                  45

Arg Asp Gln Ile Val Ile Ala Thr Lys Phe Thr Gly Asp Tyr Lys Lys
    50                  55                  60

Tyr Glu Val Gly Gly Gly Lys Ser Ala Asn Tyr Cys Gly Asn His Lys
65                  70                  75                  80

His Ser Leu His Val Ser Val Arg Asp Ser Leu Arg Lys Leu Gln Thr
                85                  90                  95

Asp Trp Ile Asp Ile Leu Tyr Val His Trp Trp Asp Tyr Met Ser Ser
            100                 105                 110

Ile Glu Glu Val Met Asp Ser Leu His Ile Leu Val Gln Gln Gly Lys
        115                 120                 125

Val Leu Tyr Leu Gly Val Ser Asp Thr Pro Ala Trp Val Val Ser Ala
    130                 135                 140

Ala Asn Tyr Tyr Ala Thr Ser His Gly Lys Thr Pro Phe Ser Ile Tyr
145                 150                 155                 160

Gln Gly Lys Trp Asn Val Leu Asn Arg Asp Phe Glu Arg Asp Ile Ile
                165                 170                 175

Pro Met Ala Arg His Phe Gly Met Ala Leu Ala Pro Trp Asp Val Met
            180                 185                 190

Gly Gly Gly Arg Phe Gln Ser Lys Lys Ala Met Glu Glu Arg Lys Lys
        195                 200                 205

Asn Gly Glu Gly Leu Arg Thr Val Ser Gly Thr Ser Lys Gln Thr Asp
    210                 215                 220

Lys Glu Val Lys Ile Ser Glu Ala Leu Ala Lys Val Ala Glu Glu His
225                 230                 235                 240

Gly Thr Glu Ser Val Thr Ala Ile Ala Ile Ala Tyr Val Arg Ser Lys
                245                 250                 255

Ala Lys Asn Val Phe Pro Leu Val Gly Gly Arg Lys Ile Glu His Leu
            260                 265                 270

Lys Gln Asn Ile Glu Ala Leu Ser Ile Lys Leu Thr Pro Glu Gln Ile
        275                 280                 285

Glu Tyr Leu Glu Ser Ile Ile Pro Phe Asp Val Gly Phe Pro Thr Asn
    290                 295                 300

Phe Ile Gly Asp Asp Pro Ala Val Thr Lys Lys Ala Ser Leu Leu Thr
305                 310                 315                 320

Ala Met Ser Ala Gln Ile Ser Phe Asp
                325
```

<210> SEQ ID NO 28
<211> LENGTH: 990
<212> TYPE: DNA
<213> ORGANISM: Saccharomyces cerevisiae

<400> SEQUENCE: 28

```
atgggctcta tgaataagga acaggctttt gaacttcttg atgcttttta tgaagcagga      60

ggtaattgca ttgatactgc aaacagttac caaaatgaag agtcagagat ttggataggt     120

gaatggatga aatcaagaaa gttgcgtgac caaattgtaa ttgccaccaa gtttaccgga     180

gattataaga agtatgaagt aggtggcggt aaaagtgcca actattgtgg taatcacaag     240
```

```
catagtttac atgtgagtgt gagggattct ctccgcaaat tgcaaactga ttggattgat    300

atactttacg ttcactggtg ggattatatg agttcaatcg aagaagttat ggatagtttg    360

catattttag ttcagcaggg caaagtcctc tatttgggtg tgtctgatac acctgcttgg    420

gttgtttctg cggcaaacta ctacgccaca tctcatggga aaactccttt tagtatctat    480

caaggtaaat ggaatgtgtt gaacagggac tttgagcgcg atatcattcc aatggccaga    540

cattttggta tggctctagc cccatgggat gttatgggag gtggaagatt tcagagtaaa    600

aaagcaatgg aggaacggaa gaagaatgga gagggtctgc gtactgtttc gggtacttct    660

aaacagacgg ataaagaggt taagatcagt gaagcattgg ccaaggttgc tgaggaacat    720

ggcactgagt ctgttactgc tattgctatt gcctatgttc gctctaaggc gaaaaatgtt    780

ttcccattgg ttggtggaag gaaaattgaa cacctcaaac agaacattga ggctttaagt    840

atcaaactga caccagaaca gatagaatac ttagaaagta ttattccttt tgatgttggt    900

tttcctacta attttatcgg tgatgatccg gctgttacca agaaggcttc acttctcacg    960

gcaatgtctg cgcagatttc cttcgattaa                                     990
```

<210> SEQ ID NO 29
<211> LENGTH: 375
<212> TYPE: PRT
<213> ORGANISM: Saccharomyces cerevisiae

<400> SEQUENCE: 29

```
Met Leu Arg Thr Ser Thr Leu Phe Thr Arg Arg Val Gln Pro Ser Leu
1               5                   10                  15

Phe Ser Arg Asn Ile Leu Arg Leu Gln Ser Thr Ala Ala Ile Pro Lys
            20                  25                  30

Thr Gln Lys Gly Val Ile Phe Tyr Glu Asn Lys Gly Lys Leu His Tyr
        35                  40                  45

Lys Asp Ile Pro Val Pro Glu Pro Lys Pro Asn Glu Ile Leu Ile Asn
    50                  55                  60

Val Lys Tyr Ser Gly Val Cys His Thr Asp Leu His Ala Trp His Gly
65                  70                  75                  80

Asp Trp Pro Leu Pro Val Lys Leu Pro Leu Val Gly Gly His Glu Gly
                85                  90                  95

Ala Gly Val Val Val Lys Leu Gly Ser Asn Val Lys Gly Trp Lys Val
            100                 105                 110

Gly Asp Leu Ala Gly Ile Lys Trp Leu Asn Gly Ser Cys Met Thr Cys
        115                 120                 125

Glu Phe Cys Glu Ser Gly His Glu Ser Asn Cys Pro Asp Ala Asp Leu
    130                 135                 140

Ser Gly Tyr Thr His Asp Gly Ser Phe Gln Gln Phe Ala Thr Ala Asp
145                 150                 155                 160

Ala Ile Gln Ala Ala Lys Ile Gln Gln Gly Thr Asp Leu Ala Glu Val
                165                 170                 175

Ala Pro Ile Leu Cys Ala Gly Val Thr Val Tyr Lys Ala Leu Lys Glu
            180                 185                 190

Ala Asp Leu Lys Ala Gly Asp Trp Val Ala Ile Ser Gly Ala Ala Gly
        195                 200                 205

Gly Leu Gly Ser Leu Ala Val Gln Tyr Ala Thr Ala Met Gly Tyr Arg
    210                 215                 220

Val Leu Gly Ile Asp Ala Gly Glu Glu Lys Glu Lys Leu Phe Lys Lys
225                 230                 235                 240
```

```
Leu Gly Gly Glu Val Phe Ile Asp Phe Thr Lys Thr Lys Asn Met Val
                245                 250                 255

Ser Asp Ile Gln Glu Ala Thr Lys Gly Gly Pro His Gly Val Ile Asn
            260                 265                 270

Val Ser Val Ser Glu Ala Ala Ile Ser Leu Ser Thr Glu Tyr Val Arg
        275                 280                 285

Pro Cys Gly Thr Val Val Leu Val Gly Leu Pro Ala Asn Ala Tyr Val
    290                 295                 300

Lys Ser Glu Val Phe Ser His Val Val Lys Ser Ile Asn Ile Lys Gly
305                 310                 315                 320

Ser Tyr Val Gly Asn Arg Ala Asp Thr Arg Glu Ala Leu Asp Phe Phe
                325                 330                 335

Ser Arg Gly Leu Ile Lys Ser Pro Ile Lys Ile Val Gly Leu Ser Glu
            340                 345                 350

Leu Pro Lys Val Tyr Asp Leu Met Glu Lys Gly Lys Ile Leu Gly Arg
        355                 360                 365

Tyr Val Val Asp Thr Ser Lys
    370                 375
```

<210> SEQ ID NO 30
<211> LENGTH: 1128
<212> TYPE: DNA
<213> ORGANISM: Saccharomyces cerevisiae

<400> SEQUENCE: 30

```
atgttgagaa cgtcaacatt gttcaccagg cgtgtccaac caagcctatt ttctagaaac     60

attcttagat tgcaatccac agctgcaatc cctaagactc aaaaaggtgt catcttttat    120

gagaataagg ggaagctgca ttacaaagat atccctgtcc ccgagcctaa gccaaatgaa    180

attttaatca acgttaaata ttctggtgta tgtcacaccg atttacatgc ttggcacggc    240

gattggccat tacctgttaa actaccatta gtaggtggtc atgaaggtgc tggtgtagtt    300

gtcaaactag gttccaatgt caagggctgg aaagtcggtg atttagcagg tatcaaatgg    360

ctgaacggtt cttgtatgac atgcgaattc tgtgaatcag gtcatgaatc aaattgtcca    420

gatgctgatt tatctggtta cactcatgat ggttctttcc aacaatttgc gaccgctgat    480

gctattcaag ccgccaaaat tcaacagggt accgacttgg ccgaagtagc cccaatatta    540

tgtgctggtg ttactgtata taaagcacta aaagaggcag acttgaaagc tggtgactgg    600

gttgccatct ctggtgctgc aggtggcttg ggttccttgg ccgttcaata tgcaactgcg    660

atgggttaca gagttctagg tattgatgca ggtgaggaaa aggaaaaact tttcaagaaa    720

ttgggggggtg aagtattcat cgactttact aaaacaaaga atatggtttc tgacattcaa    780

gaagctacca aaggtggccc tcatggtgtc attaacgttt ccgtttctga agccgctatt    840

tctctatcta cggaatatgt tagaccatgt ggtaccgtcg ttttggttgg tttgcccgct    900

aacgcctacg ttaaatcaga ggtattctct catgtggtga agtccatcaa tatcaagggt    960

tcttatgttg gtaacagagc tgatacgaga gaagccttag acttctttag cagaggtttg   1020

atcaaatcac caatcaaaat tgttggatta tctgaattac caaaggttta tgacttgatg   1080

gaaaagggca agattttggg tagatacgtc gtcgatacta gtaaataa                1128
```

<210> SEQ ID NO 31
<211> LENGTH: 382
<212> TYPE: PRT
<213> ORGANISM: Saccharomyces cerevisiae

<400> SEQUENCE: 31

```
Met Ser Ser Val Thr Gly Phe Tyr Ile Pro Pro Ile Ser Phe Phe Gly
1               5                   10                  15

Glu Gly Ala Leu Glu Glu Thr Ala Asp Tyr Ile Lys Asn Lys Asp Tyr
            20                  25                  30

Lys Lys Ala Leu Ile Val Thr Asp Pro Gly Ile Ala Ala Ile Gly Leu
        35                  40                  45

Ser Gly Arg Val Gln Lys Met Leu Glu Glu Arg Asp Leu Asn Val Ala
    50                  55                  60

Ile Tyr Asp Lys Thr Gln Pro Asn Pro Asn Ile Ala Asn Val Thr Ala
65                  70                  75                  80

Gly Leu Lys Val Leu Lys Glu Gln Asn Ser Glu Ile Val Val Ser Ile
                85                  90                  95

Gly Gly Gly Ser Ala His Asp Asn Ala Lys Ala Ile Ala Leu Leu Ala
            100                 105                 110

Thr Asn Gly Gly Glu Ile Gly Asp Tyr Glu Gly Val Asn Gln Ser Lys
        115                 120                 125

Lys Ala Ala Leu Pro Leu Phe Ala Ile Asn Thr Thr Ala Gly Thr Ala
    130                 135                 140

Ser Glu Met Thr Arg Phe Thr Ile Ile Ser Asn Glu Glu Lys Lys Ile
145                 150                 155                 160

Lys Met Ala Ile Ile Asp Asn Asn Val Thr Pro Ala Val Ala Val Asn
                165                 170                 175

Asp Pro Ser Thr Met Phe Gly Leu Pro Pro Ala Leu Thr Ala Ala Thr
            180                 185                 190

Gly Leu Asp Ala Leu Thr His Cys Ile Glu Ala Tyr Val Ser Thr Ala
        195                 200                 205

Ser Asn Pro Ile Thr Asp Ala Cys Ala Leu Lys Gly Ile Asp Leu Ile
    210                 215                 220

Asn Glu Ser Leu Val Ala Ala Tyr Lys Asp Gly Lys Asp Lys Lys Ala
225                 230                 235                 240

Arg Thr Asp Met Cys Tyr Ala Glu Tyr Leu Ala Gly Met Ala Phe Asn
                245                 250                 255

Asn Ala Ser Leu Gly Tyr Val His Ala Leu Ala His Gln Leu Gly Gly
            260                 265                 270

Phe Tyr His Leu Pro His Gly Val Cys Asn Ala Val Leu Leu Pro His
        275                 280                 285

Val Gln Glu Ala Asn Met Gln Cys Pro Lys Ala Lys Lys Arg Leu Gly
    290                 295                 300

Glu Ile Ala Leu His Phe Gly Ala Ser Gln Glu Asp Pro Glu Glu Thr
305                 310                 315                 320

Ile Lys Ala Leu His Val Leu Asn Arg Thr Met Asn Ile Pro Arg Asn
                325                 330                 335

Leu Lys Glu Leu Gly Val Lys Thr Glu Asp Phe Glu Ile Leu Ala Glu
            340                 345                 350

His Ala Met His Asp Ala Cys His Leu Thr Asn Pro Val Gln Phe Thr
        355                 360                 365

Lys Glu Gln Val Val Ala Ile Ile Lys Lys Ala Tyr Glu Tyr
    370                 375                 380
```

<210> SEQ ID NO 32
<211> LENGTH: 1149
<212> TYPE: DNA

<213> ORGANISM: Saccharomyces cerevisiae

<400> SEQUENCE: 32

```
atgtcttccg ttactgggtt ttacattcca ccaatctctt tctttggtga aggtgcttta     60
gaagaaaccg ctgattacat caaaaacaag gattacaaaa aggctttgat cgttactgat    120
cctggtattg cagctattgg tctctccggt agagtccaaa agatgttgga agaacgtgac    180
ttaaacgttg ctatctatga caaaactcaa ccaaacccaa atattgccaa tgtcacagct    240
ggtttgaagg ttttgaagga acaaaactct gaaattgttg tttccattgg tggtggttct    300
gctcacgaca atgctaaggc cattgcttta ttggctacta acggtgggga aatcggagac    360
tatgaaggtg tcaatcaatc taagaaggct gctttaccac tatttgccat caacactact    420
gctggtactg cttccgaaat gaccagattc actattatct ctaatgaaga aaagaaaatc    480
aagatggcta tcattgacaa caacgtcact ccagctgttg ctgtcaacga tccatctacc    540
atgtttggtt tgccacctgc tttgactgct gctactggtc tagatgcttt gactcactgt    600
atcgaagctt atgtttccac cgcctctaac ccaatcaccg atgcctgtgc tttgaagggt    660
attgatttga tcaatgaaag cttagtcgct gcatacaaag acggtaaaga caagaaggcc    720
agaactgaca tgtgttacgc tgaatacttg gcaggtatgg ctttcaacaa tgcttctcta    780
ggttatgttc atgcccttgc tcatcaactt ggtggtttct accacttgcc tcatggtgtt    840
tgtaacgctg tcttgttgcc tcatgttcaa gaggccaaca tgcaatgtcc aaaggccaag    900
aagagattag gtgaaattgc tttgcatttc ggtgcttctc aagaagatcc agaagaaacc    960
atcaaggctt tgcacgtttt aaacagaacc atgaacattc caagaaactt gaaagaatta   1020
ggtgttaaaa ccgaagattt tgaaattttg gctgaacacg ccatgcatga tgcctgccat   1080
ttgactaacc cagttcaatt caccaaagaa caagtggttg ccattatcaa gaaagcctat   1140
gaatattaa                                                           1149
```

<210> SEQ ID NO 33
<211> LENGTH: 500
<212> TYPE: PRT
<213> ORGANISM: Saccharomyces cerevisiae

<400> SEQUENCE: 33

```
Met Thr Lys Leu His Phe Asp Thr Ala Glu Pro Val Lys Ile Thr Leu
1               5                   10                  15

Pro Asn Gly Leu Thr Tyr Glu Gln Pro Thr Gly Leu Phe Ile Asn Asn
            20                  25                  30

Lys Phe Met Lys Ala Gln Asp Gly Lys Thr Tyr Pro Val Glu Asp Pro
        35                  40                  45

Ser Thr Glu Asn Thr Val Cys Glu Val Ser Ser Ala Thr Thr Glu Asp
    50                  55                  60

Val Glu Tyr Ala Ile Glu Cys Ala Asp Arg Ala Phe His Asp Thr Glu
65                  70                  75                  80

Trp Ala Thr Gln Asp Pro Arg Glu Arg Gly Arg Leu Leu Ser Lys Leu
                85                  90                  95

Ala Asp Glu Leu Glu Ser Gln Ile Asp Leu Val Ser Ser Ile Glu Ala
            100                 105                 110

Leu Asp Asn Gly Lys Thr Leu Ala Leu Ala Arg Gly Asp Val Thr Ile
        115                 120                 125

Ala Ile Asn Cys Leu Arg Asp Ala Ala Ala Tyr Ala Asp Lys Val Asn
    130                 135                 140
```

```
Gly Arg Thr Ile Asn Thr Gly Asp Gly Tyr Met Asn Phe Thr Thr Leu
145                 150                 155                 160

Glu Pro Ile Gly Val Cys Gly Gln Ile Ile Pro Trp Asn Phe Pro Ile
                165                 170                 175

Met Met Leu Ala Trp Lys Ile Ala Pro Ala Leu Ala Met Gly Asn Val
            180                 185                 190

Cys Ile Leu Lys Pro Ala Ala Val Thr Pro Leu Asn Ala Leu Tyr Phe
        195                 200                 205

Ala Ser Leu Cys Lys Lys Val Gly Ile Pro Ala Gly Val Val Asn Ile
    210                 215                 220

Val Pro Gly Pro Gly Arg Thr Val Gly Ala Ala Leu Thr Asn Asp Pro
225                 230                 235                 240

Arg Ile Arg Lys Leu Ala Phe Thr Gly Ser Thr Glu Val Gly Lys Ser
                245                 250                 255

Val Ala Val Asp Ser Ser Glu Ser Asn Leu Lys Lys Ile Thr Leu Glu
            260                 265                 270

Leu Gly Gly Lys Ser Ala His Leu Val Phe Asp Asp Ala Asn Ile Lys
        275                 280                 285

Lys Thr Leu Pro Asn Leu Val Asn Gly Ile Phe Lys Asn Ala Gly Gln
    290                 295                 300

Ile Cys Ser Ser Gly Ser Arg Ile Tyr Val Gln Glu Gly Ile Tyr Asp
305                 310                 315                 320

Glu Leu Leu Ala Ala Phe Lys Ala Tyr Leu Glu Thr Glu Ile Lys Val
                325                 330                 335

Gly Asn Pro Phe Asp Lys Ala Asn Phe Gln Gly Ala Ile Thr Asn Arg
            340                 345                 350

Gln Gln Phe Asp Thr Ile Met Asn Tyr Ile Asp Ile Gly Lys Lys Glu
        355                 360                 365

Gly Ala Lys Ile Leu Thr Gly Gly Glu Lys Val Gly Asp Lys Gly Tyr
    370                 375                 380

Phe Ile Arg Pro Thr Val Phe Tyr Asp Val Asn Glu Asp Met Arg Ile
385                 390                 395                 400

Val Lys Glu Glu Ile Phe Gly Pro Val Val Thr Val Ala Lys Phe Lys
                405                 410                 415

Thr Leu Glu Glu Gly Val Glu Met Ala Asn Ser Ser Glu Phe Gly Leu
            420                 425                 430

Gly Ser Gly Ile Glu Thr Glu Ser Leu Ser Thr Gly Leu Lys Val Ala
        435                 440                 445

Lys Met Leu Lys Ala Gly Thr Val Trp Ile Asn Thr Tyr Asn Asp Phe
    450                 455                 460

Asp Ser Arg Val Pro Phe Gly Gly Val Lys Gln Ser Gly Tyr Gly Arg
465                 470                 475                 480

Glu Met Gly Glu Glu Val Tyr His Ala Tyr Thr Glu Val Lys Ala Val
                485                 490                 495

Arg Ile Lys Leu
            500
```

<210> SEQ ID NO 34
<211> LENGTH: 1503
<212> TYPE: DNA
<213> ORGANISM: Saccharomyces cerevisiae

<400> SEQUENCE: 34
atgactaagc tacactttga cactgctgaa ccagtcaaga tcacacttcc aaatggtttg 60

```
acatacgagc aaccaaccgg tctattcatt aacaacaagt ttatgaaagc tcaagacggt    120

aagacctatc ccgtcgaaga tccttccact gaaaacaccg tttgtgaggt ctcttctgcc    180

accactgaag atgttgaata tgctatcgaa tgtgccgacc gtgctttcca cgacactgaa    240

tgggctaccc aagacccaag agaaagaggc cgtctactaa gtaagttggc tgacgaattg    300

gaaagccaaa ttgacttggt ttcttccatt gaagctttgg acaatggtaa aactttggcc    360

ttagcccgtg ggatgttac cattgcaatc aactgtctaa gagatgctgc tgcctatgcc    420

gacaaagtca acggtagaac aatcaacacc ggtgacggct acatgaactt caccacctta    480

gagccaatcg gtgtctgtgg tcaaattatt ccatggaact ttccaataat gatgttggct    540

tggaagatcg ccccagcatt ggccatgggt aacgtctgta tcttgaaacc cgctgctgtc    600

acacctttaa atgccctata ctttgcttct ttatgtaaga aggttggtat tccagctggt    660

gtcgtcaaca tcgttccagg tcctggtaga actgttggtg ctgctttgac caacgaccca    720

agaatcagaa agctggcttt taccggttct acagaagtcg gtaagagtgt tgctgtcgac    780

tcttctgaat ctaacttgaa gaaaatcact ttggaactag gtggtaagtc cgcccatttg    840

gtctttgacg atgctaacat taagaagact ttaccaaatc tagtaaacgg tattttcaag    900

aacgctggtc aaatttgttc ctctggttct agaatttacg ttcaagaagg tatttacgac    960

gaactattgg ctgctttcaa ggcttacttg gaaaccgaaa tcaaagttgg taatccattt   1020

gacaaggcta acttccaagg tgctatcact aaccgtcaac aattcgacac aattatgaac   1080

tacatcgata tcggtaagaa agaaggcgcc aagatcttaa ctggtggcga aaaagttggt   1140

gacaagggtt acttcatcag accaaccgtt ttctacgatg ttaatgaaga catgagaatt   1200

gttaaggaag aaatttttgg accagttgtc actgtcgcaa agttcaagac tttagaagaa   1260

ggtgtcgaaa tggctaacag ctctgaattc ggtctaggtt ctggtatcga aacagaatct   1320

ttgagcacag gtttgaaggt ggccaagatg ttgaaggccg gtaccgtctg gatcaacaca   1380

tacaacgatt ttgactccag agttccattc ggtggtgtta agcaatctgg ttacggtaga   1440

gaaatgggtg aagaagtcta ccatgcatac actgaagtaa aagctgtcag aattaagttg   1500

taa                                                                 1503
```

<210> SEQ ID NO 35
<211> LENGTH: 382
<212> TYPE: PRT
<213> ORGANISM: Saccharomyces cerevisiae

<400> SEQUENCE: 35

```
Met Arg Ala Leu Ala Tyr Phe Lys Lys Gly Asp Ile His Phe Thr Asn
1               5                   10                  15

Asp Ile Pro Arg Pro Glu Ile Gln Thr Asp Asp Glu Val Ile Ile Asp
            20                  25                  30

Val Ser Trp Cys Gly Ile Cys Gly Ser Asp Leu His Glu Tyr Leu Asp
        35                  40                  45

Gly Pro Ile Phe Met Pro Lys Asp Gly Glu Cys His Lys Leu Ser Asn
    50                  55                  60

Ala Ala Leu Pro Leu Ala Met Gly His Glu Met Ser Gly Ile Val Ser
65                  70                  75                  80

Lys Val Gly Pro Lys Val Thr Lys Val Lys Val Gly Asp His Val Val
                85                  90                  95

Val Asp Ala Ala Ser Ser Cys Ala Asp Leu His Cys Trp Pro His Ser
            100                 105                 110
```

-continued

```
Lys Phe Tyr Asn Ser Lys Pro Cys Asp Ala Cys Gln Arg Gly Ser Glu
        115                 120                 125

Asn Leu Cys Thr His Ala Gly Phe Val Gly Leu Gly Val Ile Ser Gly
    130                 135                 140

Gly Phe Ala Glu Gln Val Val Val Ser Gln His His Ile Ile Pro Val
145                 150                 155                 160

Pro Lys Glu Ile Pro Leu Asp Val Ala Ala Leu Val Glu Pro Leu Ser
                165                 170                 175

Val Thr Trp His Ala Val Lys Ile Ser Gly Phe Lys Lys Gly Ser Ser
            180                 185                 190

Ala Leu Val Leu Gly Ala Gly Pro Ile Gly Leu Cys Thr Ile Leu Val
        195                 200                 205

Leu Lys Gly Met Gly Ala Ser Lys Ile Val Val Ser Glu Ile Ala Glu
    210                 215                 220

Arg Arg Ile Glu Met Ala Lys Lys Leu Gly Val Glu Val Phe Asn Pro
225                 230                 235                 240

Ser Lys His Gly His Lys Ser Ile Glu Ile Leu Arg Gly Leu Thr Lys
                245                 250                 255

Ser His Asp Gly Phe Asp Tyr Ser Tyr Asp Cys Ser Gly Ile Gln Val
            260                 265                 270

Thr Phe Glu Thr Ser Leu Lys Ala Leu Thr Phe Lys Gly Thr Ala Thr
        275                 280                 285

Asn Ile Ala Val Trp Gly Pro Lys Pro Val Pro Phe Gln Pro Met Asp
    290                 295                 300

Val Thr Leu Gln Glu Lys Val Met Thr Gly Ser Ile Gly Tyr Val Val
305                 310                 315                 320

Glu Asp Phe Glu Glu Val Val Arg Ala Ile His Asn Gly Asp Ile Ala
                325                 330                 335

Met Glu Asp Cys Lys Gln Leu Ile Thr Gly Lys Gln Arg Ile Glu Asp
            340                 345                 350

Gly Trp Glu Lys Gly Phe Gln Glu Leu Met Asp His Lys Glu Ser Asn
        355                 360                 365

Val Lys Ile Leu Leu Thr Pro Asn Asn His Gly Glu Met Lys
    370                 375                 380
```

<210> SEQ ID NO 36
<211> LENGTH: 1149
<212> TYPE: DNA
<213> ORGANISM: Saccharomyces cerevisiae

<400> SEQUENCE: 36

```
atgagagctt tggcatattt caagaagggt gatattcact tcactaatga tatccctagg      60

ccagaaatcc aaaccgacga tgaggttatt atcgacgtct cttggtgtgg gatttgtggc     120

tcggatcttc acgagtactt ggatggtcca atcttcatgc ctaaagatgg agagtgccat     180

aaattatcca acgctgcttt acctctggca atgggccatg agatgtcagg aattgtttcc     240

aaggttggtc ctaaagtgac aaaggtgaag gttggcgacc acgtggtcgt tgatgctgcc     300

agcagttgtg cggacctgca ttgctggcca cactccaaat tttacaattc caaaccatgt     360

gatgcttgtc agaggggcag tgaaaatcta tgtacccacg ccggttttgt aggactaggt     420

gtgatcagtg gtggctttgc tgaacaagtc gtagtctctc aacatcacat tatcccggtt     480

ccaaaggaaa ttcctctaga tgtggctgct ttagttgagc ctctttctgt cacctggcat     540

gctgttaaga tttctggttt caaaaaaggc agttcagcct tggttcttgg tgcaggtccc     600
```

-continued

```
attgggttgt gtaccatttt ggtacttaag ggaatggggg ctagtaaaat tgtagtgtct     660

gaaattgcag agagaagaat agaaatggcc aagaaactgg gcgttgaggt gttcaatccc     720

tccaagcacg gtcataaatc tatagagata ctacgtggtt tgaccaagag ccatgatggg     780

tttgattaca gttatgattg ttctggtatt caagttactt tcgaaacctc tttgaaggca     840

ttaacattca aggggacagc caccaacatt gcagtttggg gtccaaaacc tgtcccattc     900

caaccaatgg atgtgactct ccaagagaaa gttatgactg gttcgatcgg ctatgttgtc     960

gaagacttcg aagaagttgt tcgtgccatc cacaacggag acatcgccat ggaagattgt    1020

aagcaactaa tcactggtaa gcaaaggatt gaggacggtt gggaaaaggg attccaagag    1080

ttgatggatc acaaggaatc caacgttaag attctattga cgcctaacaa tcacggtgaa    1140

atgaagtaa                                                            1149
```

```
<210> SEQ ID NO 37
<211> LENGTH: 417
<212> TYPE: PRT
<213> ORGANISM: Saccharomyces cerevisiae

<400> SEQUENCE: 37

Met Arg Ala Leu Ala Tyr Phe Gly Lys Gly Asn Ile Arg Phe Thr Asn
1               5                   10                  15

His Leu Lys Glu Pro His Ile Val Ala Pro Asp Glu Leu Val Ile Asp
            20                  25                  30

Ile Glu Trp Cys Gly Ile Cys Gly Thr Asp Leu His Glu Tyr Thr Asp
        35                  40                  45

Gly Pro Ile Phe Phe Pro Glu Asp Gly His Thr His Glu Ile Ser His
    50                  55                  60

Asn Pro Leu Pro Gln Ala Met Gly His Glu Met Ala Gly Thr Val Leu
65                  70                  75                  80

Glu Val Gly Pro Gly Val Lys Asn Leu Lys Val Gly Asp Lys Val Val
                85                  90                  95

Val Glu Pro Thr Gly Thr Cys Arg Asp Arg Tyr Arg Trp Pro Leu Ser
            100                 105                 110

Pro Asn Val Asp Lys Glu Trp Cys Ala Ala Cys Lys Lys Gly Tyr Tyr
        115                 120                 125

Asn Ile Cys Ser Tyr Leu Gly Leu Cys Gly Ala Gly Val Gln Ser Gly
    130                 135                 140

Gly Phe Ala Glu Arg Val Val Met Asn Glu Ser His Cys Tyr Lys Val
145                 150                 155                 160

Pro Asp Phe Val Pro Leu Asp Val Ala Ala Leu Ile Gln Pro Leu Ala
                165                 170                 175

Val Cys Trp His Ala Ile Arg Val Cys Glu Phe Lys Ala Gly Ser Thr
            180                 185                 190

Ala Leu Ile Ile Gly Ala Gly Pro Ile Gly Leu Gly Thr Ile Leu Ala
        195                 200                 205

Leu Asn Ala Ala Gly Cys Lys Asp Ile Val Val Ser Glu Pro Ala Lys
    210                 215                 220

Val Arg Arg Glu Leu Ala Glu Lys Met Gly Ala Arg Val Tyr Asp Pro
225                 230                 235                 240

Thr Ala His Ala Ala Lys Glu Ser Ile Asp Tyr Leu Arg Ser Ile Ala
                245                 250                 255

Asp Gly Gly Asp Gly Phe Asp Tyr Thr Phe Asp Cys Ser Gly Leu Glu
            260                 265                 270
```

```
Val Thr Leu Asn Ala Ala Ile Gln Cys Leu Thr Phe Arg Gly Thr Ala
        275                 280                 285

Val Asn Leu Ala Met Trp Gly His His Lys Ile Gln Phe Ser Pro Met
    290                 295                 300

Asp Ile Thr Leu His Glu Arg Lys Tyr Thr Gly Ser Met Cys Tyr Thr
305                 310                 315                 320

His His Asp Phe Glu Ala Val Ile Glu Ala Leu Glu Glu Gly Arg Ile
                325                 330                 335

Asp Ile Asp Arg Ala Arg His Met Ile Thr Gly Arg Val Asn Ile Glu
            340                 345                 350

Asp Gly Leu Asp Gly Ala Ile Met Lys Leu Ile Asn Glu Lys Glu Ser
        355                 360                 365

Thr Ile Lys Ile Ile Leu Thr Pro Asn Asn His Gly Glu Leu Asn Arg
    370                 375                 380

Glu Ala Asp Asn Glu Lys Lys Glu Ile Ser Glu Leu Ser Ser Arg Lys
385                 390                 395                 400

Asp Gln Glu Arg Leu Arg Glu Ser Ile Asn Glu Ala Lys Leu Arg His
                405                 410                 415

Thr


<210> SEQ ID NO 38
<211> LENGTH: 1254
<212> TYPE: DNA
<213> ORGANISM: Saccharomyces cerevisiae

<400> SEQUENCE: 38

atgagagcct tagcgtattt cggtaaaggt aacatcagat tcaccaacca tttaaaggag     60

ccacatattg tggcgcccga tgagcttgtg attgatatcg aatggtgtgg tatttgcggt    120

acggacctgc atgagtacac agatggtcct atctttttcc cagaagatgg acacacacat    180

gagattagtc ataacccatt gccacaggcg atgggccacg aaatggctgg taccgttttg    240

gaggtgggcc ctggtgtgaa aaacttgaaa gtgggagaca aggtagttgt cgagcccaca    300

ggtacatgca gagaccggta tcgttggccc ctgtcgccaa acgttgacaa ggaatggtgc    360

gctgcttgca aaaagggcta ctataacatt tgttcatatt tggggctttg tggtgcgggt    420

gtgcagagcg gtggatttgc agaacgtgtt gtgatgaacg aatctcactg ctacaaagta    480

ccggacttcg tgcccttaga cgttgcagct ttgattcaac cgttggctgt gtgctggcat    540

gcaattagag tctgcgagtt caaagcaggc tctacggctt tgatcattgg tgctggcccc    600

atcggactgg gcacgatact ggcgttgaac gctgcaggtt gcaaggacat cgtcgtttca    660

gagcctgcca aggtaagaag agaactggct gaaaaaatgg gtgccagggt ttacgaccca    720

actgcgcacg ctgccaagga gagcattgat tatctgaggt cgattgctga tggtggagac    780

ggcttcgatt acacatttga ttgctccggg ttggaagtca cattgaatgc tgctattcag    840

tgtctcactt tcagaggcac cgcagtgaac ttggccatgt ggggccatca caagatacag    900

ttttctccga tggacatcac attgcatgaa agaaagtaca cagggtccat gtgctacaca    960

caccacgatt ttgaggcagt aatagaagct ttggaagaag gcaggattga cattgataga   1020

gcaagacata tgataacggg cagagtcaac attgaggacg gccttgatgg cgccatcatg   1080

aagctgataa acgagaagga gtctacaatc aagattattc tgactccaaa caatcacgga   1140

gagttgaaca gggaagccga taatgagaag aaagaaattt ccgagctgag cagtcggaaa   1200

gatcaagaaa gactacgaga atcaataaac gaggctaaac tgcgtcacac atga         1254
```

<210> SEQ ID NO 39
<211> LENGTH: 900
<212> TYPE: PRT
<213> ORGANISM: Saccharomyces cerevisiae

<400> SEQUENCE: 39

Met Pro Gly Asn Leu Ser Phe Lys Asp Arg Val Val Val Ile Thr Gly
1 5 10 15

Ala Gly Gly Gly Leu Gly Lys Val Tyr Ala Leu Ala Tyr Ala Ser Arg
20 25 30

Gly Ala Lys Val Val Val Asn Asp Leu Gly Gly Thr Leu Gly Gly Ser
35 40 45

Gly His Asn Ser Lys Ala Ala Asp Leu Val Val Asp Glu Ile Lys Lys
50 55 60

Ala Gly Gly Ile Ala Val Ala Asn Tyr Asp Ser Val Asn Glu Asn Gly
65 70 75 80

Glu Lys Ile Ile Glu Thr Ala Ile Lys Glu Phe Gly Arg Val Asp Val
85 90 95

Leu Ile Asn Asn Ala Gly Ile Leu Arg Asp Val Ser Phe Ala Lys Met
100 105 110

Thr Glu Arg Glu Phe Ala Ser Val Val Asp Val His Leu Thr Gly Gly
115 120 125

Tyr Lys Leu Ser Arg Ala Ala Trp Pro Tyr Met Arg Ser Gln Lys Phe
130 135 140

Gly Arg Ile Ile Asn Thr Ala Ser Pro Ala Gly Leu Phe Gly Asn Phe
145 150 155 160

Gly Gln Ala Asn Tyr Ser Ala Ala Lys Met Gly Leu Val Gly Leu Ala
165 170 175

Glu Thr Leu Ala Lys Glu Gly Ala Lys Tyr Asn Ile Asn Val Asn Ser
180 185 190

Ile Ala Pro Leu Ala Arg Ser Arg Met Thr Glu Asn Val Leu Pro Pro
195 200 205

His Ile Leu Lys Gln Leu Gly Pro Glu Lys Ile Val Pro Leu Val Leu
210 215 220

Tyr Leu Thr His Glu Ser Thr Lys Val Ser Asn Ser Ile Phe Glu Leu
225 230 235 240

Ala Ala Gly Phe Phe Gly Gln Leu Arg Trp Glu Arg Ser Ser Gly Gln
245 250 255

Ile Phe Asn Pro Asp Pro Lys Thr Tyr Thr Pro Glu Ala Ile Leu Asn
260 265 270

Lys Trp Lys Glu Ile Thr Asp Tyr Arg Asp Lys Pro Phe Asn Lys Thr
275 280 285

Gln His Pro Tyr Gln Leu Ser Asp Tyr Asn Asp Leu Ile Thr Lys Ala
290 295 300

Lys Lys Leu Pro Pro Asn Glu Gln Gly Ser Val Lys Ile Lys Ser Leu
305 310 315 320

Cys Asn Lys Val Val Val Val Thr Gly Ala Gly Gly Gly Leu Gly Lys
325 330 335

Ser His Ala Ile Trp Phe Ala Arg Tyr Gly Ala Lys Val Val Val Asn
340 345 350

Asp Ile Lys Asp Pro Phe Ser Val Val Glu Glu Ile Asn Lys Leu Tyr
355 360 365

Gly Glu Gly Thr Ala Ile Pro Asp Ser His Asp Val Val Thr Glu Ala
370 375 380

```
Pro Leu Ile Ile Gln Thr Ala Ile Ser Lys Phe Gln Arg Val Asp Ile
385                 390                 395                 400

Leu Val Asn Asn Ala Gly Ile Leu Arg Asp Lys Ser Phe Leu Lys Met
                405                 410                 415

Lys Asp Glu Glu Trp Phe Ala Val Leu Lys Val His Leu Phe Ser Thr
            420                 425                 430

Phe Ser Leu Ser Lys Ala Val Trp Pro Ile Phe Thr Lys Gln Lys Ser
        435                 440                 445

Gly Phe Ile Ile Asn Thr Thr Ser Thr Ser Gly Ile Tyr Gly Asn Phe
    450                 455                 460

Gly Gln Ala Asn Tyr Ala Ala Ala Lys Ala Ala Ile Leu Gly Phe Ser
465                 470                 475                 480

Lys Thr Ile Ala Leu Glu Gly Ala Lys Arg Gly Ile Ile Val Asn Val
                485                 490                 495

Ile Ala Pro His Ala Glu Thr Ala Met Thr Lys Thr Ile Phe Ser Glu
            500                 505                 510

Lys Glu Leu Ser Asn His Phe Asp Ala Ser Gln Val Ser Pro Leu Val
        515                 520                 525

Val Leu Leu Ala Ser Glu Glu Leu Gln Lys Tyr Ser Gly Arg Arg Val
    530                 535                 540

Ile Gly Gln Leu Phe Glu Val Gly Gly Gly Trp Cys Gly Gln Thr Arg
545                 550                 555                 560

Trp Gln Arg Ser Ser Gly Tyr Val Ser Ile Lys Glu Thr Ile Glu Pro
                565                 570                 575

Glu Glu Ile Lys Glu Asn Trp Asn His Ile Thr Asp Phe Ser Arg Asn
            580                 585                 590

Thr Ile Asn Pro Ser Ser Thr Glu Glu Ser Ser Met Ala Thr Leu Gln
        595                 600                 605

Ala Val Gln Lys Ala His Ser Ser Lys Glu Leu Asp Asp Gly Leu Phe
    610                 615                 620

Lys Tyr Thr Thr Lys Asp Cys Ile Leu Tyr Asn Leu Gly Leu Gly Cys
625                 630                 635                 640

Thr Ser Lys Glu Leu Lys Tyr Thr Tyr Glu Asn Asp Pro Asp Phe Gln
                645                 650                 655

Val Leu Pro Thr Phe Ala Val Ile Pro Phe Met Gln Ala Thr Ala Thr
            660                 665                 670

Leu Ala Met Asp Asn Leu Val Asp Asn Phe Asn Tyr Ala Met Leu Leu
        675                 680                 685

His Gly Glu Gln Tyr Phe Lys Leu Cys Thr Pro Thr Met Pro Ser Asn
    690                 695                 700

Gly Thr Leu Lys Thr Leu Ala Lys Pro Leu Gln Val Leu Asp Lys Asn
705                 710                 715                 720

Gly Lys Ala Ala Leu Val Val Gly Gly Phe Glu Thr Tyr Asp Ile Lys
                725                 730                 735

Thr Lys Lys Leu Ile Ala Tyr Asn Glu Gly Ser Phe Phe Ile Arg Gly
            740                 745                 750

Ala His Val Pro Pro Glu Lys Glu Val Arg Asp Gly Lys Arg Ala Lys
        755                 760                 765

Phe Ala Val Gln Asn Phe Glu Val Pro His Gly Lys Val Pro Asp Phe
    770                 775                 780

Glu Ala Glu Ile Ser Thr Asn Lys Asp Gln Ala Ala Leu Tyr Arg Leu
785                 790                 795                 800
```

-continued

```
Ser Gly Asp Phe Asn Pro Leu His Ile Asp Pro Thr Leu Ala Lys Ala
                805                 810                 815

Val Lys Phe Pro Thr Pro Ile Leu His Gly Leu Cys Thr Leu Gly Ile
            820                 825                 830

Ser Ala Lys Ala Leu Phe Glu His Tyr Gly Pro Tyr Glu Glu Leu Lys
        835                 840                 845

Val Arg Phe Thr Asn Val Val Phe Pro Gly Asp Thr Leu Lys Val Lys
    850                 855                 860

Ala Trp Lys Gln Gly Ser Val Val Val Phe Gln Thr Ile Asp Thr Thr
865                 870                 875                 880

Arg Asn Val Ile Val Leu Asp Asn Ala Ala Val Lys Leu Ser Gln Ala
                885                 890                 895

Lys Ser Lys Leu
            900


<210> SEQ ID NO 40
<211> LENGTH: 2703
<212> TYPE: DNA
<213> ORGANISM: Saccharomyces cerevisiae

<400> SEQUENCE: 40

atgcctggaa atttatcctt caaagataga gttgttgtaa tcacgggcgc tggagggggc      60

ttaggtaagg tgtatgcact agcttacgca agcagaggtg caaaagtggt cgtcaatgat     120

ctaggtggca ctttgggtgg ttcaggacat aactccaaag ctgcagactt agtggtggat     180

gagataaaaa aagccggagg tatagctgtg gcaaattacg actctgttaa tgaaaatgga     240

gagaaaataa ttgaaacggc tataaaagaa ttcggcaggg ttgatgtact aattaacaac     300

gctggaatat taagggatgt ttcatttgca aagatgacag aacgtgagtt tgcatctgtg     360

gtagatgttc atttgacagg tggctataag ctatcgcgtg ctgcttggcc ttatatgcgc     420

tctcagaaat ttggtagaat cattaacacc gcttcccctg ccggtctatt tggaaatttt     480

ggtcaagcta attattcagc agctaaaatg ggcttagttg gtttggcgga aaccctcgcg     540

aaggagggtg ccaaatacaa cattaatgtt aattcaattg cgccattggc tagatcacgt     600

atgacagaaa acgtgttacc accacatatc ttgaaacagt taggaccgga aaaaattgtt     660

cccttagtac tctatttgac acacgaaagt acgaaagtgt caaactccat tttgaactc      720

gctgctggat tctttggaca gctcagatgg gagaggtctt ctggacaaat tttcaatcca     780

gaccccaaga catatactcc tgaagcaatt ttaaataagt ggaaggaaat cacagactat     840

agggacaagc catttaacaa aactcagcat ccatatcaac tctcggatta taatgattta     900

atcaccaaag caaaaaaatt acctcccaat gaacaaggct cagtgaaaat caagtcgctt     960

tgcaacaaag tcgtagtagt tacgggtgca ggaggtggtc ttgggaagtc tcatgcaatc    1020

tggtttgcac ggtacggtgc gaaggtagtt gtaaatgaca tcaaggatcc tttttcagtt    1080

gttgaagaaa taaataaact atatggtgaa ggcacagcca ttccagattc ccatgatgtg    1140

gtcaccgaag ctcctctcat tatccaaact gcaataagta agtttcagag agtagacatc    1200

ttggtcaata acgctggtat tttgcgtgac aaatcttttt taaaaatgaa agatgaggaa    1260

tggtttgctg tcctgaaagt ccaccttttt tccacatttt cattgtcaaa agcagtatgg    1320

ccaatattta ccaaacaaaa gtctggattt attatcaata ctacttctac ctcaggaatt    1380

tatggtaatt ttggacaggc caattatgcc gctgcaaaag ccgccatttt aggattcagt    1440

aaaactattg cactggaagg tgccaagaga ggaattattg ttaatgttat cgctcctcat    1500
```

-continued

```
gcagaaacgg ctatgacaaa gactatattc tcggagaagg aattatcaaa ccactttgat   1560

gcatctcaag tctccccact tgttgttttg ttggcatctg aagaactaca aaagtattct   1620

ggaagaaggg ttattggcca attattcgaa gttggcggtg gttggtgtgg gcaaaccaga   1680

tggcaaagaa gttccggtta tgtttctatt aaagagacta ttgaaccgga agaaattaaa   1740

gaaaattgga accacatcac tgatttcagt cgcaacacta tcaacccgag ctccacagag   1800

gagtcttcta tggcaacctt gcaagccgtg caaaaagcgc actcttcaaa ggagttggat   1860

gatggattat tcaagtacac taccaaggat tgtatcttgt acaatttagg acttggatgc   1920

acaagcaaag agcttaagta cacctacgag aatgatccag acttccaagt tttgcccacg   1980

ttcgccgtca ttccatttat gcaagctact gccacactag ctatggacaa tttagtcgat   2040

aacttcaatt atgcaatgtt actgcatgga gaacaatatt ttaagctctg cacgccgaca   2100

atgccaagta atggaactct aaagacactt gctaaacctt tacaagtact tgacaagaat   2160

ggtaaagccg ctttagttgt tggtggcttc gaaacttatg acattaaaac taagaaactc   2220

atagcttata acgaaggatc gttcttcatc aggggcgcac atgtacctcc agaaaaggaa   2280

gtgagggatg ggaaaagagc caagtttgct gtccaaaatt ttgaagtgcc acatggaaag   2340

gtaccagatt ttgaggcgga gatttctacg aataaagatc aagccgcatt gtacaggtta   2400

tctggcgatt tcaatccttt acatatcgat cccacgctag ccaaagcagt taaatttcct   2460

acgccaattc tgcatgggct ttgtacatta ggtattagtg cgaaagcatt gtttgaacat   2520

tatggtccat atgaggagtt gaaagtgaga tttaccaatg ttgttttccc aggtgatact   2580

ctaaaggtta aagcttggaa gcaaggctcg gttgtcgttt ttcaaacaat tgatacgacc   2640

agaaacgtca ttgtattgga taacgccgct gtaaaactat cgcaggcaaa atctaaacta   2700

taa                                                                 2703
```

<210> SEQ ID NO 41
<211> LENGTH: 312
<212> TYPE: PRT
<213> ORGANISM: Saccharomyces cerevisiae

<400> SEQUENCE: 41

```
Met Pro Ala Thr Leu His Asp Ser Thr Lys Ile Leu Ser Leu Asn Thr
1               5                   10                  15

Gly Ala Gln Ile Pro Gln Ile Gly Leu Gly Thr Trp Gln Ser Lys Glu
            20                  25                  30

Asn Asp Ala Tyr Lys Ala Val Leu Thr Ala Leu Lys Asp Gly Tyr Arg
        35                  40                  45

His Ile Asp Thr Ala Ala Ile Tyr Arg Asn Glu Asp Gln Val Gly Gln
    50                  55                  60

Ala Ile Lys Asp Ser Gly Val Pro Arg Glu Glu Ile Phe Val Thr Thr
65                  70                  75                  80

Lys Leu Trp Cys Thr Gln His His Glu Pro Glu Val Ala Leu Asp Gln
                85                  90                  95

Ser Leu Lys Arg Leu Gly Leu Asp Tyr Val Asp Leu Tyr Leu Met His
            100                 105                 110

Trp Pro Ala Arg Leu Asp Pro Ala Tyr Ile Lys Asn Glu Asp Ile Leu
        115                 120                 125

Ser Val Pro Thr Lys Lys Asp Gly Ser Arg Ala Val Asp Ile Thr Asn
    130                 135                 140

Trp Asn Phe Ile Lys Thr Trp Glu Leu Met Gln Glu Leu Pro Lys Thr
145                 150                 155                 160
```

```
Gly Lys Thr Lys Ala Val Gly Val Ser Asn Phe Ser Ile Asn Asn Leu
                165                 170                 175

Lys Asp Leu Leu Ala Ser Gln Gly Asn Lys Leu Thr Pro Ala Ala Asn
            180                 185                 190

Gln Val Glu Ile His Pro Leu Leu Pro Gln Asp Glu Leu Ile Asn Phe
        195                 200                 205

Cys Lys Ser Lys Gly Ile Val Val Glu Ala Tyr Ser Pro Leu Gly Ser
    210                 215                 220

Thr Asp Ala Pro Leu Leu Lys Glu Pro Val Ile Leu Glu Ile Ala Lys
225                 230                 235                 240

Lys Asn Asn Val Gln Pro Gly His Val Val Ile Ser Trp His Val Gln
                245                 250                 255

Arg Gly Tyr Val Val Leu Pro Lys Ser Val Asn Pro Asp Arg Ile Lys
            260                 265                 270

Thr Asn Arg Lys Ile Phe Thr Leu Ser Thr Glu Asp Phe Glu Ala Ile
        275                 280                 285

Asn Asn Ile Ser Lys Glu Lys Gly Glu Lys Arg Val Val His Pro Asn
    290                 295                 300

Trp Ser Pro Phe Glu Val Phe Lys
305                 310
```

<210> SEQ ID NO 42
<211> LENGTH: 939
<212> TYPE: DNA
<213> ORGANISM: Saccharomyces cerevisiae

<400> SEQUENCE: 42

```
atgcctgcta ctttacatga ttctacgaaa atcctttctc taaatactgg agcccaaatc      60

cctcaaatag gtttaggtac gtggcagtcg aaagagaacg atgcttataa ggctgtttta     120

accgctttga aagatggcta ccgacacatt gatactgctg ctatttaccg taatgaagac     180

caagtcggtc aagccatcaa ggattcaggt gttcctcggg aagaaatctt tgttactaca     240

aagttatggt gtacacaaca ccacgaacct gaagtagcgc tggatcaatc actaaagagg     300

ttaggattgg actacgtaga cttatatttg atgcattggc ctgccagatt agatccagcc     360

tacatcaaaa atgaagacat cttgagtgtg ccaacaaaga aggatggttc tcgtgcagtg     420

gatatcacca attggaattt catcaaaacc tgggaattaa tgcaggaact accaaagact     480

ggtaaaacta aggccgttgg agtctccaac ttttctataa ataacctgaa agatctatta     540

gcatctcaag gtaataagct tacgccagct gctaaccaag tcgaaataca tccattacta     600

cctcaagacg aattgattaa tttttgtaaa agtaaaggca ttgtggttga agcttattct     660

ccgttaggta gtaccgatgc tccactattg aaggaaccgg ttatccttga aattgcgaag     720

aaaaataacg ttcaacccgg acacgttgtt attagctggc acgtccaaag aggttatgtt     780

gtcttgccaa aatctgtgaa tcccgatcga atcaaaacga acaggaaaat atttactttg     840

tctactgagg actttgaagc tatcaataac atatcgaagg aaaagggcga aaaaagggtt     900

gtacatccaa attggtctcc tttcgaagta ttcaagtaa                            939
```

<210> SEQ ID NO 43
<211> LENGTH: 350
<212> TYPE: PRT
<213> ORGANISM: Saccharomyces cerevisiae

<400> SEQUENCE: 43

-continued

```
Met Ser Lys Lys Pro Ile Val Leu Lys Leu Gly Lys Asp Ala Phe Gly
1               5                   10                  15

Asp Gln Ala Trp Gly Glu Leu Glu Lys Ile Ala Asp Val Ile Thr Ile
            20                  25                  30

Pro Glu Ser Thr Thr Arg Glu Gln Phe Leu Arg Glu Val Lys Asp Pro
        35                  40                  45

Gln Asn Lys Leu Ser Gln Val Gln Val Ile Thr Arg Thr Ala Arg Ser
    50                  55                  60

Val Lys Asn Thr Gly Arg Phe Asp Glu Glu Leu Ala Leu Ala Leu Pro
65                  70                  75                  80

Ser Ser Val Val Ala Val Cys His Thr Gly Ala Gly Tyr Asp Gln Ile
                85                  90                  95

Asp Val Glu Pro Phe Lys Lys Arg His Ile Gln Val Ala Asn Val Pro
            100                 105                 110

Asp Leu Val Ser Asn Ala Thr Ala Asp Thr His Val Phe Leu Leu Leu
        115                 120                 125

Gly Ala Leu Arg Asn Phe Gly Ile Gly Asn Arg Arg Leu Ile Glu Gly
    130                 135                 140

Asn Trp Pro Glu Ala Gly Pro Ala Cys Gly Ser Pro Phe Gly Tyr Asp
145                 150                 155                 160

Pro Glu Gly Lys Thr Val Gly Ile Leu Gly Leu Gly Arg Ile Gly Arg
                165                 170                 175

Cys Ile Leu Glu Arg Leu Lys Pro Phe Gly Phe Glu Asn Phe Ile Tyr
            180                 185                 190

His Asn Arg His Gln Leu Pro Ser Glu Glu Glu His Gly Cys Glu Tyr
        195                 200                 205

Val Gly Phe Glu Glu Phe Leu Lys Arg Ser Asp Ile Val Ser Val Asn
    210                 215                 220

Val Pro Leu Asn His Asn Thr His His Leu Ile Asn Ala Glu Thr Ile
225                 230                 235                 240

Glu Lys Met Lys Asp Gly Val Val Ile Val Asn Thr Ala Arg Gly Ala
                245                 250                 255

Val Ile Asp Glu Gln Ala Met Thr Asp Ala Leu Arg Ser Gly Lys Ile
            260                 265                 270

Arg Ser Ala Gly Leu Asp Val Phe Glu Tyr Glu Pro Lys Ile Ser Lys
        275                 280                 285

Glu Leu Leu Ser Met Ser Gln Val Leu Gly Leu Pro His Met Gly Thr
    290                 295                 300

His Ser Val Glu Thr Arg Lys Lys Met Glu Glu Leu Val Val Glu Asn
305                 310                 315                 320

Ala Lys Asn Val Ile Leu Thr Gly Lys Val Leu Thr Ile Val Pro Glu
                325                 330                 335

Leu Gln Asn Glu Asp Trp Pro Asn Glu Ser Lys Pro Leu Val
            340                 345                 350
```

<210> SEQ ID NO 44
<211> LENGTH: 1053
<212> TYPE: DNA
<213> ORGANISM: Saccharomyces cerevisiae

<400> SEQUENCE: 44

```
atgagtaaga aaccaattgt tttgaaatta ggaaaggatg cctttggtga ccaagcctgg     60

ggggaattgg aaaagattgc ggatgtaatt accatccctg aatccaccac tagagaacag    120

tttttgcggg aggtaaaaga cccacaaaat aagctctccc aagtacaagt cattactaga    180
```

```
acagcaagga gtgtgaaaaa caccggtaga tttgatgaag agcttgctct tgctttgccc    240

tcctccgtag tggctgtatg tcatactggt gctggttatg accaaattga tgttgagcca    300

ttcaagaaaa ggcacatcca ggttgccaat gttcctgatt tagttagcaa tgctaccgct    360

gatacgcatg tatttttgct attgggtgcc ctaagaaact tcggtattgg taacagaagg    420

ttgatcgagg gaaactggcc ggaggcagga cccgcatgtg gttctccctt tggatacgac    480

cctgaaggga aaacagttgg tatactgggt ctaggtagga ttggtcgttg tattttagag    540

agattgaagc cgtttgggtt cgagaatttc atatatcata acagacacca gcttccttcc    600

gaagaagagc atggttgtga atatgtagga ttcgaggagt ttttgaagcg ttctgatata    660

gtatctgtaa acgtcccact gaaccacaat actcaccatc taatcaatgc agagactatt    720

gaaaaaatga aagatggtgt agttattgtt aacacagcgc gtggtgccgt gatagacgaa    780

caagccatga ctgatgcttt gcgttctgga aagattagaa gtgctggttt ggacgttttc    840

gaatatgagc caaaaatatc caaagagtta ttatcgatgt cccaagtctt aggactgcct    900

catatgggca cacatagtgt agaaacaaga aagaaaatgg aagaactggt cgttgaaaat    960

gcaaagaatg tgatattgac cgggaaagtc ttgactattg ttccggaatt acaaaatgaa   1020

gactggccca atgaatctaa gccattagtt tga                                1053
```

<210> SEQ ID NO 45
<211> LENGTH: 391
<212> TYPE: PRT
<213> ORGANISM: Saccharomyces cerevisiae

<400> SEQUENCE: 45

```
Met Ser Ala Ala Ala Asp Arg Leu Asn Leu Thr Ser Gly His Leu Asn
1               5                   10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
```

```
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390
```

<210> SEQ ID NO 46
<211> LENGTH: 1176
<212> TYPE: DNA
<213> ORGANISM: Saccharomyces cerevisiae

<400> SEQUENCE: 46

```
atgtctgctg ctgctgatag attaaactta acttccggcc acttgaatgc tggtagaaag     60

agaagttcct cttctgtttc tttgaaggct gccgaaaagc ctttcaaggt tactgtgatt    120

ggatctggta actggggtac tactattgcc aaggtggttg ccgaaaattg taagggatac    180

ccagaagttt tcgctccaat agtacaaatg tgggtgttcg aagaagagat caatggtgaa    240

aaattgactg aaatcataaa tactagacat caaaacgtga aatacttgcc tggcatcact    300

ctacccgaca atttggttgc taatccagac ttgattgatt cagtcaagga tgtcgacatc    360

atcgttttca acattccaca tcaatttttg ccccgtatct gtagccaatt gaaaggtcat    420

gttgattcac acgtcagagc tatctcctgt ctaaagggtt ttgaagttgg tgctaaaggt    480

gtccaattgc tatcctctta catcactgag gaactaggta ttcaatgtgg tgctctatct    540

ggtgctaaca ttgccaccga agtcgctcaa gaacactggt ctgaaacaac agttgcttac    600

cacattccaa aggatttcag aggcgagggc aaggacgtcg accataaggt tctaaaggcc    660

ttgttccaca gaccttactt ccacgttagt gtcatcgaag atgttgctgg tatctccatc    720

tgtggtgctt tgaagaacgt tgttgcctta ggttgtggtt tcgtcgaagg tctaggctgg    780

ggtaacaacg cttctgctgc catccaaaga gtcggtttgg gtgagatcat cagattcggt    840

caaatgtttt tcccagaatc tagagaagaa acatactacc aagagtctgc tggtgttgct    900

gatttgatca ccacctgcgc tggtggtaga aacgtcaagg ttgctaggct aatggctact    960

tctggtaagg acgcctggga atgtgaaaag gagttgttga atggccaatc cgctcaaggt   1020

ttaattacct gcaaagaagt tcacgaatgg ttggaaacat gtggctctgt cgaagacttc   1080
```

-continued

```
ccattatttg aagccgtata ccaaatcgtt tacaacaact acccaatgaa gaacctgccg   1140

gacatgattg aagaattaga tctacatgaa gattag                            1176


<210> SEQ ID NO 47
<211> LENGTH: 799
<212> TYPE: PRT
<213> ORGANISM: Saccharomyces cerevisiae

<400> SEQUENCE: 47

Met Val Leu Pro Ile Leu Pro Leu Ile Asp Asp Leu Ala Ser Trp Asn
1               5                   10                  15

Ser Lys Lys Glu Tyr Val Ser Leu Val Gly Gln Val Leu Leu Asp Gly
            20                  25                  30

Ser Ser Leu Ser Asn Glu Glu Ile Leu Gln Phe Ser Lys Glu Glu Glu
        35                  40                  45

Val Pro Leu Val Ala Leu Ser Leu Pro Ser Gly Lys Phe Ser Asp Asp
    50                  55                  60

Glu Ile Ile Ala Phe Leu Asn Asn Gly Val Ser Ser Leu Phe Ile Ala
65                  70                  75                  80

Ser Gln Asp Ala Lys Thr Ala Glu His Leu Val Glu Gln Leu Asn Val
                85                  90                  95

Pro Lys Glu Arg Val Val Val Glu Glu Asn Gly Val Phe Ser Asn Gln
            100                 105                 110

Phe Met Val Lys Gln Lys Phe Ser Gln Asp Lys Ile Val Ser Ile Lys
        115                 120                 125

Lys Leu Ser Lys Asp Met Leu Thr Lys Glu Val Leu Gly Glu Val Arg
    130                 135                 140

Thr Asp Arg Pro Asp Gly Leu Tyr Thr Thr Leu Val Val Asp Gln Tyr
145                 150                 155                 160

Glu Arg Cys Leu Gly Leu Val Tyr Ser Ser Lys Lys Ser Ile Ala Lys
                165                 170                 175

Ala Ile Asp Leu Gly Arg Gly Val Tyr Tyr Ser Arg Ser Arg Asn Glu
            180                 185                 190

Ile Trp Ile Lys Gly Glu Thr Ser Gly Asn Gly Gln Lys Leu Leu Gln
        195                 200                 205

Ile Ser Thr Asp Cys Asp Ser Asp Ala Leu Lys Phe Ile Val Glu Gln
    210                 215                 220

Glu Asn Val Gly Phe Cys His Leu Glu Thr Met Ser Cys Phe Gly Glu
225                 230                 235                 240

Phe Lys His Gly Leu Val Gly Leu Glu Ser Leu Leu Lys Gln Arg Leu
                245                 250                 255

Gln Asp Ala Pro Glu Glu Ser Tyr Thr Arg Arg Leu Phe Asn Asp Ser
            260                 265                 270

Ala Leu Leu Asp Ala Lys Ile Lys Glu Glu Ala Glu Glu Leu Thr Glu
        275                 280                 285

Ala Lys Gly Lys Lys Glu Leu Ser Trp Glu Ala Ala Asp Leu Phe Tyr
    290                 295                 300

Phe Ala Leu Ala Lys Leu Val Ala Asn Asp Val Ser Leu Lys Asp Val
305                 310                 315                 320

Glu Asn Asn Leu Asn Met Lys His Leu Lys Val Thr Arg Arg Lys Gly
                325                 330                 335

Asp Ala Lys Pro Lys Phe Val Gly Gln Pro Lys Ala Glu Glu Glu Lys
            340                 345                 350

Leu Thr Gly Pro Ile His Leu Asp Val Val Lys Ala Ser Asp Lys Val
```

-continued

```
        355                 360                 365

Gly Val Gln Lys Ala Leu Ser Arg Pro Ile Gln Lys Thr Ser Glu Ile
    370                 375                 380

Met His Leu Val Asn Pro Ile Ile Glu Asn Val Arg Asp Lys Gly Asn
385                 390                 395                 400

Ser Ala Leu Leu Glu Tyr Thr Glu Lys Phe Asp Gly Val Lys Leu Ser
                405                 410                 415

Asn Pro Val Leu Asn Ala Pro Phe Pro Glu Glu Tyr Phe Glu Gly Leu
            420                 425                 430

Thr Glu Glu Met Lys Glu Ala Leu Asp Leu Ser Ile Glu Asn Val Arg
        435                 440                 445

Lys Phe His Ala Ala Gln Leu Pro Thr Glu Thr Leu Glu Val Glu Thr
    450                 455                 460

Gln Pro Gly Val Leu Cys Ser Arg Phe Pro Arg Pro Ile Glu Lys Val
465                 470                 475                 480

Gly Leu Tyr Ile Pro Gly Gly Thr Ala Ile Leu Pro Ser Thr Ala Leu
                485                 490                 495

Met Leu Gly Val Pro Ala Gln Val Ala Gln Cys Lys Glu Ile Val Phe
            500                 505                 510

Ala Ser Pro Pro Arg Lys Ser Asp Gly Lys Val Ser Pro Glu Val Val
        515                 520                 525

Tyr Val Ala Glu Lys Val Gly Ala Ser Lys Ile Val Leu Ala Gly Gly
    530                 535                 540

Ala Gln Ala Val Ala Ala Met Ala Tyr Gly Thr Glu Thr Ile Pro Lys
545                 550                 555                 560

Val Asp Lys Ile Leu Gly Pro Gly Asn Gln Phe Val Thr Ala Ala Lys
                565                 570                 575

Met Tyr Val Gln Asn Asp Thr Gln Ala Leu Cys Ser Ile Asp Met Pro
            580                 585                 590

Ala Gly Pro Ser Glu Val Leu Val Ile Ala Asp Glu Asp Ala Asp Val
        595                 600                 605

Asp Phe Val Ala Ser Asp Leu Leu Ser Gln Ala Glu His Gly Ile Asp
    610                 615                 620

Ser Gln Val Ile Leu Val Gly Val Asn Leu Ser Glu Lys Lys Ile Gln
625                 630                 635                 640

Glu Ile Gln Asp Ala Val His Asn Gln Ala Leu Gln Leu Pro Arg Val
                645                 650                 655

Asp Ile Val Arg Lys Cys Ile Ala His Ser Thr Ile Val Leu Cys Asp
            660                 665                 670

Gly Tyr Glu Glu Ala Leu Glu Met Ser Asn Gln Tyr Ala Pro Glu His
        675                 680                 685

Leu Ile Leu Gln Ile Ala Asn Ala Asn Asp Tyr Val Lys Leu Val Asp
    690                 695                 700

Asn Ala Gly Ser Val Phe Val Gly Ala Tyr Thr Pro Glu Ser Cys Gly
705                 710                 715                 720

Asp Tyr Ser Ser Gly Thr Asn His Thr Leu Pro Thr Tyr Gly Tyr Ala
                725                 730                 735

Arg Gln Tyr Ser Gly Ala Asn Thr Ala Thr Phe Gln Lys Phe Ile Thr
            740                 745                 750

Ala Gln Asn Ile Thr Pro Glu Gly Leu Glu Asn Ile Gly Arg Ala Val
        755                 760                 765

Met Cys Val Ala Lys Lys Glu Gly Leu Asp Gly His Arg Asn Ala Val
    770                 775                 780
```

Lys Ile Arg Met Ser Lys Leu Gly Leu Ile Pro Lys Asp Phe Gln
785 790 795

<210> SEQ ID NO 48
<211> LENGTH: 2400
<212> TYPE: DNA
<213> ORGANISM: Saccharomyces cerevisiae

<400> SEQUENCE: 48
atggttttgc cgattctacc gttaattgat gatctggcct catggaatag taagaaggaa 60
tacgtttcac ttgttggtca ggtacttttg gatggctcga gcctgagtaa tgaagagatt 120
ctccagttct ccaaagagga agaagttcca ttggtggctt tgtccttgcc aagtggtaaa 180
ttcagcgatg atgaaatcat tgccttcttg aacaacggag tttcttctct gttcattgct 240
agccaagatg ctaaaacagc cgaacacttg gttgaacaat tgaatgtacc aaaggagcgt 300
gttgttgtgg aagagaacgg tgttttctcc aatcaattca tggtaaaaca aaaattctcg 360
caagataaaa ttgtgtccat aaagaaatta agcaaggata tgttgaccaa agaagtgctt 420
ggtgaagtac gtacagaccg tcctgacggt ttatatacca ccctagttgt cgaccaatat 480
gagcgttgtc tagggttggt gtattcttcg aagaaatcta tagcaaaggc catcgatttg 540
ggtcgtggcg tttattattc tcgttctagg aatgaaatct ggatcaaggg tgaaacttct 600
ggcaatggcc aaaagctttt acaaatctct actgactgtg attcggatgc cttaaagttt 660
atcgttgaac aagaaaacgt tggattttgc cacttggaga ccatgtcttg ctttggtgaa 720
ttcaagcatg gtttggtggg gctagaatct ttactaaaac aaaggctaca ggacgctcca 780
gaggaatctt atactagaag actattcaac gactctgcat tgttagatgc caagatcaag 840
gaagaagctg aagaactgac tgaggcaaag ggtaagaagg agctttcttg ggaggctgcc 900
gatttgttct actttgcact ggccaaatta gtggccaacg atgtttcatt gaaggacgtc 960
gagaataatc tgaatatgaa gcatctgaag gttacaagac ggaaaggtga tgctaagcca 1020
aagtttgttg gacaaccaaa ggctgaagaa gaaaaactga ccggtccaat tcacttggac 1080
gtggtgaagg cttccgacaa agttggtgtg cagaaggctt tgagcagacc aatccaaaag 1140
acttctgaaa ttatgcattt agtcaatccg atcatcgaaa atgttagaga caaaggtaac 1200
tctgcccttt tggagtacac agaaaagttt gatggtgtaa aattatccaa tcctgttctt 1260
aatgctccat tcccagaaga atactttgaa ggtttaaccg aggaaatgaa ggaagctttg 1320
gacctttcaa ttgaaaacgt ccgcaaattc catgctgctc aattgccaac agagactctt 1380
gaagttgaaa cccaacctgg tgtcttgtgt tccagattcc ctcgtcctat tgaaaaagtt 1440
ggtttgtata tccctggtgg cactgccatt ttaccaagta ctgcattaat gcttggtgtt 1500
ccagcacaag ttgcccaatg taaggagatt gtgtttgcat ctccaccaag aaaatctgat 1560
ggtaaagttt cacccgaagt tgtttatgtc gcagaaaaag ttggcgcttc caagattgtt 1620
ctagctggtg gtgcccaagc cgttgctgct atggcttacg ggacagaaac tattcctaaa 1680
gtggataaga tcttgggtcc aggtaatcaa tttgtgactg ccgccaaaat gtatgttcaa 1740
aatgacactc aagctctatg ttccattgat atgccagctg gcccaagtga agttttggtt 1800
attgccgatg aagatgccga tgtggatttt gttgcaagtg atttgctatc gcaagctgaa 1860
cacggtattg actcccaagt tatccttgtt ggtgttaact tgagcgaaaa gaaaattcaa 1920
gagattcaag atgctgtcca caatcaagct ttacaactgc cacgtgtgga tattgttcgt 1980
aaatgtattg ctcacagtac gatcgttctt tgtgacggtt acgaagaagc ccttgaaatg 2040
tccaaccaat atgcaccaga acatttgatt ctacaaatcg ccaatgctaa cgattatgtt 2100
aaattggttg acaatgcagg gtccgtattt gtgggtgctt acactccaga atcgtgcggt 2160
gactattcaa gtggtactaa ccatacatta ccaacctatg gttacgctag gcagtacagt 2220
ggtgccaaca ctgcaacctt ccaaaagttt atcactgccc aaaacattac ccctgaaggt 2280
ttagaaaaca tcggtagagc tgttatgtgc gttgccaaga aggagggtct agacggtcac 2340
agaaacgctg tgaaaatcag aatgagtaag cttgggttga tcccaaagga tttccagtag 2400

<210> SEQ ID NO 49
<211> LENGTH: 1054
<212> TYPE: PRT
<213> ORGANISM: Saccharomyces cerevisiae

<400> SEQUENCE: 49

Met Pro Pro Leu Phe Lys Gly Leu Lys Gln Met Ala Lys Pro Ile Ala
1 5 10 15

Tyr Val Ser Arg Phe Ser Ala Lys Arg Pro Ile His Ile Ile Leu Phe
20 25 30

Ser Leu Ile Ile Ser Ala Phe Ala Tyr Leu Ser Val Ile Gln Tyr Tyr
35 40 45

Phe Asn Gly Trp Gln Leu Asp Ser Asn Ser Val Phe Glu Thr Ala Pro
50 55 60

Asn Lys Asp Ser Asn Thr Leu Phe Gln Glu Cys Ser His Tyr Tyr Arg
65 70 75 80

Asp Ser Ser Leu Asp Gly Trp Val Ser Ile Thr Ala His Glu Ala Ser
85 90 95

Glu Leu Pro Ala Pro His His Tyr Tyr Leu Leu Asn Leu Asn Phe Asn
100 105 110

Ser Pro Asn Glu Thr Asp Ser Ile Pro Glu Leu Ala Asn Thr Val Phe
115 120 125

Glu Lys Asp Asn Thr Lys Tyr Ile Leu Gln Glu Asp Leu Ser Val Ser
130 135 140

Lys Glu Ile Ser Ser Thr Asp Gly Thr Lys Trp Arg Leu Arg Ser Asp
145 150 155 160

Arg Lys Ser Leu Phe Asp Val Lys Thr Leu Ala Tyr Ser Leu Tyr Asp
165 170 175

Val Phe Ser Glu Asn Val Thr Gln Ala Asp Pro Phe Asp Val Leu Ile
180 185 190

Met Val Thr Ala Tyr Leu Met Met Phe Tyr Thr Ile Phe Gly Leu Phe
195 200 205

Asn Asp Met Arg Lys Thr Gly Ser Asn Phe Trp Leu Ser Ala Ser Thr
210 215 220

Val Val Asn Ser Ala Ser Ser Leu Phe Leu Ala Leu Tyr Val Thr Gln
225 230 235 240

Cys Ile Leu Gly Lys Glu Val Ser Ala Leu Thr Leu Phe Glu Gly Leu
245 250 255

Pro Phe Ile Val Val Val Val Gly Phe Lys His Lys Ile Lys Ile Ala
260 265 270

Gln Tyr Ala Leu Glu Lys Phe Glu Arg Val Gly Leu Ser Lys Arg Ile
275 280 285

Thr Thr Asp Glu Ile Val Phe Glu Ser Val Ser Glu Glu Gly Gly Arg
290 295 300

Leu Ile Gln Asp His Leu Leu Cys Ile Phe Ala Phe Ile Gly Cys Ser

-continued

```
305                 310                 315                 320

Met Tyr Ala His Gln Leu Lys Thr Leu Thr Asn Phe Cys Ile Leu Ser
                325                 330                 335

Ala Phe Ile Leu Ile Phe Glu Leu Ile Leu Thr Pro Thr Phe Tyr Ser
            340                 345                 350

Ala Ile Leu Ala Leu Arg Leu Glu Met Asn Val Ile His Arg Ser Thr
        355                 360                 365

Ile Ile Lys Gln Thr Leu Glu Glu Asp Gly Val Val Pro Ser Thr Ala
    370                 375                 380

Arg Ile Ile Ser Lys Ala Glu Lys Lys Ser Val Ser Ser Phe Leu Asn
385                 390                 395                 400

Leu Ser Val Val Val Ile Ile Met Lys Leu Ser Val Ile Leu Leu Phe
                405                 410                 415

Val Phe Ile Asn Phe Tyr Asn Phe Gly Ala Asn Trp Val Asn Asp Ala
            420                 425                 430

Phe Asn Ser Leu Tyr Phe Asp Lys Glu Arg Val Ser Leu Pro Asp Phe
        435                 440                 445

Ile Thr Ser Asn Ala Ser Glu Asn Phe Lys Glu Gln Ala Ile Val Ser
    450                 455                 460

Val Thr Pro Leu Leu Tyr Tyr Lys Pro Ile Lys Ser Tyr Gln Arg Ile
465                 470                 475                 480

Glu Asp Met Val Leu Leu Leu Leu Arg Asn Val Ser Val Ala Ile Arg
                485                 490                 495

Asp Arg Phe Val Ser Lys Leu Val Leu Ser Ala Leu Val Cys Ser Ala
            500                 505                 510

Val Ile Asn Val Tyr Leu Leu Asn Ala Ala Arg Ile His Thr Ser Tyr
        515                 520                 525

Thr Ala Asp Gln Leu Val Lys Thr Glu Val Thr Lys Lys Ser Phe Thr
    530                 535                 540

Ala Pro Val Gln Lys Ala Ser Thr Pro Val Leu Thr Asn Lys Thr Val
545                 550                 555                 560

Ile Ser Gly Ser Lys Val Lys Ser Leu Ser Ser Ala Gln Ser Ser Ser
                565                 570                 575

Ser Gly Pro Ser Ser Ser Ser Glu Glu Asp Asp Ser Arg Asp Ile Glu
            580                 585                 590

Ser Leu Asp Lys Lys Ile Arg Pro Leu Glu Glu Leu Glu Ala Leu Leu
        595                 600                 605

Ser Ser Gly Asn Thr Lys Gln Leu Lys Asn Lys Glu Val Ala Ala Leu
    610                 615                 620

Val Ile His Gly Lys Leu Pro Leu Tyr Ala Leu Glu Lys Lys Leu Gly
625                 630                 635                 640

Asp Thr Thr Arg Ala Val Ala Val Arg Arg Lys Ala Leu Ser Ile Leu
                645                 650                 655

Ala Glu Ala Pro Val Leu Ala Ser Asp Arg Leu Pro Tyr Lys Asn Tyr
            660                 665                 670

Asp Tyr Asp Arg Val Phe Gly Ala Cys Cys Glu Asn Val Ile Gly Tyr
        675                 680                 685

Met Pro Leu Pro Val Gly Val Ile Gly Pro Leu Val Ile Asp Gly Thr
    690                 695                 700

Ser Tyr His Ile Pro Met Ala Thr Thr Glu Gly Cys Leu Val Ala Ser
705                 710                 715                 720

Ala Met Arg Gly Cys Lys Ala Ile Asn Ala Gly Gly Gly Ala Thr Thr
                725                 730                 735
```

Val Leu Thr Lys Asp Gly Met Thr Arg Gly Pro Val Val Arg Phe Pro
740 745 750

Thr Leu Lys Arg Ser Gly Ala Cys Lys Ile Trp Leu Asp Ser Glu Glu
755 760 765

Gly Gln Asn Ala Ile Lys Lys Ala Phe Asn Ser Thr Ser Arg Phe Ala
770 775 780

Arg Leu Gln His Ile Gln Thr Cys Leu Ala Gly Asp Leu Leu Phe Met
785 790 795 800

Arg Phe Arg Thr Thr Thr Gly Asp Ala Met Gly Met Asn Met Ile Ser
805 810 815

Lys Gly Val Glu Tyr Ser Leu Lys Gln Met Val Glu Glu Tyr Gly Trp
820 825 830

Glu Asp Met Glu Val Val Ser Val Ser Gly Asn Tyr Cys Thr Asp Lys
835 840 845

Lys Pro Ala Ala Ile Asn Trp Ile Glu Gly Arg Gly Lys Ser Val Val
850 855 860

Ala Glu Ala Thr Ile Pro Gly Asp Val Val Arg Lys Val Leu Lys Ser
865 870 875 880

Asp Val Ser Ala Leu Val Glu Leu Asn Ile Ala Lys Asn Leu Val Gly
885 890 895

Ser Ala Met Ala Gly Ser Val Gly Gly Phe Asn Ala His Ala Ala Asn
900 905 910

Leu Val Thr Ala Val Phe Leu Ala Leu Gly Gln Asp Pro Ala Gln Asn
915 920 925

Val Glu Ser Ser Asn Cys Ile Thr Leu Met Lys Glu Val Asp Gly Asp
930 935 940

Leu Arg Ile Ser Val Ser Met Pro Ser Ile Glu Val Gly Thr Ile Gly
945 950 955 960

Gly Gly Thr Val Leu Glu Pro Gln Gly Ala Met Leu Asp Leu Leu Gly
965 970 975

Val Arg Gly Pro His Ala Thr Ala Pro Gly Thr Asn Ala Arg Gln Leu
980 985 990

Ala Arg Ile Val Ala Cys Ala Val Leu Ala Gly Glu Leu Ser Leu Cys
995 1000 1005

Ala Ala Leu Ala Ala Gly His Leu Val Gln Ser His Met Thr His
1010 1015 1020

Asn Arg Lys Pro Ala Glu Pro Thr Lys Pro Asn Asn Leu Asp Ala
1025 1030 1035

Thr Asp Ile Asn Arg Leu Lys Asp Gly Ser Val Thr Cys Ile Lys
1040 1045 1050

Ser

<210> SEQ ID NO 50
<211> LENGTH: 3165
<212> TYPE: DNA
<213> ORGANISM: Saccharomyces cerevisiae

<400> SEQUENCE: 50
atgccgccgc tattcaaggg actgaaacag atggcaaagc caattgccta tgtttcaaga 60
ttttcggcga aacgaccaat tcatataata ctttttctc taatcatatc cgcattcgct 120
tatctatccg tcattcagta ttacttcaat ggttggcaac tagattcaaa tagtgttttt 180
gaaactgctc caaataaaga ctccaacact ctatttcaag aatgttccca ttactacaga 240

-continued

```
gattcctctc tagatggttg ggtatcaatc accgcgcatg aagctagtga gttaccagcc    300
ccacaccatt actatctatt aaacctgaac ttcaatagtc ctaatgaaac tgactccatt    360
ccagaactag ctaacacggt ttttgagaaa gataatacaa aatatattct gcaagaagat    420
ctcagtgttt ccaaagaaat ttcttctact gatggaacga aatggaggtt aagaagtgac    480
agaaaaagtc ttttcgacgt aaagacgtta gcatattctc tctacgatgt attttcagaa    540
aatgtaaccc aagcagaccc gtttgacgtc cttattatgg ttactgccta cctaatgatg    600
ttctacacca tattcggcct cttcaatgac atgaggaaga ccgggtcaaa tttttggttg    660
agcgcctcta cagtggtcaa ttctgcatca tcactttttct tagcattgta tgtcacccaa   720
tgtattctag gcaaagaagt ttccgcatta actctttttg aaggtttgcc tttcattgta    780
gttgttgttg gtttcaagca caaaatcaag attgcccagt atgccctgga gaaatttgaa    840
agagtcggtt tatctaaaag gattactacc gatgaaatcg tttttgaatc cgtgagcgaa    900
gagggtggtc gtttgattca agaccatttg ctttgtattt ttgcctttat cggatgctct    960
atgtatgctc accaattgaa gactttgaca aacttctgca tattatcagc atttatccta   1020
atttttgaat tgattttaac tcctacattt tattctgcta tcttagcgct tagactggaa   1080
atgaatgtta tccacagatc tactattatc aagcaaacat tagaagaaga cggtgttgtt   1140
ccatctacag caagaatcat ttctaaagca gaaaagaaat ccgtatcttc tttcttaaat   1200
ctcagtgtgg ttgtcattat catgaaactc tctgtcatac tgttgtttgt cttcatcaac   1260
ttttataact ttggtgcaaa ttgggtcaat gatgccttca attcattgta cttcgataag   1320
gaacgtgttt ctctaccaga ttttattacc tcgaatgcct ctgaaaactt taaagagcaa   1380
gctattgtta gtgtcacccc attattatat tacaaaccca ttaagtccta ccaacgcatt   1440
gaggatatgg ttcttctatt gcttcgtaat gtcagtgttg ccattcgtga taggttcgtc   1500
agtaaattag ttctttccgc cttagtatgc agtgctgtca tcaatgtgta tttattgaat   1560
gctgctagaa ttcataccag ttatactgca gaccaattgg tgaaaactga agtcaccaag   1620
aagtctttta ctgctcctgt acaaaaggct tctacaccag ttttaaccaa taaaacagtc   1680
atttctggat cgaaagtcaa aagtttatca tctgcgcaat cgagctcatc aggaccttca   1740
tcatctagtg aggaagatga ttcccgcgat attgaaagct tggataagaa aatacgtcct   1800
ttagaagaat tagaagcatt attaagtagt ggaaatacaa aacaattgaa gaacaaagag   1860
gtcgctgcct tggttattca cggtaagtta cctttgtacg ctttggagaa aaaattaggt   1920
gatactacga gagcggttgc ggtacgtagg aaggctcttt caattttggc agaagctcct   1980
gtattagcat ctgatcgttt accatataaa aattatgact acgaccgcgt atttggcgct   2040
tgttgtgaaa atgttatagg ttacatgcct ttgcccgttg gtgttatagg ccccttggtt   2100
atcgatggta catcttatca tataccaatg gcaactacag agggttgttt ggtagcttct   2160
gccatgcgtg gctgtaaggc aatcaatgct ggcggtggtg caacaactgt tttaactaag   2220
gatggtatga caagaggccc agtagtccgt ttcccaactt tgaaaagatc tggtgcctgt   2280
aagatatggt tagactcaga agagggacaa aacgcaatta aaaaagcttt taactctaca   2340
tcaagatttg cacgtctgca acatattcaa acttgtctag caggagattt actcttcatg   2400
agatttagaa caactactgg tgacgcaatg ggtatgaata tgatttctaa aggtgtcgaa   2460
tactcattaa agcaaatggt agaagagtat ggctgggaag atatggaggt tgtctccgtt   2520
tctggtaact actgtaccga caaaaaacca gctgccatca actggatcga aggtcgtggt   2580
aagagtgtcg tcgcagaagc tactattcct ggtgatgttg tcagaaaagt gttaaaaagt   2640
```

```
gatgtttccg cattggttga gttgaacatt gctaagaatt tggttggatc tgcaatggct   2700

gggtctgttg gtggatttaa cgcacatgca gctaatttag tgacagctgt tttcttggca   2760

ttaggacaag atcctgcaca aaatgttgaa agttccaact gtataacatt gatgaaagaa   2820

gtggacggtg atttgagaat ttccgtatcc atgccatcca tcgaagtagg taccatcggt   2880

ggtggtactg ttctagaacc acaaggtgcc atgttggact tattaggtgt aagaggcccg   2940

catgctaccg ctcctggtac caacgcacgt caattagcaa gaatagttgc ctgtgccgtc   3000

ttggcaggtg aattatcctt atgtgctgcc ctagcagccg gccatttggt tcaaagtcat   3060

atgacccaca acaggaaacc tgctgaacca acaaaaccta acaatttgga cgccactgat   3120

ataaatcgtt tgaaagatgg gtccgtcacc tgcattaaat cctaa                   3165
```

<210> SEQ ID NO 51
<211> LENGTH: 428
<212> TYPE: PRT
<213> ORGANISM: Saccharomyces cerevisiae

<400> SEQUENCE: 51

```
Met Ser Met Leu Ser Arg Arg Leu Phe Ser Thr Ser Arg Leu Ala Ala
1               5                   10                  15

Phe Ser Lys Ile Lys Val Lys Gln Pro Val Val Glu Leu Asp Gly Asp
            20                  25                  30

Glu Met Thr Arg Ile Ile Trp Asp Lys Ile Lys Lys Lys Leu Ile Leu
        35                  40                  45

Pro Tyr Leu Asp Val Asp Leu Lys Tyr Tyr Asp Leu Ser Val Glu Ser
    50                  55                  60

Arg Asp Ala Thr Ser Asp Lys Ile Thr Gln Asp Ala Ala Glu Ala Ile
65                  70                  75                  80

Lys Lys Tyr Gly Val Gly Ile Lys Cys Ala Thr Ile Thr Pro Asp Glu
                85                  90                  95

Ala Arg Val Lys Glu Phe Asn Leu His Lys Met Trp Lys Ser Pro Asn
            100                 105                 110

Gly Thr Ile Arg Asn Ile Leu Gly Gly Thr Val Phe Arg Glu Pro Ile
        115                 120                 125

Val Ile Pro Arg Ile Pro Arg Leu Val Pro Arg Trp Glu Lys Pro Ile
    130                 135                 140

Ile Ile Gly Arg His Ala His Gly Asp Gln Tyr Lys Ala Thr Asp Thr
145                 150                 155                 160

Leu Ile Pro Gly Pro Gly Ser Leu Glu Leu Val Tyr Lys Pro Ser Asp
                165                 170                 175

Pro Thr Thr Ala Gln Pro Gln Thr Leu Lys Val Tyr Asp Tyr Lys Gly
            180                 185                 190

Ser Gly Val Ala Met Ala Met Tyr Asn Thr Asp Glu Ser Ile Glu Gly
        195                 200                 205

Phe Ala His Ser Ser Phe Lys Leu Ala Ile Asp Lys Lys Leu Asn Leu
    210                 215                 220

Phe Leu Ser Thr Lys Asn Thr Ile Leu Lys Lys Tyr Asp Gly Arg Phe
225                 230                 235                 240

Lys Asp Ile Phe Gln Glu Val Tyr Glu Ala Gln Tyr Lys Ser Lys Phe
                245                 250                 255

Glu Gln Leu Gly Ile His Tyr Glu His Arg Leu Ile Asp Asp Met Val
            260                 265                 270

Ala Gln Met Ile Lys Ser Lys Gly Gly Phe Ile Met Ala Leu Lys Asn
```

```
        275                 280                 285

Tyr Asp Gly Asp Val Gln Ser Asp Ile Val Ala Gln Gly Phe Gly Ser
    290                 295                 300

Leu Gly Leu Met Thr Ser Ile Leu Val Thr Pro Asp Gly Lys Thr Phe
305                 310                 315                 320

Glu Ser Glu Ala Ala His Gly Thr Val Thr Arg His Tyr Arg Lys Tyr
                325                 330                 335

Gln Lys Gly Glu Glu Thr Ser Thr Asn Ser Ile Ala Ser Ile Phe Ala
            340                 345                 350

Trp Ser Arg Gly Leu Leu Lys Arg Gly Glu Leu Asp Asn Thr Pro Ala
        355                 360                 365

Leu Cys Lys Phe Ala Asn Ile Leu Glu Ser Ala Thr Leu Asn Thr Val
    370                 375                 380

Gln Gln Asp Gly Ile Met Thr Lys Asp Leu Ala Leu Ala Cys Gly Asn
385                 390                 395                 400

Asn Glu Arg Ser Ala Tyr Val Thr Thr Glu Glu Phe Leu Asp Ala Val
                405                 410                 415

Glu Lys Arg Leu Gln Lys Glu Ile Lys Ser Ile Glu
            420                 425


<210> SEQ ID NO 52
<211> LENGTH: 1287
<212> TYPE: DNA
<213> ORGANISM: Saccharomyces cerevisiae

<400> SEQUENCE: 52

atgagtatgt tatctagaag attattttcc acctctcgcc ttgctgcttt cagtaagatt     60

aaggtcaaac aacccgttgt cgagttggac ggtgatgaaa tgacccgtat catttgggat    120

aagatcaaga agaaattgat tctaccctac ttggacgtag atttgaagta ctacgactta    180

tctgtcgaat ctcgtgacgc cacctccgac aagattactc aggatgctgc tgaggcgatc    240

aagaagtatg gtgttggtat caaatgtgcc accatcactc ctgatgaagc tcgtgtgaag    300

gaattcaacc tgcacaagat gtggaaatct cctaatggta ccatcagaaa cattctcggc    360

ggtacagtgt tcagagagcc cattgtgatt cctagaattc ctagactggt cccacgttgg    420

gaaaaaccaa tcattattgg aagacacgcc cacggtgatc aatataaagc tacggacaca    480

ctgatcccag gcccaggatc tttggaactg gtctacaagc catccgaccc tacgactgct    540

caaccacaaa ctttgaaagt gtatgactac aagggcagtg gtgtggccat ggccatgtac    600

aatactgacg aatccatcga agggtttgct cattcgtctt tcaagctggc cattgacaaa    660

aagctaaatc ttttcttgtc aaccaagaac actattttga agaaatatga cggtcggttc    720

aaagacattt tccaagaagt ttatgaagct caatataaat ccaaattcga acaactaggg    780

atccactatg aacaccgttt aattgatgat atggtcgctc aaatgataaa atctaaaggt    840

ggctttatca tggcgctaaa gaactatgac ggtgatgtcc aatctgacat cgtcgctcaa    900

ggatttggct ccttaggttt gatgacttct atcttagtta caccagacgg taaaactttc    960

gaaagtgaag ctgctcatgg taccgtgaca agacattata gaaagtacca aaagggtgaa   1020

gaaacttcta caaactccat tgcatccatt ttcgcgtggt cgagaggtct attgaagaga   1080

ggtgaattgg acaatactcc tgctttgtgt aaatttgcca atattttgga atccgccact   1140

ttgaacacag ttcagcaaga cggtatcatg acgaaggact tggctttggc ttgcggtaac   1200

aacgaaagat ctgcttatgt taccacagaa gaatttttgg atgccgttga aaaaagacta   1260
```

caaaaagaaa tcaagtcgat cgagtaa 1287

<210> SEQ ID NO 53
<211> LENGTH: 371
<212> TYPE: PRT
<213> ORGANISM: Saccharomyces cerevisiae

<400> SEQUENCE: 53

Met Phe Arg Ser Val Ala Thr Arg Leu Ser Ala Cys Arg Gly Leu Ala
1 5 10 15

Ser Asn Ala Ala Arg Lys Ser Leu Thr Ile Gly Leu Ile Pro Gly Asp
20 25 30

Gly Ile Gly Lys Glu Val Ile Pro Ala Gly Lys Gln Val Leu Glu Asn
35 40 45

Leu Asn Ser Lys His Gly Leu Ser Phe Asn Phe Ile Asp Leu Tyr Ala
50 55 60

Gly Phe Gln Thr Phe Gln Glu Thr Gly Lys Ala Leu Pro Asp Glu Thr
65 70 75 80

Val Lys Val Leu Lys Glu Gln Cys Gln Gly Ala Leu Phe Gly Ala Val
85 90 95

Gln Ser Pro Thr Thr Lys Val Glu Gly Tyr Ser Ser Pro Ile Val Ala
100 105 110

Leu Arg Arg Glu Met Gly Leu Phe Ala Asn Val Arg Pro Val Lys Ser
115 120 125

Val Glu Gly Glu Lys Gly Lys Pro Ile Asp Met Val Ile Val Arg Glu
130 135 140

Asn Thr Glu Asp Leu Tyr Ile Lys Ile Glu Lys Thr Tyr Ile Asp Lys
145 150 155 160

Ala Thr Gly Thr Arg Val Ala Asp Ala Thr Lys Arg Ile Ser Glu Ile
165 170 175

Ala Thr Arg Arg Ile Ala Thr Ile Ala Leu Asp Ile Ala Leu Lys Arg
180 185 190

Leu Gln Thr Arg Gly Gln Ala Thr Leu Thr Val Thr His Lys Ser Asn
195 200 205

Val Leu Ser Gln Ser Asp Gly Leu Phe Arg Glu Ile Cys Lys Glu Val
210 215 220

Tyr Glu Ser Asn Lys Asp Lys Tyr Gly Gln Ile Lys Tyr Asn Glu Gln
225 230 235 240

Ile Val Asp Ser Met Val Tyr Arg Leu Phe Arg Glu Pro Gln Cys Phe
245 250 255

Asp Val Ile Val Ala Pro Asn Leu Tyr Gly Asp Ile Leu Ser Asp Gly
260 265 270

Ala Ala Ala Leu Val Gly Ser Leu Gly Val Val Pro Ser Ala Asn Val
275 280 285

Gly Pro Glu Ile Val Ile Gly Glu Pro Cys His Gly Ser Ala Pro Asp
290 295 300

Ile Ala Gly Lys Gly Ile Ala Asn Pro Ile Ala Thr Ile Arg Ser Thr
305 310 315 320

Ala Leu Met Leu Glu Phe Leu Gly His Asn Glu Ala Ala Gln Asp Ile
325 330 335

Tyr Lys Ala Val Asp Ala Asn Leu Arg Glu Gly Ser Ile Lys Thr Pro
340 345 350

Asp Leu Gly Gly Lys Ala Ser Thr Gln Gln Val Val Asp Asp Val Leu
355 360 365

Ser Arg Leu
370

<210> SEQ ID NO 54
<211> LENGTH: 1116
<212> TYPE: DNA
<213> ORGANISM: Saccharomyces cerevisiae

<400> SEQUENCE: 54
atgtttagat ctgttgctac tagattatct gcctgccgtg ggttagcatc taacgctgct 60
cgcaaatcac tcactattgg tcttatcccc ggtgacggta tcggtaagga agtcattcct 120
gctggtaagc aagttttgga aaaccttaac tccaagcacg gcctaagctt caactttatt 180
gatctctacg ccggtttcca aacattccaa gaaacaggaa aggcgttgcc tgatgagact 240
gttaaagtgt tgaaggaaca atgtcaaggt gctcttttcg gtgcagttca gtctccaact 300
actaaggtgg aaggttactc ctcaccaatt gttgctctaa ggagggaaat gggccttttc 360
gctaatgttc gtcctgttaa gtctgtagag ggagaaaagg gtaaaccaat tgacatggtt 420
atcgtcagag aaaatactga ggacctgtac attaaaattg aaaaaacata cattgacaag 480
gccacaggta caagagttgc tgatgccaca aagagaatat ccgaaattgc aacaagaaga 540
attgcaacca ttgcattaga tattgccttg aaaagattac aaacaagagg ccaagccact 600
ttgacagtga ctcataaatc aaatgttcta tctcaaagtg atggtctatt cagagaaatc 660
tgtaaggaag tctacgaatc taacaaggac aagtacggtc aaatcaaata taacgaacaa 720
attgtggatt ccatggttta taggctgttc agagaaccac aatgttttga tgtgatagtg 780
gcaccaaacc tatacgggga tatattatct gacggtgctg ctgctttagt cggttcatta 840
ggtgttgttc caagcgccaa cgtaggtcca gaaattgtca ttggtgaacc atgccatggt 900
tctgcaccag atattgctgg taaaggtatt gctaacccaa tcgccactat aagatctact 960
gctttgatgt tggaattctt gggccacaac gaagctgccc aagatatcta caaggctgtt 1020
gatgctaact taagagaggg ttctatcaag acaccagatt taggtggtaa ggcttctact 1080
caacaagtcg ttgacgacgt tttgtcgaga ttatag 1116

<210> SEQ ID NO 55
<211> LENGTH: 469
<212> TYPE: PRT
<213> ORGANISM: Saccharomyces cerevisiae

<400> SEQUENCE: 55

Met Ser Tyr Ser Ala Ala Asp Asn Leu Gln Asp Ser Phe Gln Arg Ala
1 5 10 15

Met Asn Phe Ser Gly Ser Pro Gly Ala Val Ser Thr Ser Pro Thr Gln
20 25 30

Ser Phe Met Asn Thr Leu Pro Arg Arg Val Ser Ile Thr Lys Gln Pro
35 40 45

Lys Ala Leu Lys Pro Phe Ser Thr Gly Asp Met Asn Ile Leu Leu Leu
50 55 60

Glu Asn Val Asn Ala Thr Ala Ile Lys Ile Phe Lys Asp Gln Gly Tyr
65 70 75 80

Gln Val Glu Phe His Lys Ser Ser Leu Pro Glu Asp Glu Leu Ile Glu
85 90 95

Lys Ile Lys Asp Val His Ala Ile Gly Ile Arg Ser Lys Thr Arg Leu
100 105 110

Thr Glu Lys Ile Leu Gln His Ala Arg Asn Leu Val Cys Ile Gly Cys

```
        115                 120                 125

Phe Cys Ile Gly Thr Asn Gln Val Asp Leu Lys Tyr Ala Ala Ser Lys
    130                 135                 140

Gly Ile Ala Val Phe Asn Ser Pro Phe Ser Asn Ser Arg Ser Val Ala
145                 150                 155                 160

Glu Leu Val Ile Gly Glu Ile Ile Ser Leu Ala Arg Gln Leu Gly Asp
                165                 170                 175

Arg Ser Ile Glu Leu His Thr Gly Thr Trp Asn Lys Val Ala Ala Arg
            180                 185                 190

Cys Trp Glu Val Arg Gly Lys Thr Leu Gly Ile Ile Gly Tyr Gly His
        195                 200                 205

Ile Gly Ser Gln Leu Ser Val Leu Ala Glu Ala Met Gly Leu His Val
    210                 215                 220

Leu Tyr Tyr Asp Ile Val Thr Ile Met Ala Leu Gly Thr Ala Arg Gln
225                 230                 235                 240

Val Ser Thr Leu Asp Glu Leu Leu Asn Lys Ser Asp Phe Val Thr Leu
                245                 250                 255

His Val Pro Ala Thr Pro Glu Thr Glu Lys Met Leu Ser Ala Pro Gln
            260                 265                 270

Phe Ala Ala Met Lys Asp Gly Ala Tyr Val Ile Asn Ala Ser Arg Gly
        275                 280                 285

Thr Val Val Asp Ile Pro Ser Leu Ile Gln Ala Val Lys Ala Asn Lys
    290                 295                 300

Ile Ala Gly Ala Ala Leu Asp Val Tyr Pro His Glu Pro Ala Lys Asn
305                 310                 315                 320

Gly Glu Gly Ser Phe Asn Asp Glu Leu Asn Ser Trp Thr Ser Glu Leu
                325                 330                 335

Val Ser Leu Pro Asn Ile Ile Leu Thr Pro His Ile Gly Gly Ser Thr
            340                 345                 350

Glu Glu Ala Gln Ser Ser Ile Gly Ile Glu Val Ala Thr Ala Leu Ser
        355                 360                 365

Lys Tyr Ile Asn Glu Gly Asn Ser Val Gly Ser Val Asn Phe Pro Glu
    370                 375                 380

Val Ser Leu Lys Ser Leu Asp Tyr Asp Gln Glu Asn Thr Val Arg Val
385                 390                 395                 400

Leu Tyr Ile His Arg Asn Val Pro Gly Val Leu Lys Thr Val Asn Asp
                405                 410                 415

Ile Leu Ser Asp His Asn Ile Glu Lys Gln Phe Ser Asp Ser His Gly
            420                 425                 430

Glu Ile Ala Tyr Leu Met Ala Asp Ile Ser Ser Val Asn Gln Ser Glu
        435                 440                 445

Ile Lys Asp Ile Tyr Glu Lys Leu Asn Gln Thr Ser Ala Lys Val Ser
    450                 455                 460

Ile Arg Leu Leu Tyr
465
```

<210> SEQ ID NO 56
<211> LENGTH: 1410
<212> TYPE: DNA
<213> ORGANISM: Saccharomyces cerevisiae

<400> SEQUENCE: 56

```
atgtcttatt cagctgccga taatttacaa gattcattcc aacgtgccat gaacttttct      60

ggctctcctg gtgcagtctc aacctcacca actcagtcat ttatgaacac actacctcgt     120
```

```
cgtgtaagca ttacaaagca accaaaggct ttaaaacctt tttctactgg tgacatgaat    180

attctactgt tggaaaatgt caatgcaact gcaatcaaaa tcttcaagga tcagggttac    240

caagtagagt tccacaagtc ttctctacct gaggatgaat tgattgaaaa aatcaaagac    300

gtacacgcta tcggtataag atccaaaact agattgactg aaaaaatact acagcatgcc    360

aggaatctag tttgtattgg ttgtttttgc ataggtacca atcaagtaga cctaaaatat    420

gccgctagta aaggtattgc tgttttcaat tcgccattct ccaattcaag atccgtagca    480

gaattggtaa ttggtgagat cattagttta gcaagacaat taggtgatag atccattgaa    540

ctgcatacag gtacatggaa taaagtcgct gctaggtgtt gggaagtaag aggaaaaact    600

ctcggtatta ttgggtatgg tcacattggt tcgcaattat cagttcttgc agaagctatg    660

ggcctgcatg tgctatacta tgatatcgtg acaattatgg ccttaggtac tgccagacaa    720

gtttctacat tagatgaatt gttgaataaa tctgattttg taacactaca tgtaccagct    780

actccagaaa ctgaaaaaat gttatctgct ccacaattcg ctgctatgaa ggacggggct    840

tatgttatta atgcctcaag aggtactgtc gtggacattc catctctgat ccaagccgtc    900

aaggccaaca aaattgcagg tgctgcttta gatgtttatc cacatgaacc agctaagaac    960

ggtgaaggtt catttaacga tgaacttaac agctggactt ctgagttggt ttcattacca   1020

aatataatcc tgacaccaca tattggtggc tctacagaag aagctcaaag ttcaatcggt   1080

attgaggtgg ctactgcatt gtccaaatac atcaatgaag gtaactctgt cggttctgtg   1140

aacttcccag aagtcagttt gaagtctttg gactacgatc aagagaacac agtacgtgtc   1200

ttgtatattc atcgtaacgt tcctggtgtt ttgaagaccg ttaatgatat cttatccgat   1260

cataatatcg agaaacagtt ttctgattct cacggcgaga tcgcttatct aatggcagac   1320

atctcttctg ttaatcaaag tgaaatcaag gatatatatg aaaagttgaa ccaaacttct   1380

gccaaagttt ccatcaggtt attatactaa                                     1410
```

<210> SEQ ID NO 57
<211> LENGTH: 505
<212> TYPE: PRT
<213> ORGANISM: Saccharomyces cerevisiae

<400> SEQUENCE: 57

```
Met Ser Glu Gly Pro Val Lys Phe Glu Lys Asn Thr Val Ile Ser Val
1               5                   10                  15

Phe Gly Ala Ser Gly Asp Leu Ala Lys Lys Lys Thr Phe Pro Ala Leu
            20                  25                  30

Phe Gly Leu Phe Arg Glu Gly Tyr Leu Asp Pro Ser Thr Lys Ile Phe
        35                  40                  45

Gly Tyr Ala Arg Ser Lys Leu Ser Met Glu Glu Asp Leu Lys Ser Arg
    50                  55                  60

Val Leu Pro His Leu Lys Lys Pro His Gly Glu Ala Asp Asp Ser Lys
65                  70                  75                  80

Val Glu Gln Phe Phe Lys Met Val Ser Tyr Ile Ser Gly Asn Tyr Asp
                85                  90                  95

Thr Asp Glu Gly Phe Asp Glu Leu Arg Thr Gln Ile Glu Lys Phe Glu
            100                 105                 110

Lys Ser Ala Asn Val Asp Val Pro His Arg Leu Phe Tyr Leu Ala Leu
        115                 120                 125

Pro Pro Ser Val Phe Leu Thr Val Ala Lys Gln Ile Lys Ser Arg Val
    130                 135                 140
```

```
Tyr Ala Glu Asn Gly Ile Thr Arg Val Ile Val Glu Lys Pro Phe Gly
145                 150                 155                 160

His Asp Leu Ala Ser Ala Arg Glu Leu Gln Lys Asn Leu Gly Pro Leu
                165                 170                 175

Phe Lys Glu Glu Glu Leu Tyr Arg Ile Asp His Tyr Leu Gly Lys Glu
            180                 185                 190

Leu Val Lys Asn Leu Leu Val Leu Arg Phe Gly Asn Gln Phe Leu Asn
        195                 200                 205

Ala Ser Trp Asn Arg Asp Asn Ile Gln Ser Val Gln Ile Ser Phe Lys
    210                 215                 220

Glu Arg Phe Gly Thr Glu Gly Arg Gly Gly Tyr Phe Asp Ser Ile Gly
225                 230                 235                 240

Ile Ile Arg Asp Val Met Gln Asn His Leu Leu Gln Ile Met Thr Leu
                245                 250                 255

Leu Thr Met Glu Arg Pro Val Ser Phe Asp Pro Glu Ser Ile Arg Asp
            260                 265                 270

Glu Lys Val Lys Val Leu Lys Ala Val Ala Pro Ile Asp Thr Asp Asp
        275                 280                 285

Val Leu Leu Gly Gln Tyr Gly Lys Ser Glu Asp Gly Ser Lys Pro Ala
    290                 295                 300

Tyr Val Asp Asp Asp Thr Val Asp Lys Asp Ser Lys Cys Val Thr Phe
305                 310                 315                 320

Ala Ala Met Thr Phe Asn Ile Glu Asn Glu Arg Trp Glu Gly Val Pro
                325                 330                 335

Ile Met Met Arg Ala Gly Lys Ala Leu Asn Glu Ser Lys Val Glu Ile
            340                 345                 350

Arg Leu Gln Tyr Lys Ala Val Ala Ser Gly Val Phe Lys Asp Ile Pro
        355                 360                 365

Asn Asn Glu Leu Val Ile Arg Val Gln Pro Asp Ala Ala Val Tyr Leu
    370                 375                 380

Lys Phe Asn Ala Lys Thr Pro Gly Leu Ser Asn Ala Thr Gln Val Thr
385                 390                 395                 400

Asp Leu Asn Leu Thr Tyr Ala Ser Arg Tyr Gln Asp Phe Trp Ile Pro
                405                 410                 415

Glu Ala Tyr Glu Val Leu Ile Arg Asp Ala Leu Leu Gly Asp His Ser
            420                 425                 430

Asn Phe Val Arg Asp Asp Glu Leu Asp Ile Ser Trp Gly Ile Phe Thr
        435                 440                 445

Pro Leu Leu Lys His Ile Glu Arg Pro Asp Gly Pro Thr Pro Glu Ile
    450                 455                 460

Tyr Pro Tyr Gly Ser Arg Gly Pro Lys Gly Leu Lys Glu Tyr Met Gln
465                 470                 475                 480

Lys His Lys Tyr Val Met Pro Glu Lys His Pro Tyr Ala Trp Pro Val
                485                 490                 495

Thr Lys Pro Glu Asp Thr Lys Asp Asn
            500                 505
```

<210> SEQ ID NO 58
<211> LENGTH: 1518
<212> TYPE: DNA
<213> ORGANISM: Saccharomyces cerevisiae

<400> SEQUENCE: 58

```
atgagtgaag gccccgtcaa attcgaaaaa aataccgtca tatctgtctt tggtgcgtca      60
```

-continued

```
ggtgatctgg caaagaagaa gacttttccc gccttatttg ggcttttcag agaaggttac    120

cttgatccat ctaccaagat cttcggttat gcccggtcca aattgtccat ggaggaggac    180

ctgaagtccc gtgtcctacc ccacttgaaa aaacctcacg gtgaagccga tgactctaag    240

gtcgaacagt tcttcaagat ggtcagctac atttcgggaa attacgacac agatgaaggc    300

ttcgacgaat taagaacgca gatcgagaaa ttcgagaaaa gtgccaacgt cgatgtccca    360

caccgtctct tctatctggc cttgccgcca agcgtttttt tgacggtggc caagcagatc    420

aagagtcgtg tgtacgcaga gaatggcatc acccgtgtaa tcgtagagaa acctttcggc    480

cacgacctgg cctctgccag ggagctgcaa aaaaacctgg ggcccctctt taaagaagaa    540

gagttgtaca gaattgacca ttacttgggt aaagagttgg tcaagaatct tttagtcttg    600

aggttcggta accagttttt gaatgcctcg tggaatagag acaacattca aagcgttcag    660

atttcgttta aagagaggtt cggcaccgaa ggccgtggcg gctatttcga ctctataggc    720

ataatcagag acgtgatgca gaaccatctg ttacaaatca tgactctctt gactatggaa    780

agaccggtgt cttttgaccc ggaatctatt cgtgacgaaa aggttaaggt tctaaaggcc    840

gtggccccca tcgacacgga cgacgtcctc ttgggccagt acggtaaatc tgaggacggg    900

tctaagcccg cctacgtgga tgatgacact gtagacaagg actctaaatg tgtcactttt    960

gcagcaatga ctttcaacat cgaaaacgag cgttgggagg gcgtccccat catgatgcgt   1020

gccggtaagg ctttgaatga gtccaaggtg gagatcagac tgcagtacaa agcggtcgca   1080

tcgggtgtct tcaaagacat tccaaataac gaactggtca tcagagtgca gcccgatgcc   1140

gctgtgtacc taaagtttaa tgctaagacc cctggtctgt caaatgctac ccaagtcaca   1200

gatctgaatc taacttacgc aagcaggtac caagactttt ggattccaga ggcttacgag   1260

gtgttgataa gagacgccct actgggtgac cattccaact ttgtcagaga tgacgaattg   1320

gatatcagtt ggggcatatt caccccatta ctgaagcaca tagagcgtcc ggacggtcca   1380

acaccggaaa tttaccccta cggatcaaga ggtccaaagg gattgaagga atatatgcaa   1440

aaacacaagt atgttatgcc cgaaaagcac ccttacgctt ggcccgtgac taagccagaa   1500

gatacgaagg ataattag                                                 1518
```

<210> SEQ ID NO 59
<211> LENGTH: 342
<212> TYPE: PRT
<213> ORGANISM: Saccharomyces cerevisiae

<400> SEQUENCE: 59

```
Met Val Leu Val Lys Gln Val Arg Leu Gly Asn Ser Gly Leu Lys Ile
1               5                   10                  15

Ser Pro Ile Val Ile Gly Cys Met Ser Tyr Gly Ser Lys Lys Trp Ala
            20                  25                  30

Asp Trp Val Ile Glu Asp Lys Thr Gln Ile Phe Lys Ile Met Lys His
        35                  40                  45

Cys Tyr Asp Lys Gly Leu Arg Thr Phe Asp Thr Ala Asp Phe Tyr Ser
    50                  55                  60

Asn Gly Leu Ser Glu Arg Ile Ile Lys Glu Phe Leu Glu Tyr Tyr Ser
65                  70                  75                  80

Ile Lys Arg Glu Thr Val Val Ile Met Thr Lys Ile Tyr Phe Pro Val
                85                  90                  95

Asp Glu Thr Leu Asp Leu His His Asn Phe Thr Leu Asn Glu Phe Glu
            100                 105                 110
```

```
Glu Leu Asp Leu Ser Asn Gln Arg Gly Leu Ser Arg Lys His Ile Ile
        115                 120                 125

Ala Gly Val Glu Asn Ser Val Lys Arg Leu Gly Thr Tyr Ile Asp Leu
    130                 135                 140

Leu Gln Ile His Arg Leu Asp His Glu Thr Pro Met Lys Glu Ile Met
145                 150                 155                 160

Lys Ala Leu Asn Asp Val Val Glu Ala Gly His Val Arg Tyr Ile Gly
                165                 170                 175

Ala Ser Ser Met Leu Ala Thr Glu Phe Ala Glu Leu Gln Phe Thr Ala
            180                 185                 190

Asp Lys Tyr Gly Trp Phe Gln Phe Ile Ser Ser Gln Ser Tyr Tyr Asn
        195                 200                 205

Leu Leu Tyr Arg Glu Asp Glu Arg Glu Leu Ile Pro Phe Ala Lys Arg
    210                 215                 220

His Asn Ile Gly Leu Leu Pro Trp Ser Pro Asn Ala Arg Gly Met Leu
225                 230                 235                 240

Thr Arg Pro Leu Asn Gln Ser Thr Asp Arg Ile Lys Ser Asp Pro Thr
                245                 250                 255

Phe Lys Ser Leu His Leu Asp Asn Leu Glu Glu Glu Gln Lys Glu Ile
            260                 265                 270

Ile Asn Arg Val Glu Lys Val Ser Lys Asp Lys Lys Val Ser Met Ala
        275                 280                 285

Met Leu Ser Ile Ala Trp Val Leu His Lys Gly Cys His Pro Ile Val
    290                 295                 300

Gly Leu Asn Thr Thr Ala Arg Val Asp Glu Ala Ile Ala Ala Leu Gln
305                 310                 315                 320

Val Thr Leu Thr Glu Glu Glu Ile Lys Tyr Leu Glu Glu Pro Tyr Lys
                325                 330                 335

Pro Gln Arg Gln Arg Cys
            340
```

<210> SEQ ID NO 60
<211> LENGTH: 1029
<212> TYPE: DNA
<213> ORGANISM: Saccharomyces cerevisiae

<400> SEQUENCE: 60

```
atggttttag ttaagcaggt aagactcggt aactcaggtc ttaagatatc accgatagtg      60

ataggatgta tgtcatacgg gtccaagaaa tgggcggact gggtcataga ggacaagacc     120

caaattttca agattatgaa gcattgttac gataaaggtc ttcgtacttt tgacacagca     180

gatttttatt ctaatggttt gagtgaaaga ataattaagg agtttctgga gtactacagt     240

ataaagagag aaacggtggt gattatgacc aaaatttact tcccagttga tgaaacgctt     300

gatttgcatc ataacttcac tttaaatgaa tttgaagaat tggacttgtc caaccagcgg     360

ggtttatcca gaaagcatat aattgctggt gtcgagaact ctgtgaaaag actgggcaca     420

tatatagacc ttttacaaat tcacagatta gatcatgaaa cgccaatgaa agagatcatg     480

aaggcattga atgatgttgt tgaagcgggc cacgttagat acattggggc ttcgagtatg     540

ttggcaactg aatttgcaga actgcagttc acagccgata aatatggctg gtttcagttc     600

atttcttcgc agtcttacta caatttgctc tatcgtgaag atgaacgcga attgattcct     660

tttgccaaaa gacacaatat tggtttactt ccatggtctc ctaacgcacg aggcatgttg     720

actcgtcctc tgaaccaaag cacggacagg attaagagtg atccaacttt caagtcgtta     780
```

```
catttggata atctcgaaga agaacaaaag gaaattataa atcgtgtgga aaaggtgtcg    840

aaggacaaaa aagtctcgat ggctatgctc tccattgcat gggttttgca taaaggatgt    900

caccctattg tgggattgaa cactacagca agagtagacg aagcgattgc cgcactacaa    960

gtaactctaa cagaagaaga gataaagtac ctcgaggagc cctacaaacc ccagaggcaa   1020

agatgttaa                                                           1029


<210> SEQ ID NO 61
<211> LENGTH: 344
<212> TYPE: PRT
<213> ORGANISM: Saccharomyces cerevisiae

<400> SEQUENCE: 61

Met Ser Ser Ser Val Ala Ser Thr Glu Asn Ile Val Glu Asn Met Leu
1               5                   10                  15

His Pro Lys Thr Thr Glu Ile Tyr Phe Ser Leu Asn Asn Gly Val Arg
            20                  25                  30

Ile Pro Ala Leu Gly Leu Gly Thr Ala Asn Pro His Glu Lys Leu Ala
        35                  40                  45

Glu Thr Lys Gln Ala Val Lys Ala Ala Ile Lys Ala Gly Tyr Arg His
    50                  55                  60

Ile Asp Thr Ala Trp Ala Tyr Glu Thr Glu Pro Phe Val Gly Glu Ala
65                  70                  75                  80

Ile Lys Glu Leu Leu Glu Asp Gly Ser Ile Lys Arg Glu Asp Leu Phe
                85                  90                  95

Ile Thr Thr Lys Val Trp Pro Val Leu Trp Asp Glu Val Asp Arg Ser
            100                 105                 110

Leu Asn Glu Ser Leu Lys Ala Leu Gly Leu Glu Tyr Val Asp Leu Leu
        115                 120                 125

Leu Gln His Trp Pro Leu Cys Phe Glu Lys Ile Lys Asp Pro Lys Gly
    130                 135                 140

Ile Ser Gly Leu Val Lys Thr Pro Val Asp Asp Ser Gly Lys Thr Met
145                 150                 155                 160

Tyr Ala Ala Asp Gly Asp Tyr Leu Glu Thr Tyr Lys Gln Leu Glu Lys
                165                 170                 175

Ile Tyr Leu Asp Pro Asn Asp His Arg Val Arg Ala Ile Gly Val Ser
            180                 185                 190

Asn Phe Ser Ile Glu Tyr Leu Glu Arg Leu Ile Lys Glu Cys Arg Val
        195                 200                 205

Lys Pro Thr Val Asn Gln Val Glu Thr His Pro His Leu Pro Gln Met
    210                 215                 220

Glu Leu Arg Lys Phe Cys Phe Met His Asp Ile Leu Leu Thr Ala Tyr
225                 230                 235                 240

Ser Pro Leu Gly Ser His Gly Ala Pro Asn Leu Lys Ile Pro Leu Val
                245                 250                 255

Lys Lys Leu Ala Glu Lys Tyr Asn Val Thr Gly Asn Asp Leu Leu Ile
            260                 265                 270

Ser Tyr His Ile Arg Gln Gly Thr Ile Val Ile Pro Arg Ser Leu Asn
        275                 280                 285

Pro Val Arg Ile Ser Ser Ser Ile Glu Phe Ala Ser Leu Thr Lys Asp
    290                 295                 300

Glu Leu Gln Glu Leu Asn Asp Phe Gly Glu Lys Tyr Pro Val Arg Phe
305                 310                 315                 320
```

```
Ile Asp Glu Pro Phe Ala Ala Ile Leu Pro Glu Phe Thr Gly Asn Gly
            325                 330                 335

Pro Asn Leu Asp Asn Leu Lys Tyr
        340


<210> SEQ ID NO 62
<211> LENGTH: 1035
<212> TYPE: DNA
<213> ORGANISM: Saccharomyces cerevisiae

<400> SEQUENCE: 62

atgtcttctt cagtagcctc aaccgaaaac atagtcgaaa atatgttgca tccaaagact      60

acagaaatat acttttcact caacaatggt gttcgtatcc cagcactggg tttggggaca     120

gcaaatcctc acgaaaagtt agctgaaaca aaacaagccg taaaagctgc aatcaaagct     180

ggatacaggc acattgatac tgcttgggcc tacgagacag agccattcgt aggtgaagcc     240

atcaaggagt tattagaaga tggatctatc aaaagggagg atcttttcat aaccacaaaa     300

gtgtggccgg ttctatggga cgaagtggac agatcattga atgaatcttt gaaagcttta     360

ggcttggaat acgtcgactt gctcttgcaa cattggccgc tatgttttga aaagattaag     420

gaccctaagg ggatcagcgg actggtgaag actccggttg atgattctgg aaaaacaatg     480

tatgctgccg acggtgacta tttagaaact tacaagcaat tggaaaaaat ttaccttgat     540

cctaacgatc atcgtgtgag agccattggt gtctcaaatt tttccattga gtatttggaa     600

cgtctcatta aggaatgcag agttaagcca acggtgaacc aagtggaaac tcaccctcac     660

ttaccacaaa tggaactaag aaagttctgc tttatgcacg acattctgtt aacagcatac     720

tcaccattag gttcccatgg cgcaccaaac ttgaaaatcc cactagtgaa aaagcttgcc     780

gaaaagtaca atgtcacagg aaatgacttg ctaatttctt accatattag acaaggcact     840

atcgtaattc cgagatcctt gaatccagtt aggatttcct cgagtattga attcgcatct     900

ttgacaaagg atgaattaca agagttgaac gacttcggtg aaaaatacccc agtgagattc     960

atcgatgagc catttgcagc catccttcca gagtttactg gtaacggacc aaacttggac    1020

aatttaaagt attaa                                                     1035


<210> SEQ ID NO 63
<211> LENGTH: 6311
<212> TYPE: DNA
<213> ORGANISM: Artificial Sequence
<220> FEATURE:
<223> OTHER INFORMATION: vector pEVE2120

<400> SEQUENCE: 63

ctgcattaat gaatcggcca acgcgcgggg agaggcggtt tgcgtattgg gcgctcttcc      60

gcttcctcgc tcactgactc gctgcgctcg gtcgttcggc tgcggcgagc ggtatcagct     120

cactcaaagg cggtaatacg gttatccaca gaatcagggg ataacgcagg aaagaacatg     180

tgagcaaaag gccagcaaaa ggccaggaac cgtaaaaagg ccgcgttgct ggcgtttttc     240

cataggctcc gcccccctga cgagcatcac aaaaatcgac gctcaagtca gaggtggcga     300

aacccgacag gactataaag ataccaggcg tttccccctg gaagctccct cgtgcgctct     360

cctgttccga ccctgccgct taccggatac ctgtccgcct ttctcccttc gggaagcgtg     420

gcgctttctc atagctcacg ctgtaggtat ctcagttcgg tgtaggtcgt tcgctccaag     480

ctgggctgtg tgcacgaacc ccccgttcag cccgaccgct gcgccttatc cggtaactat     540

cgtcttgagt ccaacccggt aagacacgac ttatcgccac tggcagcagc cactggtaac     600
```

aggattagca gagcgaggta tgtaggcggt gctacagagt tcttgaagtg gtggcctaac 660
tacggctaca ctagaaggac agtatttggt atctgcgctc tgctgaagcc agttaccttc 720
ggaaaaagag ttggtagctc ttgatccggc aaacaaacca ccgctggtag cggtggtttt 780
tttgtttgca agcagcagat tacgcgcaga aaaaaaggat ctcaagaaga tcctttgatc 840
ttttctacgg ggtctgacgc tcagtggaac gaaaactcac gttaagggat tttggtcatg 900
agattatcaa aaaggatctt cacctagatc cttttaaatt aaaaatgaag ttttaaatca 960
atctaaagta tatatgagta aacttggtct gacagttacc aatgcttaat cagtgaggca 1020
cctatctcag cgatctgtct atttcgttca tccatagttg cctgactccc cgtcgtgtag 1080
ataactacga tacgggaggg cttaccatct ggccccagtg ctgcaatgat accgcgagac 1140
ccacgctcac cggctccaga tttatcagca ataaaccagc cagccggaag ggccgagcgc 1200
agaagtggtc ctgcaacttt atccgcctcc atccagtcta ttaattgttg ccgggaagct 1260
agagtaagta gttcgccagt taatagtttg cgcaacgttg ttgccattgc tacaggcatc 1320
gtggtgtcac gctcgtcgtt tggtatggct tcattcagct ccggttccca acgatcaagg 1380
cgagttacat gatcccccat gttgtgcaaa aaagcggtta gctccttcgg tcctccgatc 1440
gttgtcagaa gtaagttggc cgcagtgtta tcactcatgg ttatggcagc actgcataat 1500
tctcttactg tcatgccatc cgtaagatgc ttttctgtga ctggtgagta ctcaaccaag 1560
tcattctgag aatagtgtat gcggcgaccg agttgctctt gcccggcgtc aatacgggat 1620
aataccgcgc cacatagcag aactttaaaa gtgctcatca ttggaaaacg ttcttcgggg 1680
cgaaaactct caaggatctt accgctgttg agatccagtt cgatgtaacc cactcgtgca 1740
cccaactgat cttcagcatc ttttactttc accagcgttt ctgggtgagc aaaaacagga 1800
aggcaaaatg ccgcaaaaaa gggaataagg gcgacacgga aatgttgaat actcatactc 1860
ttcctttttc aatattattg aagcatttat cagggttatt gtctcatgag cggatacata 1920
tttgaatgta tttagaaaaa taaacaaata ggggttccgc gcacatttcc ccgaaaagtg 1980
ccacctgggt ccttttcatc acgtgctata aaaataatta taatttaaat tttttaatat 2040
aaatatataa attaaaaata gaaagtaaaa aaagaaatta aagaaaaaat agtttttgtt 2100
ttccgaagat gtaaaagact ctagggggat cgccaacaaa tactaccttt tatcttgctc 2160
ttcctgctct caggtattaa tgccgaattg tttcatcttg tctgtgtaga agaccacaca 2220
cgaaaatcct gtgattttac attttactta tcgttaatcg aatgtatatc tatttaatct 2280
gcttttcttg tctaataaat atatatgtaa agtacgcttt ttgttgaaat tttttaaacc 2340
tttgtttatt ttttttttctt cattccgtaa ctcttctacc ttctttattt actttctaaa 2400
atccaaatac aaaacataaa aataaataaa cacagagtaa attcccaaat tattccatca 2460
ttaaaagata cgaggcgcgt gtaagttaca ggcaagcgat ccgtcctaag aaaccattat 2520
tatcatgaca ttaacctata aaaataggcg tatcacgagg ccctttcgtc tcgcgcgttt 2580
cggtgatgac ggtgaaaacc tctgacacat gcagctcccg gagacggtca cagcttgtct 2640
gtaagcggat gccgggagca gacaagcccg tcagggcgcg tcagcgggtg ttggcgggtg 2700
tcggggctgg cttaactatg cggcatcaga gcagattgta ctgagagtgc accataccac 2760
agcttttcaa ttcaattcat catttttttt ttattctttt ttttgatttc ggtttctttg 2820
aaattttttt gattcggtaa tctccgaaca gaaggaagaa cgaaggaagg agcacagact 2880
tagattggta tatatacgca tatgtagtgt tgaagaaaca tgaaattgcc cagtattctt 2940

```
aacccaactg cacagaacaa aaacctgcag gaaacgaaga taaatcatgt cgaaagctac   3000
atataaggaa cgtgctgcta ctcatcctag tcctgttgct gccaagctat ttaatatcat   3060
gcacgaaaag caaacaaact tgtgtgcttc attggatgtt cgtaccacca aggaattact   3120
ggagttagtt gaagcattag gtcccaaaat ttgtttacta aaaacacatg tggatatctt   3180
gactgatttt tccatggagg gcacagttaa gccgctaaag gcattatccg ccaagtacaa   3240
tttttactc ttcgaagaca gaaaatttgc tgacattggt aatacagtca aattgcagta   3300
ctctgcgggt gtatacagaa tagcagaatg ggcagacatt acgaatgcac acggtgtggt   3360
gggcccaggt attgttagcg gtttgaagca ggcggcagaa gaagtaacaa aggaacctag   3420
aggccttttg atgttagcag aattgtcatg caagggctcc ctatctactg gagaatatac   3480
taagggtact gttgacattg cgaagagcga caaagatttt gttatcggct ttattgctca   3540
aagagacatg ggtggaagag atgaaggtta cgattggttg attatgacac ccggtgtggg   3600
tttagatgac aagggagacg cattgggtca acagtataga accgtggatg atgtggtctc   3660
tacaggatct gacattatta ttgttggaag aggactattt gcaaagggaa gggatgctaa   3720
ggtagagggt gaacgttaca gaaaagcagg ctgggaagca tatttgagaa gatgcggcca   3780
gcaaaactaa aaaactgtat tataagtaaa tgcatgtata ctaaactcac aaattagagc   3840
ttcaatttaa ttatatcagt tattacccta tgcggtgtga aataccgcac agatgcgtaa   3900
ggagaaaata ccgcatcagg aaattgtaaa cgttaatatt ttgttaaaat tcgcgttaaa   3960
tttttgttaa atcagctcat tttttaacca ataggccgaa atcggcaaaa tcccttataa   4020
atcaaaagaa tagaccgaga tagggttgag tgttgttcca gtttggaaca agagtccact   4080
attaaagaac gtggactcca acgtcaaagg gcgaaaaacc gtctatcagg gcgatggccc   4140
actacgtgaa ccatcaccct aatcaagttt tttggggtcg aggtgccgta aagcactaaa   4200
tcggaaccct aaagggagcc cccgatttag agcttgacgg ggaaagccgg cgaacgtggc   4260
gagaaaggaa gggaagaaag cgaaaggagc gggcgctagg gcgctggcaa gtgtagcggt   4320
cacgctgcgc gtaaccacca cacccgccgc gcttaatgcg ccgctacagg gcgcgtcgcg   4380
ccattcgcca ttcaggctgc gcaactgttg ggaagggcga tcggtgcggg cctcttcgct   4440
attacgccag ctgatttgcc cgggcagttc aggctcatca ggcgcgccat gcaggatgca   4500
ttgatcagtt aacccatggg catgcgaagg aaaatgagaa atatcgaggg agacgattca   4560
gaggagcagg acaaactata accgactgtt tgttggagga tgccgtacat aacgaacact   4620
gctgaagcta ccatgtctac agtttagagg aatgggtaca actcacaggc gagggatggt   4680
gttcactcgt gctagcaaac gcggtgggag caaaaagtag aatattatct tttattcgtg   4740
aaacttcgaa cactgtcatc taaagatgct atatactaat ataggcatac ttgataatga   4800
aaactataaa tcgtaaagac ataagagatc cgcggatccc cgggtcgagc ctgaacggcc   4860
tcgaggcctg aacggcctcg acgaattcat tatttgtaga gctcatccat gccatgtgta   4920
atcccagcag cagttacaaa ctcaagaagg accatgtggt cacgcttttc gttgggatct   4980
ttcgaaaggg cagattgtgt cgacaggtaa tggttgtctg gtaaaaggac agggccatcg   5040
ccaattggag tattttgttg ataatggtct gctagttgaa cggatccatc ttcaatgttg   5100
tggcgaattt tgaagttagc tttgattcca ttcttttgtt tgtctgccgt gatgtataca   5160
ttgtgtgagt tatagttgta ctcgagtttg tgtccgagaa tgtttccatc ttctttaaaa   5220
tcaatacctt ttaactcgat acgattaaca agggtatcac cttcaaactt gacttcagca   5280
cgcgtcttgt agttcccgtc atctttgaaa gatatagtgc gttcctgtac ataaccttcg   5340
```

```
ggcatggcac tcttgaaaaa gtcatgccgt ttcatatgat ccggataacg ggaaaagcat   5400

tgaacaccat aagagaaagt agtgacaagt gttggccatg gaacaggtag ttttccagta   5460

gtgcaaataa atttaagggt aagctggccc tgcaggccaa gctttgtttt atatttgttg   5520

taaaaagtag ataattactt ccttgatgat ctgtaaaaaa gagaaaaaga aagcatctaa   5580

gaacttgaaa aactacgaat tagaaaagac caaatatgta tttcttgcat tgaccaattt   5640

atgcaagttt atatatatgt aaatgtaagt ttcacgaggt tctactaaac taaaccaccc   5700

ccttggttag aagaaaagag tgtgtgagaa caggctgttg ttgtcacacg attcggacaa   5760

ttctgtttga aagagagaga gtaacagtac gatcgaacga actttgctct ggagatcaca   5820

gtgggcatca tagcatgtgg tactaaaccc tttcccgcca ttccagaacc ttcgattgct   5880

tgttacaaaa cctgtgagcc gtcgctagga ccttgttgtg tgacgaaatt ggaagctgca   5940

atcaatagga agacaggaag tcgagcgtgt ctgggttttt tcagttttgt tctttttgca   6000

aacaaatcac gagcgacggt aatttctttc tcgataagag gccacgtgct ttatgagggt   6060

aacatcaatt caagaaggag ggaaacactt ccttttttctg gccctgataa tagtatgagg   6120

gtgaagccaa aataaaggat tcgcgcccaa atcggcatct ttaaatgcag gtatgcgata   6180

gttcctcact ctttccttac tcacgagtaa ttcttgcaaa tgcctattat gcagatgtta   6240

taatatctgt gcgtagatct gatatccctg catggcgcgc ctgatgagcc tgaactgccc   6300

gggcaaatca g                                                        6311
```

<210> SEQ ID NO 64
<211> LENGTH: 6248
<212> TYPE: DNA
<213> ORGANISM: Artificial Sequence
<220> FEATURE:
<223> OTHER INFORMATION: vector pEVE27735

<400> SEQUENCE: 64

```
ctgatttgcc cgggcagttc aggctcatca ggcgcgccat gcagggatat cagatctacg     60

cacagatatt ataacatctg cataataggc atttgcaaga attactcgtg agtaaggaaa    120

gagtgaggaa ctatcgcata cctgcattta aagatgccga tttgggcgcg aatcctttat    180

tttggcttca ccctcatact attatcaggg ccagaaaaag gaagtgtttc cctccttctt    240

gaattgatgt taccctcata aagcacgtgg cctcttatcg agaaagaaat taccgtcgct    300

cgtgatttgt ttgcaaaaag aacaaaactg aaaaaaccca gacacgctcg acttcctgtc    360

ttcctattga ttgcagcttc caatttcgtc acacaacaag gtcctagcga cggctcacag    420

gttttgtaac aagcaatcga aggttctgga atggcgggaa agggtttagt accacatgct    480

atgatgccca ctgtgatctc cagagcaaag ttcgttcgat cgtactgtta ctctctctct    540

ttcaaacaga attgtccgaa tcgtgtgaca acaacagcct gttctcacac actcttttct    600

tctaaccaag gggtggttt agtttagtag aacctcgtga aacttacatt tacatatata    660

taaacttgca taaattggtc aatgcaagaa atacatattt ggtcttttct aattcgtagt    720

ttttcaagtt cttagatgct ttcttttct cttttttaca gatcatcaag gaagtaatta    780

tctacttttt acaacaaata taaaacaaag cttaaaatga gaatggaagt cgtcttggtc    840

gttttcttga tgttcattgg tactatcaac tgcgaaagat tgatcttcaa tggtagacct    900

ttgttgcaca gagttaccaa agaagaaacc gttatgttgt accacgaatt ggaagttgct    960

gcttctgctg atgaagtttg gtctgttgaa ggttctccag aattgggttt acatttgcca   1020
```

```
gatttgttgc cagctggtat ttttgccaag ttcgaaatta ctggtgatgg tggtgaaggt   1080
tccattttgg atatgacttt tccaccaggt caattcccac atcattacag agaaaagttc   1140
gtctttttcg accacaagaa cagatacaag ttggtcgaac aaatcgatgg tgatttcttc   1200
gatttgggtg ttacttacta catggacacc attagagttg ttgctactgg tccagattct   1260
tgcgttatta agtctactac tgaataccac gtcaagccag aatttgctaa aatcgttaag   1320
ccattgatcg ataccgttcc attggctatt atgtctgaag ctattgccaa ggttgtcttg   1380
gaaaacaaac acaagtcatc tgaatgaaag actccgcgga tctcttatgt ctttacgatt   1440
tatagttttc attatcaagt atgcctatat tagtatatag catctttaga tgacagtgtt   1500
cgaagtttca cgaataaaag ataatattct actttttgct cccaccgcgt ttgctagcac   1560
gagtgaacac catccctcgc ctgtgagttg tacccattcc tctaaactgt agacatggta   1620
gcttcagcag tgttcgttat gtacggcatc ctccaacaaa cagtcggtta tagtttgtcc   1680
tgctcctctg aatcgtctcc ctcgatattt ctcattttcc ttcgcatgcc catgggttaa   1740
ctgatcaatg catcctgcat ggcgcgcctg atgagcctga actgcccggg caaatcagct   1800
ggcgtaatag cgaagaggcc cgcaccgatc gcccttccca acagttgcgc agcctgaatg   1860
gcgaatggcg cgacgcgccc tgtagcggcg cattaagcgc ggcgggtgtg gtggttacgc   1920
gcagcgtgac cgctacactt gccagcgccc tagcgcccgc tcctttcgct ttcttccctt   1980
cctttctcgc cacgttcgcc ggctttcccc gtcaagctct aaatcggggg ctccctttag   2040
ggttccgatt tagtgcttta cggcacctcg accccaaaaa acttgattag ggtgatggtt   2100
cacgtagtgg gccatcgccc tgatagacgg tttttcgccc tttgacgttg gagtccacgt   2160
tctttaatag tggactcttg ttccaaactg gaacaacact caaccctatc tcggtctatt   2220
cttttgattt ataagggatt ttgccgattt cggcctattg gttaaaaaat gagctgattt   2280
aacaaaaatt taacgcgaat tttaacaaaa tattaacgtt tacaatttcc tgatgcggta   2340
ttttctcctt acgcatctgt gcggtatttc acaccgcata gggtaataac tgatataatt   2400
aaattgaagc tctaatttgt gagtttagta tacatgcatt tacttataat acagtttttt   2460
agttttgctg gccgcatctt ctcaaatatg cttcccagcc tgcttttctg taacgttcac   2520
cctctacctt agcatccctt ccctttgcaa atagtcctct tccaacaata ataatgtcag   2580
atcctgtaga gaccacatca tccacggttc tatactgttg acccaatgcg tctcccttgt   2640
catctaaacc cacaccgggt gtcataatca accaatcgta accttcatct cttccaccca   2700
tgtctctttg agcaataaag ccgataacaa aatctttgtc gctcttcgca atgtcaacag   2760
tacccttagt atattctcca gtagataggg agcccttgca tgacaattct gctaacatca   2820
aaaggcctct aggttccttt gttacttctt ctgccgcctg cttcaaaccg ctaacaatac   2880
ctgggcccac cacaccgtgt gcattcgtaa tgtctgccca ttctgctatt ctgtatacac   2940
ccgcagagta ctgcaatttg actgtattac caatgtcagc aaattttctg tcttcgaaga   3000
gtaaaaaatt gtacttggcg gataatgcct ttagcggctt aactgtgccc tccatggaaa   3060
aatcagtcaa gatatccaca tgtgttttta gtaaacaaat tttgggacct aatgcttcaa   3120
ctaactccag taattccttg gtggtacgaa catccaatga agcacacaag tttgtttgct   3180
tttcgtgcat gatattaaat agcttggcag caacaggact aggatgagta gcagcacgtt   3240
ccttatatgt agctttcgac atgatttatc ttcgtttcct gcaggttttt gttctgtgca   3300
gttgggttaa gaatactggg caatttcatg tttcttcaac actacatatg cgtatatata   3360
ccaatctaag tctgtgctcc ttccttcgtt cttccttctg ttcggagatt accgaatcaa   3420
```

-continued

```
aaaaatttca aagaaaccga aatcaaaaaa aagaataaaa aaaaaatgat gaattgaatt   3480
gaaaagctgt ggtatggtgc actctcagta caatctgctc tgatgccgca tagttaagcc   3540
agccccgaca cccgccaaca cccgctgacg cgccctgacg ggcttgtctg ctcccggcat   3600
ccgcttacag acaagctgtg accgtctccg ggagctgcat gtgtcagagg ttttcaccgt   3660
catcaccgaa acgcgcgaga cgaaagggcc tcgtgatacg cctattttta taggttaatg   3720
tcatgataat aatggtttct taggacggat cgcttgcctg taacttacac gcgcctcgta   3780
tcttttaatg atggaataat ttgggaattt actctgtgtt tatttatttt tatgttttgt   3840
atttggattt tagaaagtaa ataaagaagg tagaagagtt acggaatgaa gaaaaaaaaa   3900
taaacaaagg tttaaaaaat ttcaacaaaa agcgtacttt acatatatat ttattagaca   3960
agaaaagcag attaaataga tatacattcg attaacgata agtaaaatgt aaaatcacag   4020
gattttcgtg tgtggtcttc tacacagaca agatgaaaca attcggcatt aatacctgag   4080
agcaggaaga gcaagataaa aggtagtatt tgttggcgat ccccctagag tcttttacat   4140
cttcggaaaa caaaaactat tttttcttta atttcttttt ttactttcta tttttaattt   4200
atatatttat attaaaaaat ttaaattata attattttta tagcacgtga tgaaaaggac   4260
ccaggtggca cttttcgggg aaatgtgcgc ggaaccccta tttgtttatt tttctaaata   4320
cattcaaata tgtatccgct catgagacaa taaccctgat aaatgcttca ataatattga   4380
aaaaggaaga gtatgagtat tcaacatttc cgtgtcgccc ttattccctt ttttgcggca   4440
ttttgccttc ctgtttttgc tcacccagaa acgctggtga aagtaaaaga tgctgaagat   4500
cagttgggtg cacgagtggg ttacatcgaa ctggatctca acagcggtaa gatccttgag   4560
agttttcgcc ccgaagaacg ttttccaatg atgagcactt ttaaagttct gctatgtggc   4620
gcggtattat cccgtattga cgccgggcaa gagcaactcg gtcgccgcat acactattct   4680
cagaatgact tggttgagta ctcaccagtc acagaaaagc atcttacgga tggcatgaca   4740
gtaagagaat tatgcagtgc tgccataacc atgagtgata acactgcggc caacttactt   4800
ctgacaacga tcggaggacc gaaggagcta accgcttttt tgcacaacat gggggatcat   4860
gtaactcgcc ttgatcgttg ggaaccggag ctgaatgaag ccataccaaa cgacgagcgt   4920
gacaccacga tgcctgtagc aatggcaaca acgttgcgca aactattaac tggcgaacta   4980
cttactctag cttcccggca acaattaata gactggatgg aggcggataa agttgcagga   5040
ccacttctgc gctcggccct tccggctggc tggtttattg ctgataaatc tggagccggt   5100
gagcgtgggt ctcgcggtat cattgcagca ctggggccag atggtaagcc ctcccgtatc   5160
gtagttatct acacgacggg gagtcaggca actatggatg aacgaaatag acagatcgct   5220
gagataggtg cctcactgat taagcattgg taactgtcag accaagttta ctcatatata   5280
ctttagattg atttaaaact tcatttttaa tttaaaagga tctaggtgaa gatccttttt   5340
gataatctca tgaccaaaat cccttaacgt gagttttcgt tccactgagc gtcagacccc   5400
gtagaaaaga tcaaaggatc ttcttgagat cctttttttc tgcgcgtaat ctgctgcttg   5460
caaacaaaaa aaccaccgct accagcggtg gtttgtttgc cggatcaaga gctaccaact   5520
ctttttccga aggtaactgg cttcagcaga gcgcagatac caaatactgt ccttctagtg   5580
tagccgtagt taggccacca cttcaagaac tctgtagcac cgcctacata cctcgctctg   5640
ctaatcctgt taccagtggc tgctgccagt ggcgataagt cgtgtcttac cgggttggac   5700
tcaagacgat agttaccgga taaggcgcag cggtcgggct gaacgggggg ttcgtgcaca   5760
```

-continued

```
cagcccagct tggagcgaac gacctacacc gaactgagat acctacagcg tgagctatga   5820

gaaagcgcca cgcttcccga agggagaaag gcggacaggt atccggtaag cggcagggtc   5880

ggaacaggag agcgcacgag ggagcttcca gggggaaacg cctggtatct ttatagtcct   5940

gtcgggtttc gccacctctg acttgagcgt cgatttttgt gatgctcgtc aggggggcgg   6000

agcctatgga aaaacgccag caacgcggcc tttttacggt tcctggcctt ttgctggcct   6060

tttgctcaca tgttctttcc tgcgttatcc cctgattctg tggataaccg tattaccgcc   6120

tttgagtgag ctgataccgc tcgccgcagc cgaacgaccg agcgcagcga gtcagtgagc   6180

gaggaagcgg aagagcgccc aatacgcaaa ccgcctctcc ccgcgcgttg gccgattcat   6240

taatgcag                                                            6248
```

INCREASED BIOSYNTHESIS OF BENZYLISOQUINOLINE ALKALOIDS AND BENZYLISOQUINOLINE ALKALOID PRECURSORS IN A RECOMBINANT HOST CELL

CROSS-REFERENCE TO RELATED APPLICATIONS

This application is a national stage application under 35 U.S.C. § 371 of International Application No. PCT/EP2017/070253, filed Aug. 9, 2017, which claims the benefit of U.S. Provisional Application Ser. No. 62/372,356, filed Aug. 9, 2016, and U.S. Provisional Application Ser. No. 62,524,120, filed Jun. 23, 2017, each entitled "BIOSYNTHESIS OF BENZYLISOQUINOLINE ALKALOIDS AND BENZYLISOQUINOLINE ALKALOID PRECURSORS", the disclosures of each of which are explicitly incorporated herein by reference.

BACKGROUND OF THE INVENTION

Field of the Invention

The invention disclosed herein relates generally to the field of genetic engineering. Particularly, the invention disclosed herein provides methods for biosynthetic production of benzylisoquinoline alkaloid compounds and benzylisoquinoline alkaloid precursors in a genetically modified cell.

Description of Related Art

Benzylisoquinoline alkaloids (BIAs) are a broad class of plant secondary metabolites with diverse pharmaceutical properties including, for example, analgesic, antimicrobial, antitussive, antiparasitic, cytotoxic, and anticancer properties (Hagel & Facchini, 2013, *Plant Cell Physiol.* 54(5); 647-672). Thousands of distinct BIAs have been identified in plants, each of which derive from a common precursor: (S)-norcoclaurine (see e.g., Hagel & Facchini, 2013, *Plant Cell Physiol.* 54(5); 647-672; Fossati et al., 2015, *PLoS ONE* 10(4): e0124459).

While BIAs are widely used in human health and nutrition, current production is achieved mainly by extraction from plants. However, extraction of these compounds from plants often provides low yields due, in part, to low levels of the metabolites within the plant cells (Nakagawa et al., 2011, Nature Communications, 2:326; DOI:10.1028/ncomms1327). Extraction of sufficient quantities of just the opiate morphine, a widely-prescribed analgesic BIA, to meet medical needs requires industrial processing of tens to hundreds of thousand tons of *Papaver somniferum* (opium poppy) biomass per year (Thodey and Smolke, 2014, *Nat Chem Biol.,* 10(10):837-844). Chemical synthesis of BIAs is not a viable alternative for commercial production due to the complex regio- and stereochemistry of BIAs (see e.g., Thodey and Smolke, 2014; Hagel and Facchini, 2013).

Recently, synthesis of BIA branch point intermediate reticuline has been reported from simple carbon sources in *E. coli* (Nakagawa et al., 2014, *Sci Rep.,* 4:6695) and from (R,S)-norlaudanosoline in *S. cerevisiae* (Hawkins and Smolke, 2008, *Nat Chem Biol.,* 4:564-573), and production of morphine and semi-synthetic opioids from thebaine in *S. cerevisiae* was also recently reported (Thodey et al., 2014, *Nat Chem Biol.,* 10:837-844). However, low yields of intermediates at the beginning of the BIA pathway and the corresponding inability to reconstitute a complete BIA pathway from a low cost substrate currently prevent BIA synthesis from being a viable microbial process (Fossati et al., 2015, *PLoS ONE* 10(4): e0124459). One such problem to be resolved is the extreme inefficiency in yeast of the initial conversion of dopamine and 4-HPAA (4-hydroxyphenylacetaldehyde) (or 3,4-DHPAA (3,4-Dihydroxyphenylacetaldehyde) in the alternative pathway) via norcoclaurine synthase (NCS), which results in low yields of intermediate (S)—Norcoclaurine ((S)-Norlaudanosoline in the alternative pathway) (see e.g., Hawkins and Smolke, 2008, *Nat Chem Biol.,* 4:564-573). This inefficiency has resulted in requiring fed dopamine concentrations of approximately 100 mM, or bypassing the reaction altogether in favor of using Norcoclaurine or Norlaudanosoline as the initial substrate for conversion to (S)-Reticuline (see Hawkins and Smolke, 2008, Nat Chem Biol., 4:564-573).

There is thus a need in this art to increase production of metabolic intermediates at the beginning of the BIA pathway to enable production of valuable products of the BIA pathway more efficiently and economically.

SUMMARY OF THE INVENTION

It is against the above background that this invention provides certain advantages and advancements over the prior art.

Although this invention disclosed herein is not limited to specific advantages or functionality, the invention disclosed herein provides recombinant host cells capable of increased production of one or more benzylisoquinoline alkaloids or benzylisoquinoline alkaloid precursors, or both, having:

(a) reduced or eliminated enzymatic activity of a first alcohol dehydrogenase or aldehyde reductase; and, optionally, (b) reduced or eliminated enzymatic activity of one or more second alcohol dehydrogenases or aldehyde reductases, or a combination thereof, wherein the activity of each of the enzymes in (a) and (b) is reduced or eliminated by having disrupted or deleted one or more genes encoding said enzyme, and whereby the host cell is thereby capable of increased production of one or more benzylisoquinoline alkaloids or benzylisoquinoline alkaloid precursors, or both, than are produced in wild-type cell.

The invention further provides methods for producing a benzylisoquinoline alkaloid or a benzylisoquinoline alkaloid precursor, comprising:

(a) providing a recombinant host that has reduced or eliminated activity of (i) a first alcohol dehydrogenase or aldehyde reductase and, optionally, (ii) one or more second alcohol dehydrogenases or aldehyde reductases, or a combination thereof, wherein the activity of each of the enzymes in (i) and (ii) is reduced or eliminated by disrupting or deleting one or more genes encoding said enzyme, wherein said cell has been genetically engineered to produce a benzylisoquinoline alkaloid and/or a benzylisoquinoline alkaloid precursor;

(b) cultivating said recombinant host for a time sufficient for said recombinant host to produce a benzylisoquinoline alkaloid and/or a benzylisoquinoline alkaloid precursor; and, optionally, (c) isolating the benzylisoquinoline alkaloid and/or a benzylisoquinoline alkaloid precursor from said recombinant host or from the cultivation supernatant, thereby producing a benzylisoquinoline alkaloid and/or a benzylisoquinoline alkaloid precursor.

In certain embodiments of the recombinant host cells or the methods disclosed herein, the cells produce one or more benzylisoquinoline alkaloid precursors. Particular benzylisoquinoline alkaloid precursors produced in said embodiments are (S)-reticuline or (S)-norcoclaurine.

In some aspects, the first alcohol dehydrogenase is Alcohol Dehydrogenase 3 (ADH3) (SEQ ID NOs: 29 & 30), Alcohol Dehydrogenase 4 (ADH4) (SEQ ID NOs: 31 & 32), Alcohol Dehydrogenase 5 (ADH5) (SEQ ID NOs:1 & 2), Alcohol Dehydrogenase 6 (ADH6) (SEQ ID NOs: 3 & 4), Alcohol Dehydrogenase 7 (ADH7) (SEQ ID NOs: 5 & 6), Genes de Respuesta a Estres 2 (GRE2) (SEQ ID NOs: 7 & 8), Aryl-alcohol Dehydrogenase 3 (AAD3) (SEQ ID NOs: 25 & 26), Aryl-alcohol Dehydrogenase 4 (AAD4) (SEQ ID NOs: 27 & 28), Butanediol dehydrogenase 1 (BDH1) (SEQ ID NOs: 35 & 36), medium-chain alcohol dehydrogenase BDH2 (SEQ ID NOs: 37 & 38), arabinose dehydrogenase ARA1 (SEQ ID NOs: 61 & 62), glycerol dehydrogenase GCY1 (SEQ ID NOs: 41 & 42), 3-hydroxyacyl-CoA dehydrogenase FOX2 (SEQ ID NOs: 39 & 40), Aryl-alcohol Dehydrogenase YPL088W (SEQ ID NOs: 59 & 60), glucose-6-phosphate dehydrogenase ZWF1 (SEQ ID NOs: 57 & 58), Glycerol-3-Phosphate Dehydrogenase (GPD1) (SEQ ID NOs: 45 & 46), HIS4 (SEQ ID NOs: 47 & 48), NADP-specific Isocitrate Dehydrogenase (IDP1) (SEQ ID NOs: 51 & 52), homo-isocitrate dehyrogenases (LYS12) (SEQ ID NOs: 53 & 54), or a homolog thereof.

In some aspects, the first aldehyde reductase is Aldehyde Reductase Intermediate 1 (ARI1) (SEQ ID NOs: 15 & 16), Genes de Respuesta a Estres 3 (GRE3) (SEQ ID NOs: 9 & 10), aldehyde reductase YCR102C (SEQ ID NOs: 19 & 20), aldehyde reductase YDR541C (SEQ ID NOs: 11 & 12), SER33 (SEQ ID NOs: 55 & 56), aldehyde reductase YGL039W (SEQ ID NOs: 17 & 18), aldehyde reductase YLR460C (SEQ ID NOs: 13 & 14), aldehyde reductase YPR127W (SEQ ID NOs: 21 & 22), aldehyde dehydrogenase 6 (ALD6) (SEQ ID NOs: 33 & 34), GlyOxylate Reductase (GOR1) (SEQ ID NOs: 43 & 44), 3-Hydroxy-3-MethylGlutaryl-coenzyme a reductase (HMG1) (SEQ ID NOs: 49 & 50), or a homolog thereof.

In some aspects, the one or more second alcohol dehydrogenases or aldehyde reductases, or a combination thereof, is ADH3 (SEQ ID NOs: 29 & 30), ADH4 (SEQ ID NOs: 31 & 32), ADH5 (SEQ ID NOs:1 & 2), ADH6 (SEQ ID NOs: 3 & 4), ADH7 (SEQ ID NOs: 5 & 6), GRE2 (SEQ ID NOs: 7 & 8), AAD3 (SEQ ID NOs: 25 & 26), AAD4 (SEQ ID NOs: 27 & 28), BDH1(SEQ ID NOs: 35 & 36, BDH2 (SEQ ID NOs: 37 & 38), ARA1 (SEQ ID NOs: 61 & 62), GCY1 (SEQ ID NOs: 41 & 42), FOX2 (SEQ ID NOs: 39 & 40), Aryl-alcohol Dehydrogenase YPL088W (SEQ ID NOs: 59 & 60), glucose-6-phosphate dehydrogenase ZWF1 (SEQ ID NOs: 57 & 58), GPD1 (SEQ ID NOs: 45 & 46), HIS4 (SEQ ID NOs: 47 & 48), IDP1 (SEQ ID NOs: 51 & 52), LYS12 (SEQ ID NOs: 53 & 54), ARI1 (SEQ ID NOs: 15 & 16), GRE3 (SEQ ID NOs: 9 & 10), aldehyde reductase YCR102C (SEQ ID NOs: 19 & 20), aldehyde reductase YDR541C (SEQ ID NOs: 11 & 12), SER33 (SEQ ID NOs: 55 & 56), aldehyde reductase YGL039W (SEQ ID NOs: 17 & 18), aldehyde reductase YLR460C (SEQ ID NOs: 13 & 14), aldehyde reductase YPR127W (SEQ ID NOs: 21 & 22), ALD6 (SEQ ID NOs: 33 & 34), GOR1 (SEQ ID NOs: 43 & 44), HMG1 (SEQ ID NOs: 49 & 50), or a homolog thereof.

In some aspects of the recombinant host cell or methods disclosed herein, the recombinant host is a microorganism.

In some aspects of the recombinant host cell or methods disclosed herein, the microorganism is *Saccharomyces cerevisiae, Schizosaccharomyces pombe, Escherichia coli*, or *Yarrowia lipolytica*.

In some aspects of the recombinant host cell or methods disclosed herein, the recombinant host is a plant, an alga, or a cell thereof.

These and other features and advantages of this invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of this invention can be best understood when read in conjunction with the following drawings.

FIG. 1 is a schematic of biosynthesis of benzylisoquinoline alkaloids and benzylisoquinoline alkaloid precursors from L-tyrosine. FIG. 1 includes biosynthesis of (S)-Reticuline via the natural plant pathway, the alternative pathway in bacteria (with bacterial enzymes italicized and underlined), and yeast, which can utilize both the plant and bacterial pathways. Enzymatic examples (with GenBank accession numbers) and other protein abbreviations within FIG. 1 are as follows: TYDC (Tyrosine decarboxylase) of *Papaver somniferum* (GenBank accession nos. P54768 or U08597) or *Thalictrum flavum* (GenBank accession no. AF314150); TYR (Tyrosinase) of *Rattus norvegicus* (GenBank accession no. NM012740) or *Streptomyces castaneoglobisporus* (ScTYR containing tyrosinase and adaptor protein, ORF378, GenBank accession nos. AY254101 and AY254102); HPPDC (hydroxyphenylpyruvate decarboxylase) of *S. cerevisiae* (GenBank accession no. NP_010668.3); DODC (aromatic-L-amino-acid decarboxylase) of *Pseudomonas putida* (GenBank accession no. AE015451); MAO (monoamine oxidase) of *Micrococcus luteus* (GenBank accession no. AB010716); NCS ((S)-norcoclaurine synthase) of *Coptis japonica* (GenBank accession no. AB267399.2) and *S. cerevisiae* codon-optimized (SEQ ID NOs: 23 & 24); 6OMT (Norcoclaurine 6-O-methyltransferase) of *P. somniferum* (GenBank accession no. Q6WUC1) or *C. japonica* (GenBank accession no. D29811); SAM (S-adenosyl-L-methionine); CNMT (Coclaurine-N-methyltransferase) of *C. japonica* (GenBank accession no. Q948P7) or *T. flavum* (GenBank accession no. AY610508) or *P. somniferum* (GenBank accession no. AY217336); CYP80B (N-methylcoclaurine 3'-monooxygenase) of *P. somniferum* (GenBank accession no. 064899); 4'OMT (3'-hydrozy-N-methyl-(S)-coclaurine 4'-O-methyltransferase) of *C. japonica* (GenBank accession no. Q9LEL5); STORR ((S)-to-(R)-reticuline) of *P. somniferum* (GenBank accession no. PODKI7); SAS (salutaridine synthase) of *P. somniferum* (GenBank accession no. EF451150); SAR (salutaridine reductase) of *P. somniferum* (GenBank accession no. DQ316261); NADPH (nicotinamide adenine dinucleotide phosphate); SAT (salutaridinol acetyl transferase) with acetyl-CoA of *P. somniferum* (GenBank accession no. AF339913); T6ODM (thebaine 6-O-demethylase) of *P. somniferum* (GenBank accession no. GQ500139); 2-OG (2-oxoglutarate); CODM (codeine 3-O-demethylase) of *P. somniferum* (GenBank accession no. GQ500141); NADH (nicotinamide adenine dinucleotide); morA (morphine 6-dehydrogenase) of *Pseudomonas putida* (GenBank accession no. T2HEI8); morB (morphinone reductase) of *P. putida* (GenBank accession no. Q51990); COR (codeinone reductase) of *P. somniferum* (GenBank accession no. AF108432); CODM (codeine 3-O-demethylase) of *P. somniferum* (GenBank accession no. D4N502).

DETAILED DESCRIPTION OF THE INVENTION

Figure 2A:
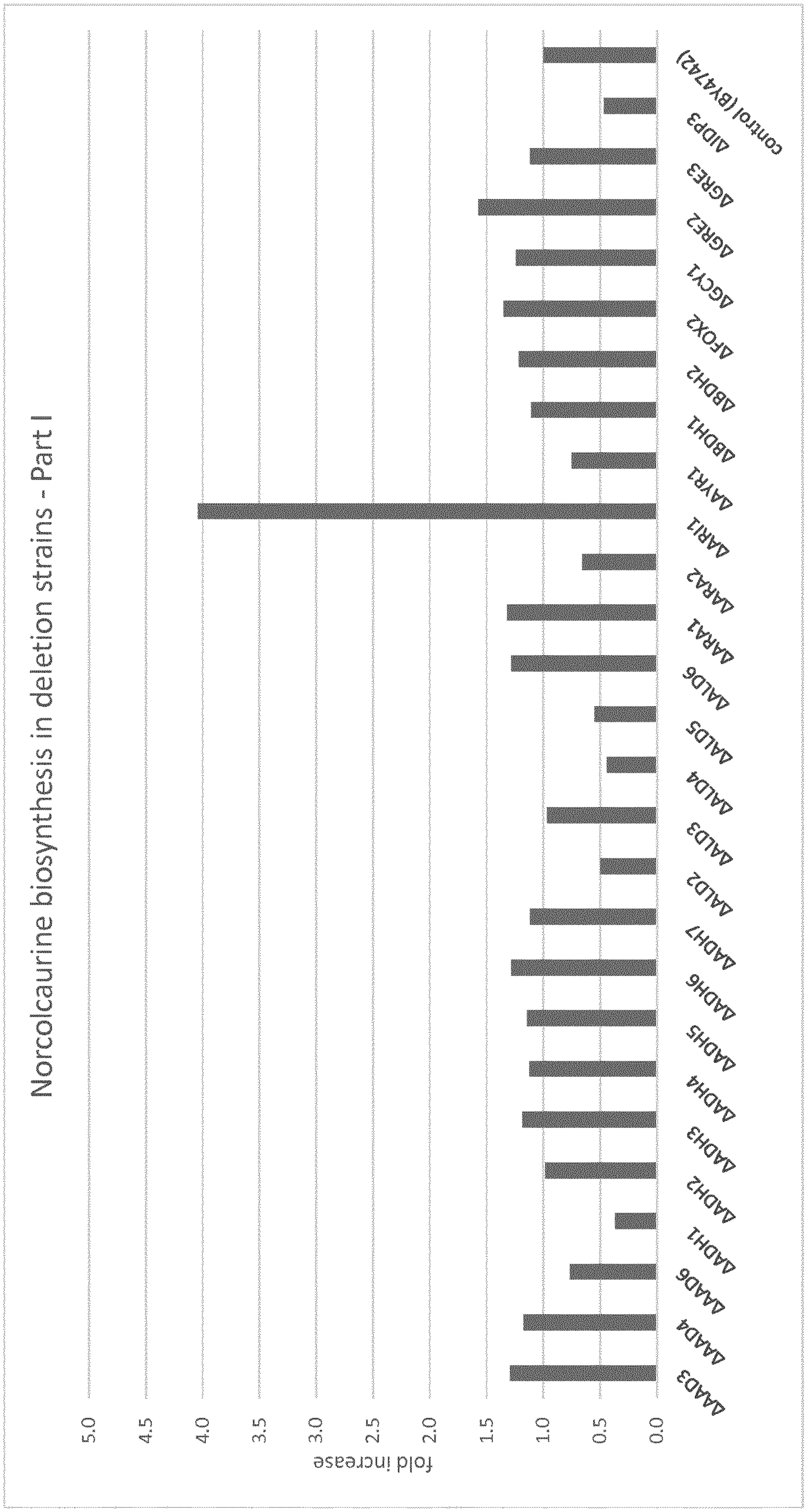
FIG. 2(A) provides results from a first part of a data set of fold-increase of norcoclaurine over the control strain (EVST25620, MATalpha his3Δ1 leu2Δ0 lys2Δ0 ura3Δ0 [ARS/CEN/URA3/pPGK1-Cj_NCS_co-tADH1]). Norcoclaurine concentrations were measured in duplicate cultures by LC/MS in cell culture supernatants of norcoclaurine synthase expressing single gene deletion strains. Positives singe gene deletions in this dataset with an increase of norcolaurine biosynthesis of at least 10%: ΔAAD3, ΔAAD4, ΔADH3, ΔADH4, ΔADH5, ΔADH6, ΔADH7, ΔARA1, ΔARI1, ΔALD6, ΔBDH1, ΔBDH2, ΔFOX2, ΔGCY1, ΔGRE2, ΔGRE3.

All publications, patents and patent applications cited herein are hereby expressly incorporated by reference for all purposes.

Methods well known to those skilled in the art can be used to construct genetic expression constructs and recombinant cells according to this invention. These methods include in vitro recombinant DNA techniques, synthetic techniques, in vivo recombination techniques, and PCR techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

Before describing this invention in detail, a number of terms are defined. As used herein, the singular forms "a", "an", and "the" include plural referents unless the context clearly dictates otherwise. For example, reference to a "nucleic acid" means one or more nucleic acids.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of this invention.

For the purposes of describing and defining this invention it is noted that the terms "reduced", "reduction", "increase", "increases", "increased", "greater", 'higher", and "lower" are utilized herein to represent comparisons, values, measurements, or other representations to a stated reference or control.

For the purposes of describing and defining this invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the terms "polynucleotide", "nucleotide", "oligonucleotide", and "nucleic acid" can be used interchangeably to refer to nucleic acid comprising DNA, RNA, derivatives thereof, or combinations thereof.

Synthesis of Benzylisoquinoline Alkaloids

With reference to the metabolic pathway illustrated in FIG. 1, in plants, BIA synthesis proceeds through condensation of the L-tyrosine derivatives L-dopamine and 4-hydroxyphenylacetaldehyde (4-HPAA) to produce (S)-norcoclaurine, which is catalyzed by the enzyme norcoclaurine synthase (NCS) of *Coptis japonica* (GenBank accession no. AB267399.2) (*S. cerevisiae* codon-optimized: SEQ ID NOs: 23 & 24) (see e.g., Fossati et al., 2015, *PLoS ONE* 10(4): e0124459; Ilari et al., *J Biol Chem*, 2009, 284:897-904; FIG. 1). (S)-Norcoclaurine is then converted to (S)-Coclaurine by the enzyme 6-O-methyltransferase (6-OMT) of *P. somniferum* (GenBank accession no. Q6WUC1) or *C. japonica* (GenBank accession no. D29811), followed by conversion of (S)-Coclaurine to (S)—N-Methylcoclaurine by (CNMT) of *C. japonica* (GenBank accession no. Q948P7) or *T. flavum* (GenBank accession no. AY610508) or *P. somniferum* (GenBank accession no. AY217336); conversion of (S)—N-Methylcoclaurine to (S)-3'-Hydroxy-N-methylcoclaurine by N-methylcoclaurine 3'-hydroxylase (CYP80B) of *P. somniferum* (GenBank accession no. 064899); and finally conversion of (S)-3'-Hydroxy-N-methylcoclaurine to the branch point intermediate (S)-reticuline via 4'-O-methyltransferase (4'OMT) of *C. japonica* (GenBank accession no. Q9LEL5). Yeast can also utilize the pathway traditionally used by plants.

An alternative pathway to biosynthesis of (S)-Reticuline also set forth in FIG. 1 has been developed in bacteria, but which yeast are also able to utilize, in which the L-tyrosine derivatives L-dopamine and 3,4-Dihydroxyphenylacetaldehyde (3,4-DHPAA) are condensed by norcoclaurine synthase (NCS) of *Coptis japonica* (GenBank accession no. AB267399.2) and *S. cerevisiae* codon-optimized (SEQ ID NOs: 23 & 24) to produce (S)-Norlaudanosoline. This alternative pathway continues to produce (S)-Reticuline via conversion of (S)-Norlaudanosoline to (S)-3'-Hydroxycoclaurine by 6-OMT of *P. somniferum* (GenBank accession no. Q6WUC1) or *C. japonica* (GenBank accession no. D29811); conversion of (S)-3'-Hydroxycoclaurine to (S)-3'-Hydroxy-N-methylcoclaurine by CNMT of *C. japonica*

(GenBank accession no. Q948P7) or *T. flavum* (GenBank accession no. AY610508) or *P. somniferum* (GenBank accession no. AY217336); and, finally, conversion of (S)-3'-Hydroxy-N-methylcoclaurine to (S)-Reticuline by 4'OMT of *C. japonica* (GenBank accession no. Q9LEL5) (FIG. 1). In plants and microorganisms, synthesis of BIAs from the intermediate (S)-Reticuline proceeds via known enzymatic reactions (see FIG. 1).

As disclosed herein, disrupting or knocking out certain enzymes, including alcohol dehydrogenases, and/or aldehyde reductases, or similar enzymes, decreases the amount of 4-hydroxyphenylacetaldehyde (4-HPAA) that is reduced to the byproduct 4-hydroxyphenylacetalcohol. See FIG. 1. This is of commercial importance because retention of 4-HPAA in the plant reticuline pathway, or 3,4-DHPAA in the alternative bacterial reticuline pathway improves conversion of dopamine and 4-HPAA or 3,4-DHPAA to (S)—Norcoclaurine and (S)-Norlaudanosoline, respectively, via norcoclaurine synthase (NCS).

This invention provides a recombinant host that is capable of producing increased amounts of benzylisoquinoline alkaloids (BIAs) and/or benzylisoquinoline alkaloid (BIA) precursors, as disclosed herein, and does not produce, or has reduced production of, one or more alcohol dehydrogenases and/or, one or more aldehyde reductases. A recombinant host that produces or is capable of producing BIAs and/or BIA precursors as disclosed herein is a host cell that expresses the necessary biosynthetic enzymes to produce BIAs and/or BIA precursor from a primary substrate, e.g., glucose, or from an intermediate molecule, e.g., L-tyrosine. See e.g., Fossati et al., 2015*, PLoS ONE* 10(4): e0124459; Ilari et al., *J Biol Chem,* 2009, 284:897-904; Hawkins and Smolke, 2008*, Nat Chem Biol.,* 4:564-573; FIG. 1.

As used herein a recombinant host that fails to produce an enzyme, has reduced production of an enzyme, or lacks a functional enzyme, includes an organism that has been recombinantly modified such that the gene encoding the enzyme is knocked out, an organism in which the gene encoding the enzyme contains one or more mutations that reduce or diminish the activity of the enzyme compared to a wild-type organism, or an organism wherein the promoter of the gene encoding the enzyme has been modified or deleted so that the enzyme is expressed at a reduced level compared to a wild-type organism or is not expressed.

Many methods for genetic modification of target genes are known to one skilled in the art and may be used to create recombinant hosts of this invention. Modifications that may be used to reduce or eliminate expression of a target enzyme are disruptions that include, but are not limited to, deletion of the entire gene or a portion of the gene encoding an enzyme; inserting a DNA fragment into a gene encoding the enzyme (in either the promoter or coding region) so that the enzyme is not expressed or expressed at lower levels; introducing a mutation into the coding region for the enzyme, which adds a stop codon or frame shift such that a functional enzyme is not expressed; and introducing one or more mutations, including insertions and deletions, into the coding region of an enzyme to alter amino acids so that a non-functional or a less enzymatically active enzyme is expressed. In addition, expression of an enzyme can be blocked by expression of an antisense RNA or an interfering RNA, and constructs can be introduced that result in co-suppression. In addition, the synthesis or stability of the transcript can be lessened by mutation. Similarly, the efficiency by which an enzyme is translated from mRNA can be modulated by mutation. All of these methods can be readily practiced by one skilled in the art making use of the known sequences encoding the alcohol dehydrogenases and/or aldehyde reductases of this invention.

Alcohol dehydrogenase and aldehyde reductase sequences from a variety of organisms are known in the art and selection of target gene(s) is dependent upon the host selected. Representative alcohol dehydrogenase (ADH) and aldehyde reductase sequences, which can be targeted in accordance with this invention are listed in Table 1. One skilled in the art can choose specific modification strategies to eliminate or lower the expression of an alcohol dehydrogenase and/or aldehyde reductase as desired to facilitate production of BIAs and/or BIA precursors.

TABLE 1

| | | Amino Acid Sequence | | Nucleotide Sequence | |
|---|---|---|---|---|---|
| | Target | Accession No. | SEQ ID NO: | Accession No. | SEQ ID NO: |
| *S. cerevisiae* | ADH5 | NP_009703 | 1 | NM_001178493 | 2 |
| *S. cerevisiae* | ADH6 | NP_014051 | 3 | NM_001182831 | 4 |
| *S. cerevisiae* | ADH7 | NP_010030 | 5 | NM_001178812 | 6 |
| *S. cerevisiae* | GRE2 | NP_014490 | 7 | NM_001183405 | 8 |
| *S. cerevisiae* | GRE3 | NP_011972 | 9 | NM_001179234 | 10 |
| *S. cerevisiae* | YDR541C | NP_010830 | 11 | NM_001180849 | 12 |
| *S. cerevisiae* | YLR460C | NP_013565 | 13 | NM_001182348 | 14 |
| *S. cerevisiae* | ARI1 | NP_011358 | 15 | NM_001181022 | 16 |
| *S. cerevisiae* | YCR102C | NP_010026 | 19 | NM_001178809 | 20 |
| *S. cerevisiae* | YPR127W | NP_015452 | 21 | NM_001184224 | 22 |

In some aspects, the recombinant host cell disclosed herein has reduced or zero activity of a first alcohol dehydrogenase or aldehyde reductase and, optionally, reduced or zero activity of one or more second alcohol dehydrogenases, one or more aldehyde dehyrogenases, or a combination thereof, wherein the activity of each of the alcohol dehydrogenases or aldehyde reductases is reduced or eliminated by having disrupted or deleted one or more genes encoding the enzyme, and whereby the host cell is capable of increased production of one or more benzylisoquinoline alkaloids or benzylisoquinoline alkaloid precursors, or both, than are produced in wild-type cell capable of producing one or more benzylisoquinoline alkaloids or benzylisoquinoline alkaloid precursors.

In some aspects, a first alcohol dehydrogenase is ADH6 or a homolog thereof, e.g., CAD9, CAD3 or CAD2 from *A. thaliana*. In some aspects, one or more second alcohol dehydrogenases are ADH7, GRE2 (Genes de Respuesta a Estres 2), or a homolog thereof, e.g., AT1G51410 or AT5G19440; and the aldehyde reductase is ARI1 (Aldehyde Reductase Intermediate 1), Aldehyde Reductase YGL039W, or a homolog thereof, e.g., SPAC513.07 or YDR541C).

DNA sequences surrounding one or more of the above-referenced sequences are also useful in some modification procedures and are available for yeasts such as for *Saccharomyces cerevisiae* in the complete genome sequence coordinated by NCBI (National Center for Biotechnology Information) with identifying BioProject Nos. PRJNA128, PRJNA13838, PRJNA43747, PRJNA48559, PRJNA52955, PRJNA48569, PRJNA39317. Additional examples of yeast genomic sequences include that of *Schizosaccharomyces pombe*, which is included in BioProject Nos. PRJNA127, PRJNA13836, and PRJNA20755. Genomic sequences of plants are also known in the art and the genomic sequence of *Arabidopsis thaliana* is included in BioProject Nos. PRJNA116, PRJNA10719, PRJNA13190, and PRJNA30811. Other genomic sequences can be readily found by one of skill in the art in publicly available databases.

In particular, DNA sequences surrounding an alcohol dehydrogenase or aldehyde reductase coding sequence are useful for modification methods using homologous recombination. For example, sequences flanking the gene of interest are placed on either side of a selectable marker gene to mediate homologous recombination whereby the marker gene replaces the gene of interest. Also partial gene sequences and flanking sequences bounding a selectable marker gene may be used to mediate homologous recombination whereby the marker gene replaces a portion of the target gene. In addition, the selectable marker may be bounded by site-specific recombination sites, so that following expression of the corresponding site-specific recombinase, the resistance gene is excised from the gene of interest without reactivating the latter. The site-specific recombination leaves behind a recombination site which disrupts expression of the alcohol dehydrogenase or aldehyde reductase. A homologous recombination vector can be constructed to also leave a deletion in the gene of interest following excision of the selectable marker, as is well known to one skilled in the art.

Deletions can be made using mitotic recombination as described in Wach et al. (1994, *Yeast* 10:1793-1808). This method involves preparing a DNA fragment that contains a selectable marker between genomic regions that may be as short as 20 bp, and which bind a target DNA sequence. This DNA fragment can be prepared by PCR amplification of the selectable marker gene using as primers oligonucleotides that hybridize to the ends of the marker gene and that include the genomic regions that can recombine with the yeast genome. The linear DNA fragment can be efficiently transformed into yeast and recombined into the genome resulting in gene replacement including with deletion of the target DNA sequence.

Moreover, promoter replacement methods may be used to change endogenous transcriptional control elements allowing another means to modulate expression such as described in Mnaimneh et al. (2004, *Cell* 118:31-44).

Hosts cells of use in this invention include any organism capable of producing BIAs and/or BIA precursors as disclosed herein, either naturally or synthetically, e.g., by recombinant expression of one or more genes of the BIA biosynthetic pathway (FIG. 1). A number of prokaryotes and eukaryotes are suitable for use in constructing the recombinant microorganisms described herein, e.g., gram-negative bacteria, gram-positive bacteria, yeast or other fungi. A species and strain selected for use as a BIA and/or BIA precursor production strain is first analyzed to determine which production genes are endogenous to the strain and which genes are not present. Genes for which an endogenous counterpart is not present in the strain are assembled in one or more recombinant constructs, which are then transformed into the strain in order to supply the missing function(s).

Exemplary prokaryotic and eukaryotic species are described in more detail below. However, it will be appreciated that other species may be suitable. For example, suitable species may be in a genus *Agaricus, Aspergillus, Bacillus, Candida, Corynebacterium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces, Yarrowia* and *Lactobacillus*. Exemplary species from such genera include *Lentinus tigrinus, Laetiporus sulphureus, Phanerochaete chrysosporium, Pichia pastoris, Physcomitrella patens, Rhodoturula glutinis* 32, *Rhodoturula mucilaginosa, Phaffia rhodozyma* UBV-AX, *Xanthophyllomyces dendrorhous, Fusarium fujikurol/Gibberella fujikuroi, Candida utilis* and *Yarrowia lipolytica*. In some aspects, a microorganism can be an Ascomycete such as *Gibberella fujikuroi, Kluyveromyces lactis, Schizosaccharomyces pombe, Aspergillus niger*, or *Saccharomyces cerevisiae*. In some aspects, a microorganism can be a prokaryote such as *Escherichia coli, Rhodobacter sphaeroides*, or *Rhodobacter capsulatus*. It will be appreciated that certain microorganisms can be used to screen and test genes of interest in a high throughput manner, while other microorganisms with desired productivity or growth characteristics can be used for large-scale production of BIAs and/or BIA precursors.

In some aspects, the recombinant host used with this invention is *S. cerevisiae*, which can be genetically engineered as described herein. *S. cerevisiae* is a widely used organism in synthetic biology, and can be used as the recombinant microorganism platform herein. There are libraries of mutants, plasmids, detailed computer models of metabolism and other information available for *S. cerevisiae*, permitting rational design of various modules to enhance product yield. Methods are known for making recombinant microorganisms. In some aspects, the *S. cerevisiae* strain is S288C (Mortimer and Johnston, 1986, *Genetics* 113:35-43).

*Aspergillus* species such as *A. oryzae, A. niger* and *A. sojae* are widely used microorganisms in food production, and can also be used as the recombinant microorganism platform. Thus, the recombinant host may be *Aspergillus* spp. Nucleotide sequences are available for genomes of *A. nidulans, A. fumigatus, A. oryzae, A. clavatus, A. flavus, A. niger*, and *A. terreus*, allowing rational design and modification of endogenous pathways to enhance flux and increase product yield. Metabolic models have been developed for *Aspergillus*, as well as transcriptomic studies and proteomics studies.

*E. coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Rhodobacter* can be used as the recombinant microorganism platform. Similar to *E. coli*, there are libraries of mutants available as well as suitable plasmid vectors, allowing for rational design of various modules to enhance product yield. Methods similar to those described above for *E. coli* can be used to make recombinant *Rhodobacter* microorganisms.

*Physcomitrella* mosses, when grown in suspension culture, have characteristics similar to yeast or other fungal cultures. These genera are becoming an important type of cell for production of plant secondary metabolites, which can be difficult to produce in other types of cells. Thus, the recombinant host may be a *Physcomitrella* spp.

In some aspects, the recombinant host is a plant or plant cells that includes a sufficient number of genes from the BIA biosynthetic pathway set forth in FIG. 1 to produce one or more benzylisoquinoline alkaloids or benzylisoquinoline alkaloid precursors, or both. As disclosed herein, a plant or plant cell modified to express the BIA biosynthetic pathway can also contain a knockout of one or more alcohol dehydrogenases and/or aldehyde reductases to advantageously increase the yield thereof. Plant or plant cells can be stably transformed to retain the introduced nucleic acid with each cell division. A plant or plant cell can also be transiently transformed such that the heterologous nucleic acid is not integrated into its genome. Transiently transformed cells typically lose all or some portion of the introduced nucleic acid with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a heterologous nucleic acid, for example a recombinant nucleic acid construct into other lines, to transfer a heterologous nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Certain transgenic plants or plant cells can be grown in suspension culture. For the purposes of this invention, solid and/or liquid culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation; see U.S. Pat. Nos. 5,538,880; 5,204,253; 6,329,571; and 6,013,863. If a cell or cultured tissue is used as the recipient tissue for transformation, plants can be regenerated from transformed cultures if desired, by techniques known to those skilled in the art.

A population of transgenic plants can be screened and/or selected for those members of the population that have a trait or phenotype conferred by expression of the transgene. For example, a population of progeny of a single transformation event can be screened for those plants having a desired level of expression of a polypeptide or nucleic acid described herein. Physical and biochemical methods can be used to identify expression levels. These include Southern analysis or PCR amplification for detection of a polynucleotide; northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, western blots, immunoprecipitation, and enzyme-linked immunoassays to detect polypeptides. Other techniques such as in situ hybridization, enzyme staining, and immunostaining also can be used to detect the presence or expression of polypeptides and/or nucleic acids. Methods for performing all of the referenced techniques are known.

As an alternative, a population of plants with independent transformation events can be screened for those plants having a desired trait, such as production of BIAs and/or BIA precursors, and/or lack of conversion of 4-HPAA and/or 3,4-DHPAA to 4-hydroxyphenylacetalcohol and 3,4-Dihydroxyphenylacetalcohol, respectively. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant.

Depending on the particular organism used in this invention, the recombinant host cell can naturally or recombinantly express genes encoding a 6-OMT (6-O-methyltransferase) of *P. somniferum* (GenBank accession no. Q6WUC1) or *C. japonica* (GenBank accession no. D29811), CNMT (Coclaurine N-methyltransferase) of *C. japonica* (GenBank accession no. Q948P7) or *T. flavum* (GenBank accession no. AY610508) or *P. somniferum* (GenBank accession no. AY217336), CYP80B (N-methylcoclaurine 3'-hydroxylase) of *P. somniferum* (GenBank accession no. 064899), or 4'OMT (4'-O-methyltransferase) of *C. japonica* (GenBank accession no. Q9LEL5) (FIG. 1).

As used herein, "recombinant expression" means that the genome of a host cell has been augmented through the introduction of one or more recombinant genes, which include regulatory sequences that facilitate the transcription and translation of a protein of interest. While embodiments include stable introduction of recombinant genes into the host genome, autonomous or replicative plasmids or vectors can also be used within the scope of this invention. Moreover, this invention can be practiced using a low copy number, e.g., a single copy, or high copy number (as exemplified herein) plasmid or vector.

Generally, the introduced recombinant gene is not originally resident in the host that is the recipient of the recombinant gene, but it is within the scope of the invention to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms, plant cells, and plants.

The term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene may be a DNA sequence from another species, or may be a DNA sequence that originated from or is present in the same species, but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA.

A recombinant gene encoding a polypeptide described herein includes the coding sequence for that polypeptide, operably linked, in sense orientation, to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. The term "heterologous nucleic acid" as used herein, refers to a nucleic acid introduced into a recombinant host, wherein said nucleic acid is not naturally present in said host or members of the host species. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically includes at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

One or more genes, for example one or more heterologous nucleic acids, can be combined in a recombinant nucleic acid construct in "modules" useful for a discrete aspect of BIA and/or BIA precursor production. Combining a plurality of genes or heterologous nucleic acids in a module facilitates the use of the module in a variety of species. For example, a BIA and/or BIA precursor gene cluster can be combined such that each coding sequence is operably linked to a separate regulatory region, to form a BIA and/or BIA precursor module for production in eukaryotic organisms. Alternatively, the module can express a polycistronic message for production of BIAs and/or BIA precursors in prokaryotic hosts such as species of *Rodobacter, E. coli, Bacillus* or *Lactobacillus*. In addition to genes useful for production of BIAs and/or BIA precursors, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

Functional Homologs

Functional homologs of the polypeptides described herein are also suitable for use in producing benzylisoquinoline alkaloid compounds and benzylisoquinoline alkaloid precursors in a recombinant host. A functional homolog is a polypeptide that has sequence similarity to a reference polypeptide, and that carries out one or more of the biochemical or physiological function(s) of the reference polypeptide. A functional homolog and the reference polypeptide can be a naturally occurring polypeptide, and the sequence similarity can be due to convergent or divergent evolutionary events. As such, functional homologs are sometimes designated in the literature as homologs or orthologs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of benzylisoquinoline alkaloid compounds and benzylisoquinoline alkaloid precursors. Amino acid sequence similarity allows for conservative amino acid substitutions, such as inter alia substitution of one hydrophobic residue for another or substitution of one polar residue for another. If desired, manual inspection of such candidates can be carried out in order to narrow the number of candidates to be further evaluated.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

A candidate sequence typically has a length that is from 80% to 200% of the length of the reference sequence, e.g., 82, 85, 87, 89, 90, 93, 95, 97, 99, 100, 105, 110, 115, 120, 130, 140, 150, 160, 170, 180, 190, or 200% of the length of the reference sequence. A functional homolog polypeptide typically has a length that is from 95% to 125% of the length of the reference sequence, e.g., 90, 93, 95, 97, 99, 100, 105, 110, 115, or 120% of the length of the reference sequence, or any range between. A % identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using the computer program ClustalW (version 1.83, default parameters), which allows alignments of nucleic acid or polypeptide sequences to be carried out across their entire length (global alignment). See, Chenna et al., 2003, *Nucleic Acids Res.* 31(13):3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: % age; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method:% age; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine %-identity of a candidate nucleic acid or amino acid sequence to a reference sequence, the sequences are aligned using ClustalW, the number of identical matches in the alignment is divided by the length of the reference sequence, and the result is multiplied by 100. It is noted that the % identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

To demonstrate expression and activity of one or more of the above-referenced enzymes expressed by the recombinant host, levels of products, substrates and intermediates, e.g., 4-HPAA, 3,4-DHPAA, (S)—Norcoclaurine, (S)-Norlaudanosoline, L-Tyrosine, Dopamine, and/or benzylisoquinoline alkaloids produced by the recombinant host can be determined by extracting samples from culture media for analysis according to published methods.

Recombinant hosts described herein can be used in methods to produce BIAs and/or BIA precursors. For example, if the recombinant host is a microorganism, the method can include growing a recombinant microorganism genetically engineered to produce BIAs and/or BIA precursors in a culture medium under conditions in which biosynthesis genes for BIAs and/or BIA precursors are expressed. The recombinant microorganism may be grown in a batch, fed batch or continuous process or combinations thereof. Typically, the recombinant microorganism is grown in a fermenter at a defined temperature(s) in the presence of a suitable nutrient source, e.g., a carbon source, for a desired period of time to produce a desired amount of BIAs and/or BIA precursors.

Therefore, this invention also provides an improved method for producing BIAs and/or BIA precursors as disclosed herein by providing a recombinant host that produces BIAs and/or BIA precursors as disclosed herein and has reduced production or activity of at least one alcohol dehydrogenase, at least one aldehyde reductase, or at least one alcohol dehydrogenase and at least one aldehyde reductase; cultivating said recombinant host, e.g., in the presence of a suitable carbon source, for a time sufficient for said recombinant host to produce BIAs and/or BIA precursors as disclosed herein; and isolating BIAs and/or BIA precursors as disclosed herein from said recombinant host or from the cultivation supernatant. In some aspects, the recombinant host produces a reduced amount of 4-hydroxyphenylacetalcohol or 3,4-dihydroxyphenylacetalcohol in comparison to a host that expresses the one or more functional alcohol dehydrogenases or one or more aldehyde reductases.

The level of 4-hydroxyphenylacetaldehyde (4-HPAA) and 4-hydroxyphenylacetalcohol, and/or 3,4-dihydroxyphenylacetaldehyde (3,4-DHPAA) and 3,4-dihydroxyphenylacetalcohol may be determined by any suitable method useful for detecting these compounds. Such methods include, for example, HPLC. Similarly, the level of a specific BIA and/or BIA precursor, such as but not limited to, Dopamine, 4-HPAA, 3,4-DHPAA, (S)-Norcoclaurine, (S)-Norlaudanosoline, and (S)-Reticuline may be determined using any suitable method useful for detecting these compounds. Such methods include, for example, HPLC.

Carbon sources of use in the method of this invention include any molecule that can be metabolized by a suitably modified recombinant host cell to facilitate growth and/or production of BIAs and/or BIA precursors as disclosed herein. Examples of suitable carbon sources include, but are not limited to, sucrose (e.g., as found in molasses), fructose, xylose, ethanol, glycerol, glucose, cellulose, starch, cellobiose or other glucose containing polymer. In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

After a suitably modified recombinant host has been grown in culture for the desired period of time, BIAs and/or BIA precursors can then be recovered from the culture using various techniques known in the art, e.g., isolation and purification by extraction, vacuum distillation and multi-stage re-crystallization from aqueous solutions and ultrafiltration (Boddeker, et al. (1997) *J. Membrane Sci.* 137:155-158; Borges da Silva, et al. (2009) *Chem. Eng. Des.* 87:1276-1292). If the recombinant host is a plant or plant cells, BIAs and/or BIA precursors can be extracted from the plant tissue using various techniques known in the art.

In some embodiments, BIAs and/or BIA precursors can be produced using suitably modified whole cells that are fed raw materials that contain precursor molecules. The raw materials may be fed during cell growth or after cell growth. The whole cells may be in suspension or immobilized. The whole cells may be in fermentation broth or in a reaction buffer. In some embodiments a permeabilizing agent may be required for efficient transfer of substrate into the cells.

In some aspects, a BIA and/or BIA precursor is isolated and purified to homogeneity (e.g., at least 90%, 92%, 94%, 96%, or 98% pure). In some aspects, the BIA and/or BIA precursor is isolated as an extract from a suitably modified recombinant host. In this respect, BIA and/or BIA precursor may be isolated, but not necessarily purified to homogeneity. Desirably, the amount of BIA and/or BIA precursor produced can be from about 1 mg/l to about 20,000 mg/L or higher. For example about 1 to about 100 mg/L, about 30 to about 100 mg/L, about 50 to about 200 mg/L, about 100 to about 500 mg/L, about 100 to about 1,000 mg/L, about 250 to about 5,000 mg/L, about 1,000 to about 15,000 mg/L, or about 2,000 to about 10,000 mg/L of BIA and/or BIA precursor can be produced. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of suitably modified recombinant microorganisms is used, they can be grown in a mixed culture to produce BIAs and/or BIA precursors.

Extracts of isolated, and optionally purified, BIAs and/or BIA precursors find use in a wide variety of pharmaceutical compositions.

The invention is further described in the following examples, which do not limit the scope of the invention described in the claims.

EXAMPLES

Example 1: Identification of Gene Candidates

Figure 2B:
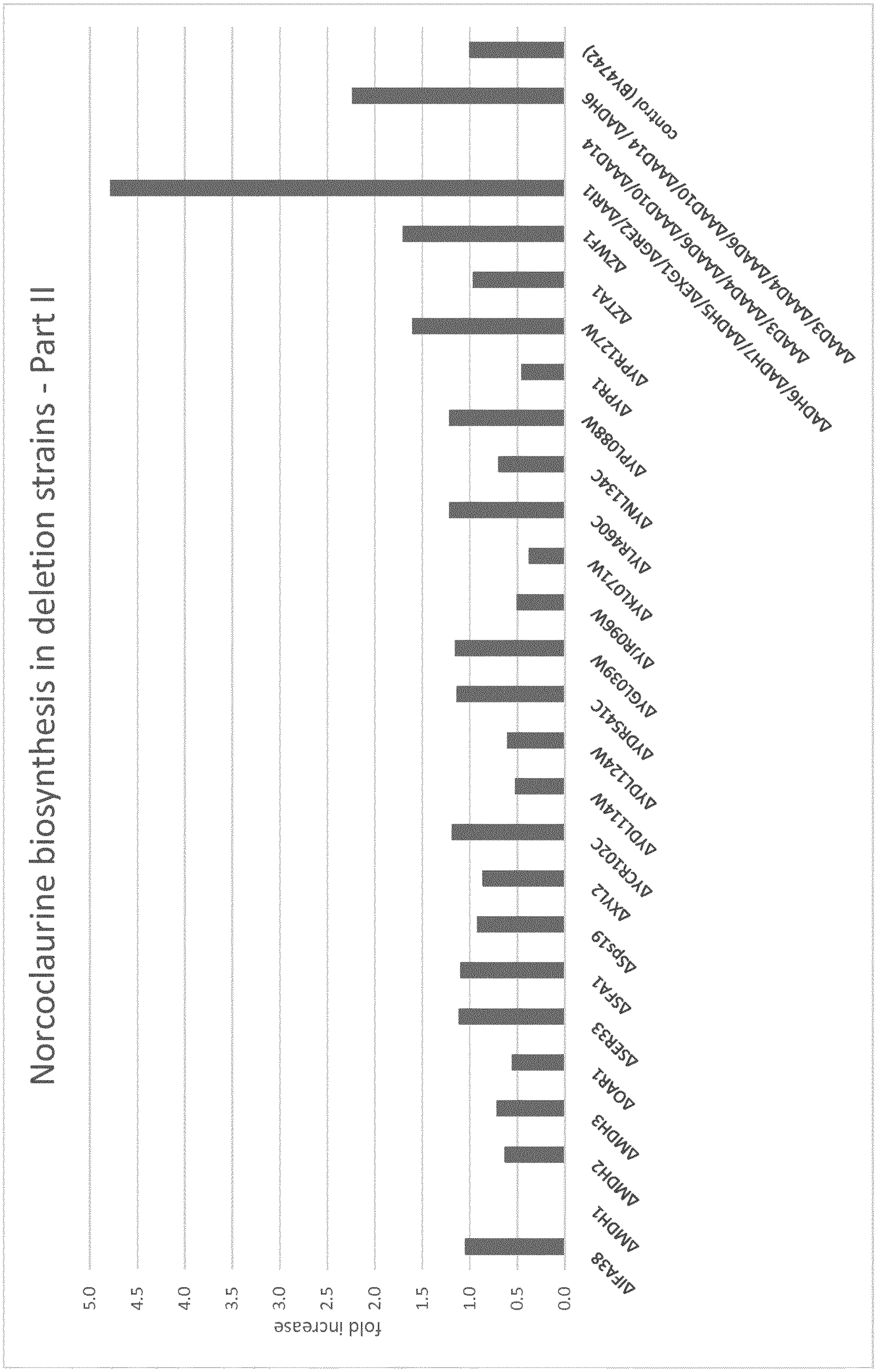
FIG. 2(B) provides results from the remaining part of data set of fold increase of norcoclaurine over the control strain (EVST25620, MATalpha his3Δ1 leu2Δ0 lys2Δ0 ura3Δ0 [ARS/CEN/URA3/pPGK1-Cj_NCS_co-tADH1]). Norcoclaurine concentrations were measured in duplicate cultures by LC/MS in cell culture supernatants of norcoclaurine synthase expressing single gene deletion strains and multiple deletion strains. Positives single gene deletions in this dataset with an increase of norcolaurine biosynthesis of at least 10%: ΔSER33, ΔYCR102C, ΔYDR541C, ΔYGL039W, ΔYLR460C, ΔYPL088W, ΔYPR127, ΔZWF1. Positive combinations of gene deletions in this data set:
ΔADH6/ΔADH7/ΔADH5/ΔBGL1/ΔGRE2/ΔARI1,
ΔAAD3/ΔAAD4/ΔAAD6/ΔAAD10/ΔAAD14/ΔADH6.
Figure 3:
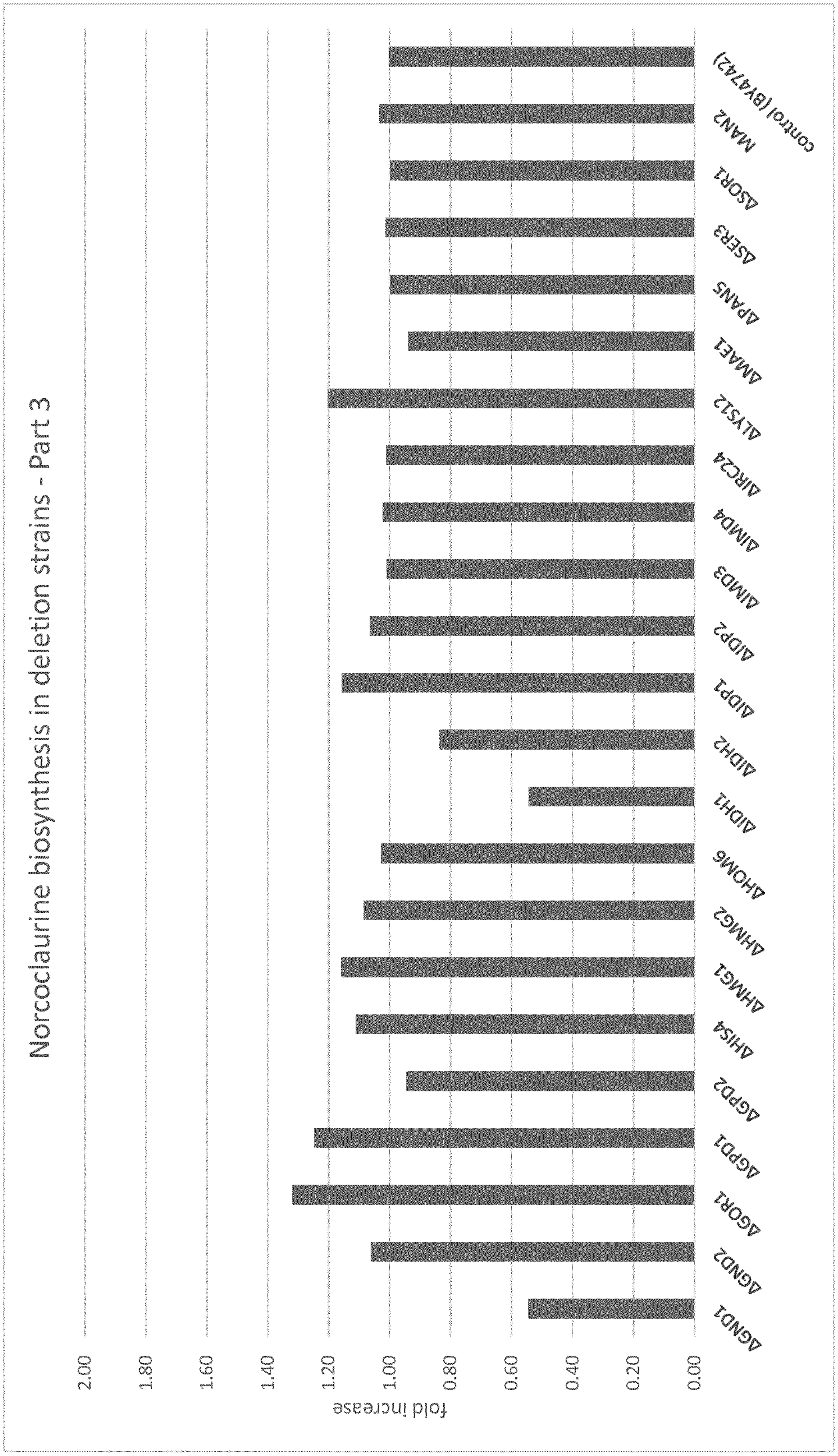
FIG. 3 provides the fold-increase of norcoclaurine concentration in the cell culture supernatant measured by LC/MS over the control strain (EVST25620, MATalpha his3Δ1 leu2Δ0 lys2Δ0 ura3Δ0 [ARS/CEN/URA3/pPGK1-Cj_NCS_co-tADH1]). Norcoclaurine concentrations were measured after 72h of cultivation in two independent experiments, average fold increase of norcoclaurine concentrations was calculated. Positive single gene deletions in this dataset with an increase of norcolaurine biosynthesis of at least 10%: ΔGOR1, ΔGPD1, ΔHIS4, ΔHMG1, ΔIDP1, ΔLYS12.

Gene candidates shown in FIGS. 2A and 2B were identified in the *S. cerevisiae* genome either by annotated information on alcohol- and/or aldehyde dehydrogenases in the *Saccharomyces* Genome Database (http://www.yeastgenome.org/) or by sequence homology searches against the *S. cerevisiae* genome. In addition, all RefSeq Protein sequences were downloaded from NCBI on Nov. 13, 2015 (totally 5915 Sequences). Those sequences were scanned with PRIAM (Claudel-Renard et al. 2003, *Nucleic Acids Res.* 31(22):6633-39) for hits to EC 1.1.1 in order to identify further candidates (FIG. 3). Seventy-two single gene deletions (generated as described in Example 2) were tested and list of the single gene deletions which were shown to work is presented in Table 2 and gene combinations are shown in Table 3.

TABLE 2

Single gene deletions shown to increase norcoclaurine biosynthesis.

| Standard Name | Systematic Name | Strain number | Annotation |
|---|---|---|---|
| AAD3 | YCR107W | EVST25702 | Putative aryl-alcohol dehydrogenase |
| AAD4 | YDL243C | EVST25704 | Putative aryl-alcohol dehydrogenase |
| ADH3 | YMR083W | EVST25572 | Mitochondrial alcohol dehydrogenase isozyme III |
| ADH4 | YGL256W | EVST25573 | Alcohol dehydrogenase isoenzyme type IV |
| ADH5 | YBR145W | EVST25574 | Alcohol dehydrogenase isoenzyme V |
| ADH6 | YMR318C | EVST25575 | NADPH-dependent medium chain alcohol dehydrogenase |
| ADH7 | YCR105W | EVST25576 | NADPH-dependent medium chain alcohol dehydrogenase |
| ALD6 | YPL061W/ | EVST25611 | Cytosolic aldehyde dehydrogenase |
| ARA1 | YBR149W | EVST25591 | NADP+ dependent arabinose dehydrogenase |
| ARI1 | YGL157W | EVST25577 | NADPH-dependent aldehyde reductase |
| BDH1 | YAL060W | EVST25586 | NAD-dependent (R,R)-butanediol dehydrogenase |
| BDH2 | YAL061W | EVST25587 | Putative medium-chain alcohol dehydrogenase with similarity to BDH1 |
| FOX2 | YKR009C | EVST25593 | 3-hydroxyacyl-CoA dehydrogenase and enoyl-CoA hydratase |
| GCY1 | YOR120W | EVST25594 | Glycerol dehydrogenase |
| GOR1 | YNL274C | EVST27673 | Glyoxylate reductase |
| GPD1 | YDL022W | EVST27687 | NAD-dependent glycerol-3-phosphate dehydrogenase |
| GRE2 | YOL151W | EVST25578 | 3-methylbutanal reductase and NADPH-dependent methylglyoxal reductase |
| GRE3 | YHR104W | EVST25579 | Aldose reductase |
| HIS4 | YCL030C | EVST27654 | Multifunctional enzyme containing phosphoribosyl-ATP pyrophosphatase, phosphoribosyl-AMP cyclohydrolase, and histidinol dehydrogenase activities |
| HMG1 | YML075C | EVST27685 | HMG-CoA reductase |
| IDP1 | YDL066W | EVST27690 | Mitochondrial NADP-specific isocitrate dehydrogenase |
| LYS12 | YIL094C | EVST27692 | Homo-isocitrate dehydrogenase |
| SER33 | YIL074C | EVST25600 | 3-phosphoglycerate dehydrogenase and alpha-ketoglutarate reductase |
| ZWF1 | YNL241C | EVST25705 | Glucose-6-phosphate dehydrogenase |
| | YCR102C | EVST25581 | Putative protein of unknown function |
| | YDR541C | EVST25582 | Aldehyde reductase |
| | YGL039W | EVST25583 | Aldehyde reductase |
| | YLR460C | EVST25584 | Member of the quinone oxidoreductase family |
| | YPL088W | EVST25701 | Putative aryl alcohol dehydrogenase |

TABLE 2-continued

Single gene deletions shown to increase norcoclaurine biosynthesis.

| Standard Name | Systematic Name | Strain number | Annotation |
|---|---|---|---|
| | YPR127W | EVST25698 | Putative pyridoxine 4-dehydrogenase |

TABLE 3

Multiple Gene Deletions tested for increase of norcoclaurine biosynthesis.

| Standard Name | Systematic Name | Strain | Annotation |
|---|---|---|---|
| ADH6/ADH7/ADH5/EXG1/GRE2/ARI1 | YMR318C/YCR105W/YBR145W/YLR300W/YOL151W/YGL157W | EVST25619 | Combination of alcohol dehydrogenases and aldehyde reductases |
| AAD3/AAD4/AAD6/AAD10/AAD14/ADH6 | YCR107W/YDL243C/YFL056C/YJR155W/YNL331C | EVST25618 | Combination of putative aryl-alcohol dehydrogenases with alcohol dehydrogenase |

Example 2: Construction and Cultivation of Assay Strains

All single gene deletion strains were constructed from the Yeast MATalpha Collection YSC1054 (GE Dharmacon) which is based on the strain BY4742 with the genotype MAT alpha his3Δ1 leu2Δ0 lys2Δ0 ura3Δ0 (GenBank accession no. JRIR00000000). Deletion strains were generated using homologous recombination methods, by deletion of the respective target gene, as identified for each strain in Table 2. As an indirect measure for 4-hydroyxphenyl acetaldehyde (4-HPAA), strains overexpressing norcoclaurine synthase from a plasmid were generated. Control strain EVST25620 (MAT alpha his3Δ1 leu2Δ0 lys2Δ0 ura3Δ0 [ARS/CEN/URA3/pPGK1-Cj_NCS_co-tADH1]) was prepared accordingly in the BY4742 background, as described above, that did not carry any additional deletions.

Multiple deletion strains EVST25618 and EVST25619 were constructed from the previously described strain YSC1054 (based on strain BY4742; genotype MAT alpha his3Δ1 leu2Δ0 lys2Δ0 ura3Δ0). Deletion strains were generated using homologous recombination methods, with sequential deletion of either the genes: (1) AAD3, AAD4, AAD6, (Putative aryl-alcohol dehydrogenase 6; YFL056C), AAD10 (Putative aryl-alcohol dehydrogenase 10), AAD14 (Putative aryl-alcohol dehydrogenase), ADH6; or (2) ADH6, ADH7, ADH5, EXG1 (EXo-1,3-beta-Glucanase), GRE2, ARI1, respectively.

*Coptis japonica* norcoclaurine synthase (GenBank accession number AB267399.2) was codon optimized for *S. cerevisiae* (SEQ ID NOs: 23 & 24) and synthesized de novo (GeneArt). An open reading frame flanked by HindIII and SacII restriction enzyme recognition sites was cloned into HindIII/SacII linearized vector backbone pEVE2120 (SEQ ID NO: 63) resulting in plasmid pEV27735 (SEQ ID NO: 64). Clones were verified by sequencing, and the yeast single deletion mutant strains, as well as the non-deleted control strain, were transformed with plasmid pEV27735 (SEQ ID NO: 64). Single clones grown on selective SC-agar plates lacking uracil were singled out on selective SC-agar plates. One single clone in duplicates was used to inoculate 500 μl SC minus uracil selective media, supplemented with 1 mM tyrosine and 9.8 mM dopamine, in single wells of 96-deep well plates. Cultures were grown for 72 h at 30° C. with shaking at 300 rpm. Optical density of the cultures was measured at 600 nm either by a standard method using a spectrophotometer or a plate reader. For analysis of norcoclaurine biosynthesis the plates were centrifuged for 5 min at 3000 rpm and 100 μl of the supernatant were withdrawn.

TABLE 4

Average absorption values ($OD_{600}$) of duplicate cultures after cultivation time of 72 h measured with a standard spectrophotometer.

| Gene deletion | Average $OD_{600}$ | Gene deletion | Average $OD_{600}$ |
|---|---|---|---|
| ΔAAD3 | 12.3 | ΔALD6 | 13.8 |
| ΔAAD4 | 12.5 | ΔARA1 | 12.8 |
| ΔADH3 | 12.0 | ΔARI1 | 13.0 |
| ΔADH4 | 12.8 | ΔBDH1 | 11.8 |
| ΔADH5 | 13.3 | ΔBDH2 | 13.8 |
| ΔADH6 | 13.0 | ΔFOX2 | 13.8 |
| ΔADH7 | 12.3 | ΔGCY1 | 11.5 |
| | | ΔGRE2 | 13.5 |
| | | ΔGRE3 | 12.3 |
| | | control (BY4742) | 13.3 |

TABLE 5

Average absorption values (OD600) of duplicate cultures after cultivation time of 72 h measured with a standard spectrophotometer.

| Gene deletion | Average final $OD_{600}$ |
|---|---|
| ΔYGL039W | 11.8 |
| ΔYLR460C | 13.5 |
| ΔYPL088W | 11.8 |
| ΔSER33 | 12.3 |
| ΔYPR127W | 8.9 |
| ΔZWF1 | 13.0 |
| ΔYCR102C | 15.3 |
| ΔADH6/ΔADH7/ΔADH5Δ/EXG1/ΔGRE2/ΔARI1 | 14.3 |
| ΔAAD3/ΔAAD4/ΔAAD6/ΔAAD10/ΔAAD14/ΔADH6 | 6.0 |
| control (BY4742) | 13.3 |

TABLE 6

Absorption values (OD600) of cultures of one of the two independent experiments carried out in this study after a cultivation time of 72 h measured with a standard plate reader.

| Genotype | Absorption |
|---|---|
| ΔGOR1 | 6.1 |
| ΔGPD1 | 9.7 |
| ΔLYS12 | 5.5 |
| ΔHIS4 | 5.2 |
| ΔHMG1 | 5.7 |
| ΔIDP1 | 6.0 |
| control BY4742) | 5.2 |

Example 3: Measurement of Norcoclaurine in Cell Culture Media

Norcoclaurine analysis was carried out on an Acquity UPLC-SQD apparatus (Waters) equipped with an Acquity BEH C18 1.7 μm 2.1×100 mm reverse phase column (Waters) kept at 35° C. 5 μl of culture supernatant were loaded onto the column and separated using a gradient from 2% Solvent B to 30% Solvent B in 5 min, then washed with 100% Solvent B for 1 minute and reconditioned at 2% Solvent B for another minute. Solvent A consisted of water with 0.1% formic acid and Solvent B consisted of acetonitrile with 0.1% formic acid. The flow rate was 0.4 ml/min. Norcoclaurine was quantified by single ion monitoring of m/z 272 $[M+H]^+$ at 2.42 min and a calibration curve prepared in culture medium covering the concentration range of 78 µg/L to 10 mg/L.

Norcoclaurine concentrations were normalized to the optical density ($OD_{600}$) of the cultures after cultivation (72 h), and fold increase of norcoclaurine concentrations were calculated from the normalized results. The control strain (EVST25620, MATalpha his3Δ1 Leu2Δ0 lys2Δ0 ura3Δ0 [ARS/CEN/URA3/pPGK1-Cj_NCS_co-tADH1]) was set at a fold increase of 1.0. Positives singe gene deletions with an increase of norcolaurine biosynthesis of at least 10% were shown for: ΔAAD3, ΔAAD4, ΔADH3, ΔADH4, ΔADH5, ΔADH6, ΔADH7, ΔARA1, ΔARI1, ΔALD6, ΔBDH1, ΔBDH2, ΔFOX2, ΔGCY1, ΔGRE2, ΔGRE3, ΔSER33, ΔYCR102C, ΔYDR541C, ΔYGL039W, ΔYLR460C, ΔYPL088W, ΔYPR127, ΔZWF1, ΔGOR1, ΔGPD1, ΔHIS4, ΔHMG1, ΔIDP1, ΔLYS12 (FIGS. 2 and 3).

TABLE 7

| Disclosed Nucleic Acid and Amino Acid Sequences |
|---|
| Protein sequence from alcohol dehydrogenase<br>5 (ADH5) of *Saccharomyces cerevisiae*<br>SEQ ID NO: 1<br>MPSQVIPEKQKAIVFYETDGKLEYKDVTVPEPKPNEILVHVKYSGVCHSDLHAWHGDWP<br>FQLKFPLIGGHEGAGVVVKLGSNVKGWKVGDFAGIKWLNGTCMSCEYCEVGNESQCP<br>YLDGTGFTHDGTFQEYATADAVQAAHIPPNVNLAEVAPILCAGITVYKALKRANVIPGQW<br>VTISGACGGLGSLAIQYALAMGYRVIGIDGGNAKRKLFEQLGGEIFIDFTEEKDIVGAIIKA<br>TNGGSHGVINVSVSEAAIEASTRYCRPNGTVVLVGMPAHAYCNSDVFNQVVKSISIVGS<br>CVGNRADTREALDFFARGLIKSPIHLAGLSDVPEIFAKMEKGEIVGRYVVETSK |
| DNA sequence encoding alcohol dehydrogenase<br>5 (ADH5) of *Saccharomyces cerevisiae*<br>SEQ ID NO: 2<br>ATGCCTTCGCAAGTCATTCCTGAAAAACAAAAGGCTATTGTCTTTTATGAGACAGATG<br>GAAAATTGGAATATAAAGACGTCACAGTTCCGGAACCTAAGCCTAACGAAATTTTAG<br>TCCACGTTAAATATTCTGGTGTTTGTCATAGTGACTTGCACGCGTGGCACGGTGATT<br>GGCCATTTCAATTGAAATTTCCATTAATCGGTGGTCACGAAGGTGCTGGTGTTGTTG<br>TTAAGTTGGGATCTAACGTTAAGGGCTGGAAAGTCGGTGATTTTGCAGGTATAAAAT<br>GGTTGAATGGGACTTGCATGTCCTGTGAATATTGTGAAGTAGGTAATGAATCTCAAT<br>GTCCTTATTTGGATGGTACTGGCTTCACACATGATGGTACTTTTCAAGAATACGCAA<br>CTGCCGATGCCGTTCAAGCTGCCCATATTCCACCAAACGTCAATCTTGCTGAAGTTG<br>CCCCAATCTTGTGTGCAGGTATCACTGTTTATAAGGCGTTGAAAAGAGCCAATGTGA<br>TACCAGGCCAATGGGTCACTATATCCGGTGCATGCGGTGGCTTGGGTTCTCTGGCA<br>ATCCAATACGCCCTTGCTATGGGTTACAGGGTCATTGGTATCGATGGTGGTAATGCC<br>AAGCGAAAGTTATTTGAACAATTAGGCGGAGAAATATTCATCGATTTCACGGAAGAA<br>AAAGACATTGTTGGTGCTATAATAAAGGCCACTAATGGCGGTTCTCATGGAGTTATT<br>AATGTGTCTGTTTCTGAAGCAGCTATCGAGGCTTCTACGAGGTATTGTAGGCCCAAT<br>GGTACTGTCGTCCTGGTTGGTATGCCAGCTCATGCTTACTGCAATTCCGATGTTTTC<br>AATCAAGTTGTAAAATCAATCTCCATCGTTGGATCTTGTGTTGGAAATAGAGCTGATA<br>CAAGGGAGGCTTTAGATTTCTTCGCCAGAGGTTTGATCAAATCTCCGATCCACTTAG<br>CTGGCCTATCGGATGTTCCTGAAATTTTTGCAAAGATGGAGAAGGGTGAAATTGTTG<br>GTAGATATGTTGTTGAGACTTCTAAATGA |
| Protein sequence from alcohol dehydrogenase<br>6 (ADH6) of *Saccharomyces cerevisiae*<br>SEQ ID NO: 3<br>MSYPEKFEGIAIQSHEDWKNPKKTKYDPKPFYDHDIDIKIEACGVCGSDIHCAAGHWGN<br>MKMPLVVGHEIVGKVVKLGPKSNSGLKVGQRVGVGAQVFSCLECDRCKNDNEPYCTK<br>FVTTYSQPYEDGYVSQGGYANYVRVHEHFVVPIPENIPSHLAAPLLCGGLTVYSPLVRN<br>GCGPGKKVGIVGLGGIGSMGTLISKAMGAETYVISRSSRKREDAMKMGADHYIATLEEG<br>DWGEKYFDTFDLIVVCASSLTDIDFNIMPKAMKVGGRIVSISIPEQHEMLSLKPYGLKAVS<br>ISYSALGSIKELNQLLKLVSEKDIKIWVETLPVGEAGVHEAFERMEKGDVRYRFTLVGYD<br>KEFSD |
| DNA sequence encoding alcohol dehydrogenase<br>6 (ADH6) of *Saccharomyces cerevisiae*<br>SEQ ID NO: 4<br>ATGTCTTATCCTGAGAAATTTGAAGGTATCGCTATTCAATCACACGAAGATTGGAAAA<br>ACCCAAAGAAGACAAAGTATGACCCAAAACCATTTTACGATCATGACATTGACATTAA<br>GATCGAAGCATGTGGTGTCTGCGGTAGTGATATTCATTGTGCAGCTGGTCATTGGG<br>GCAATATGAAGATGCCGCTAGTCGTTGGTCATGAAATCGTTGGTAAAGTTGTCAAGC<br>TAGGGCCCAAGTCAAACAGTGGGTTGAAAGTCGGTCAACGTGTTGGTGTAGGTGCT<br>CAAGTCTTTTCATGCTTGGAATGTGACCGTTGTAAGAATGATAATGAACCATACTGCA<br>CCAAGTTTGTTACCACATACAGTCAGCCTTATGAAGACGGCTATGTGTCGCAGGGTG<br>GCTATGCAAACTACGTCAGAGTTCATGAACATTTTGTGGTGCCTATCCCAGAGAATA<br>TTCCATCACATTTGGCTGCTCCACTATTATGTGGTGGTTTGACTGTGTACTCTCCATT<br>GGTTCGTAACGGTTGCGGTCCAGGTAAAAAAGTTGGTATAGTTGGTCTTGGTGGTAT<br>CGGCAGTATGGGTACATTGATTTCCAAAGCCATGGGGGCAGAGACGTATGTTATTTC<br>TCGTTCTTCGAGAAAAAGAGAAGATGCAATGAAGATGGGCGCCGATCACTACATTG<br>CTACATTAGAAGAAGGTGATTGGGGTGAAAAGTACTTTGACACCTTCGACCTGATTG<br>TAGTCTGTGCTTCCTCCCTTACCGACATTGACTTCAACATTATGCCAAAGGCTATGAA<br>GGTTGGTGGTAGAATTGTCTCAATCTCTATACCAGAACAACACGAAATGTTATCGCT |

TABLE 7-continued

| Disclosed Nucleic Acid and Amino Acid Sequences |
|---|
| AAAGCCATATGGCTTAAAGGCTGTCTCCATTTCTTACAGTGCTTTAGGTTCCATCAAA<br>GAATTGAACCAACTCTTGAAATTAGTCTCTGAAAAAGATATCAAAATTTGGGTGGAAA<br>CATTACCTGTTGGTGAAGCCGGCGTCCATGAAGCCTTCGAAAGGATGGAAAAGGGT<br>GACGTTAGATATAGATTTACCTTAGTCGGCTACGACAAAGAATTTTCAGACTAG |
| Protein sequence from alcohol dehydrogenase 7 (ADH7) of *Saccharomyces cerevisiae*<br>SEQ ID NO: 5<br>MLYPEKFQGIGISNAKDWKHPKLVSFDPKPFGDHDVDVEIEACGICGSDFHIAVGNWGP<br>VPENQILGHEIIGRVVKVGSKCHTGVKIGDRVGVGAQALACFECERCKSDNEQYCTNDH<br>VLTMWTPYKDGYISQGGFASHVRLHEHFAIQIPENIPSPLAAPLLCGGITVFSPLLRNGC<br>GPGKRVGIVGIGGIGHMGILLAKAMGAEVYAFSRGHSKREDSMKLGADHYIAMLEDKG<br>WTEQYSNALDLLVVCSSSLSKVNFDSIVKIMKIGGSIVSIAAPEVNEKLVLKPLGLMGVSIS<br>SSAIGSRKEIEQLLKLVSEKNVKIWVEKLPISEEGVSHAFTRMESGDVKYRFTLVDYDKK<br>FHK |
| DNA sequence encoding alcohol dehydrogenase 7 (ADH7) of *Saccharomyces cerevisiae*<br>SEQ ID NO: 6<br>ATGCTTTACCCAGAAAAATTTCAGGGCATCGGTATTTCCAACGCAAAGGATTGGAAG<br>CATCCTAAATTAGTGAGTTTTGACCCAAAACCCTTTGGCGATCATGACGTTGATGTT<br>GAAATTGAAGCCTGTGGTATCTGCGGATCTGATTTTCATATAGCCGTTGGTAATTGG<br>GGTCCAGTCCCAGAAAATCAAATCCTTGGACATGAAATAATTGGCCGCGTGGTGAA<br>GGTTGGATCCAAGTGCCACACTGGGGTAAAAATCGGTGACCGTGTTGGTGTTGGTG<br>CCCAAGCCTTGGCGTGTTTTGAGTGTGAACGTTGCAAAAGTGACAACGAGCAATACT<br>GTACCAATGACCACGTTTTGACTATGTGGACTCCTTACAAGGACGGCTACATTTCAC<br>AAGGAGGCTTTGCCTCCCACGTGAGGCTTCATGAACACTTTGCTATTCAAATACCAG<br>AAAATATTCCAAGTCCGCTAGCCGCTCCATTATTGTGTGGTGGTATTACAGTTTTCTC<br>TCCACTACTAAGAAATGGCTGTGGTCCAGGTAAGAGGGTAGGTATTGTTGGCATCG<br>GTGGTATTGGGCATATGGGGATTCTGTTGGCTAAAGCTATGGGAGCCGAGGTTTAT<br>GCGTTTTCGCGAGGCCACTCCAAGCGGGAGGATTCTATGAAACTCGGTGCTGATCA<br>CTATATTGCTATGTTGGAGGATAAAGGCTGGACAGAACAATACTCTAACGCTTTGGA<br>CCTTCTTGTCGTTTGCTCATCATCTTTGTCGAAAGTTAATTTTGACAGTATCGTTAAG<br>ATTATGAAGATTGGAGGCTCCATCGTTTCAATTGCTGCTCCTGAAGTTAATGAAAAG<br>CTTGTTTTAAAACCGTTGGGCCTAATGGGAGTATCAATCTCAAGCAGTGCTATCGGA<br>TCTAGGAAGGAAATCGAACAACTATTGAAATTAGTTTCCGAAAAGAATGTCAAAATAT<br>GGGTGGAAAAACTTCCGATCAGCGAAGAAGGCGTCAGCCATGCCTTTACAAGGATG<br>GAAAGCGGAGACGTCAAATACAGATTTACTTTGGTCGATTATGATAAGAAATTCCATA<br>AATAG |
| Protein sequence from Genes de Respuesta a Estres 2 (GRE2) of *Saccharomyces cerevisiae*<br>SEQ ID NO: 7<br>MSVFVSGANGFIAQHIVDLLLKEDYKVIGSARSQEKAENLTEAFGNNPKFSMEVVPDISK<br>LDAFDHVFQKHGKDIKIVLHTASPFCFDITDSERDLLIPAVNGVKGILHSIKKYAADSVERV<br>VLTSSYAAVFDMAKENDKSLTFNEESWNPATWESCQSDPVNAYCGSKKFAEKAAWEF<br>LEENRDSVKFELTAVNPVYVFGPQMFDKDVKKHLNTSCELVNSLMHLSPEDKIPELFGG<br>YIDVRDVAKAHLVAFQKRETIGQRLIVSEARFTMQDVLDILNEDFPVLKGNIPVGKPGSG<br>ATHNTLGATLDNKKSKKLLGFKFRNLKETIDDTASQILKFEGRI |
| DNA sequence encoding Genes de Respuesta a Estres 2 (GRE2) of *Saccharomyces cerevisiae*<br>SEQ ID NO: 8<br>ATGTCAGTTTTCGTTTCAGGTGCTAACGGGTTCATTGCCCAACACATTGTCGATCTC<br>CTGTTGAAGGAAGACTATAAGGTCATCGGTTCTGCCAGAAGTCAAGAAAAGGCCGA<br>GAATTTAACGGAGGCCTTTGGTAACAACCCAAAATTCTCCATGGAAGTTGTCCCAGA<br>CATATCTAAGCTGGACGCATTTGACCATGTTTTCCAAAAGCACGGCAAGGATATCAA<br>GATAGTTCTACATACGGCCTCTCCATTCTGCTTTGATATCACTGACAGTGAACGCGA<br>TTTATTAATTCCTGCTGTGAACGGTGTTAAGGGAATTCTCCACTCAATTAAAAAATAC<br>GCCGCTGATTCTGTAGAACGTGTAGTTCTCACCTCTTCTTATGCAGCTGTGTTCGAT<br>ATGGCAAAAGAAAACGATAAGTCTTTAACATTTAACGAAGAATCCTGGAACCCAGCT<br>ACCTGGGAGAGTTGCCAAAGTGACCCAGTTAACGCCTACTGTGGTTCTAAGAAGTTT<br>GCTGAAAAAGCAGCTTGGGAATTTCTAGAGGAGAATAGAGACTCTGTAAAATTCGAA<br>TTAACTGCCGTTAACCCAGTTTACGTTTTTGGTCCGCAAATGTTTGACAAAGATGTGA<br>AAAAACACTTGAACACATCTTGCGAACTCGTCAACAGCTTGATGCATTTATCACCAG<br>AGGACAAGATACCGGAACTATTTGGTGGATACATTGATGTTCGTGATGTTGCAAAGG<br>CTCATTTAGTTGCCTTCCAAAAGAGGGAAACAATTGGTCAAAGACTAATCGTATCGG<br>AGGCCAGATTTACTATGCAGGATGTTCTCGATATCCTTAACGAAGACTTCCCTGTTC<br>TAAAAGGCAATATTCCAGTGGGGAAACCAGGTTCTGGTGCTACCCATAACACCCTTG<br>GTGCTACTCTTGATAATAAAAAGAGTAAGAAATTGTTAGGTTTCAAGTTCAGGAACTT<br>GAAAGAGACCATTGACGACACTGCCTCCCAAATTTTAAAATTTGAGGGCAGAATATA<br>A |
| Protein sequence from Genes de Respuesta a Estres 3 (GRE3) of *Saccharomyces cerevisiae*<br>SEQ ID NO: 9<br>MSSLVTLNNGLKMPLVGLGCWKIDKKVCANQIYEAIKLGYRLFDGACDYGNEKEVGEGI<br>RKAISEGLVSRKDIFVVSKLWNNFHHPDHVKLALKKTLSDMGLDYLDLYYIHFPIAFKYVP |

TABLE 7-continued

| Disclosed Nucleic Acid and Amino Acid Sequences |
|---|

FEEKYPPGFYTGADDEKKGHITEAHVPIIDTYRALEECVDEGLIKSIGVSNFQGSLIQDLL
RGCRIKPVALQIEHHPYLTQEHLVEFCKLHDIQVVAYSSFGPQSFIEMDLQLAKTTPTLFE
NDVIKKVSQNHPGSTTSQVLLRWATQRGIAVIPKSSKKERLLGNLEIEKKFTLTEQELKDI
SALNANIRFNDPWTWLDGKFPTFA

DNA sequence encoding Genes de Respuesta a
Estres 3 (GRE3) of *Saccharomyces cerevisiae*
SEQ ID NO: 10
ATGTCTTCACTGGTTACTCTTAATAACGGTCTGAAAATGCCCCTAGTCGGCTTAGGG
TGCTGGAAAATTGACAAAAAAGTCTGTGCGAATCAAATTTATGAAGCTATCAAATTAG
GCTACCGTTTATTCGATGGTGCTTGCGACTACGGCAACGAAAAGGAAGTTGGTGAA
GGTATCAGGAAAGCCATCTCCGAAGGTCTTGTTTCTAGAAAGGATATATTTGTTGTTT
CAAAGTTATGGAACAATTTTCACCATCCTGATCATGTAAAATTAGCTTTAAAGAAGAC
CTTAAGCGATATGGGACTTGATTATTTAGACCTGTATTATATTCACTTCCCAATCGCC
TTCAAATATGTTCCATTTGAAGAGAAATACCCTCCAGGATTCTATACGGGCGCAGAT
GACGAGAAGAAAGGTCACATCACCGAAGCACATGTACCAATCATAGATACGTACCG
GGCTCTGGAAGAATGTGTTGATGAAGGCTTGATTAAGTCTATTGGTGTTTCCAACTT
TCAGGGAAGCTTGATTCAAGATTTATTACGTGGTTGTAGAATCAAGCCCGTGGCTTT
GCAAATTGAACACCATCCTTATTTGACTCAAGAACACCTAGTTGAGTTTTGTAAATTA
CACGATATCCAAGTAGTTGCTTACTCCTCCTTCGGTCCTCAATCATTCATTGAGATG
GACTTACAGTTGGCAAAAACCACGCCAACTCTGTTCGAGAATGATGTAATCAAGAAG
GTCTCACAAAACCATCCAGGCAGTACCACTTCCCAAGTATTGCTTAGATGGGCAACT
CAGAGAGGCATTGCCGTCATTCCAAAATCTTCCAAGAAGGAAAGGTTACTTGGCAAC
CTAGAAATCGAAAAAAAGTTCACTTTAACGGAGCAAGAATTGAAGGATATTTCTGCA
CTAAATGCCAACATCAGATTTAATGATCCATGGACCTGGTTGGATGGTAAATTCCCC
ACTTTTGCCTGA Protein sequence from carbonyl reductase (NADPH-dependent)
(YDR541C) of *Saccharomyces cerevisiae*
SEQ ID NO: 11
MSNTVLVSGASGFIALHILSQLLKQDYKVIGTVRSHEKEAKLLRQFQHNPNLTLEIVPDIS
HPNAFDKVLQKRGREIRYVLHTASPFHYDTTEYEKDLLIPALEGTKNILNSIKKYAADTVE
RVVVTSSCTAIITLAKMDDPSVVFTEESWNEATWESCQIDCINAYFASKKFAEKAAWEFT
KENEDHIKFKLTTVNPSLLFGPQLFDEDVHGHLNTSCEMINGLIHTPVNASVPDFHSIFID
VRDVALAHLYAFQKENTAGKRLVVTNGKFGNQDILDILNEDFPQLRGLIPLGKPGTGDQV
IDRGSTTDNSATRKILGFEFRSLHESVHDTAAQILKKQNRL DNA sequence encoding carbonyl reductase (NADPH-dependent)
(YDR541C) of *Saccharomyces cerevisiae*
SEQ ID NO: 12
ATGTCTAATACAGTTCTAGTTTCTGGCGCTTCAGGTTTTATTGCCTTGCATATCCTGT
CACAATTGTTAAAACAAGATTATAAGGTTATTGGAACTGTGAGATCCCATGAAAAAGA
AGCAAAATTGCTAAGACAATTTCAACATAACCCTAATTTAACTTTAGAAATTGTTCCG
GACATTTCTCATCCAAATGCTTTCGATAAGGTTCTGCAGAAACGTGGACGTGAGATT
AGGTATGTTCTACACACGGCCTCTCCTTTTCATTATGATACTACCGAATATGAAAAAG
ACTTATTGATTCCCGCGTTAGAAGGTACAAAAAACATCCTAAATTCTATCAAGAAATA
TGCAGCAGACACTGTAGAGCGTGTTGTTGTGACTTCTTCTTGTACTGCTATTATAAC
CCTTGCAAAGATGGACGATCCCAGTGTGGTTTTTACAGAAGAGAGTTGGAACGAAG
CAACCTGGGAAAGCTGTCAAATTGATGGGATAAATGCTTACTTTGCATCCAAGAAGT
TTGCTGAAAAGGCTGCCTGGGAGTTCACAAAAGAGAATGAAGATCACATCAAATTCA
AACTAACAACAGTCAACCCTTCTCTTCTTTTTGGTCCTCAACTTTTCGATGAAGATGT
GCATGGCCATTTGAATACTTCTTGCGAAATGATCAATGGCCTAATTCATACCCCAGT
AAATGCCAGTGTTCCTGATTTTCATTCCATTTTTATTGATGTAAGGGATGTGGCCCTA
GCTCATCTGTATGCTTTCCAGAAGGAAAATACCGCGGGTAAAAGATTAGTGGTAACT
AACGGTAAATTTGGAAACCAAGATATCCTGGATATTTTGAACGAAGATTTTCCACAAT
TAAGAGGTCTCATTCCTTTGGGTAAGCCTGGCACAGGTGATCAAGTCATTGACCGC
GGTTCAACTACAGATAATAGTGCAACGAGGAAAATACTTGGCTTTGAGTTCAGAAGT
TTACACGAAAGTGTCCATGATACTGCTGCCCAAATTTTGAAGAAGCAGAACAGATTA
TGA Protein sequence from YLR460C of *Saccharomyces cerevisiae*
SEQ ID NO: 13
MQVAIPETMKAVVIEDGKAVVKEGIPIPELEEGFVLIKTLAVAGNPTDWAHIDYKIGPQGSI
LGCDAAGQIVKLGPAVNPKDFSIGDYIYGFlHGSSVRFPSNGAFAEYSAISTVVAYKSPN
ELKFLGEDVLPAGPVRSLEGVATIPVSLTTAGLVLTYNLGLDLKWEPSTPQRKGPILLWG
GATAVGQSLIQLANKLNGFTKIIVVASRKHEKLLKEYGADELFDYHDIDVVEQIKHKYNNIS
YLVDCVANQDTLQQVYKCAADKQDATIVELKNLTEENVKKENRRQNVTIDIIRLYSIGGH
EVPFGNITLPADSEARKAAIKFIKFINPKINDGQIRHIPVRVYKNGLCDVPHILKDIKYGKNS
GEKLVAVLN DNA sequence encoding YLR460C of *Saccharomyces cerevisiae*
SEQ ID NO: 14
ATGCAAGTTGCAATTCCAGAAACCATGAAGGCTGTCGTCATTGAAGACGGTAAAGC
GGTTGTTAAAGAGGGCATTCCCATTCCTGAATTGGAAGAAGGATTCGTATTGATTAA
GACACTCGCTGTTGCTGGTAACCCCACTGATTGGGCACACATTGACTACAAGATCG
GGCCTCAAGGATCTATTCTGGGATGTGATGCTGCTGGCCAAATTGTCAAATTGGGC
CCAGCTGTCAATCCTAAAGACTTTTCTATCGGTGATTATATTTATGGGTTCATTCACG
GATCTTCCGTAAGGTTTCCTTCCAATGGTGCTTTTGCTGAATATTCTGCTATTTCAAC TABLE 7-continued

| Disclosed Nucleic Acid and Amino Acid Sequences |
|---|
| TGTGGTTGCCTACAAATCACCCAATGAACTCAAATTTTTGGGTGAGGATGTTCTACC<br>TGCCGGCCCTGTCAGGTCTTTGGAAGGTGTAGCCACTATCCCAGTGTCACTGACCA<br>CAGCCGGCTTGGTGTTGACCTATAACTTGGGCTTGGACCTGAAGTGGGAGCCATCA<br>ACCCCACAAAGAAAAGGCCCCATCTTATTATGGGGCGGTGCAACTGCAGTAGGTCA<br>GTCGCTCATCCAATTAGCCAATAAATTGAATGGCTTCACCAAGATCATTGTTGTGGC<br>TTCTCGGAAGCACGAAAAACTTTTGAAAGAATATGGTGCTGATGAATTATTTGATTAT<br>CATGATATTGACGTGGTAGAACAAATTAAACACAAGTACAACAATATCTCGTATTTAG<br>TCGACTGTGTCGCGAATCAAGATACGCTTCAACAAGTGTACAAATGTGCGGCCGATA<br>AACAGGATGCTACAATTGTTGAATTAAAAAATTTGACAGAAGAAAACGTCAAAAAAGA<br>GAACAGGAGACAAAACGTTACTATTGACATAATAAGGCTATATTCAATAGGTGGCCA<br>TGAAGTACCATTTGGAAACATTACTTTACCAGCCGACTCAGAAGCTAGGAAAGCTGC<br>AATAAAATTTATCAAATTCATCAATCCAAAGATTAATGATGGACAAATTCGCCATATTC<br>CAGTAAGGGTCTATAAGAACGGGCTTTGTGATGTTCCTCATATCCTAAAAGACATCA<br>AATATGGTAAGAACTCTGGTGAAAAACTCGTTGCCGTATTAAACTAG |
| Protein sequence from carbonyl reductase (NADPH-dependent)<br>(ARI1) of *Saccharomyces cerevisiae*<br>SEQ ID NO: 15<br>MTTDTTVFVSGATGFIALHIMNDLLKAGYTVIGSGRSQEKNDGLLKKFNNNPKLSMEIVE<br>DIAAPNAFDEVFKKHGKEIKIVLHTASPFHFETTNFEKDLLTPAVNGTKSILEAIKKYAADT<br>VEKVIVTSSTAALVTPTDMNKGDLVITEESWNKDTWDSCQANAVAAYCGSKKFAEKTA<br>WEFLKENKSSVKFTLSTINPGFVFGPQMFADSLKHGINTSSGIVSELIHSKVGGEFYNYC<br>GPFIDVRDVSKAHLVAIEKPECTGQRLVLSEGLFCCQEIVDILNEEFPQLKGKIATGEPAT<br>GPSFLEKNSCKFDNSKTKKLLGFQFYNLKDCIVDTAAQMLEVQNEA |
| DNA sequence encoding carbonyl reductase (NADPH-dependent)<br>(ARI1) of *Saccharomyces cerevisiae*<br>SEQ ID NO: 16<br>ATGACTACTGATACCACTGTTTTCGTTTCTGGCGCAACCGGTTTCATTGCTCTACACA<br>TTATGAACGATCTGTTGAAAGCTGGCTATACAGTCATCGGCTCAGGTAGATCTCAAG<br>AAAAAAATGATGGCTTGCTCAAAAAATTTAATAACAATCCCAAACTATCGATGGAAAT<br>TGTGGAAGATATTGCTGCTCCAAACGCCTTTGATGAAGTTTTCAAAAAACATGGTAA<br>GGAAATTAAGATTGTGCTACACACTGCCTCCCCATTCCATTTTGAAACTACCAATTTT<br>GAAAAGGATTTACTAACCCCTGCAGTGAACGGTACAAAATCTATCTTGGAAGCGATT<br>AAAAAATATGCTGCAGACACTGTTGAAAAAGTTATTGTTACTTCGTCTACTGCTGCTC<br>TGGTGACACCTACAGACATGAACAAAGGAGATTTGGTGATCACGGAGGAGAGTTGG<br>AATAAGGATACATGGGACAGTTGTCAAGCCAACGCCGTTGCCGCATATTGTGGCTC<br>GAAAAAGTTTGCTGAAAAAACTGCTTGGGAATTTCTTAAAGAAAACAAGTCTAGTGTC<br>AAATTCACACTATCCACTATCAATCCGGGATTCGTTTTTGGTCCTCAAATGTTTGCAG<br>ATTCGCTAAAACATGGCATAAATACCTCCTCAGGGATCGTATCTGAGTTAATTCATTC<br>CAAGGTAGGTGGAGAATTTTATAATTACTGTGGCCCATTTATTGACGTGCGTGACGT<br>TTCTAAAGCCCACCTAGTTGCAATTGAAAAACCAGAATGTACCGGCCAAAGATTAGT<br>ATTGAGTGAAGGTTTATTCTGCTGTCAAGAAATCGTTGACATCTTGAACGAGGAATT<br>CCCTCAATTAAAGGGCAAGATAGCTACAGGTGAACCTGCGACCGGTCCAAGCTTTTT<br>AGAAAAAAACTCTTGCAAGTTTGACAATTCTAAGACAAAAAAACTACTGGGATTCCAG<br>TTTTACAATTTAAAGGATTGCATAGTTGACACCGCGGCGCAAATGTTAGAAGTTCAAA<br>ATGAAGCCTAA |
| Protein sequence from carbonyl reductase (NADPH-dependent)<br>(YGL039W) of *Saccharomyces cerevisiae*<br>SEQ ID NO: 17<br>MTTEKTVVFVSGATGFIALHVVDDLLKTGYKVIGSGRSQEKNDGLLKKFKSNPNLSMEIV<br>EDIAAPNAFDKVFQKHGKEIKVVLHIASPVHFNTTDFEKDLLIPAVNGTKSILEAIKNYAAD<br>TVEKVVITSSVAALASPGDMKDTSFVVNEESWNKDTWESCQANAVSAYCGSKKFAEKT<br>AWDFLEENQSSIKFTLSTINPGFVFGPQLFADSLRNGINSSSAIIANLVSYKLGDNFYNYS<br>GPFIDVRDVSKAHLLAFEKPECAGQRLFLCEDMFCSQEALDILNEEFPQLKGKIATGEPG<br>SGSTFLTKNCCKCDNRKTKNLLGFQFNKFRDCIVDTASQLLEVQSKS |
| DNA sequence encoding carbonyl reductase (NADPH-dependent)<br>(YGL039W) of *Saccharomyces cerevisiae*<br>SEQ ID NO: 18<br>ATGACTACTGAAAAAACCGTTGTTTTTGTTTCTGGTGCTACTGGTTTCATTGCTCTAC<br>ACGTAGTGGACGATTTATTAAAAACTGGTTACAAGGTCATCGGTTCGGGTAGGTCCC<br>AAGAAAAGAATGATGGATTGCTGAAAAAATTTAAGAGCAATCCCAACCTTTCAATGG<br>AGATTGTCGAAGACATTGCTGCTCCAAACGCTTTTGACAAAGTTTTTCAAAAGCACG<br>GCAAAGAGATCAAGGTTGTCTTGCACATAGCTTCTCCGGTTCACTTCAACACCACTG<br>ATTTCGAAAAGGATCTGCTAATTCCTGCTGTGAATGGTACCAAGTCCATTCTAGAAG<br>CAATCAAAAATTATGCCGCAGACACAGTCGAAAAAGTCGTTATTACTTCTTCTGTTGC<br>TGCCCTTGCATCTCCCGGAGATATGAAGGACACTAGTTTCGTTGTCAATGAGGAAAG<br>TTGGAACAAAGATACTTGGGAAAGTTGTCAAGCTAACGCGGTTTCCGCATACTGTGG<br>TTCCAAGAAATTTGCTGAAAAAACTGCTTGGGATTTTCTCGAGGAAAACCAATCAAG<br>CATCAAATTTACGCTATCAACCATCAACCCAGGATTTGTTTTTGGCCCTCAGCTATTT<br>GCCGACTCTCTTAGAAATGGAATAAATAGCTCTTCAGCCATTATTGCCAATTTGGTTA<br>GTTATAAATTAGGCGACAATTTTTATAATTACAGTGGTCCTTTTATTGACGTTCGCGA<br>TGTTTCAAAAGCTCATTTACTTGCATTTGAGAAACCCGAATGCGCTGGCCAAAGACT<br>ATTCTTATGTGAAGATATGTTTTGCTCTCAAGAAGCGCTGGATATCTTGAATGAGGAA<br>TTTCCACAGTTAAAAGGCAAGATAGCAACTGGCGAACCTGGTAGCGGCTCAACCTTT<br>TTGACAAAAAACTGCTGCAAGTGCGACAACCGCAAAACCAAAAATTTATTAGGATTC |

TABLE 7-continued

Disclosed Nucleic Acid and Amino Acid Sequences

CAATTTAATAAGTTCAGAGATTGCATTGTCGATACTGCCTCGCAATTACTAGAAGTTC
AAAGTAAAAGCTAA

Protein sequence from YCR102C of *Saccharomyces cerevisiae*
SEQ ID NO: 19
MKAVVIEDGKAVVKEGVPIPELEEGFVLIKTLAVAGNPTDWAHIDYKVGPQGSILGCDAA
GQIVKLGPAVDPKDFSIGDYIYGFIHGSSVRFPSNGAFAEYSAISTVVAYKSPNELKFLGE
DVLPAGPVRSLEGAATIPVSLTTAGLVLTYNLGLNLKWEPSTPQRNGPILLWGGATAVG
QSLIQLANKLNGFTKIIVVASRKHEKLLKEYGADQLFDYHDIDVVEQIKHKYNNISYLVDCV
ANQNTLQQVYKCAADKQDATVVELTNLTEENVKKENRRQNVTIDRTRLYSIGGHEVPFG
GITFPADPEARRAATEFVKFINPKISDGQIHHIPARVYKNGLYDVPRILEDIKIGKNSGEKL
VAVLN DNA sequence encoding YCR102C of *Saccharomyces cerevisiae*
SEQ ID NO: 20
ATGAAGGCTGTCGTCATTGAAGACGGTAAAGCGGTTGTCAAAGAGGGCGTTCCCAT
TCCTGAATTGGAAGAAGGATTCGTATTGATTAAGACACTCGCTGTTGCTGGTAACCC
GACTGATTGGGCACACATTGACTACAAGGTCGGGCCTCAAGGATCTATTCTGGGAT
GTGACGCTGCCGGCCAAATTGTCAAATTGGGCCCAGCCGTCGATCCTAAAGACTTT
TCTATTGGTGATTATATTTATGGGTTCATTCACGGATCTTCCGTAAGGTTTCCTTCCA
ATGGTGCTTTTGCTGAATATTCTGCTATTTCAACTGTGGTTGCCTACAAATCACCCAA
TGAACTCAAATTTTTGGGTGAAGATGTTCTACCTGCCGGCCCTGTCAGGTCTTTGGA
AGGGGCAGCCACTATCCCAGTGTCACTGACCACAGCTGGCTTGGTGTTGACCTATA
ACTTGGGCTTGAACCTGAAGTGGGAGCCATCAACCCCACAAAGAAACGGCCCCATC
TTATTATGGGGCGGTGCAACTGCAGTAGGTCAGTCGCTCATCCAATTAGCCAATAAA
TTGAATGGCTTCACCAAGATCATTGTTGTGGCTTCTCGGAAACACGAAAAACTGTTG
AAAGAATATGGTGCTGATCAACTATTTGATTACCATGATATTGACGTGGTAGAACAAA
TTAAACACAAGTACAACAATATCTCGTATTTAGTCGACTGTGTCGCGAATCAAAATAC
GCTTCAACAAGTGTACAAATGTGCGGCCGATAAACAGGATGCTACCGTTGTCGAATT
AACTAATTTGACAGAAGAAAACGTCAAAAAGGAGAATAGGAGGCAAAATGTCACTAT
TGACAGAACAAGACTGTATTCAATAGGCGGCCATGAAGTACCATTTGGTGGCATTAC
TTTCCCTGCTGACCCAGAAGCCAGGAGAGCTGCCACCGAATTCGTCAAGTTCATCA
ATCCAAAGATTAGTGATGGGCAAATTCACCATATTCCAGCAAGGGTCTATAAGAACG
GGCTTTACGATGTTCCTCGTATCCTGGAAGACATTAAAATCGGTAAGAACTCTGGTG
AAAAACTAGTTGCCGTATTAAACTAG Protein sequence from pyridoxine 4-dehydrogenase (YPR127W) of *Saccharomyces cerevisiae*
SEQ ID NO: 21
MSVADLKNNIHKLDTGYGLMSLTWRAEPIPQSQAFEAMHRVVELSRERGHKAFFNVGE
FYGPDFINLSYVHDFFAKYPDLRKDVVISCKGGADNATLTPRGSHDDVVQSVKNSVSAI
GGYIDIFEVARIDTSLCTKGEVYPYESFEALAEMISEGVIGGISLSEVNEEQIRAIHKDWGK
FLTCVEVELSLFSNDILHNGIAKTCAELGLSIICYSPLGRGLLTGQLKSNADIPEGDFRKSL
KRFSDESLKKNLTLVRFLQEEIVDKRPQNNSITLAQLALGWVKHWNKVPEYSGAKFIPIP
SGSSISKVNENFDEQKTKLTDQEFNAINKYLTTFHTVGDRYEMA DNA sequence encoding pyridoxine 4-dehydrogenase (YPR127W) of *Saccharomyces cerevisiae*
SEQ ID NO: 22
ATGTCTGTCGCCGATTTGAAAAACAACATCCACAAGTTAGATACTGGCTATGGTTTAA
TGAGTTTGACTTGGAGAGCCGAGCCTATCCCTCAGTCGCAGGCTTTCGAGGCCATG
CACAGAGTGGTTGAGTTATCCAGAGAACGTGGGCACAAGGCCTTTTTCAACGTTGG
TGAATTCTATGGTCCCGATTTTATTAATTTGTCGTATGTTCACGACTTCTTTGCGAAAT
ACCCAGATTTGAGAAAGGATGTGGTTATCAGTTGTAAAGGTGGTGCAGACAATGCTA
CCTTAACCCCCAGAGGCAGTCACGATGATGTTGTACAAAGCGTAAAGAATTCAGTTA
GTGCTATTGGTGGCTACATCGACATCTTCGAAGTCGCAAGAATCGACACTTCCCTAT
GCACGAAAGGAGAGGTCTACCCCTACGAATCGTTCGAAGCGCTTGCTGAGATGATC
TCCGAAGGCGTTATTGGCGGTATTTCATTAAGTGAAGTTAATGAAGAGCAAATTAGA
GCTATTCACAAGGATTGGGGAAAGTTTTTGACCTGCGTTGAAGTGGAACTTTCTTTG
TTCAGTAATGACATTTTACACAACGGAATTGCTAAAACATGTGCTGAATTGGGGTTGT
CCATCATCTGCTACTCCCCACTGGGCAGAGGATTGTTGACAGGTCAATTGAAGTCAA
ACGCTGATATCCCTGAGGGTGACTTTAGAAAGTCGTTAAAGAGATTTAGCGACGAGT
CTTTGAAAAAAAACCTGACCTTGGTCAGGTTTCTACAGGAAGAAATAGTCGACAAGC
GCCCACAAAACAACTCCATTACTCTTGCACAACTGGCTTTGGGATGGGTTAAGCACT
GGAACAAAGTTCCGGAATACAGTGGCGCCAAATTTATCCCAATTCCAAGTGGCTCTT
CTATTTCCAAGGTTAATGAAAACTTTGATGAACAGAAAACCAAACTTACCGATCAAGA
GTTCAATGCCATTAACAAATATTTGACTACTTTCCATACTGTTGGTGACAGATACGAA
ATGGCGTAA DNA sequence encoding norcoclaurine synthase of *Coptis japonica*, codon optimized for *S. cerevisiae* with HindIII and SacII cloning sites
SEQ ID NO: 23
AAGCTTAAAATGAGAATGGAAGTCGTCTTGGTCGTTTTCTTGATGTTCATTGGTACTA
TCAACTGCGAAAGATTGATCTTCAATGGTAGACCTTTGTTGCACAGAGTTACCAAAG
AAGAAACCGTTATGTTGTACCACGAATTGGAAGTTGCTGCTTCTGCTGATGAAGTTT
GGTCTGTTGAAGGTTCTCCAGAATTGGGTTTACATTTGCCAGATTTGTTGCCAGCTG
GTATTTTTGCCAAGTTCGAAATTACTGGTGATGGTGGTGAAGGTTCCATTTTGGATAT TABLE 7-continued

| Disclosed Nucleic Acid and Amino Acid Sequences |
|---|
| GACTTTTCCACCAGGTCAATTCCCACATCATTACAGAGAAAAGTTCGTCTTTTTCGAC<br>CACAAGAACAGATACAAGTTGGTCGAACAAATCGATGGTGATTTCTTCGATTTGGGT<br>GTTACTTACTACATGGACACCATTAGAGTTGTTGCTACTGGTCCAGATTCTTGCGTTA<br>TTAAGTCTACTACTGAATACCACGTCAAGCCAGAATTTGCTAAAATCGTTAAGCCATT<br>GATCGATACCGTTCCATTGGCTATTATGTCTGAAGCTATTGCCAAGGTTGTCTTGGA<br>AAACAAACACAAGTCATCTGAATGAAAGACTCCGCGG |
| Protein sequence from norcoclaurine synthase of *Coptis japonica*<br>SEQ ID NO: 24<br>MRMEVVLVVFLMFIGTINCERLIFNGRPLLHRVTKEETVMLYHELEVAASADEVWSVEGS<br>PELGLHLPDLLPAGIFAKFEITGDGGEGSILDMTFPPGQFPHHYREKFVFFDHKNRYKLV<br>EQIDGDFFDLGVTYYMDTIRVVATGPDSCVIKSTTEYHVKPEFAKIVKPLIDTVPLAIMSEA<br>IAKVVLENKHKSSE |
| Protein sequence from Aryl-alcohol Dehydrogenase 3 (AAD3) of<br>*Saccharomyces cerevisiae*<br>SEQ ID NO: 25<br>MIGSASDSSSKLGRLRFLSETAAIKVSPLILGEVSYDGARSDFLKSMNKNRAFELLDTFYE<br>AGGNFIDAANNCQNEQSEEWIGEWIQSRRLRDQIVIATKFIKSDKKYKAGESNTANYCGN<br>HKRSLHVSVRDSLRKLQTDWIDILYVHWWDYMSSIEEFMDSLHILVQQGKVLYLGVSDTP<br>AWVVSAANYYATSYGKTPFSIYQGKWNVLNRDFERDIIPMARHFGMALAPWDVMGGGR<br>FQSKKAMEERRKNGEGIRSFVGASEQTDAEIKISEALAKIAEEHGTESVTAIAIAYVRSKAK<br>NFFPSVEGGKIEDLKENIKALSIDLTPDNIKYLESIVPFDIGFPNNFIVLNSLTQKYGTNNV |
| DNA sequence encoding Aryl-alcohol Dehydrogenase 3 (AAD3) of<br>*Saccharomyces cerevisiae*<br>SEQ ID NO: 26<br>ATGATTGGGTCCGCGTCCGACTCATCTAGCAAGTTAGGACGCCTCCGATTTCTTTCT<br>GAAACTGCCGCTATTAAAGTATCCCCGTTAATCCTAGGAGAAGTCTCATACGATGGA<br>GCACGTTCGGATTTTCTCAAATCAATGAACAAGAATCGAGCTTTTGAATTGCTTGATA<br>CTTTTTACGAGGCAGGTGGAAATTTCATTGATGCCGCAAACAACTGCCAAAACGAGC<br>AATCAGAAGAATGGATTGGTGAATGGATACAGTCCAGAAGGTTACGTGATCAAATTG<br>TCATTGCAACCAAGTTTATAAAAAGCGATAAAAAGTATAAAGCAGGTGAAAGTAACAC<br>TGCCAACTACTGTGGTAATCACAAGCGTAGTTTACATGTGAGTGTGAGGGATTCTCT<br>CCGCAAATTGCAAACTGATTGGATTGATATACTTTACGTTCACTGGTGGGATTATATG<br>AGTTCAATCGAAGAATTTATGGATAGTTTGCATATTCTGGTCCAGCAGGGCAAGGTC<br>CTCTATTTGGGTGTATCTGATACACCTGCTTGGGTTGTTTCTGCGGCAAACTACTACG<br>CTACATCTTATGGTAAAACTCCCTTTAGTATCTACCAAGGTAAATGGAACGTGTTGAA<br>CAGAGATTTTGAGCGTGATATTATTCCAATGGCTAGGCATTTCGGTATGGCCCTCGC<br>CCCATGGGATGTCATGGGAGGTGGAAGATTTCAGAGTAAAAAAGCAATGGAGGAAC<br>GGAGGAAGAATGGAGAGGGTATTCGTTCTTTCGTTGGCGCCTCCGAACAAACAGAT<br>GCAGAAATCAAGATTAGTGAAGCATTGGCCAAGATTGCTGAGGAACATGGCACTGAG<br>TCTGTTACTGCTATTGCTATTGCCTATGTTCGCTCTAAGGCGAAAAATTTTTTTCCGTC<br>GGTTGAAGGAGGAAAAATTGAGGATCTCAAAGAGAACATTAAGGCTCTCAGTATCGA<br>TCTAACGCCAGACAATATAAAATACTTAGAAAGTATAGTTCCTTTTGACATCGGATTTC<br>CTAATAATTTTATCGTGTTAAATTCCTTGACTCAAAAATATGGTACGAATAATGTTTAG |
| Protein sequence from Aryl-alcohol Dehydrogenase 4 (AAD4) of<br>*Saccharomyces cerevisiae*<br>SEQ ID NO: 27<br>MGSMNKEQAFELLDAFYEAGGNCIDTANSYQNEESEIWIGEWMKSRKLRDQIVIATKFTG<br>DYKKYEVGGGKSANYCGNHKHSLHVSVRDSLRKLQTDWIDILYVHVWVDYMSSIEEVMD<br>SLHILVQQGKVLYLGVSDTPAWVVSAANYYATSHGKTPFSIYQGKWNVLNRDFERDIIPM<br>ARHFGMALAPWDVMGGGRFQSKKAMEERKKNGEGLRTVSGTSKQTDKEVKISEALAKV<br>AEEHGTESVTAIAIAYVRSKAKNVFPLVGGRKIEHLKQNIEALSIKLTPEQIEYLESIIPFDVG<br>FPTNFIGDDPAVTKKASLLTAMSAQISFD |
| DNA sequence encoding Aryl-alcohol Dehydrogenase 4 (AAD4) of<br>*Saccharomyces cerevisiae*<br>SEQ ID NO: 28<br>ATGGGCTCTATGAATAAGGAACAGGCTTTTGAACTTCTTGATGCTTTTTATGAAGCAG<br>GAGGTAATTGCATTGATACTGCAAACAGTTACCAAAATGAAGAGTCAGAGATTTGGAT<br>AGGTGAATGGATGAAATCAAGAAAGTTGCGTGACCAAATTGTAATTGCCACCAAGTTT<br>ACCGGAGATTATAAGAAGTATGAAGTAGGTGGCGGTAAAAGTGCCAACTATTGTGGT<br>AATCACAAGCATAGTTTACATGTGAGTGTGAGGGATTCTCTCCGCAAATTGCAAACTG<br>ATTGGATTGATATACTTTACGTTCACTGGTGGGATTATATGAGTTCAATCGAAGAAGT<br>TATGGATAGTTTGCATATTTTAGTTCAGCAGGGCAAAGTCCTCTATTTGGGTGTGTCT<br>GATACACCTGCTTGGGTTGTTTCTGCGGCAAACTACTACGCCACATCTCATGGGAAA<br>ACTCCTTTTAGTATCTATCAAGGTAAATGGAATGTGTTGAACAGGGACTTTGAGCGCG<br>ATATCATTCCAATGGCCAGACATTTTGGTATGGCTCTAGCCCCATGGGATGTTATGG<br>GAGGTGGAAGATTTCAGAGTAAAAAAGCAATGGAGGAACGGAAGAAGAATGGAGAG<br>GGTCTGCGTACTGTTTCGGGTACTTCTAAACAGACGGATAAAGAGGTTAAGATCAGT<br>GAAGCATTGGCCAAGGTTGCTGAGGAACATGGCACTGAGTCTGTTACTGCTATTGCT<br>ATTGCCTATGTTCGCTCTAAGGCGAAAAATGTTTTCCCATTGGTTGGTGGAAGGAAAA<br>TTGAACACCTCAAACAGAACATTGAGGCTTTAAGTATCAAACTGACACCAGAACAGAT<br>AGAATACTTAGAAAGTATTATTCCTTTTGATGTTGGTTTTCCTACTAATTTTATCGGTG<br>ATGATCCGGCTGTTACCAAGAAGGCTTCACTTCTCACGGCAATGTCTGCGCAGATTT<br>CCTTCGATTAA |

TABLE 7-continued

| Disclosed Nucleic Acid and Amino Acid Sequences |
|---|
| Protein sequence from Mitochondrial alcohol dehydrogenase isozyme III (ADH3) of *Saccharomyces cerevisiae*<br>SEQ ID NO: 29<br>MLRTSTLFTRRVQPSLFSRNILRLQSTAAIPKTQKGVIFYENKGKLHYKDIPVPEPKPNEIL<br>INVKYSGVCHTDLHAWHGDWPLPVKLPLVGGHEGAGVVVKLGSNVKGWKVGDLAGIK<br>WLNGSCMTCEFCESGHESNCPDADLSGYTHDGSFQQFATADAIQAAKIQQGTDLAEVA<br>PILCAGVTVYKALKEADLKAGDWVAISGAAGGLGSLAVQYATAMGYRVLGIDAGEEKEK<br>LFKKLGGEVFIDFTKTKNMVSDIQEATKGGPHGVINVSVSEAAISLSTEYVRPCGTVVLV<br>GLPANAYVKSEVFSHVVKSINIKGSYVGNRADTREALDFFSRGLIKSPIKIVGLSELPKVY<br>DLMEKGKILGRYVVDTSK |
| DNA sequence encoding Mitochondrial alcohol dehydrogenase isozyme III (ADH3) of *Saccharomyces cerevisiae*<br>SEQ ID NO: 30<br>ATGTTGAGAACGTCAACATTGTTCACCAGGCGTGTCCAACCAAGCCTATTTTCTAGA<br>AACATTCTTAGATTGCAATCCACAGCTGCAATCCCTAAGACTCAAAAAGGTGTCATCT<br>TTTATGAGAATAAGGGGAAGCTGCATTACAAAGATATCCCTGTCCCCGAGCCTAAGC<br>CAAATGAAATTTTAATCAACGTTAAATATTCTGGTGTATGTCACACCGATTTACATGC<br>TTGGCACGGCGATTGGCCATTACCTGTTAAACTACCATTAGTAGGTGGTCATGAAGG<br>TGCTGGTGTAGTTGTCAAACTAGGTTCCAATGTCAAGGGCTGGAAAGTCGGTGATTT<br>AGCAGGTATCAAATGGCTGAACGGTTCTTGTATGACATGCGAATTCTGTGAATCAGG<br>TCATGAATCAAATTGTCCAGATGCTGATTTATCTGGTTACACTCATGATGGTTCTTTC<br>CAACAATTTGCGACCGCTGATGCTATTCAAGCCGCCAAAATTCAACAGGGTACCGAC<br>TTGGCCGAAGTAGCCCCAATATTATGTGCTGGTGTTACTGTATATAAAGCACTAAAA<br>GAGGCAGACTTGAAAGCTGGTGACTGGGTTGCCATCTCTGGTGCTGCAGGTGGCTT<br>GGGTTCCTTGGCCGTTCAATATGCAACTGCGATGGGTTACAGAGTTCTAGGTATTGA<br>TGCAGGTGAGGAAAAGGAAAAACTTTTCAAGAAATTGGGGGGTGAAGTATTCATCGA<br>CTTTACTAAAACAAAGAATATGGTTTCTGACATTCAAGAAGCTACCAAAGGTGGCCC<br>TCATGGTGTCATTAACGTTTCCGTTTCTGAAGCCGCTATTTCTCTATCTACGGAATAT<br>GTTAGACCATGTGGTACCGTCGTTTTGGTTGGTTTGCCCGCTAACGCCTACGTTAAA<br>TCAGAGGTATTCTCTCATGTGGTGAAGTCCATCAATATCAAGGGTTCTTATGTTGGTA<br>ACAGAGCTGATACGAGAGAAGCCTTAGACTTCTTTAGCAGAGGTTTGATCAAATCAC<br>CAATCAAAATTGTTGGATTATCTGAATTACCAAAGGTTTATGACTTGATGGAAAAGGG<br>CAAGATTTTGGGTAGATACGTCGTCGATACTAGTAAATAA |
| Protein sequence from Alcohol dehydrogenase isoenzyme type IV (ADH4) of *Saccharomyces cerevisiae*<br>SEQ ID NO: 31<br>MSSVTGFYIPPISFFGEGALEETADYIKNKDYKKALIVTDPGIAAIGLSGRVQKMLEERDL<br>NVAIYDKTQPNPNIANVTAGLKVLKEQNSEIVVSIGGGSAHDNAKAIALLATNGGEIGDYE<br>GVNQSKKAALPLFAINTTAGTASEMTRFTIISNEEKKIKMAIIDNNVTPAVAVNDPSTMFGL<br>PPALTAATGLDALTHCIEAYVSTASNPITDACALKGIDLINESLVAAYKDGKDKKARTDMC<br>YAEYLAGMAFNNASLGYVHALAHQLGGFYHLPHGVCNAVLLPHVQEANMQCPKAKKRL<br>GEIALHFGASQEDPEETIKALHVLNRTMNIPRNLKELGVKTEDFEILAEHAMHDACHLTN<br>PVQFTKEQVVAIIKKAYEY |
| DNA sequence encoding Alcohol dehydrogenase isoenzyme type IV (ADH4) of *Saccharomyces cerevisiae*<br>SEQ ID NO: 32<br>ATGTCTTCCGTTACTGGGTTTTACATTCCACCAATCTCTTTCTTTGGTGAAGGTGCTTT<br>AGAAGAAACCGCTGATTACATCAAAAACAAGGATTACAAAAAGGCTTTGATCGTTACT<br>GATCCTGGTATTGCAGCTATTGGTCTCTCCGGTAGAGTCCAAAAGATGTTGGAAGAA<br>CGTGACTTAAACGTTGCTATCTATGACAAAACTCAACCAAACCCAAATATTGCCAATG<br>TCACAGCTGGTTTGAAGGTTTTGAAGGAACAAAACTCTGAAATTGTTGTTTCCATTGG<br>TGGTGGTTCTGCTCACGACAATGCTAAGGCCATTGCTTTATTGGCTACTAACGGTGG<br>GGAAATCGGAGACTATGAAGGTGTCAATCAATCTAAGAAGGCTGCTTTACCACTATTT<br>GCCATCAACACTACTGCTGGTACTGCTTCCGAAATGACCAGATTCACTATTATCTCTA<br>ATGAAGAAAAGAAAATCAAGATGGCTATCATTGACAACAACGTCACTCCAGCTGTTGC<br>TGTCAACGATCCATCTACCATGTTTGGTTTGCCACCTGCTTTGACTGCTGCTACTGGT<br>CTAGATGCTTTGACTCACTGTATCGAAGCTTATGTTTCCACCGCCTCTAACCCAATCA<br>CCGATGCCTGTGCTTTGAAGGGTATTGATTTGATCAATGAAAGCTTAGTCGCTGCATA<br>CAAAGACGGTAAAGACAAGAAGGCCAGAACTGACATGTGTTACGCTGAATACTTGGC<br>AGGTATGGCTTTCAACAATGCTTCTCTAGGTTATGTTCATGCCCTTGCTCATCAACTT<br>GGTGGTTTCTACCACTTGCCTCATGGTGTTTGTAACGCTGTCTTGTTGCCTCATGTTC<br>AAGAGGCCAACATGCAATGTCCAAAGGCCAAGAAGAGATTAGGTGAAATTGCTTTGC<br>ATTTCGGTGCTTCTCAAGAAGATCCAGAAGAAACCATCAAGGCTTTGCACGTTTTAAA<br>CAGAACCATGAACATTCCAAGAAACTTGAAAGAATTAGGTGTTAAAACCGAAGATTTT<br>GAAATTTTGGCTGAACACGCCATGCATGATGCCTGCCATTTGACTAACCCAGTTCAAT<br>TCACCAAAGAACAAGTGGTTGCCATTATCAAGAAAGCCTATGAATATTAA |
| Protein sequence from Cytosolic aldehyde dehydrogenase (ALD6) of *Saccharomyces cerevisiae*<br>SEQ ID NO: 33<br>MTKLHFDTAEPVKITLPNGLTYEQPTGLFINNKFMKAQDGKTYPVEDPSTENTVCEVSSA<br>TTEDVEYAIECADRAFHDTEWATQDPRERGRLLSKLADELESQIDLVSSIEALDNGKTLA<br>LARGDVTIAINCLRDAAAYADKVNGRTINTGDGYMNFTTLEPIGVCGQIIPWNFPIMLA<br>WKIAPALAMGNVCILKPAAVTPLNALYFASLCKKVGIPAGVVNIVPGPGRTVGAALTNDP |

TABLE 7-continued

| Disclosed Nucleic Acid and Amino Acid Sequences |
|---|
| RIRKLAFTGSTEVGKSVAVDSSESNLKKITLELGGKSAHLVFDDANIKKTLPNLVNGIFKN<br>AGQICSSGSRIYVQEGIYDELLAAFKAYLETEIKVGNPFDKANFQGAITNRQQFDTIMNYI<br>DIGKKEGAKILTGGEKVGDKGYFIRPTVFYDVNEDMRIVKEEIFGPVVTVAKFKTLEEGVE<br>MANSSEFGLGSGIETESLSTGLKVAKMLKAGTVWINTYNDFDSRVPFGGVKQSGYGRE<br>MGEEVYHAYTEVKAVRIKL |
| DNA sequence encoding Cytosolic aldehyde dehydrogenase (ALD6) of *Saccharomyces cerevisiae*<br>SEQ ID NO: 34<br>ATGACTAAGCTACACTTTGACACTGCTGAACCAGTCAAGATCACACTTCCAAATGGT<br>TTGACATACGAGCAACCAACCGGTCTATTCATTAACAACAAGTTTATGAAAGCTCAA<br>GACGGTAAGACCTATCCCGTCGAAGATCCTTCCACTGAAAACACCGTTTGTGAGGT<br>CTCTTCTGCCACCACTGAAGATGTTGAATATGCTATCGAATGTGCCGACCGTGCTTT<br>CCACGACACTGAATGGGCTACCCAAGACCCAAGAGAAAGAGGCCGTCTACTAAGTA<br>AGTTGGCTGACGAATTGGAAAGCCAAATTGACTTGGTTTCTTCCATTGAAGCTTTGG<br>ACAATGGTAAAACTTTGGCCTTAGCCCGTGGGGATGTTACCATTGCAATCAACTGTC<br>TAAGAGATGCTGCTGCCTATGCCGACAAAGTCAACGGTAGAACAATCAACACCGGT<br>GACGGCTACATGAACTTCACCACCTTAGAGCCAATCGGTGTCTGTGGTCAAATTATT<br>CCATGGAACTTTCCAATAATGATGTTGGCTTGGAAGATCGCCCCAGCATTGGCCATG<br>GGTAACGTCTGTATCTTGAAACCCGCTGCTGTCACACCTTTAAATGCCCTATACTTT<br>GCTTCTTTATGTAAGAAGGTTGGTATTCCAGCTGGTGTCGTCAACATCGTTCCAGGT<br>CCTGGTAGAACTGTTGGTGCTGCTTTGACCAACGACCCAAGAATCAGAAAGCTGGC<br>TTTTACCGGTTCTACAGAAGTCGGTAAGAGTGTTGCTGTCGACTCTTCTGAATCTAA<br>CTTGAAGAAAATCACTTTGGAACTAGGTGGTAAGTCCGCCCATTTGGTCTTTGACGA<br>TGCTAACATTAAGAAGACTTTACCAAATCTAGTAAACGGTATTTTCAAGAACGCTGGT<br>CAAATTTGTTCCTCTGGTTCTAGAATTTACGTTCAAGAAGGTATTTACGACGAACTAT<br>TGGCTGCTTTCAAGGCTTACTTGGAAACCGAAATCAAAGTTGGTAATCCATTTGACA<br>AGGCTAACTTCCAAGGTGCTATCACTAACCGTCAACAATTCGACACAATTATGAACT<br>ACATCGATATCGGTAAGAAAGAAGGCGCCAAGATCTTAACTGGTGGCGAAAAAGTT<br>GGTGACAAGGGTTACTTCATCAGACCAACCGTTTTCTACGATGTTAATGAAGACATG<br>AGAATTGTTAAGGAAGAAATTTTTGGACCAGTTGTCACTGTCGCAAAGTTCAAGACTT<br>TAGAAGAAGGTGTCGAAATGGCTAACAGCTCTGAATTCGGTCTAGGTTCTGGTATCG<br>AAACAGAATCTTTGAGCACAGGTTTGAAGGTGGCCAAGATGTTGAAGGCCGGTACC<br>GTCTGGATCAACACATACAACGATTTTGACTCCAGAGTTCCATTCGGTGGTGTTAAG<br>CAATCTGGTTACGGTAGAGAAATGGGTGAAGAAGTCTACCATGCATACACTGAAGTA<br>AAAGCTGTCAGAATTAAGTTGTAA |
| Protein sequence from NAD-dependent (R,R)-butanediol dehydrogenase (BDH1) of *Saccharomyces cerevisiae*<br>SEQ ID NO: 35<br>MRALAYFKKGDIHFTNDIPRPEIQTDDEVIIDVSWCGICGSDLHEYLDGPIFMPKDGECHK<br>LSNAALPLAMGHEMSGIVSKVGPKVTKVKVGDHVVVDAASSCADLHCWPHSKFYNSKP<br>CDACQRGSENLCTHAGFVGLGVISGGFAEQVVVSQHHIIPVPKEIPLDVAALVEPLSVTW<br>HAVKISGFKKGSSALVLGAGPIGLCTILVLKGMGASKIVVSEIAERRIEMAKKLGVEVFNP<br>SKHGHKSIEILRGLTKSHDGFDYSYDCSGIQVTFETSLKALTFKGTATNIAVWGPKPVPF<br>QPMDVTLQEKVMTGSIGYVVEDFEEVVRAIHNGDIAMEDCKQLITGKQRIEDGWEKGFQ<br>ELMDHKESNVKILLTPNNHGEMK |
| DNA sequence encoding NAD-dependent (R,R)-butanediol dehydrogenase (BDH1) of *Saccharomyces cerevisiae*<br>SEQ ID NO: 36<br>ATGAGAGCTTTGGCATATTTCAAGAAGGGTGATATTCACTTCACTAATGATATCCCTA<br>GGCCAGAAATCCAAACCGACGATGAGGTTATTATCGACGTCTCTTGGTGTGGGATTT<br>GTGGCTCGGATCTTCACGAGTACTTGGATGGTCCAATCTTCATGCCTAAAGATGGAG<br>AGTGCCATAAATTATCCAACGCTGCTTTACCTCTGGCAATGGGCCATGAGATGTCAG<br>GAATTGTTTCCAAGGTTGGTCCTAAAGTGACAAAGGTGAAGGTTGGCGACCACGTGG<br>TCGTTGATGCTGCCAGCAGTTGTGCGGACCTGCATTGCTGGCCACACTCCAAATTTT<br>ACAATTCCAAACCATGTGATGCTTGTCAGAGGGGCAGTGAAAATCTATGTACCCACG<br>CCGGTTTTGTAGGACTAGGTGTGATCAGTGGTGGCTTTGCTGAACAAGTCGTAGTCT<br>CTCAACATCACATTATCCCGGTTCCAAAGGAAATTCCTCTAGATGTGGCTGCTTTAGT<br>TGAGCCTCTTTCTGTCACCTGGCATGCTGTTAAGATTTCTGGTTTCAAAAAAGGCAGT<br>TCAGCCTTGGTTCTTGGTGCAGGTCCCATTGGGTTGTGTACCATTTTGGTACTTAAG<br>GGAATGGGGGCTAGTAAAATTGTAGTGTCTGAAATTGCAGAGAGAAGAATAGAAATG<br>GCCAAGAAACTGGGCGTTGAGGTGTTCAATCCCTCCAAGCACGGTCATAAATCTATA<br>GAGATACTACGTGGTTTGACCAAGAGCCATGATGGGTTTGATTACAGTTATGATTGTT<br>CTGGTATTCAAGTTACTTTCGAAACCTCTTTGAAGGCATTAACATTCAAGGGGACAGC<br>CACCAACATTGCAGTTTGGGGTCCAAAACCTGTCCCATTCCAACCAATGGATGTGAC<br>TCTCCAAGAGAAAGTTATGACTGGTTCGATCGGCTATGTTGTCGAAGACTTCGAAGA<br>AGTTGTTCGTGCCATCCACAACGGAGACATCGCCATGGAAGATTGTAAGCAACTAAT<br>CACTGGTAAGCAAAGGATTGAGGACGGTTGGGAAAAGGGATTCCAAGAGTTGATGG<br>ATCACAAGGAATCCAACGTTAAGATTCTATTGACGCCTAACAATCACGGTGAAATGAA<br>GTAA |

TABLE 7-continued

| Disclosed Nucleic Acid and Amino Acid Sequences |
|---|

Protein sequence from Putative medium-chain alcohol dehydrogenase with similarity to BDH2 (BDH2) of *Saccharomyces cerevisiae*

SEQ ID NO: 37

MRALAYFGKGNIRFTNHLKEPHIVAPDELVIDIEWCGICGTDLHEYTDGPIFFPEDGHTHE
ISHNPLPQAMGHEMAGTVLEVGPGVKNLKVGDKVVVEPTGTCRDRYRWPLSPNVDKE
WCAACKKGYYNICSYLGLCGAGVQSGGFAERVVMNESHCYKVPDFVPLDVAALIQPLA
VCWHAIRVCEFKAGSTALIIGAGPIGLGTILALNAAGCKDIVVSEPAKVRRELAEKMGARV
YDPTAHAAKESIDYLRSIADGGDGFDYTFDCSGLEVTLNAAIQCLTFRGTAVNLAMWGH
HKIQFSPMDITLHERKYTGSMCYTHHDFEAVIEALEEGRIDIDRARHMITGRVNIEDGLDG
AIMKLINEKESTIKIILTPNNHGELNREADNEKKEISELSSRKDQERLRESINEAKLRHT

DNA sequence encoding Putative medium-chain alcohol dehydrogenase with similarity to BDH2 (BDH2) of *Saccharomyces cerevisiae*

SEQ ID NO: 38

ATGAGAGCCTTAGCGTATTTCGGTAAAGGTAACATCAGATTCACCAACCATTTAAAGG
AGCCACATATTGTGGCGCCCGATGAGCTTGTGATTGATATCGAATGGTGTGGTATTT
GCGGTACGGACCTGCATGAGTACACAGATGGTCCTATCTTTTTCCCAGAAGATGGAC
ACACACATGAGATTAGTCATAACCCATTGCCACAGGCGATGGGCCACGAAATGGCTG
GTACCGTTTTGGAGGTGGGCCCTGGTGTGAAAAACTTGAAAGTGGGAGACAAGGTA
GTTGTCGAGCCCACAGGTACATGCAGAGACCGGTATCGTTGGCCCCTGTCGCCAAA
CGTTGACAAGGAATGGTGCGCTGCTTGCAAAAAGGGCTACTATAACATTTGTTCATAT
TTGGGGCTTTGTGGTGCGGGTGTGCAGAGCGGTGGATTTGCAGAACGTGTTGTGAT
GAACGAATCTCACTGCTACAAAGTACCGGACTTCGTGCCCTTAGACGTTGCAGCTTT
GATTCAACCGTTGGCTGTGTGCTGGCATGCAATTAGAGTCTGCGAGTTCAAAGCAGG
CTCTACGGCTTTGATCATTGGTGCTGGCCCCATCGGACTGGGCACGATACTGGCGTT
GAACGCTGCAGGTTGCAAGGACATCGTCGTTTCAGAGCCTGCCAAGGTAAGAAGAG
AACTGGCTGAAAAAATGGGTGCCAGGGTTTACGACCCAACTGCGCACGCTGCCAAG
GAGAGCATTGATTATCTGAGGTCGATTGCTGATGGTGGAGACGGCTTCGATTACACA
TTTGATTGCTCCGGGTTGGAAGTCACATTGAATGCTGCTATTCAGTGTCTCACTTTCA
GAGGCACCGCAGTGAACTTGGCCATGTGGGGCCATCACAAGATACAGTTTTCTCCG
ATGGACATCACATTGCATGAAAGAAAGTACACAGGGTCCATGTGCTACACACACCAC
GATTTTGAGGCAGTAATAGAAGCTTTGGAAGAAGGCAGGATTGACATTGATAGAGCA
AGACATATGATAACGGGCAGAGTCAACATTGAGGACGGCCTTGATGGCGCCATCAT
GAAGCTGATAAACGAGAAGGAGTCTACAATCAAGATTATTCTGACTCCAAACAATCAC
GGAGAGTTGAACAGGGAAGCCGATAATGAGAAGAAAGAAATTTCCGAGCTGAGCAG
TCGGAAAGATCAAGAAAGACTACGAGAATCAATAAACGAGGCTAAACTGCGTCACAC
ATGA

Protein sequence from 3-hydroxyacyl-CoA dehydrogenase and enoyl-CoA hydratase (FOX2) of *Saccharomyces cerevisiae*

SEQ ID NO: 39

MPGNLSFKDRVVVITGAGGGLGKVYALAYASRGAKVVVNDLGGTLGGSGHNSKAADLV
VDEIKKAGGIAVANYDSVNENGEKIIETAIKEFGRVDVLINNAGILRDVSFAKMTEREFASV
VDVHLTGGYKLSRAAWPYMRSQKFGRIINTASPAGLFGNFGQANYSAAKMGLVGLAET
LAKEGAKYNINVNSIAPLARSRMTENVLPPHILKQLGPEKIVPLVLYLTHESTKVSNSIFEL
AAGFFGQLRWERSSGQIFNPDPKTYTPEAILNKWKEITDYRDKPFNKTQHPYQLSDYND
LITKAKKLPPNEQGSVKIKSLCNKVVVVTGAGGGLGKSHAIWFARYGAKVVVNDIKDPFS
VVEEINKLYGEGTAIPDSHDVVTEAPLIIQTAISKFQRVDILVNNAGILRDKSFLKMKDEEW
FAVLKVHLFSTFSLSKAVWPIFTKQKSGFIINTTSTSGIYGNFGQANYAAAKAAILGFSKTI
ALEGAKRGIIVNVIAPHAETAMTKTIFSEKELSNHFDASQVSPLVVLLASEELQKYSGRRV
IGQLFEVGGGWCGQTRWQRSSGYVSIKETIEPEEIKENWNHITDFSRNTINPSSTEESS
MATLQAVQKAHSSKELDDGLFKYTTKDCILYNLGLGCTSKELKYTYENDPDFQVLPTFA
VIPFMQATATLAMDNLVDNFNYAMLLHGEQYFKLCTPTMPSNGTLKTLAKPLQVLDKNG
KAALVVGGFETYDIKTKKLIAYNEGSFFIRGAHVPPEKEVRDGKRAKFAVQNFEVPHGKV
PDFEAEISTNKDQAALYRLSGDFNPLHIDPTLAKAVKFPTPILHGLCTLGISAKALFEHYG
PYEELKVRFTNVVFPGDTLKVKAWKQGSVVVFQTIDTTRNVIVLDNAAVKLSQAKSKL

DNA sequence encoding 3-hydroxyacyl-CoA dehydrogenase and enoyl-CoA hydratase (FOX2) of *Saccharomyces cerevisiae*

SEQ ID NO: 40

ATGCCTGGAAATTTATCCTTCAAAGATAGAGTTGTTGTAATCACGGGCGCTGGAGGG
GGCTTAGGTAAGGTGTATGCACTAGCTTACGCAAGCAGAGGTGCAAAAGTGGTCGT
CAATGATCTAGGTGGCACTTTGGGTGGTTCAGGACATAACTCCAAAGCTGCAGACTT
AGTGGTGGATGAGATAAAAAAAGCCGGAGGTATAGCTGTGGCAAATTACGACTCTGT
TAATGAAAATGGAGAGAAAATAATTGAAACGGCTATAAAAGAATTCGGCAGGGTTGAT
GTACTAATTAACAACGCTGGAATATTAAGGGATGTTTCATTTGCAAAGATGACAGAAC
GTGAGTTTGCATCTGTGGTAGATGTTCATTTGACAGGTGGCTATAAGCTATCGCGTG
CTGCTTGGCCTTATATGCGCTCTCAGAAATTTGGTAGAATCATTAACACCGCTTCCCC
TGCCGGTCTATTTGGAAATTTTGGTCAAGCTAATTATTCAGCAGCTAAAATGGGCTTA
GTTGGTTTGGCGGAAACCCTCGCGAAGGAGGGTGCCAAATACAACATTAATGTTAAT
TCAATTGCGCCATTGGCTAGATCACGTATGACAGAAAACGTGTTACCACCACATATCT
TGAAACAGTTAGGACCGGAAAAAATTGTTCCCTTAGTACTCTATTTGACACACGAAAG
TACGAAAGTGTCAAACTCCATTTTTGAACTCGCTGCTGGATTCTTTGGACAGCTCAGA
TGGGAGAGGTCTTCTGGACAAATTTTCAATCCAGACCCCAAGACATATACTCCTGAA
GCAATTTTAAATAAGTGGAAGGAAATCACAGACTATAGGGACAAGCCATTTAACAAAA

TABLE 7-continued

| Disclosed Nucleic Acid and Amino Acid Sequences |
|---|
| CTCAGCATCCATATCAACTCTCGGATTATAATGATTTAATCACCAAAGCAAAAAAATTA<br>CCTCCCAATGAACAAGGCTCAGTGAAAATCAAGTCGCTTTGCAACAAAGTCGTAGTA<br>GTTACGGGTGCAGGAGGTGGTCTTGGGAAGTCTCATGCAATCTGGTTTGCACGGTA<br>CGGTGCGAAGGTAGTTGTAAATGACATCAAGGATCCTTTTTCAGTTGTTGAAGAAATA<br>AATAAACTATATGGTGAAGGCACAGCCATTCCAGATTCCCATGATGTGGTCACCGAA<br>GCTCCTCTCATTATCCAAACTGCAATAAGTAAGTTTCAGAGAGTAGACATCTTGGTCA<br>ATAACGCTGGTATTTTGCGTGACAAATCTTTTTTAAAAATGAAAGATGAGGAATGGTTT<br>GCTGTCCTGAAAGTCCACCTTTTTTCCACATTTTCATTGTCAAAAGCAGTATGGCCAA<br>TATTTACCAAACAAAAGTCTGGATTTATTATCAATACTACTTCTACCTCAGGAATTTAT<br>GGTAATTTTGGACAGGCCAATTATGCCGCTGCAAAAGCCGCCATTTTAGGATTCAGT<br>AAAACTATTGCACTGGAAGGTGCCAAGAGAGGAATTATTGTTAATGTTATCGCTCCTC<br>ATGCAGAAACGGCTATGACAAAGACTATATTCTCGGAGAAGGAATTATCAAACCACTT<br>TGATGCATCTCAAGTCTCCCCACTTGTTGTTTTGTTGGCATCTGAAGAACTACAAAAG<br>TATTCTGGAAGAAGGGTTATTGGCCAATTATTCGAAGTTGGCGGTGGTTGGTGTGGG<br>CAAACCAGATGGCAAAGAAGTTCCGGTTATGTTTCTATTAAAGAGACTATTGAACCGG<br>AAGAAATTAAAGAAAATTGGAACCACATCACTGATTTCAGTCGCAACACTATCAACCC<br>GAGCTCCACAGAGGAGTCTTCTATGGCAACCTTGCAAGCCGTGCAAAAAGCGCACT<br>CTTCAAAGGAGTTGGATGATGGATTATTCAAGTACACTACCAAGGATTGTATCTTGTA<br>CAATTTAGGACTTGGATGCACAAGCAAAGAGCTTAAGTACACCTACGAGAATGATCC<br>AGACTTCCAAGTTTTGCCCACGTTCGCCGTCATTCCATTTATGCAAGCTACTGCCACA<br>CTAGCTATGGACAATTTAGTCGATAACTTCAATTATGCAATGTTACTGCATGGAGAAC<br>AATATTTTAAGCTCTGCACGCCGACAATGCCAAGTAATGGAACTCTAAAGACACTTGC<br>TAAACCTTTACAAGTACTTGACAAGAATGGTAAAGCCGCTTTAGTTGTTGGTGGCTTC<br>GAAACTTATGACATTAAAACTAAGAAACTCATAGCTTATAACGAAGGATCGTTCTTCAT<br>CAGGGGCGCACATGTACCTCCAGAAAAGGAAGTGAGGGATGGGAAAAGAGCCAAGT<br>TTGCTGTCCAAAATTTTGAAGTGCCACATGGAAAGGTACCAGATTTTGAGCCCGAGA<br>TTTCTACGAATAAAGATCAAGCCGCATTGTACAGGTTATCTGGCGATTTCAATCCTTT<br>ACATATCGATCCCACGCTAGCCAAAGCAGTTAAATTTCCTACGCCAATTCTGCATGG<br>GCTTTGTACATTAGGTATTAGTGCGAAAGCATTGTTTGAACATTATGGTCCATATGAG<br>GAGTTGAAAGTGAGATTTACCAATGTTGTTTTCCCAGGTGATACTCTAAAGGTTAAAG<br>CTTGGAAGCAAGGCTCGGTTGTCGTTTTTCAAACAATTGATACGACCAGAAACGTCAT<br>TGTATTGGATAACGCCGCTGTAAAACTATCGCAGGCAAAATCTAAACTATAA |
| Protein sequence from Glycerol dehydrogenase<br>(GCY1) of *Saccharomyces cerevisiae*<br>SEQ ID NO: 41<br>MPATLHDSTKILSLNTGAQIPQIGLGTWQSKENDAYKAVLTALKDGYRHIDTAAIYRNED<br>QVGQAIKDSGVPREEIFVTTKLWCTQHHEPEVALDQSLKRLGLDYVDLYLMHWPARLD<br>PAYIKNEDILSVPTKKDGSRAVDITNWNFIKTWELMQELPKTGKTKAVGVSNFSINNLKDL<br>LASQGNKLTPAANQVEIHPLLPQDELINFCKSKGIVVEAYSPLGSTDAPLLKEPVILEIAKK<br>NNVQPGHVVISWHVQRGYVVLPKSVNPDRIKTNRKIFTLSTEDFEAINNISKEKGEKRVV<br>HPNWSPFEVFK |
| DNA sequence encoding Glycerol dehydrogenase<br>(GCY1) of *Saccharomyces cerevisiae*<br>SEQ ID NO: 42<br>ATGCCTGCTACTTTACATGATTCTACGAAAATCCTTTCTCTAAATACTGGAGCCCAAAT<br>CCCTCAAATAGGTTTAGGTACGTGGCAGTCGAAAGAGAACGATGCTTATAAGGCTGT<br>TTTAACCGCTTTGAAAGATGGCTACCGACACATTGATACTGCTGCTATTTACCGTAAT<br>GAAGACCAAGTCGGTCAAGCCATCAAGGATTCAGGTGTTCCTCGGGAAGAAATCTTT<br>GTTACTACAAAGTTATGGTGTACACAACACCACGAACCTGAAGTAGCGCTGGATCAA<br>TCACTAAAGAGGTTAGGATTGGACTACGTAGACTTATATTTGATGCATTGGCCTGCCA<br>GATTAGATCCAGCCTACATCAAAAATGAAGACATCTTGAGTGTGCCAACAAAGAAGG<br>ATGGTTCTCGTGCAGTGGATATCACCAATTGGAATTTCATCAAAACCTGGGAATTAAT<br>GCAGGAACTACCAAAGACTGGTAAAACTAAGGCCGTTGGAGTCTCCAACTTTTCTAT<br>AAATAACCTGAAAGATCTATTAGCATCTCAAGGTAATAAGCTTACGCCAGCTGCTAAC<br>CAAGTCGAAATACATCCATTACTACCTCAAGACGAATTGATTAATTTTTGTAAAAGTAA<br>AGGCATTGTGGTTGAAGCTTATTCTCCGTTAGGTAGTACCGATGCTCCACTATTGAAG<br>GAACCGGTTATCCTTGAAATTGCGAAGAAAAATAACGTTCAACCCGGACACGTTGTTA<br>TTAGCTGGCACGTCCAAAGAGGTTATGTTGTCTTGCCAAAATCTGTGAATCCCGATC<br>GAATCAAAACGAACAGGAAAATATTTACTTTGTCTACTGAGGACTTTGAAGCTATCAA<br>TAACATATCGAAGGAAAAGGGCGAAAAAAGGGTTGTACATCCAAATTGGTCTCCTTTC<br>GAAGTATTCAAGTAA |
| Protein sequence from Glyoxylate reductase<br>(GOR1) of *Saccharomyces cerevisiae*<br>SEQ ID NO: 43<br>MSKKPIVLKLGKDAFGDQAWGELEKIADVITIPESTTREQFLREVKDPQNKLSQVQVITRT<br>ARSVKNTGRFDEELALALPSSVVAVCHTGAGYDQIDVEPFKKRHIQVANVPDLVSNATA<br>DTHVFLLLGALRNFGIGNRRLIEGNWPEAGPACGSPFGYDPEGKTVGILGLGRIGRCILE<br>RLKPFGFENFIYHNRHQLPSEEEHGCEYVGFEEFLKRSDIVSVNVPLNHNTHHLINAETIE<br>KMKDGVVIVNTARGAVIDEQAMTDALRSGKIRSAGLDVFEYEPKISKELLSMSQVLGLPH<br>MGTHSVETRKKMEELVVENAKNVILTGKVLTIVPELQNEDWPNESKPLV |

TABLE 7-continued

| Disclosed Nucleic Acid and Amino Acid Sequences |
|---|

DNA sequence encoding Glyoxylate reductase (GOR1) of *Saccharomyces cerevisiae*

SEQ ID NO: 44

ATGAGTAAGAAACCAATTGTTTTGAAATTAGGAAAGGATGCCTTTGGTGACCAAGCC
TGGGGGGAATTGGAAAAGATTGCGGATGTAATTACCATCCCTGAATCCACCACTAGA
GAACAGTTTTTGCGGGAGGTAAAAGACCCACAAAATAAGCTCTCCCAAGTACAAGTC
ATTACTAGAACAGCAAGGAGTGTGAAAAACACCGGTAGATTTGATGAAGAGCTTGCT
CTTGCTTTGCCCTCCTCCGTAGTGGCTGTATGTCATACTGGTGCTGGTTATGACCAA
ATTGATGTTGAGCCATTCAAGAAAAGGCACATCCAGGTTGCCAATGTTCCTGATTTA
GTTAGCAATGCTACCGCTGATACGCATGTATTTTTGCTATTGGGTGCCCTAAGAAAC
TTCGGTATTGGTAACAGAAGGTTGATCGAGGGAAACTGGCCGGAGGCAGGACCCG
CATGTGGTTCTCCCTTTGGATACGACCCTGAAGGGAAAACAGTTGGTATACTGGGTC
TAGGTAGGATTGGTCGTTGTATTTTAGAGAGATTGAAGCCGTTTGGGTTCGAGAATT
TCATATATCATAACAGACACCAGCTTCCTTCCGAAGAAGAGCATGGTTGTGAATATG
TAGGATTCGAGGAGTTTTTGAAGCGTTCTGATATAGTATCTGTAAACGTCCCACTGA
ACCACAATACTCACCATCTAATCAATGCAGAGACTATTGAAAAAATGAAAGATGGTGT
AGTTATTGTTAACACAGCGCGTGGTGCCGTGATAGACGAACAAGCCATGACTGATG
CTTTGCGTTCTGGAAAGATTAGAAGTGCTGGTTTGGACGTTTTCGAATATGAGCCAA
AAATATCCAAAGAGTTATTATCGATGTCCCAAGTCTTAGGACTGCCTCATATGGGCA
CACATAGTGTAGAAACAAGAAAGAAAATGGAAGAACTGGTCGTTGAAAATGCAAAGA
ATGTGATATTGACCGGGAAAGTCTTGACTATTGTTCCGGAATTACAAAATGAAGACT
GGCCCAATGAATCTAAGCCATTAGTTTGA

Protein sequence from NAD-dependent glycerol-3-phosphate dehydrogenase (GPD1) of *Saccharomyces cerevisiae*

SEQ ID NO: 45

MSAAADRLNLTSGHLNAGRKRSSSSVSLKAAEKPFKVTVIGSGNWGTTIAKVVAENCKG
YPEVFAPIVQMWVFEEEINGEKLTEIINTRHQNVKYLPGITLPDNLVANPDLIDSVKDVDII
VFNIPHQFLPRICSQLKGHVDSHVRAISCLKGFEVGAKGVQLLSSYITEELGIQCGALSGA
NIATEVAQEHWSETTVAYHIPKDFRGEGKDVDHKVLKALFHRPYFHVSVIEDVAGISICG
ALKNVVALGCGFVEGLGWGNNASAAIQRVGLGEIIRFGQMFFPESREETYYQESAGVA
DLITTCAGGRNVKVARLMATSGKDAWECEKELLNGQSAQGLITCKEVHEWLETCGSVE
DFPLFEAVYQIVYNNYPMKNLPDMIEELDLHED

DNA sequence encoding NAD-dependent glycerol-3-phosphate dehydrogenase (GPD1) of *Saccharomyces cerevisiae*

SEQ ID NO: 46

ATGTCTGCTGCTGCTGATAGATTAAACTTAACTTCCGGCCACTTGAATGCTGGTAGAA
AGAGAAGTTCCTCTTCTGTTTCTTTGAAGGCTGCCGAAAAGCCTTTCAAGGTTACTGT
GATTGGATCTGGTAACTGGGGTACTACTATTGCCAAGGTGGTTGCCGAAAATTGTAA
GGGATACCCAGAAGTTTTCGCTCCAATAGTACAAATGTGGGTGTTCGAAGAAGAGAT
CAATGGTGAAAAATTGACTGAAATCATAAATACTAGACATCAAAACGTGAAATACTTG
CCTGGCATCACTCTACCCGACAATTTGGTTGCTAATCCAGACTTGATTGATTCAGTCA
AGGATGTCGACATCATCGTTTTCAACATTCCACATCAATTTTTGCCCCGTATCTGTAG
CCAATTGAAAGGTCATGTTGATTCACACGTCAGAGCTATCTCCTGTCTAAAGGGTTTT
GAAGTTGGTGCTAAAGGTGTCCAATTGCTATCCTCTTACATCACTGAGGAACTAGGTA
TTCAATGTGGTGCTCTATCTGGTGCTAACATTGCCACCGAAGTCGCTCAAGAACACT
GGTCTGAAACAACAGTTGCTTACCACATTCCAAAGGATTTCAGAGGCGAGGGCAAGG
ACGTCGACCATAAGGTTCTAAAGGCCTTGTTCCACAGACCTTACTTCCACGTTAGTGT
CATCGAAGATGTTGCTGGTATCTCCATCTGTGGTGCTTTGAAGAACGTTGTTGCCTTA
GGTTGTGGTTTCGTCGAAGGTCTAGGCTGGGGTAACAACGCTTCTGCTGCCATCCAA
AGAGTCGGTTTGGGTGAGATCATCAGATTCGGTCAAATGTTTTTCCCAGAATCTAGA
GAAGAAACATACTACCAAGAGTCTGCTGGTGTTGCTGATTTGATCACCACCTGCGCT
GGTGGTAGAAACGTCAAGGTTGCTAGGCTAATGGCTACTTCTGGTAAGGACGCCTG
GGAATGTGAAAAGGAGTTGTTGAATGGCCAATCCGCTCAAGGTTTAATTACCTGCAA
AGAAGTTCACGAATGGTTGGAAACATGTGGCTCTGTCGAAGACTTCCCATTATTTGAA
GCCGTATACCAAATCGTTTACAACAACTACCCAATGAAGAACCTGCCGGACATGATT
GAAGAATTAGATCTACATGAAGATTAG

Protein sequence from Multifunctional enzyme containing phosphoribosyl-ATP pyrophosphatase, phosphoribosyl-AMP cyclohydrolase, and histidinol dehydrogenase activities (HIS4) of *Saccharomyces cerevisiae*

SEQ ID NO: 47

MVLPILPLIDDLASWNSKKEYVSLVGQVLLDGSSLSNEEILQFSKEEEVPLVALSLPSGKF
SDDEIIAFLNNGVSSLFIASQDAKTAEHLVEQLNVPKERVVVEENGVFSNQFMVKQKFSQ
DKIVSIKKLSKDMLTKEVLGEVRTDRPDGLYTTLVVDQYERCLGLVYSSKKSIAKAIDLGR
GVYYSRSRNEIWIKGETSGNGQKLLQISTDCDSDALKFIVEQENVGFCHLETMSCFGEF
KHGLVGLESLLKQRLQDAPEESYTRRLFNDSALLDAKIKEEAEELTEAKGKKELSWEAA
DLFYFALAKLVANDVSLKDVENNLNMKHLKVTRRKGDAKPKFVGQPKAEEEKLTGPIHL
DVVKASDKVGVQKALSRPIQKTSEIMHLVNPIIENVRDKGNSALLEYTEKFDGVKLSNPV
LNAPFPEEYFEGLTEEMKEALDLSIENVRKFHAAQLPTETLEVETQPGVLCSRFPRPIEK

TABLE 7-continued

Disclosed Nucleic Acid and Amino Acid Sequences

VGLYIPGGTAILPSTALMLGVPAQVAQCKEIVFASPPRKSDGKVSPEVVYVAEKVGASKI
VLAGGAQAVAAMAYGTETIPKVDKILGPGNQFVTAAKMYVQNDTQALCSIDMPAGPSEV
LVIADEDADVDFVASDLLSQAEHGIDSQVILVGVNLSEKKIQEIQDAVHNQALQLPRVDIV
RKCIAHSTIVLCDGYEEALEMSNQYAPEHLILQIANANDYVKLVDNAGSVFVGAYTPESC
GDYSSGTNHTLPTYGYARQYSGANTATFQKFITAQNITPEGLENIGRAVMCVAKKEGLD
GHRNAVKIRMSKLGLIPKDFQ

DNA sequence Multifunctional enzyme containing phosphoribosyl-ATP pyro-phosphatase, phosphoribosyl-AMP cyclohydrolase, and histidinol dehydrogenase activities (HIS4) of *Saccharomyces cerevisiae*

SEQ ID NO: 48

ATGGTTTTGCCGATTCTACCGTTAATTGATGATCTGGCCTCATGGAATAGTAAGAAG
GAATACGTTTCACTTGTTGGTCAGGTACTTTTGGATGGCTCGAGCCTGAGTAATGAA
GAGATTCTCCAGTTCTCCAAAGAGGAAGAAGTTCCATTGGTGGCTTTGTCCTTGCCA
AGTGGTAAATTCAGCGATGATGAAATCATTGCCTTCTTGAACAACGGAGTTTCTTCTC
TGTTCATTGCTAGCCAAGATGCTAAAACAGCCGAACACTTGGTTGAACAATTGAATG
TACCAAAGGAGCGTGTTGTTGTGGAAGAGAACGGTGTTTTCTCCAATCAATTCATGG
TAAAACAAAAATTCTCGCAAGATAAAATTGTGTCCATAAAGAAATTAAGCAAGGATAT
GTTGACCAAAGAAGTGCTTGGTGAAGTACGTACAGACCGTCCTGACGGTTTATATAC
CACCCTAGTTGTCGACCAATATGAGCGTTGTCTAGGGTTGGTGTATTCTTCGAAGAA
ATCTATAGCAAAGGCCATCGATTTGGGTCGTGGCGTTTATTATTCTCGTTCTAGGAA
TGAAATCTGGATCAAGGGTGAAACTTCTGGCAATGGCCAAAAGCTTTTACAAATCTC
TACTGACTGTGATTCGGATGCCTTAAAGTTTATCGTTGAACAAGAAAACGTTGGATTT
TGCCACTTGGAGACCATGTCTTGCTTTGGTGAATTCAAGCATGGTTTGGTGGGGCTA
GAATCTTTACTAAAACAAAGGCTACAGGACGCTCCAGAGGAATCTTATACTAGAAGA
CTATTCAACGACTCTGCATTGTTAGATGCCAAGATCAAGGAAGAAGCTGAAGAACTG
ACTGAGGCAAAGGGTAAGAAGGAGCTTTCTTGGGAGGCTGCCGATTTGTTCTACTTT
GCACTGGCCAAATTAGTGGCCAACGATGTTTCATTGAAGGACGTCGAGAATAATCTG
AATATGAAGCATCTGAAGGTTACAAGACGGAAAGGTGATGCTAAGCCAAAGTTTGTT
GGACAACCAAAGGCTGAAGAAGAAAAACTGACCGGTCCAATTCACTTGGACGTGGT
GAAGGCTTCCGACAAAGTTGGTGTGCAGAAGGCTTTGAGCAGACCAATCCAAAAGA
CTTCTGAAATTATGCATTTAGTCAATCCGATCATCGAAAATGTTAGAGACAAAGGTAA
CTCTGCCCTTTTGGAGTACACAGAAAAGTTTGATGGTGTAAAATTATCCAATCCTGTT
CTTAATGCTCCATTCCCAGAAGAATACTTTGAAGGTTTAACCGAGGAAATGAAGGAA
GCTTTGGACCTTTCAATTGAAAACGTCCGCAAATTCCATGCTGCTCAATTGCCAACA
GAGACTCTTGAAGTTGAAACCCAACCTGGTGTCTTGTGTTCCAGATTCCCTCGTCCT
ATTGAAAAAGTTGGTTTGTATATCCCTGGTGGCACTGCCATTTTACCAAGTACTGCAT
TAATGCTTGGTGTTCCAGCACAAGTTGCCCAATGTAAGGAGATTGTGTTTGCATCTC
CACCAAGAAAATCTGATGGTAAAGTTTCACCCGAAGTTGTTTATGTCGCAGAAAAAG
TTGGCGCTTCCAAGATTGTTCTAGCTGGTGGTGCCCAAGCCGTTGCTGCTATGGCT
TACGGGACAGAAACTATTCCTAAAGTGGATAAGATCTTGGGTCCAGGTAATCAATTT
GTGACTGCCGCCAAAATGTATGTTCAAAATGACACTCAAGCTCTATGTTCCATTGATA
TGCCAGCTGGCCCAAGTGAAGTTTTGGTTATTGCCGATGAAGATGCCGATGTGGAT
TTTGTTGCAAGTGATTTGCTATCGCAAGCTGAACACGGTATTGACTCCCAAGTTATC
CTTGTTGGTGTTAACTTGAGCGAAAAGAAAATTCAAGAGATTCAAGATGCTGTCCAC
AATCAAGCTTTACAACTGCCACGTGTGGATATTGTTCGTAAATGTATTGCTCACAGTA
CGATCGTTCTTTGTGACGGTTACGAAGAAGCCCTTGAAATGTCCAACCAATATGCAC
CAGAACATTTGATTCTACAAATCGCCAATGCTAACGATTATGTTAAATTGGTTGACAA
TGCAGGGTCCGTATTTGTGGGTGCTTACACTCCAGAATCGTGCGGTGACTATTCAA
GTGGTACTAACCATACATTACCAACCTATGGTTACGCTAGGCAGTACAGTGGTGCCA
ACACTGCAACCTTCCAAAAGTTTATCACTGCCCAAAACATTACCCCTGAAGGTTTAG
AAAACATCGGTAGAGCTGTTATGTGCGTTGCCAAGAAGGAGGGTCTAGACGGTCAC
AGAAACGCTGTGAAAATCAGAATGAGTAAGCTTGGGTTGATCCCAAAGGATTTCCAG
TAG

Protein sequence from HMG-CoA reductase (HMG1) of *Saccharomyces cerevisiae*

SEQ ID NO: 49

MPPLFKGLKQMAKPIAYVSRFSAKRPIHIILFSLIISAFAYLSVIQYYFNGWQLDSNSVFET
APNKDSNTLFQECSHYYRDSSLDGWVSITAHEASELPAPHHYYLLNLNFNSPNETDSIP
ELANTVFEKDNTKYILQEDLSVSKEISSTDGTKWRLRSDRKSLFDVKTLAYSLYDVFSEN
VTQADPFDVLIMVTAYLMMFYTIFGLFNDMRKTGSNFWLSASTVVNSASSLFLALYVTQ
CILGKEVSALTLFEGLPFIVVVVGFKHKIKIAQYALEKFERVGLSKRITTDEIVFESVSEEG
GRLIQDHLLCIFAFIGCSMYAHQLKTLTNFCILSAFILIFELILTPTFYSAILALRLEMNVIHRS
TIIKQTLEEDGVVPSTARIISKAEKKSVSSFLNLSVVVIIMKLSVILLFVFINFYNFGANWVN
DAFNSLYFDKERVSLPDFITSNASENFKEQAIVSVTPLLYYKPIKSYQRIEDMVLLLLRNVS
VAIRDRFVSKLVLSALVCSAVINVYLLNAARIHTSYTADQLVKTEVTKKSFTAPVQKASTP
VLTNKTVISGSKVKSLSSAQSSSSGPSSSSEEDDSRDIESLDKKIRPLEELEALLSSGNTK
QLKNKEVAALVIHGKLPLYALEKKLGDTTRAVAVRRKALSILAEAPVLASDRLPYKNYDY
DRVFGACCENVIGYMPLPVGVIGPLVIDGTSYHIPMATTEGCLVASAMRGCKAINAGGG
ATTVLTKDGMTRGPVVRFPTLKRSGACKIWLDSEEGQNAIKKAFNSTSRFARLQHIQTC
LAGDLLFMRFRTTTGDAMGMNMISKGVEYSLKQMVEEYGWEDMEVVSVSGNYCTDKK
PAAINWIEGRGKSVVAEATIPGDVVRKVLKSDVSALVELNIAKNLVGSAMAGSVGGFNA
HAANLVTAVFLALGQDPAQNVESSNCITLMKEVDGDLRISVSMPSIEVGTIGGGTVLEPQ
GAMLDLLGVRGPHATAPGTNARQLARIVACAVLAGELSLCAALAAGHLVQSHMTHNRK
PAEPTKPNNLDATDINRLKDGSVTCIKS

TABLE 7-continued

| Disclosed Nucleic Acid and Amino Acid Sequences |
|---|

DNA sequence encoding HMG-CoA reductase
(HMG1) of *Saccharomyces cerevisiae*

SEQ ID NO: 50

ATGCCGCCGCTATTCAAGGGACTGAAACAGATGGCAAAGCCAATTGCCTATGTTTCA
AGATTTTCGGCGAAACGACCAATTCATATAATACTTTTTTCTCTAATCATATCCGCATT
CGCTTATCTATCCGTCATTCAGTATTACTTCAATGGTTGGCAACTAGATTCAAATAGT
GTTTTTGAAACTGCTCCAAATAAAGACTCCAACACTCTATTTCAAGAATGTTCCCATTA
CTACAGAGATTCCTCTCTAGATGGTTGGGTATCAATCACCGCGCATGAAGCTAGTGA
GTTACCAGCCCCACACCATTACTATCTATTAAACCTGAACTTCAATAGTCCTAATGAA
ACTGACTCCATTCCAGAACTAGCTAACACGGTTTTTGAGAAAGATAATACAAAATATA
TTCTGCAAGAAGATCTCAGTGTTTCCAAAGAAATTTCTTCTACTGATGGAACGAAATG
GAGGTTAAGAAGTGACAGAAAAAGTCTTTTCGACGTAAAGACGTTAGCATATTCTCTC
TACGATGTATTTTCAGAAAATGTAACCCAAGCAGACCCGTTTGACGTCCTTATTATGG
TTACTGCCTACCTAATGATGTTCTACACCATATTCGGCCTCTTCAATGACATGAGGAA
GACCGGGTCAAATTTTTGGTTGAGCGCCTCTACAGTGGTCAATTCTGCATCATCACTT
TTCTTAGCATTGTATGTCACCCAATGTATTCTAGGCAAAGAAGTTTCCGCATTAACTCT
TTTTGAAGGTTTGCCTTTCATTGTAGTTGTTGTTGGTTTCAAGCACAAAATCAAGATTG
CCCAGTATGCCCTGGAGAAATTTGAAAGAGTCGGTTTATCTAAAAGGATTACTACCGA
TGAAATCGTTTTTGAATCCGTGAGCGAAGAGGGTGGTCGTTTGATTCAAGACCATTT
GCTTTGTATTTTTGCCTTTATCGGATGCTCTATGTATGCTCACCAATTGAAGACTTTGA
CAAACTTCTGCATATTATCAGCATTTATCCTAATTTTTGAATTGATTTTAACTCCTACAT
TTTATTCTGCTATCTTAGCGCTTAGACTGGAAATGAATGTTATCCACAGATCTACTATT
ATCAAGCAAACATTAGAAGAAGACGGTGTTGTTCCATCTACAGCAAGAATCATTTCTA
AAGCAGAAAAGAAATCCGTATCTTCTTTCTTAAATCTCAGTGTGGTTGTCATTATCATG
AAACTCTCTGTCATACTGTTGTTTGTCTTCATCAACTTTTATAACTTTGGTGCAAATTG
GGTCAATGATGCCTTCAATTCATTGTACTTCGATAAGGAACGTGTTTCTCTACCAGAT
TTTATTACCTCGAATGCCTCTGAAAACTTTAAAGAGCAAGCTATTGTTAGTGTCACCC
CATTATTATATTACAAACCCATTAAGTCCTACCAACGCATTGAGGATATGGTTCTTCTA
TTGCTTCGTAATGTCAGTGTTGCCATTCGTGATAGGTTCGTCAGTAAATTAGTTCTTT
CCGCCTTAGTATGCAGTGCTGTCATCAATGTGTATTTATTGAATGCTGCTAGAATTCA
TACCAGTTATACTGCAGACCAATTGGTGAAAACTGAAGTCACCAAGAAGTCTTTTACT
GCTCCTGTACAAAAGGCTTCTACACCAGTTTTAACCAATAAAACAGTCATTTCTGGAT
CGAAAGTCAAAAGTTTATCATCTGCGCAATCGAGCTCATCAGGACCTTCATCATCTAG
TGAGGAAGATGATTCCCGCGATATTGAAAGCTTGGATAAGAAAATACGTCCTTTAGAA
GAATTAGAAGCATTATTAAGTAGTGGAAATACAAAACAATTGAAGAACAAAGAGGTCG
CTGCCTTGGTTATTCACGGTAAGTTACCTTTGTACGCTTTGGAGAAAAAATTAGGTGA
TACTACGAGAGCGGTTGCGGTACGTAGGAAGGCTCTTTCAATTTTGGCAGAAGCTCC
TGTATTAGCATCTGATCGTTTACCATATAAAAATTATGACTACGACCGCGTATTTGGC
GCTTGTTGTGAAAATGTTATAGGTTACATGCCTTTGCCCGTTGGTGTTATAGGCCCCT
TGGTTATCGATGGTACATCTTATCATATACCAATGGCAACTACAGAGGGTTGTTTGGT
AGCTTCTGCCATGCGTGGCTGTAAGGCAATCAATGCTGGCGGTGGTGCAACAACTG
TTTTAACTAAGGATGGTATGACAAGAGGCCCAGTAGTCCGTTTCCCAACTTTGAAAAG
ATCTGGTGCCTGTAAGATATGGTTAGACTCAGAAGAGGGACAAAACGCAATTAAAAA
AGCTTTTAACTCTACATCAAGATTTGCACGTCTGCAACATATTCAAACTTGTCTAGCA
GGAGATTTACTCTTCATGAGATTTAGAACAACTACTGGTGACGCAATGGGTATGAATA
TGATTTCTAAAGGTGTCGAATACTCATTAAAGCAAATGGTAGAAGAGTATGGCTGGGA
AGATATGGAGGTTGTCTCCGTTTCTGGTAACTACTGTACCGACAAAAAACCAGCTGC
CATCAACTGGATCGAAGGTCGTGGTAAGAGTGTCGTCGCAGAAGCTACTATTCCTGG
TGATGTTGTCAGAAAAGTGTTAAAAAGTGATGTTTCCGCATTGGTTGAGTTGAACATT
GCTAAGAATTTGGTTGGATCTGCAATGGCTGGGTCTGTTGGTGGATTTAACGCACAT
GCAGCTAATTTAGTGACAGCTGTTTTCTTGGCATTAGGACAAGATCCTGCACAAAATG
TTGAAAGTTCCAACTGTATAACATTGATGAAAGAAGTGGACGGTGATTTGAGAATTTC
CGTATCCATGCCATCCATCGAAGTAGGTACCATCGGTGGTGGTACTGTTCTAGAACC
ACAAGGTGCCATGTTGGACTTATTAGGTGTAAGAGGCCCGCATGCTACCGCTCCTGG
TACCAACGCACGTCAATTAGCAAGAATAGTTGCCTGTGCCGTCTTGGCAGGTGAATT
ATCCTTATGTGCTGCCCTAGCAGCCGGCCATTTGGTTCAAAGTCATATGACCCACAA
CAGGAAACCTGCTGAACCAACAAAACCTAACAATTTGGACGCCACTGATATAAATCGT
TTGAAAGATGGGTCCGTCACCTGCATTAAATCCTAA

Protein sequence from Mitochondrial NADP-specific isocitrate
dehydrogenase (IPD1) of *Saccharomyces cerevisiae*

SEQ ID NO: 51

MSMLSRRLFSTSRLAAFSKIKVKQPVVELDGDEMTRIIWDKIKKKLILPYLDVDLKYYDLS
VESRDATSDKITQDAAEAIKKYGVGIKCATITPDEARVKEFNLHKMWKSPNGTIRNILGGT
VFREPIVIPRIPRLVPRWEKPIIIGRHAHGDQYKATDTLIPGPGSLELVYKPSDPTTAQPQT
LKVYDYKGSGVAMAMYNTDESIEGFAHSSFKLAIDKKLNLFLSTKNTILKKYDGRFKDIFQ
EVYEAQYKSKFEQLGIHYEHRLIDDMVAQMIKSKGGFIMALKNYDGDVQSDIVAQGFGS
LGLMTSILVTPDGKTFESEAAHGTVTRHYRKYQKGEETSTNSIASIFAWSRGLLKRGELD
NTPALCKFANILESATLNTVQQDGIMTKDLALACGNNERSAYVTTEEFLDAVEKRLQKEI
KSIE

DNA sequence encoding Mitochondrial NADP-specific isocitrate
dehydrogenase (IPD1) of *Saccharomyces cerevisiae*

SEQ ID NO: 52

ATGAGTATGTTATCTAGAAGATTATTTTCCACCTCTCGCCTTGCTGCTTTCAGTAAGAT
TAAGGTCAAACAACCCGTTGTCGAGTTGGACGGTGATGAAATGACCCGTATCATTTG
GGATAAGATCAAGAAGAAATTGATTCTACCCTACTTGGACGTAGATTTGAAGTACTAC
GACTTATCTGTCGAATCTCGTGACGCCACCTCCGACAAGATTACTCAGGATGCTGCT

TABLE 7-continued

| Disclosed Nucleic Acid and Amino Acid Sequences |
|---|
| GAGGCGATCAAGAAGTATGGTGTTGGTATCAAATGTGCCACCATCACTCCTGATGAA<br>GCTCGTGTGAAGGAATTCAACCTGCACAAGATGTGGAAATCTCCTAATGGTACCATC<br>AGAAACATTCTCGGCGGTACAGTGTTCAGAGAGCCCATTGTGATTCCTAGAATTCCT<br>AGACTGGTCCCACGTTGGGAAAAACCAATCATTATTGGAAGACACGCCCACGGTGAT<br>CAATATAAAGCTACGGACACACTGATCCCAGGCCCAGGATCTTTGGAACTGGTCTAC<br>AAGCCATCCGACCCTACGACTGCTCAACCACAAACTTTGAAAGTGTATGACTACAAG<br>GGCAGTGGTGTGGCCATGGCCATGTACAATACTGACGAATCCATCGAAGGGTTTGCT<br>CATTCGTCTTTCAAGCTGGCCATTGACAAAAAGCTAAATCTTTTCTTGTCAACCAAGA<br>ACACTATTTTGAAGAAATATGACGGTCGGTTCAAAGACATTTTCCAAGAAGTTTATGA<br>AGCTCAATATAAATCCAAATTCGAACAACTAGGGATCCACTATGAACACCGTTTAATT<br>GATGATATGGTCGCTCAAATGATAAAATCTAAAGGTGGCTTTATCATGGCGCTAAAGA<br>ACTATGACGGTGATGTCCAATCTGACATCGTCGCTCAAGGATTTGGCTCCTTAGGTTT<br>GATGACTTCTATCTTAGTTACACCAGACGGTAAAACTTTCGAAAGTGAAGCTGCTCAT<br>GGTACCGTGACAAGACATTATAGAAAGTACCAAAAGGGTGAAGAAACTTCTACAAAC<br>TCCATTGCATCCATTTTCGCGTGGTCGAGAGGTCTATTGAAGAGAGGTGAATTGGAC<br>AATACTCCTGCTTTGTGTAAATTTGCCAATATTTTGGAATCCGCCACTTTGAACACAGT<br>TCAGCAAGACGGTATCATGACGAAGGACTTGGCTTTGGCTTGCGGTAACAACGAAAG<br>ATCTGCTTATGTTACCACAGAAGAATTTTTGGATGCCGTTGAAAAAGACTACAAAAA<br>GAAATCAAGTCGATCGAGTAA |
| Protein sequence from Homo-isocitrate dehydrogenase (LYS12) of *Saccharomyces cerevisiae*<br>SEQ ID NO: 53<br>MFRSVATRLSACRGLASNAARKSLTIGLIPGDGIGKEVIPAGKQVLENLNSKHGLSFNFID<br>LYAGFQTFQETGKALPDETVKVLKEQCQGALFGAVQSPTTKVEGYSSPIVALRREMGLF<br>ANVRPVKSVEGEKGKPIDMVIVRENTEDLYIKIEKTYIDKATGTRVADATKRISEIATRRIAT<br>IALDIALKRLQTRGQATLTVTHKSNVLSQSDGLFREICKEVYESNKDKYGQIKYNEQIVDS<br>MVYRLFREPQCFDVIVAPNLYGDILSDGAAALVGSLGVVPSANVGPEIVIGEPCHGSAPD<br>IAGKGIANPIATIRSTALMLEFLGHNEAAQDIYKAVDANLREGSIKTPDLGGKASTQQVVD<br>DVLSRL |
| DNA sequence encoding Homo-isocitrate dehydrogenase (LYS12) of *Saccharomyces cerevisiae*<br>SEQ ID NO: 54<br>ATGTTTAGATCTGTTGCTACTAGATTATCTGCCTGCCGTGGGTTAGCATCTAACGCT<br>GCTCGCAAATCACTCACTATTGGTCTTATCCCCGGTGACGGTATCGGTAAGGAAGTC<br>ATTCCTGCTGGTAAGCAAGTTTTGGAAAACCTTAACTCCAAGCACGGCCTAAGCTTC<br>AACTTTATTGATCTCTACGCCGGTTTCCAAACATTCCAAGAAACAGGAAAGGCGTTG<br>CCTGATGAGACTGTTAAAGTGTTGAAGGAACAATGTCAAGGTGCTCTTTTCGGTGCA<br>GTTCAGTCTCCAACTACTAAGGTGGAAGGTTACTCCTCACCAATTGTTGCTCTAAGG<br>AGGGAAATGGGCCTTTTCGCTAATGTTCGTCCTGTTAAGTCTGTAGAGGGAGAAAAG<br>GGTAAACCAATTGACATGGTTATCGTCAGAGAAAATACTGAGGACCTGTACATTAAA<br>ATTGAAAAAACATACATTGACAAGGCCACAGGTACAAGAGTTGCTGATGCCACAAAG<br>AGAATATCCGAAATTGCAACAAGAAGAATTGCAACCATTGCATTAGATATTGCCTTGA<br>AAAGATTACAAACAAGAGGCCAAGCCACTTTGACAGTGACTCATAAATCAAATGTTC<br>TATCTCAAAGTGATGGTCTATTCAGAGAAATCTGTAAGGAAGTCTACGAATCTAACAA<br>GGACAAGTACGGTCAAATCAAATATAACGAACAAATTGTGGATTCCATGGTTTATAG<br>GCTGTTCAGAGAACCACAATGTTTTGATGTGATAGTGGCACCAAACCTATACGGGGA<br>TATATTATCTGACGGTGCTGCTGCTTTAGTCGGTTCATTAGGTGTTGTTCCAAGCGC<br>CAACGTAGGTCCAGAAATTGTCATTGGTGAACCATGCCATGGTTCTGCACCAGATAT<br>TGCTGGTAAAGGTATTGCTAACCCAATCGCCACTATAAGATCTACTGCTTTGATGTT<br>GGAATTCTTGGGCCACAACGAAGCTGCCCAAGATATCTACAAGGCTGTTGATGCTAA<br>CTTAAGAGAGGGTTCTATCAAGACACCAGATTTAGGTGGTAAGGCTTCTACTCAACA<br>AGTCGTTGACGACGTTTTGTCGAGATTATAG |
| Protein sequence from 3-phospho-glycerate dehydrogenase and alpha-ketoglutarate reductase (SER33) of *Saccharomyces cerevisiae*<br>SEQ ID NO: 55<br>MSYSAADNLQDSFQRAMNFSGSPGAVSTSPTQSFMNTLPRRVSITKQPKALKPFSTGD<br>MNILLLENVNATAIKIFKDQGYQVEFHKSSLPEDELIEKIKDVHAIGIRSKTRLTEKILQHAR<br>NLVCIGCFCIGTNQVDLKYAASKGIAVFNSPFSNSRSVAELVIGEIISLARQLGDRSIELHT<br>GTWNKVAARCWEVRGKTLGIIGYGHIGSQLSVLAEAMGLHVLYYDIVTIMALGTARQVST<br>LDELLNKSDFVTLHVPATPETEKMLSAPQFAAMKDGAYVINASRGTVVDIPSLIQAVKAN<br>KIAGAALDVYPHEPAKNGEGSFNDELNSWTSELVSLPNIILTPHIGGSTEEAQSSIGIEVA<br>TALSKYINEGNSVGSVNFPEVSLKSLDYDQENTVRVLYIHRNVPGVLKTVNDILSDHNIEK<br>QFSDSHGEIAYLMADISSVNQSEIKDIYEKLNQTSAKVSIRLLY |
| DNA sequence encoding 3-phospho-glycerate dehydrogenase and alpha-ketoglutarate reductase (SER33) of *Saccharomyces cerevisiae*<br>SEQ ID NO: 56<br>ATGTCTTATTCAGCTGCCGATAATTTACAAGATTCATTCCAACGTGCCATGAACTTTTC<br>TGGCTCTCCTGGTGCAGTCTCAACCTCACCAACTCAGTCATTTATGAACACACTACCT<br>CGTCGTGTAAGCATTACAAAGCAACCAAAGGCTTTAAAACCTTTTTCTACTGGTGACA<br>TGAATATTCTACTGTTGGAAAATGTCAATGCAACTGCAATCAAAATCTTCAAGGATCA<br>GGGTTACCAAGTAGAGTTCCACAAGTCTTCTCTACCTGAGGATGAATTGATTGAAAAA<br>ATCAAAGACGTACACGCTATCGGTATAAGATCCAAAACTAGATTGACTGAAAAAATAC<br>TACAGCATGCCAGGAATCTAGTTTGTATTGGTTGTTTTTGCATAGGTACCAATCAAGT |

TABLE 7-continued

| Disclosed Nucleic Acid and Amino Acid Sequences |
|---|
| AGACCTAAAATATGCCGCTAGTAAAGGTATTGCTGTTTTCAATTCGCCATTCTCCAAT<br>TCAAGATCCGTAGCAGAATTGGTAATTGGTGAGATCATTAGTTTAGCAAGACAATTAG<br>GTGATAGATCCATTGAACTGCATACAGGTACATGGAATAAAGTCGCTGCTAGGTGTT<br>GGGAAGTAAGAGGAAAAACTCTCGGTATTATTGGGTATGGTCACATTGGTTCGCAAT<br>TATCAGTTCTTGCAGAAGCTATGGGCCTGCATGTGCTATACTATGATATCGTGACAAT<br>TATGGCCTTAGGTACTGCCAGACAAGTTTCTACATTAGATGAATTGTTGAATAAATCT<br>GATTTTGTAACACTACATGTACCAGCTACTCCAGAAACTGAAAAAATGTTATCTGCTC<br>CACAATTCGCTGCTATGAAGGACGGGGCTTATGTTATTAATGCCTCAAGAGGTACTG<br>TCGTGGACATTCCATCTCTGATCCAAGCCGTCAAGGCCAACAAAATTGCAGGTGCTG<br>CTTTAGATGTTTATCCACATGAACCAGCTAAGAACGGTGAAGGTTCATTTAACGATGA<br>ACTTAACAGCTGGACTTCTGAGTTGGTTTCATTACCAAATATAATCCTGACACCACAT<br>ATTGGTGGCTCTACAGAAGAAGCTCAAAGTTCAATCGGTATTGAGGTGGCTACTGCA<br>TTGTCCAAATACATCAATGAAGGTAACTCTGTCGGTTCTGTGAACTTCCCAGAAGTCA<br>GTTTGAAGTCTTTGGACTACGATCAAGAGAACACAGTACGTGTCTTGTATATTCATCG<br>TAACGTTCCTGGTGTTTTGAAGACCGTTAATGATATCTTATCCGATCATAATATCGAG<br>AAACAGTTTTCTGATTCTCACGGCGAGATCGCTTATCTAATGGCAGACATCTCTTCTG<br>TTAATCAAAGTGAAATCAAGGATATATATGAAAAGTTGAACCAAACTTCTGCCAAAGTT<br>TCCATCAGGTTATTATACTAA |
| Protein sequence from Glucose-6-phosphate<br>dehydrogenase (ZWF1) of *Saccharomyces cerevisiae*<br>SEQ ID NO: 57<br>MSEGPVKFEKNTVISVFGASGDLAKKKTFPALFGLFREGYLDPSTKIFGYARSKLSMEED<br>LKSRVLPHLKKPHGEADDSKVEQFFKMVSYISGNYDTDEGFDELRTQIEKFEKSANVDV<br>PHRLFYLALPPSVFLTVAKQIKSRVYAENGITRVIVEKPFGHDLASARELQKNLGPLFKEE<br>ELYRIDHYLGKELVKNLLVLRFGNQFLNASWNRDNIQSVQISFKERFGTEGRGGYFDSIG<br>IIRDVMQNHLLQIMTLLTMERPVSFDPESIRDEKVKVLKAVAPIDTDDVLLGQYGKSEDGS<br>KPAYVDDDTVDKDSKCVTFAAMTFNIENERWEGVPIMMRAGKALNESKVEIRLQYKAVA<br>SGVFKDIPNNELVIRVQPDAAVYLKFNAKTPGLSNATQVTDLNLTYASRYQDFWIPEAYE<br>VLIRDALLGDHSNFVRDDELDISWGIFTPLLKHIERPDGPTPEIYPYGSRGPKGLKEYMQ<br>KHKYVMPEKHPYAWPVTKPEDTKDN |
| DNA sequence encoding Glucose-6-phosphate<br>dehydrogenase (ZWF1) of *Saccharomyces cerevisiae*<br>SEQ ID NO: 58<br>ATGAGTGAAGGCCCCGTCAAATTCGAAAAAAATACCGTCATATCTGTCTTTGGTGCGT<br>CAGGTGATCTGGCAAAGAAGAAGACTTTTCCCGCCTTATTTGGGCTTTTCAGAGAAG<br>GTTACCTTGATCCATCTACCAAGATCTTCGGTTATGCCCGGTCCAAATTGTCCATGGA<br>GGAGGACCTGAAGTCCCGTGTCCTACCCCACTTGAAAAAACCTCACGGTGAAGCCG<br>ATGACTCTAAGGTCGAACAGTTCTTCAAGATGGTCAGCTACATTTCGGGAAATTACGA<br>CACAGATGAAGGCTTCGACGAATTAAGAACGCAGATCGAGAAATTCGAGAAAAGTGC<br>CAACGTCGATGTCCCACACCGTCTCTTCTATCTGGCCTTGCCGCCAAGCGTTTTTTT<br>GACGGTGGCCAAGCAGATCAAGAGTCGTGTGTACGCAGAGAATGGCATCACCCGTG<br>TAATCGTAGAGAAACCTTTCGGCCACGACCTGGCCTCTGCCAGGGAGCTGCAAAAAA<br>ACCTGGGGCCCCTCTTTAAAGAAGAAGAGTTGTACAGAATTGACCATTACTTGGGTA<br>AAGAGTTGGTCAAGAATCTTTTAGTCTTGAGGTTCGGTAACCAGTTTTTGAATGCCTC<br>GTGGAATAGAGACAACATTCAAAGCGTTCAGATTTCGTTTAAAGAGAGGTTCGGCAC<br>CGAAGGCCGTGGCGGCTATTTCGACTCTATAGGCATAATCAGAGACGTGATGCAGAA<br>CCATCTGTTACAAATCATGACTCTCTTGACTATGGAAAGACCGGTGTCTTTTGACCCG<br>GAATCTATTCGTGACGAAAAGGTTAAGGTTCTAAAGGCCGTGGCCCCCATCGACACG<br>GACGACGTCCTCTTGGGCCAGTACGGTAAATCTGAGGACGGGTCTAAGCCCGCCTA<br>CGTGGATGATGACACTGTAGACAAGGACTCTAAATGTGTCACTTTTGCAGCAATGAC<br>TTTCAACATCGAAAACGAGCGTTGGGAGGGCGTCCCCATCATGATGCGTGCCGGTA<br>AGGCTTTGAATGAGTCCAAGGTGGAGATCAGACTGCAGTACAAAGCGGTCGCATCG<br>GGTGTCTTCAAAGACATTCCAAATAACGAACTGGTCATCAGAGTGCAGCCCGATGCC<br>GCTGTGTACCTAAAGTTTAATGCTAAGACCCCTGGTCTGTCAAATGCTACCCAAGTCA<br>CAGATCTGAATCTAACTTACGCAAGCAGGTACCAAGACTTTTGGATTCCAGAGGCTTA<br>CGAGGTGTTGATAAGAGACGCCCTACTGGGTGACCATTCCAACTTTGTCAGAGATGA<br>CGAATTGGATATCAGTTGGGGCATATTCACCCCATTACTGAAGCACATAGAGCGTCC<br>GGACGGTCCAACACCGGAAATTTACCCCTACGGATCAAGAGGTCCAAAGGGATTGA<br>AGGAATATATGCAAAAACACAAGTATGTTATGCCCGAAAAGCACCCTTACGCTTGGC<br>CCGTGACTAAGCCAGAAGATACGAAGGATAATTAG |
| Protein sequence from Putative aryl alcohol dehydrogenase<br>(YPL088W) of *Saccharomyces cerevisiae*<br>SEQ ID NO: 59<br>MVLVKQVRLGNSGLKISPIVIGCMSYGSKKWADWVIEDKTQIFKIMKHCYDKGLRTFDTA<br>DFYSNGLSERIIKEFLEYYSIKRETVVIMTKIYFPVDETLDLHHNFTLNEFEELDLSNQRGL<br>SRKHIIAGVENSVKRLGTYIDLLQIHRLDHETPMKEIMKALNDVVEAGHVRYIGASSMLAT<br>EFAELQFTADKYGWFQFISSQSYYNLLYREDERELIPFAKRHNIGLLPWSPNARGMLTR<br>PLNQSTDRIKSDPTFKSLHLDNLEEEQKEIINRVEKVSKDKKVSMAMLSIAWVLHKGCHPI<br>VGLNTTARVDEAIAALQVTLTEEEIKYLEEPYKPQRQRC |
| DNA sequence encoding Putative aryl alcohol dehydrogenase<br>(YPL088W) of *Saccharomyces cerevisiae*<br>SEQ ID NO: 60<br>ATGGTTTTAGTTAAGCAGGTAAGACTCGGTAACTCAGGTCTTAAGATATCACCGATA<br>GTGATAGGATGTATGTCATACGGGTCCAAGAAATGGGCGGACTGGGTCATAGAGGA |

TABLE 7-continued

| Disclosed Nucleic Acid and Amino Acid Sequences |
|---|
| CAAGACCCAAATTTTCAAGATTATGAAGCATTGTTACGATAAAGGTCTTCGTACTTTT<br>GACACAGCAGATTTTTATTCTAATGGTTTGAGTGAAAGAATAATTAAGGAGTTTCTGG<br>AGTACTACAGTATAAAGAGAGAAACGGTGGTGATTATGACCAAAATTTACTTCCCAG<br>TTGATGAAACGCTTGATTTGCATCATAACTTCACTTTAAATGAATTTGAAGAATTGGA<br>CTTGTCCAACCAGCGGGGTTTATCCAGAAAGCATATAATTGCTGGTGTCGAGAACTC<br>TGTGAAAAGACTGGGCACATATATAGACCTTTTACAAATTCACAGATTAGATCATGAA<br>ACGCCAATGAAAGAGATCATGAAGGCATTGAATGATGTTGTTGAAGCGGGCCACGT<br>TAGATACATTGGGGCTTCGAGTATGTTGGCAACTGAATTTGCAGAACTGCAGTTCAC<br>AGCCGATAAATATGGCTGGTTTCAGTTCATTTCTTCGCAGTCTTACTACAATTTGCTC<br>TATCGTGAAGATGAACGCGAATTGATTCCTTTTGCCAAAAGACACAATATTGGTTTAC<br>TTCCATGGTCTCCTAACGCACGAGGCATGTTGACTCGTCCTCTGAACCAAAGCACG<br>GACAGGATTAAGAGTGATCCAACTTTCAAGTCGTTACATTTGGATAATCTCGAAGAA<br>GAACAAAAGGAAATTATAAATCGTGTGGAAAAGGTGTCGAAGGACAAAAAAGTCTCG<br>ATGGCTATGCTCTCCATTGCATGGGTTTTGCATAAAGGATGTCACCCTATTGTGGGA<br>TTGAACACTACAGCAAGAGTAGACGAAGCGATTGCCGCACTACAAGTAACTCTAACA<br>GAAGAAGAGATAAAGTACCTCGAGGAGCCCTACAAACCCCAGAGGCAAAGATGTTA<br>A |
| Protein sequence NADP + dependent arabinose<br>dehydrogenase (ARA1) of *Saccharomyces cerevisiae*<br>SEQ ID NO: 61<br>MSSSVASTENIVENMLHPKTTEIYFSLNNGVRIPALGLGTANPHEKLAETKQAVKAAIKAG<br>YRHIDTAWAYETEPFVGEAIKELLEDGSIKREDLFITTKVWPVLWDEVDRSLNESLKALG<br>LEYVDLLLQHWPLCFEKIKDPKGISGLVKTPVDDSGKTMYAADGDYLETYKQLEKIYLDP<br>NDHRVRAIGVSNFSIEYLERLIKECRVKPTVNQVETHPHLPQMELRKFCFMHDILLTAYS<br>PLGSHGAPNLKIPLVKKLAEKYNVTGNDLLISYHIRQGTIVIPRSLNPVRISSSIEFASLTKD<br>ELQELNDFGEKYPVRFIDEPFAAILPEFTGNGPNLDNLKY |
| DNA Encoding NADP + dependent arabinose<br>dehydrogenase (ARA1) of *Saccharomyces cerevisiae*<br>SEQ ID NO: 62<br>ATGTCTTCTTCAGTAGCCTCAACCGAAAACATAGTCGAAAATATGTTGCATCCAAAGA<br>CTACAGAAATATACTTTTCACTCAACAATGGTGTTCGTATCCCAGCACTGGGTTTGGG<br>GACAGCAAATCCTCACGAAAAGTTAGCTGAAACAAAACAAGCCGTAAAAGCTGCAAT<br>CAAAGCTGGATACAGGCACATTGATACTGCTTGGGCCTACGAGACAGAGCCATTCGT<br>AGGTGAAGCCATCAAGGAGTTATTAGAAGATGGATCTATCAAAAGGGAGGATCTTTT<br>CATAACCACAAAAGTGTGGCCGGTTCTATGGGACGAAGTGGACAGATCATTGAATGA<br>ATCTTTGAAAGCTTTAGGCTTGGAATACGTCGACTTGCTCTTGCAACATTGGCCGCTA<br>TGTTTTGAAAAGATTAAGGACCCTAAGGGGATCAGCGGACTGGTGAAGACTCCGGTT<br>GATGATTCTGGAAAAACAATGTATGCTGCCGACGGTGACTATTTAGAAACTTACAAGC<br>AATTGGAAAAAATTTACCTTGATCCTAACGATCATCGTGTGAGAGCCATTGGTGTCTC<br>AAATTTTTCCATTGAGTATTTGGAACGTCTCATTAAGGAATGCAGAGTTAAGCCAACG<br>GTGAACCAAGTGGAAACTCACCCTCACTTACCACAAATGGAACTAAGAAAGTTCTGC<br>TTTATGCACGACATTCTGTTAACAGCATACTCACCATTAGGTTCCCATGGCGCACCAA<br>ACTTGAAAATCCCACTAGTGAAAAAGCTTGCCGAAAAGTACAATGTCACAGGAAATGA<br>CTTGCTAATTTCTTACCATATTAGACAAGGCACTATCGTAATTCCGAGATCCTTGAATC<br>CAGTTAGGATTTCCTCGAGTATTGAATTCGCATCTTTGACAAAGGATGAATTACAAGA<br>GTTGAACGACTTCGGTGAAAAATACCCAGTGAGATTCATCGATGAGCCATTTGCAGC<br>CATCCTTCCAGAGTTTACTGGTAACGGACCAAACTTGGACAATTTAAAGTATTAA |
| DNA sequence from vector pEVE2120<br>SEQ ID NO: 63<br>CTGCATTAATGAATCGGCCAACGCGCGGGGAGAGGCGGTTTGCGTATTGGGCGCT<br>CTTCCGCTTCCTCGCTCACTGACTCGCTGCGCTCGGTCGTTCGGCTGCGGCGAGC<br>GGTATCAGCTCACTCAAAGGCGGTAATACGGTTATCCACAGAATCAGGGGATAACG<br>CAGGAAAGAACATGTGAGCAAAAGGCCAGCAAAAGGCCAGGAACCGTAAAAAGGC<br>CGCGTTGCTGGCGTTTTTCCATAGGCTCCGCCCCCCTGACGAGCATCACAAAAATC<br>GACGCTCAAGTCAGAGGTGGCGAAACCCGACAGGACTATAAAGATACCAGGCGTTT<br>CCCCCTGGAAGCTCCCTCGTGCGCTCTCCTGTTCCGACCCTGCCGCTTACCGGATA<br>CCTGTCCGCCTTTCTCCCTTCGGGAAGCGTGGCGCTTTCTCATAGCTCACGCTGTA<br>GGTATCTCAGTTCGGTGTAGGTCGTTCGCTCCAAGCTGGGCTGTGTGCACGAACCC<br>CCCGTTCAGCCCGACCGCTGCGCCTTATCCGGTAACTATCGTCTTGAGTCCAACCC<br>GGTAAGACACGACTTATCGCCACTGGCAGCAGCCACTGGTAACAGGATTAGCAGAG<br>CGAGGTATGTAGGCGGTGCTACAGAGTTCTTGAAGTGGTGGCCTAACTACGGCTAC<br>ACTAGAAGGACAGTATTTGGTATCTGCGCTCTGCTGAAGCCAGTTACCTTCGGAAAA<br>AGAGTTGGTAGCTCTTGATCCGGCAAACAAACCACCGCTGGTAGCGGTGGTTTTTTT<br>GTTTGCAAGCAGCAGATTACGCGCAGAAAAAAAGGATCTCAAGAAGATCCTTTGATC<br>TTTTCTACGGGGTCTGACGCTCAGTGGAACGAAAACTCACGTTAAGGGATTTTGGTC<br>ATGAGATTATCAAAAAGGATCTTCACCTAGATCCTTTTAAATTAAAAATGAAGTTTTAA<br>ATCAATCTAAAGTATATATGAGTAAACTTGGTCTGACAGTTACCAATGCTTAATCAGT<br>GAGGCACCTATCTCAGCGATCTGTCTATTTCGTTCATCCATAGTTGCCTGACTCCCC<br>GTCGTGTAGATAACTACGATACGGGAGGGCTTACCATCTGGCCCCAGTGCTGCAAT<br>GATACCGCGAGACCCACGCTCACCGGCTCCAGATTTATCAGCAATAAACCAGCCAG<br>CCGGAAGGGCCGAGCGCAGAAGTGGTCCTGCAACTTTATCCGCCTCCATCCAGTCT<br>ATTAATTGTTGCCGGGAAGCTAGAGTAAGTAGTTCGCCAGTTAATAGTTTGCGCAAC<br>GTTGTTGCCATTGCTACAGGCATCGTGGTGTCACGCTCGTCGTTTGGTATGGCTTCA<br>TTCAGCTCCGGTTCCCAACGATCAAGGCGAGTTACATGATCCCCCATGTTGTGCAAA<br>AAAGCGGTTAGCTCCTTCGGTCCTCCGATCGTTGTCAGAAGTAAGTTGGCCGCAGT |

TABLE 7-continued

| Disclosed Nucleic Acid and Amino Acid Sequences |
|---|
| GTTATCACTCATGGTTATGGCAGCACTGCATAATTCTCTTACTGTCATGCCATCCGTA<br>AGATGCTTTTCTGTGACTGGTGAGTACTCAACCAAGTCATTCTGAGAATAGTGTATG<br>CGGCGACCGAGTTGCTCTTGCCCGGCGTCAATACGGGATAATACCGCGCCACATAG<br>CAGAACTTTAAAAGTGCTCATCATTGGAAAACGTTCTTCGGGGCGAAAACTCTCAAG<br>GATCTTACCGCTGTTGAGATCCAGTTCGATGTAACCCACTCGTGCACCCAACTGATC<br>TTCAGCATCTTTTACTTTCACCAGCGTTTCTGGGTGAGCAAAAACAGGAAGGCAAAA<br>TGCCGCAAAAAAGGGAATAAGGGCGACACGGAAATGTTGAATACTCATACTCTTCCT<br>TTTTCAATATTATTGAAGCATTTATCAGGGTTATTGTCTCATGAGCGGATACATATTTG<br>AATGTATTTAGAAAAATAAACAAATAGGGGTTCCGCGCACATTTCCCCGAAAAGTGC<br>CACCTGGGTCCTTTTCATCACGTGCTATAAAAATAATTATAATTTAAATTTTTTAATAT<br>AAATATATAAATTAAAAATAGAAAGTAAAAAAAGAAATTAAAGAAAAAATAGTTTTTGT<br>TTTCCGAAGATGTAAAAGACTCTAGGGGGATCGCCAACAAATACTACCTTTTATCTT<br>GCTCTTCCTGCTCTCAGGTATTAATGCCGAATTGTTTCATCTTGTCTGTGTAGAAGAC<br>CACACACGAAAATCCTGTGATTTTACATTTTACTTATCGTTAATCGAATGTATATCTAT<br>TTAATCTGCTTTTCTTGTCTAATAAATATATATGTAAAGTACGCTTTTTGTTGAAATTTT<br>TTAAACCTTTGTTTATTTTTTTTTCTTCATTCCGTAACTCTTCTACCTTCTTTATTTACT<br>TTCTAAAATCCAAATACAAAACATAAAAATAAATAAACACAGAGTAAATTCCCAAATTA<br>TTCCATCATTAAAAGATACGAGGCGCGTGTAAGTTACAGGCAAGCGATCCGTCCTAA<br>GAAACCATTATTATCATGACATTAACCTATAAAAATAGGCGTATCACGAGGCCCTTTC<br>GTCTCGCGCGTTTCGGTGATGACGGTGAAAACCTCTGACACATGCAGCTCCCGGAG<br>ACGGTCACAGCTTGTCTGTAAGCGGATGCCGGGAGCAGACAAGCCCGTCAGGGCG<br>CGTCAGCGGGTGTTGGCGGGTGTCGGGGCTGGCTTAACTATGCGGCATCAGAGCA<br>GATTGTACTGAGAGTGCACCATACCACAGCTTTTCAATTCAATTCATCATTTTTTTTTT<br>ATTCTTTTTTTTGATTTCGGTTTCTTTGAAATTTTTTTGATTCGGTAATCTCCGAACAG<br>AAGGAAGAACGAAGGAAGGAGCACAGACTTAGATTGGTATATATACGCATATGTAGT<br>GTTGAAGAAACATGAAATTGCCCAGTATTCTTAACCCAACTGCACAGAACAAAAACC<br>TGCAGGAAACGAAGATAAATCATGTCGAAAGCTACATATAAGGAACGTGCTGCTACT<br>CATCCTAGTCCTGTTGCTGCCAAGCTATTTAATATCATGCACGAAAAGCAAACAAACT<br>TGTGTGCTTCATTGGATGTTCGTACCACCAAGGAATTACTGGAGTTAGTTGAAGCAT<br>TAGGTCCCAAAATTTGTTTACTAAAAACACATGTGGATATCTTGACTGATTTTTCCAT<br>GGAGGGCACAGTTAAGCCGCTAAAGGCATTATCCGCCAAGTACAATTTTTTACTCTT<br>CGAAGACAGAAAATTTGCTGACATTGGTAATACAGTCAAATTGCAGTACTCTGCGGG<br>TGTATACAGAATAGCAGAATGGGCAGACATTACGAATGCACACGGTGTGGTGGGCC<br>CAGGTATTGTTAGCGGTTTGAAGCAGGCGGCAGAAGAAGTAACAAAGGAACCTAGA<br>GGCCTTTTGATGTTAGCAGAATTGTCATGCAAGGGCTCCCTATCTACTGGAGAATAT<br>ACTAAGGGTACTGTTGACATTGCGAAGAGCGACAAAGATTTTGTTATCGGCTTTATT<br>GCTCAAAGAGACATGGGTGGAAGAGATGAAGGTTACGATTGGTTGATTATGACACC<br>CGGTGTGGGTTTAGATGACAAGGGAGACGCATTGGGTCAACAGTATAGAACCGTGG<br>ATGATGTGGTCTCTACAGGATCTGACATTATTATTGTTGGAAGAGGACTATTTGCAAA<br>GGGAAGGGATGCTAAGGTAGAGGGTGAACGTTACAGAAAAGCAGGCTGGGAAGCA<br>TATTTGAGAAGATGCGGCCAGCAAAACTAAAAAACTGTATTATAAGTAAATGCATGTA<br>TACTAAACTCACAAATTAGAGCTTCAATTTAATTATATCAGTTATTACCCTATGCGGTG<br>TGAAATACCGCACAGATGCGTAAGGAGAAAATACCGCATCAGGAAATTGTAAACGTT<br>AATATTTTGTTAAAATTCGCGTTAAATTTTTGTTAAATCAGCTCATTTTTTAACCAATAG<br>GCCGAAATCGGCAAAATCCCTTATAAATCAAAAGAATAGACCGAGATAGGGTTGAGT<br>GTTGTTCCAGTTTGGAACAAGAGTCCACTATTAAAGAACGTGGACTCCAACGTCAAA<br>GGGCGAAAAACCGTCTATCAGGGCGATGGCCCACTACGTGAACCATCACCCTAATC<br>AAGTTTTTTGGGGTCGAGGTGCCGTAAAGCACTAAATCGGAACCCTAAAGGGAGCC<br>CCCGATTTAGAGCTTGACGGGGAAAGCCGGCGAACGTGGCGAGAAAGGAAGGGAA<br>GAAAGCGAAAGGAGCGGGCGCTAGGGCGCTGGCAAGTGTAGCGGTCACGCTGCG<br>CGTAACCACCACACCCGCCGCGCTTAATGCGCCGCTACAGGGCGCGTCGCGCCAT<br>TCGCCATTCAGGCTGCGCAACTGTTGGGAAGGGCGATCGGTGCGGGCCTCTTCGC<br>TATTACGCCAGCTGATTTGCCCGGGCAGTTCAGGCTCATCAGGCGCGCCATGCAGG<br>ATGCATTGATCAGTTAACCCATGGGCATGCGAAGGAAAATGAGAAATATCGAGGGA<br>GACGATTCAGAGGAGCAGGACAAACTATAACCGACTGTTTGTTGGAGGATGCCGTA<br>CATAACGAACACTGCTGAAGCTACCATGTCTACAGTTTAGAGGAATGGGTACAACTC<br>ACAGGCGAGGGATGGTGTTCACTCGTGCTAGCAAACGCGGTGGGAGCAAAAAGTA<br>GAATATTATCTTTTATTCGTGAAACTTCGAACACTGTCATCTAAAGATGCTATATACTA<br>ATATAGGCATACTTGATAATGAAAACTATAAATCGTAAAGACATAAGAGATCCGCGG<br>ATCCCCGGGTCGAGCCTGAACGGCCTCGAGGCCTGAACGGCCTCGACGAATTCAT<br>TATTTGTAGAGCTCATCCATGCCATGTGTAATCCCAGCAGCAGTTACAAACTCAAGA<br>AGGACCATGTGGTCACGCTTTTCGTTGGGATCTTTCGAAAGGGCAGATTGTGTCGA<br>CAGGTAATGGTTGTCTGGTAAAAGGACAGGGCCATCGCCAATTGGAGTATTTTGTTG<br>ATAATGGTCTGCTAGTTGAACGGATCCATCTTCAATGTTGTGGCGAATTTTGAAGTTA<br>GCTTTGATTCCATTCTTTTGTTTGTCTGCCGTGATGTATACATTGTGTGAGTTATAGT<br>TGTACTCGAGTTTGTGTCCGAGAATGTTTCCATCTTCTTTAAAATCAATACCTTTTAAC<br>TCGATACGATTAACAAGGGTATCACCTTCAAACTTGACTTCAGCACGCGTCTTGTAG<br>TTCCCGTCATCTTTGAAAGATATAGTGCGTTCCTGTACATAACCTTCGGGCATGGCA<br>CTCTTGAAAAAGTCATGCCGTTTCATATGATCCGGATAACGGGAAAAGCATTGAACA<br>CCATAAGAGAAAGTAGTGACAAGTGTTGGCCATGGAACAGGTAGTTTTCCAGTAGTG<br>CAAATAAATTTAAGGGTAAGCTGGCCCTGCAGGCCAAGCTTTGTTTTATATTTGTTGT<br>AAAAAGTAGATAATTACTTCCTTGATGATCTGTAAAAAAGAGAAAAAGAAAGCATCTA<br>AGAACTTGAAAAACTACGAATTAGAAAAGACCAAATATGTATTTCTTGCATTGACCAA<br>TTTATGCAAGTTTATATATATGTAAATGTAAGTTTCACGAGGTTCTACTAAACTAAACC<br>ACCCCCTTGGTTAGAAGAAAAGAGTGTGTGAGAACAGGCTGTTGTTGTCACACGATT<br>CGGACAATTCTGTTTGAAAGAGAGAGAGTAACAGTACGATCGAACGAACTTTGCTCT<br>GGAGATCACAGTGGGCATCATAGCATGTGGTACTAAACCCTTTCCCGCCATTCCAG<br>AACCTTCGATTGCTTGTTACAAAACCTGTGAGCCGTCGCTAGGACCTTGTTGTGTGA |

TABLE 7-continued

| Disclosed Nucleic Acid and Amino Acid Sequences |
| --- |

CGAAATTGGAAGCTGCAATCAATAGGAAGACAGGAAGTCGAGCGTGTCTGGGTTTT
TTCAGTTTTGTTCTTTTTGCAAACAAATCACGAGCGACGGTAATTTCTTTCTCGATAA
GAGGCCACGTGCTTTATGAGGGTAACATCAATTCAAGAAGGAGGGAAACACTTCCTT
TTTCTGGCCCTGATAATAGTATGAGGGTGAAGCCAAAATAAAGGATTCGCGCCCAAA
TCGGCATCTTTAAATGCAGGTATGCGATAGTTCCTCACTCTTTCCTTACTCACGAGTA
ATTCTTGCAAATGCCTATTATGCAGATGTTATAATATCTGTGCGTAGATCTGATATCC
CTGCATGGCGCGCCTGATGAGCCTGAACTGCCCGGGCAAATCAG

DNA sequence from vector pEVE27735

SEQ ID NO: 64

CTGATTTGCCCGGGCAGTTCAGGCTCATCAGGCGCGCCATGCAGGGATATCAGATC
TACGCACAGATATTATAACATCTGCATAATAGGCATTTGCAAGAATTACTCGTGAGTA
AGGAAAGAGTGAGGAACTATCGCATACCTGCATTTAAAGATGCCGATTTGGGCGCGA
ATCCTTTATTTTGGCTTCACCCTCATACTATTATCAGGGCCAGAAAAAGGAAGTGTTT
CCCTCCTTCTTGAATTGATGTTACCCTCATAAAGCACGTGGCCTCTTATCGAGAAAGA
AATTACCGTCGCTCGTGATTTGTTTGCAAAAAGAACAAAACTGAAAAAACCCAGACAC
GCTCGACTTCCTGTCTTCCTATTGATTGCAGCTTCCAATTTCGTCACACAACAAGGTC
CTAGCGACGGCTCACAGGTTTTGTAACAAGCAATCGAAGGTTCTGGAATGGCGGGA
AAGGGTTTAGTACCACATGCTATGATGCCCACTGTGATCTCCAGAGCAAAGTTCGTT
CGATCGTACTGTTACTCTCTCTCTTTCAAACAGAATTGTCCGAATCGTGTGACAACAA
CAGCCTGTTCTCACACACTCTTTTCTTCTAACCAAGGGGGTGGTTTAGTTTAGTAGAA
CCTCGTGAAACTTACATTTACATATATATAAACTTGCATAAATTGGTCAATGCAAGAAA
TACATATTTGGTCTTTTCTAATTCGTAGTTTTTCAAGTTCTTAGATGCTTTCTTTTTCTC
TTTTTTACAGATCATCAAGGAAGTAATTATCTACTTTTTACAACAAATATAAAACAAAG
CTTAAAATGAGAATGGAAGTCGTCTTGGTCGTTTTCTTGATGTTCATTGGTACTATCA
ACTGCGAAAGATTGATCTTCAATGGTAGACCTTTGTTGCACAGAGTTACCAAAGAAGA
AACCGTTATGTTGTACCACGAATTGGAAGTTGCTGCTTCTGCTGATGAAGTTTGGTCT
GTTGAAGGTTCTCCAGAATTGGGTTTACATTTGCCAGATTTGTTGCCAGCTGGTATTT
TTGCCAAGTTCGAAATTACTGGTGATGGTGGTGAAGGTTCCATTTTGGATATGACTTT
TCCACCAGGTCAATTCCCACATCATTACAGAGAAAAGTTCGTCTTTTTCGACCACAAG
AACAGATACAAGTTGGTCGAACAAATCGATGGTGATTTCTTCGATTTGGGTGTTACTT
ACTACATGGACACCATTAGAGTTGTTGCTACTGGTCCAGATTCTTGCGTTATTAAGTC
TACTACTGAATACCACGTCAAGCCAGAATTTGCTAAAATCGTTAAGCCATTGATCGAT
ACCGTTCCATTGGCTATTATGTCTGAAGCTATTGCCAAGGTTGTCTTGGAAAACAAAC
ACAAGTCATCTGAATGAAAGACTCCGCGGATCTCTTATGTCTTTACGATTTATAGTTTT
CATTATCAAGTATGCCTATATTAGTATATAGCATCTTTAGATGACAGTGTTCGAAGTTT
CACGAATAAAAGATAATATTCTACTTTTTGCTCCCACCGCGTTTGCTAGCACGAGTGA
ACACCATCCCTCGCCTGTGAGTTGTACCCATTCCTCTAAACTGTAGACATGGTAGCTT
CAGCAGTGTTCGTTATGTACGGCATCCTCCAACAAACAGTCGGTTATAGTTTGTCCTG
CTCCTCTGAATCGTCTCCCTCGATATTTCTCATTTTCCTTCGCATGCCCATGGGTTAA
CTGATCAATGCATCCTGCATGGCGCGCCTGATGAGCCTGAACTGCCCGGGCAAATC
AGCTGGCGTAATAGCGAAGAGGCCCGCACCGATCGCCCTTCCCAACAGTTGCGCAG
CCTGAATGGCGAATGGCGCGACGCGCCCTGTAGCGGCGCATTAAGCGCGGCGGGT
GTGGTGGTTACGCGCAGCGTGACCGCTACACTTGCCAGCGCCCTAGCGCCCGCTCC
TTTCGCTTTCTTCCCTTCCTTTCTCGCCACGTTCGCCGGCTTTCCCCGTCAAGCTCTA
AATCGGGGGCTCCCTTTAGGGTTCCGATTTAGTGCTTTACGGCACCTCGACCCCAAA
AAACTTGATTAGGGTGATGGTTCACGTAGTGGGCCATCGCCCTGATAGACGGTTTTT
CGCCCTTTGACGTTGGAGTCCACGTTCTTTAATAGTGGACTCTTGTTCCAAACTGGAA
CAACACTCAACCCTATCTCGGTCTATTCTTTTGATTTATAAGGGATTTTGCCGATTTCG
GCCTATTGGTTAAAAAATGAGCTGATTTAACAAAAATTTAACGCGAATTTTAACAAAAT
ATTAACGTTTACAATTTCCTGATGCGGTATTTTCTCCTTACGCATCTGTGCGGTATTTC
ACACCGCATAGGGTAATAACTGATATAATTAAATTGAAGCTCTAATTTGTGAGTTTAGT
ATACATGCATTTACTTATAATACAGTTTTTTAGTTTTGCTGGCCGCATCTTCTCAAATA
TGCTTCCCAGCCTGCTTTTCTGTAACGTTCACCCTCTACCTTAGCATCCCTTCCCTTT
GCAAATAGTCCTCTTCCAACAATAATAATGTCAGATCCTGTAGAGACCACATCATCCA
CGGTTCTATACTGTTGACCCAATGCGTCTCCCTTGTCATCTAAACCCACACCGGGTG
TCATAATCAACCAATCGTAACCTTCATCTCTTCCACCCATGTCTCTTTGAGCAATAAAG
CCGATAACAAAATCTTTGTCGCTCTTCGCAATGTCAACAGTACCCTTAGTATATTCTC
CAGTAGATAGGGAGCCCTTGCATGACAATTCTGCTAACATCAAAAGGCCTCTAGGTT
CCTTTGTTACTTCTTCTGCCGCCTGCTTCAAACCGCTAACAATACCTGGGCCCACCA
CACCGTGTGCATTCGTAATGTCTGCCCATTCTGCTATTCTGTATACACCCGCAGAGTA
CTGCAATTTGACTGTATTACCAATGTCAGCAAATTTTCTGTCTTCGAAGAGTAAAAAAT
TGTACTTGGCGGATAATGCCTTTAGCGGCTTAACTGTGCCCTCCATGGAAAAATCAG
TCAAGATATCCACATGTGTTTTTAGTAAACAAATTTTGGGACCTAATGCTTCAACTAAC
TCCAGTAATTCCTTGGTGGTACGAACATCCAATGAAGCACACAAGTTTGTTTGCTTTT
CGTGCATGATATTAAATAGCTTGGCAGCAACAGGACTAGGATGAGTAGCAGCACGTT
CCTTATATGTAGCTTTCGACATGATTTATCTTCGTTTCCTGCAGGTTTTTGTTCTGTGC
AGTTGGGTTAAGAATACTGGGCAATTTCATGTTTCTTCAACACTACATATGCGTATATA
TACCAATCTAAGTCTGTGCTCCTTCCTTCGTTCTTCCTTCTGTTCGGAGATTACCGAA
TCAAAAAAATTTCAAAGAAACCGAAATCAAAAAAAAGAATAAAAAAAAAATGATGAATT
GAATTGAAAAGCTGTGGTATGGTGCACTCTCAGTACAATCTGCTCTGATGCCGCATA
GTTAAGCCAGCCCCGACACCCGCCAACACCCGCTGACGCGCCCTGACGGGCTTGTC
TGCTCCCGGCATCCGCTTACAGACAAGCTGTGACCGTCTCCGGGAGCTGCATGTGT
CAGAGGTTTTCACCGTCATCACCGAAACGCGCGAGACGAAAGGGCCTCGTGATACG
CCTATTTTTATAGGTTAATGTCATGATAATAATGGTTTCTTAGGACGGATCGCTTGCCT
GTAACTTACACGCGCCTCGTATCTTTTAATGATGGAATAATTTGGGAATTTACTCTGT
GTTTATTTATTTTTATGTTTTGTATTTGGATTTTAGAAAGTAAATAAAGAAGGTAGAAGA
GTTACGGAATGAAGAAAAAAAAATAAACAAAGGTTTAAAAAATTTCAACAAAAAGCGT

TABLE 7-continued

| Disclosed Nucleic Acid and Amino Acid Sequences |
|---|
| ACTTTACATATATATTTATTAGACAAGAAAAGCAGATTAAATAGATATACATTCGATTAA<br>CGATAAGTAAAATGTAAAATCACAGGATTTTCGTGTGTGGTCTTCTACACAGACAAGA<br>TGAAACAATTCGGCATTAATACCTGAGAGCAGGAAGAGCAAGATAAAAGGTAGTATTT<br>GTTGGCGATCCCCCTAGAGTCTTTTACATCTTCGGAAAACAAAAACTATTTTTTCTTTA<br>ATTTCTTTTTTTACTTTCTATTTTTAATTTATATATTTATATTAAAAAATTTAAATTATAAT<br>TATTTTTATAGCACGTGATGAAAAGGACCCAGGTGGCACTTTTCGGGGAAATGTGCG<br>CGGAACCCCTATTTGTTTATTTTTCTAAATACATTCAAATATGTATCCGCTCATGAGAC<br>AATAACCCTGATAAATGCTTCAATAATATTGAAAAAGGAAGAGTATGAGTATTCAACAT<br>TTCCGTGTCGCCCTTATTCCCTTTTTTGCGGCATTTTGCCTTCCTGTTTTTGCTCACC<br>CAGAAACGCTGGTGAAAGTAAAAGATGCTGAAGATCAGTTGGGTGCACGAGTGGGT<br>TACATCGAACTGGATCTCAACAGCGGTAAGATCCTTGAGAGTTTTCGCCCCGAAGAA<br>CGTTTTCCAATGATGAGCACTTTTAAAGTTCTGCTATGTGGCGCGGTATTATCCCGTA<br>TTGACGCCGGGCAAGAGCAACTCGGTCGCCGCATACACTATTCTCAGAATGACTTGG<br>TTGAGTACTCACCAGTCACAGAAAAGCATCTTACGGATGGCATGACAGTAAGAGAAT<br>TATGCAGTGCTGCCATAACCATGAGTGATAACACTGCGGCCAACTTACTTCTGACAA<br>CGATCGGAGGACCGAAGGAGCTAACCGCTTTTTTGCACAACATGGGGGATCATGTAA<br>CTCGCCTTGATCGTTGGGAACCGGAGCTGAATGAAGCCATACCAAACGACGAGCGT<br>GACACCACGATGCCTGTAGCAATGGCAACAACGTTGCGCAAACTATTAACTGGCGAA<br>CTACTTACTCTAGCTTCCCGGCAACAATTAATAGACTGGATGGAGGCGGATAAAGTT<br>GCAGGACCACTTCTGCGCTCGGCCCTTCCGGCTGGCTGGTTTATTGCTGATAAATCT<br>GGAGCCGGTGAGCGTGGGTCTCGCGGTATCATTGCAGCACTGGGGCCAGATGGTA<br>AGCCCTCCCGTATCGTAGTTATCTACACGACGGGGAGTCAGGCAACTATGGATGAAC<br>GAAATAGACAGATCGCTGAGATAGGTGCCTCACTGATTAAGCATTGGTAACTGTCAG<br>ACCAAGTTTACTCATATATACTTTAGATTGATTTAAAACTTCATTTTTAATTTAAAAGGA<br>TCTAGGTGAAGATCCTTTTTGATAATCTCATGACCAAAATCCCTTAACGTGAGTTTTC<br>GTTCCACTGAGCGTCAGACCCCGTAGAAAAGATCAAAGGATCTTCTTGAGATCCTTTT<br>TTTCTGCGCGTAATCTGCTGCTTGCAAACAAAAAAACCACCGCTACCAGCGGTGGTT<br>TGTTTGCCGGATCAAGAGCTACCAACTCTTTTTCCGAAGGTAACTGGCTTCAGCAGA<br>GCGCAGATACCAAATACTGTCCTTCTAGTGTAGCCGTAGTTAGGCCACCACTTCAAG<br>AACTCTGTAGCACCGCCTACATACCTCGCTCTGCTAATCCTGTTACCAGTGGCTGCT<br>GCCAGTGGCGATAAGTCGTGTCTTACCGGGTTGGACTCAAGACGATAGTTACCGGAT<br>AAGGCGCAGCGGTCGGGCTGAACGGGGGGTTCGTGCACACAGCCCAGCTTGGAGC<br>GAACGACCTACACCGAACTGAGATACCTACAGCGTGAGCTATGAGAAAGCGCCACG<br>CTTCCCGAAGGGAGAAAGGCGGACAGGTATCCGGTAAGCGGCAGGGTCGGAACAG<br>GAGAGCGCACGAGGGAGCTTCCAGGGGGAAACGCCTGGTATCTTTATAGTCCTGTC<br>GGGTTTCGCCACCTCTGACTTGAGCGTCGATTTTTGTGATGCTCGTCAGGGGGGCG<br>GAGCCTATGGAAAAACGCCAGCAACGCGGCCTTTTTACGGTTCCTGGCCTTTTGCTG<br>GCCTTTTGCTCACATGTTCTTTCCTGCGTTATCCCCTGATTCTGTGGATAACCGTATT<br>ACCGCCTTTGAGTGAGCTGATACCGCTCGCCGCAGCCGAACGACCGAGCGCAGCG<br>AGTCAGTGAGCGAGGAAGCGGAAGAGCGCCCAATACGCAAACCGCCTCTCCCCGC<br>GCGTTGGCCGATTCATTAATGCAG |

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A recombinant yeast cell capable of producing one or more benzylisoquinoline alkaloids or benzylisoquinoline alkaloid precursors, or both, comprising:

(a) reduced or eliminated enzymatic activity of Aldehyde Reductase Intermediate 1 (ARI1) comprising the amino acid sequence of SEQ ID NO:15 and encoded by the nucleotide sequence SEQ ID NO:16, or the amino acid sequence of ARI1 yeast ortholog YDR541C comprising the amino acid sequence of SEQ ID NO: 11 and encoded by the nucleotide sequence SEQ ID NO: 12, or an amino acid sequence having at least 90% identity to SEQ ID NO: 11 or 15; and, optionally, (b) reduced or eliminated enzymatic activity of one or more alcohol dehydrogenases or other aldehyde reductases, or a combination thereof, Wherein the activity of each of the enzymes in (a) and (b) is reduced or eliminated, and whereby the recombinant yeast cell is thereby capable of increased production of one or more benzylisoquinoline alkaloids or benzylisoquinoline alkaloid precursors, or both, than are produced in cells without reduced or eliminated activity of said enzymes, and wherein the recombinant cell comprises a native gene encoding YDR541C or ARI1 comprising the amino acid sequence of SEQ ID NO: 11 or 15, respectively, or an amino acid sequence having at least 90% identity to SEQ ID NO: 11 or 15.

2. The recombinant cell according to claim 1, wherein the cell produces one or more benzylisoquinoline alkaloid precursors.

3. The recombinant cell according to claim 1, wherein the cell produces (S)-reticuline.

4. The recombinant cell according to claim 1, wherein the cell produces (S)-norcoclaurine.

5. The recombinant yeast cell of claim 1, wherein the one or more alcohol dehydrogenases or other aldehyde reductases, or combination thereof, is ADH3 comprising the amino acid sequence SEQ ID NO:29 encoded by the nucleotide sequence SEQ ID NO: 30, ADH4 comprising the amino acid sequence SEQ ID NO: 31 encoded by the nucleotide sequence SEQ ID NO:32, ADH5 comprising the amino acid sequence SEQ ID NO: 1 encoded by the nucleotide sequence SEQ ID NO:2, ADH6 comprising the amino acid sequence SEQ ID NO:3 encoded by the nucleotide sequence SEQ ID NO:4, ADH7 comprising the amino acid sequence SEQ ID NO:5 encoded by the nucleotide sequence SEQ ID NO:6, GRE2 comprising the amino acid sequence SEQ ID NO:7 encoded by the nucleotide sequence SEQ ID NO:8, AAD3 comprising the amino acid sequence SEQ ID NO:25 encoded by the nucleotide sequence SEQ ID NO:26, AAD4 comprising the amino acid sequence SEQ ID NO:27 encoded by the nucleotide sequence SEQ ID NO:28, BDH1 comprising the amino acid sequence SEQ ID NO:35 encoded by the nucleotide sequence SEQ ID NO:36, BDH2 comprising the amino acid sequence SEQ ID NO:37 encoded by the nucleotide sequence SEQ ID NO:38, ARA1 comprising the amino acid sequence SEQ ID NO:61 encoded by the nucleotide sequence SEQ ID NO:62, GCY1 comprising the amino acid sequence SEQ ID NO:41 encoded by the nucleotide sequence SEQ ID NO:42, FOX2 comprising the amino acid sequence SEQ ID NO:39 encoded by the nucleotide sequence SEQ ID NO:40, Aryl-alcohol Dehydrogenase YPL088W comprising the amino acid sequence SEQ ID NO:59 encoded by the nucleotide sequence SEQ ID NO:60, glucose-6-phosphate dehydrogenase ZWF1 comprising the amino acid sequence SEQ ID NO:57 encoded by the nucleotide sequence SEQ ID NO:58, GPD1 comprising the amino acid sequence SEQ ID NO:45 encoded by the nucleotide sequence SEQ ID NO:46, HIS4 comprising the amino acid sequence SEQ ID NO:47 encoded by the nucleotide sequence SEQ ID NO:48, IDP1 comprising the amino acid sequence SEQ ID NO:51 encoded by the nucleotide sequence SEQ ID NO:52, LYS12 comprising the amino acid sequence SEQ ID NO:53 encoded by the nucleotide sequence SEQ ID NO:54, GRE3 comprising the amino acid sequence SEQ ID NO:9 encoded by the nucleotide sequence SEQ ID NO:10, aldehyde reductase YCR102C comprising the amino acid sequence SEQ ID NO: s19 encoded by the nucleotide sequence SEQ ID NO:20, aldehyde reductase YDR541C comprising the amino acid sequence SEQ ID NO:11 encoded by the nucleotide sequence SEQ ID NO:12, SER33 comprising the amino acid sequence SEQ ID NO:55 encoded by the nucleotide sequence SEQ ID NO:56, aldehyde reductase YGL039W comprising the amino acid sequence SEQ ID NO:17 encoded by the nucleotide sequence SEQ ID NO:18, aldehyde reductase YLR460C comprising the amino acid sequence SEQ ID NO:13 encoded by the nucleotide sequence SEQ ID NO:14, aldehyde reductase YPR127W comprising the amino acid sequence SEQ ID NO:21 encoded by the nucleotide sequence SEQ ID NO:22, ALD6 comprising the amino acid sequence SEQ ID NO:33 encoded by the nucleotide sequence SEQ ID NO:34, GOR1 comprising the amino acid sequence SEQ ID NO:43 encoded by the nucleotide sequence SEQ ID NO:44, HMG1 comprising the amino acid sequence SEQ ID NO:49 encoded by the nucleotide sequence SEQ ID NO:50, or an amino acid sequence having at least 90% identity to SEQ ID NO: 29, 31, 1, 3, 5, 7, 25, 27, 35, 37, 61, 41, 39, 59, 57, 45, 47, 51, 53, 15, 9, 19, 11, 55, 17, 13, 21, 33, 43 or 49, and wherein the yeast cell comprises a native gene of the corresponding one or more alcohol dehydrogenases or other aldehyde reductases.

6. The recombinant yeast cell of claim 1, wherein the recombinant yeast cell is *Saccharomyces cerevisiae, Schizosaccharomyces pombe* or *Yarrowia lipolytica.*

7. A method for producing of a benzylisoquinoline alkaloid or a benzylisoquinoline alkaloid precursor, comprising:

(a) providing a recombinant yeast capable of producing one or more benzylisoquinoline alkaloids or benzylisoquinoline alkaloid precursors, or both, that has reduced or eliminated activity of (i) Aldehyde Reductase Intermediate 1 (ARI1) comprising the amino acid sequence SEQ ID NO:15 encoded by the nucleotide sequence SEQ ID NO:16, or the amino acid sequence of ARI1 yeast ortholog YDR541C comprising the amino acid sequence of SEQ ID NO: 11 encoded by the nucleotide sequence SEQ ID NO: 12, or an amino acid sequence having at least 90% identity to SEQ ID NO: 11 or 15; and, optionally, (ii) one or more alcohol dehydrogenases or other aldehyde reductases, or a combination thereof, wherein the activity of each of the enzymes in (i) and (ii) is reduced or eliminated, and wherein the recombinant yeast cell comprises a native gene encoding YDR541C or ARI1 comprising the amino acid sequence of SEQ ID NO: 11 or 15, respectively, or an amino acid sequence having at least 90% identity to SEQ ID NO: 11 or 15, (b) cultivating said recombinant cell for a time sufficient for said recombinant yeast cell to produce a benzylisoquinoline alkaloid and/or a benzylisoquinoline alkaloid precursor; and, optionally, (c) isolating the benzylisoquinoline alkaloid and/or a benzylisoquinoline alkaloid precursor from said recombinant cell or from the cultivation supernatant, thereby producing a benzylisoquinoline alkaloid and/or a benzylisoquinoline alkaloid precursor.

8. The method of claim 7, wherein the recombinant yeast cell produces one or more benzylisoquinoline alkaloid precursors.

9. The method of claim 7, wherein the recombinant yeast cell produces (S)-reticuline.

10. The method of claim, wherein the recombinant yeast cell produces (S)-norcoclaurine.

11. The method of claim 7, wherein the one or more alcohol dehydrogenases or other aldehyde reductases, or combination thereof, is ADH3 comprising the amino acid sequence SEQ ID NO:29 encoded by the nucleotide sequence SEQ ID NO: 30, ADH4 comprising the amino acid sequence SEQ ID NO: 31 encoded by the nucleotide sequence SEQ ID NO:32, ADH5 comprising the amino acid sequence SEQ ID NO: 1 encoded by the nucleotide sequence SEQ ID NO:2, ADH6 comprising the amino acid sequence SEQ ID NO:3 encoded by the nucleotide sequence SEQ ID NO:4, ADH7 comprising the amino acid sequence SEQ ID NO:5 encoded by the nucleotide sequence SEQ ID NO:6, GRE2 comprising the amino acid sequence SEQ ID NO:7 encoded by the nucleotide sequence SEQ ID NO:8, AAD3 comprising the amino acid sequence SEQ ID NO:25 encoded by the nucleotide sequence SEQ ID NO:26, AAD4 comprising the amino acid sequence SEQ ID NO:27 encoded by the nucleotide sequence SEQ ID NO:28, BDH1 comprising the amino acid sequence SEQ ID NO:35 encoded by the nucleotide sequence SEQ ID NO:36, BDH2 comprising the amino acid sequence SEQ ID NO:37 encoded by the nucleotide sequence SEQ ID NO:38, ARA1 comprising the amino acid sequence SEQ ID NO:61 encoded by the nucleotide sequence SEQ ID NO:62, GCY1 comprising the amino acid sequence SEQ ID NO:41 encoded by the nucleotide sequence SEQ ID NO:42, FOX2 comprising the amino acid sequence SEQ ID NO:39 encoded by the nucleotide sequence SEQ ID NO:40, Aryl-alcohol Dehydrogenase YPL088W comprising the amino acid sequence SEQ ID NO:59 encoded by the nucleotide sequence SEQ ID NO:60, glucose-6-phosphate dehydrogenase ZWF1 comprising the amino acid sequence SEQ ID NO:57 encoded by the nucleotide sequence SEQ ID NO:58, GPD1 comprising the amino acid sequence SEQ ID NO:45 encoded by the nucleotide sequence SEQ ID NO:46, HIS4 comprising the amino acid sequence SEQ ID NO:47 encoded by the nucleotide sequence SEQ ID NO:48, IDP1 comprising the amino acid sequence SEQ ID NO:51 encoded by the nucleotide sequence SEQ ID NO:52, LYS12 comprising the amino acid sequence SEQ ID NO:53 encoded by the nucleotide sequence SEQ ID NO:54, GRE3 comprising the amino acid sequence SEQ ID NO:9 encoded by the nucleotide sequence SEQ ID NO:10, aldehyde reductase YCR102C comprising the amino acid sequence SEQ ID NO:19 encoded by the nucleotide sequence SEQ ID NO:20, aldehyde reductase YDR541C comprising the amino acid sequence SEQ ID NO:11 encoded by the nucleotide sequence SEQ ID NO:12, SER33 comprising the amino acid sequence SEQ ID NO:55 encoded by the nucleotide sequence SEQ ID NO:56, aldehyde reductase YGL039W comprising the amino acid sequence SEQ ID NO:17 encoded by the nucleotide sequence SEQ ID NO:18, aldehyde reductase YLR460C comprising the amino acid sequence SEQ ID NO:13 encoded by the nucleotide sequence SEQ ID NO:14, aldehyde reductase YPR127W comprising the amino acid sequence SEQ ID NO:21 encoded by the nucleotide sequence SEQ ID NO:22, ALD6 comprising the amino acid sequence SEQ ID NO:33 encoded by the nucleotide sequence SEQ ID NO:34, GOR1 comprising the amino acid sequence SEQ ID NO:43 encoded by the nucleotide sequence SEQ ID NO:44, HMG1 comprising the amino acid sequence SEQ ID NO:49 encoded by the nucleotide sequence SEQ ID NO:50, or an amino acid sequence having at least 90% identity to SEQ ID NO: 29, 31, 1, 3, 5, 7, 25, 27, 35, 37, 61, 41, 39, 59, 57, 45, 47, 51, 53, 15, 9, 19, 11, 55, 17, 13, 21, 33, 43 or 49, and wherein the yeast cell comprises a native gene of the corresponding one or more alcohol dehydrogenases or other aldehyde reductases.

12. The method of claim 7, wherein the recombinant yeast is *Saccharomyces cerevisiae, Schizosaccharomyces pombe* or *Yarrowia lipolytica.*

13. The recombinant yeast cell of claim 1, wherein the cell produces one or more benzylisoquinoline alkaloids selected from thebaine, morphine, neomorphine, hydrocodone, Codeine, Oxycodone, Oxymorphone and Dihydromorphine.

14. The method of claim 7, wherein the recombinant yeast cell produces one or more benzylisoquinoline alkaloid selected from thebaine, morphine, neomorphine, hydrocodone, Codeine, Oxycodone, Oxymorphone and Dihydromorphine.

* * * * *